(12) United States Patent
De Juan, Jr. et al.

(10) Patent No.: US 10,555,804 B2
(45) Date of Patent: Feb. 11, 2020

(54) THERAPEUTIC DEVICE FOR PAIN MANAGEMENT AND VISION

(71) Applicant: Journey1, Inc., Brisbane, CA (US)

(72) Inventors: Eugene De Juan, Jr., San Francisco, CA (US); Cary J. Reich, Los Gatos, CA (US); Stephen Boyd, Murrieta, CA (US); Yair Alster, Menlo Park, CA (US); David Sierra, Aptos, CA (US); Hanson S. Gifford, Woodside, CA (US); Jose D. Alejandro, Sunnyvale, CA (US); Richard L. Lindstrom, Minneapolis, MN (US); K. Angela MacFarlane, Woodside, CA (US); Douglas Sutton, Pacifica, CA (US); John Anthony Scholl, San Ramon, CA (US)

(73) Assignee: JOURNEY1, INC., Brisbane, CA (US)

( * ) Notice: Subject to any disclaimer, the term of this patent is extended or adjusted under 35 U.S.C. 154(b) by 0 days.

(21) Appl. No.: 15/917,071

(22) Filed: Mar. 9, 2018

(65) Prior Publication Data

US 2018/0193133 A1    Jul. 12, 2018

Related U.S. Application Data

(63) Continuation of application No. 12/384,659, filed on Apr. 6, 2009, now Pat. No. 9,943,401.
(Continued)

(51) Int. Cl.
*A61F 2/14* (2006.01)
*A61F 9/00* (2006.01)
*G02C 7/04* (2006.01)

(52) U.S. Cl.
CPC .......... *A61F 2/142* (2013.01); *A61F 2/14* (2013.01); *A61F 9/00* (2013.01); *A61F 2250/0067* (2013.01); *G02C 7/047* (2013.01)

(58) Field of Classification Search
CPC .......... A61F 2/142; A61F 2/145; A61F 2/147; A61F 2/16; A61F 2/14; A61F 9/0061; G02C 7/047
See application file for complete search history.

(56) References Cited

U.S. PATENT DOCUMENTS

| 2,641,161 A | 6/1953 | Silverstein et al. |
| 2,714,721 A | 8/1955 | Stone, Jr. et al. |

(Continued)

FOREIGN PATENT DOCUMENTS

| CA | 993401 A | 7/1976 |
| CA | 2174967 A1 | 5/1995 |

(Continued)

OTHER PUBLICATIONS

Alio et al. Contact Lens Fitting to Correct Irregular Astigmatic After Corneal Refractive Surgery. Journal of Cataract & Refractive Surgery 28(10):1750-1757 (2002).

(Continued)

*Primary Examiner* — David H Willse
*Assistant Examiner* — Tiffany P Shipmon
(74) *Attorney, Agent, or Firm* — Wilson Sonsini Goodrich & Rosati

(57) ABSTRACT

A therapeutic lens for the treatment of an epithelial defect comprises a layer of therapeutic material disposed over the stroma and/or Bowman's membrane to inhibit water flow from the tear liquid to the stroma and/or Bowman's membrane, such that corneal deturgescence can be restored to decrease corneal swelling and light scattering. The layer may cover and protect nerve fibers to decrease pain. The (Continued)

layer may comprise an index of refraction to inhibit light scatter from an anterior surface of the stroma and/or Bowman's membrane. The lens may comprise a curved anterior surface that provides functional vision for the patient when the epithelium regenerates. The layer of therapeutic material can be positioned on the eye in many ways, for example with a spray that is cured to adhere the layer to the exposed surface of the stroma and/or Bowman's membrane.

25 Claims, 137 Drawing Sheets

Related U.S. Application Data

(60) Provisional application No. 61/211,815, filed on Apr. 3, 2009, provisional application No. 61/119,712, filed on Dec. 3, 2008, provisional application No. 61/191,915, filed on Sep. 11, 2008, provisional application No. 61/050,147, filed on May 2, 2008, provisional application No. 61/042,594, filed on Apr. 4, 2008.

(56) References Cited

U.S. PATENT DOCUMENTS

| | | |
|---|---|---|
| 2,952,023 A | 9/1960 | Hyman et al. |
| 3,246,941 A | 4/1966 | Moss et al. |
| 3,431,046 A | 3/1969 | Conrad et al. |
| 3,468,602 A | 9/1969 | Rosen et al. |
| 3,488,111 A | 1/1970 | Isen et al. |
| 3,489,491 A | 1/1970 | Creighton et al. |
| 3,495,899 A | 2/1970 | Biri et al. |
| 3,594,074 A | 7/1971 | Rosen et al. |
| 3,619,044 A | 11/1971 | Kamath et al. |
| 3,688,386 A | 9/1972 | Pereira et al. |
| 3,833,786 A | 9/1974 | Brucker et al. |
| 3,915,609 A | 10/1975 | Robinson et al. |
| 3,944,347 A | 3/1976 | Barkdoll et al. |
| 3,973,837 A | 8/1976 | Page et al. |
| 3,973,838 A | 8/1976 | Page et al. |
| 4,037,866 A | 7/1977 | Price et al. |
| 4,053,442 A | 10/1977 | Jungr et al. |
| 4,068,933 A | 1/1978 | Seiderman et al. |
| 4,071,272 A | 1/1978 | Drdlik et al. |
| 4,121,885 A | 10/1978 | Erickson et al. |
| 4,126,904 A | 11/1978 | Shepard et al. |
| 4,166,255 A | 8/1979 | Graham et al. |
| 4,171,878 A | 10/1979 | Arbuzova et al. |
| 4,194,815 A | 3/1980 | Trombley et al. |
| 4,198,132 A | 4/1980 | Jacobson et al. |
| 4,200,320 A | 4/1980 | Durham et al. |
| 4,208,362 A | 6/1980 | Deichert et al. |
| 4,211,476 A | 7/1980 | Brummel et al. |
| 4,268,131 A | 5/1981 | Miyata et al. |
| 4,268,133 A | 5/1981 | Fischer et al. |
| 4,312,575 A | 1/1982 | Peyman et al. |
| 4,346,482 A | 8/1982 | Tennant et al. |
| 4,381,007 A | 4/1983 | Doss et al. |
| 4,407,766 A | 10/1983 | Haardt et al. |
| 4,452,776 A | 6/1984 | Refojo et al. |
| 4,452,925 A | 6/1984 | Kuzma et al. |
| 4,487,905 A | 12/1984 | Mitchell et al. |
| 4,563,779 A | 1/1986 | Kelman et al. |
| 4,581,030 A | 4/1986 | Bruns et al. |
| 4,593,981 A | 6/1986 | Scilipoti et al. |
| 4,621,912 A | 11/1986 | Meyer et al. |
| 4,624,669 A | 11/1986 | Grendahl et al. |
| 4,640,594 A | 2/1987 | Berger et al. |
| 4,666,249 A | 5/1987 | Bauman et al. |
| 4,666,267 A | 5/1987 | Wichterle et al. |
| 4,676,790 A | 6/1987 | Kern et al. |
| 4,693,715 A | 9/1987 | Abel, Jr. et al. |
| 4,701,288 A | 10/1987 | Cook et al. |
| 4,715,858 A | 12/1987 | Lindstrom et al. |
| 4,772,283 A | 9/1988 | White et al. |
| 4,799,931 A | 1/1989 | Lindstrom et al. |
| 4,806,382 A | 2/1989 | Goldberg et al. |
| 4,810,082 A | 3/1989 | Abel, Jr. et al. |
| 4,834,748 A | 5/1989 | McDonald et al. |
| 4,851,003 A | 7/1989 | Lindstrom et al. |
| 4,866,350 A | 9/1989 | Counts et al. |
| 4,886,350 A | 12/1989 | Wichterle et al. |
| 4,890,911 A | 1/1990 | Sulc et al. |
| 4,909,896 A | 3/1990 | Ikushima et al. |
| 4,923,467 A | 5/1990 | Thompson et al. |
| 4,940,751 A | 7/1990 | Frances et al. |
| 4,943,150 A | 7/1990 | Deichert et al. |
| 4,952,045 A | 8/1990 | Stoyan et al. |
| 4,969,912 A | 11/1990 | Kelman et al. |
| 4,973,493 A | 11/1990 | Guire et al. |
| 4,978,481 A | 12/1990 | Janssen et al. |
| 4,979,959 A | 12/1990 | Guire et al. |
| 4,981,841 A | 1/1991 | Gibson et al. |
| 4,983,181 A | 1/1991 | Civerchia et al. |
| 4,994,081 A | 2/1991 | Civerchia et al. |
| 4,997,583 A | 3/1991 | Itzhak et al. |
| 5,008,289 A | 4/1991 | Bernstein et al. |
| 5,019,097 A | 5/1991 | Knight et al. |
| 5,030,230 A | 7/1991 | White et al. |
| 5,073,021 A | 12/1991 | Marron et al. |
| 5,104,213 A | 4/1992 | Wolfson et al. |
| 5,108,428 A | 4/1992 | Capecchi et al. |
| 5,112,350 A | 5/1992 | Civerchia et al. |
| 5,114,627 A | 5/1992 | Civerchia et al. |
| 5,143,660 A | 9/1992 | Hamilton et al. |
| 5,152,786 A | 10/1992 | Hanna et al. |
| 5,156,622 A | 10/1992 | Thompson et al. |
| 5,159,360 A | 10/1992 | Stoy et al. |
| 5,163,596 A | 11/1992 | Ravoo et al. |
| 5,163,934 A | 11/1992 | Munnerlyn et al. |
| 5,166,710 A | 11/1992 | Hoefer et al. |
| 5,171,318 A | 12/1992 | Gibson et al. |
| 5,178,879 A | 1/1993 | Adekunle et al. |
| 5,191,365 A | 3/1993 | Stoyan et al. |
| 5,192,316 A | 3/1993 | Ting et al. |
| 5,196,027 A | 3/1993 | Thompson et al. |
| 5,213,720 A | 5/1993 | Civerchia et al. |
| 5,236,236 A | 8/1993 | Girimont et al. |
| 5,244,799 A | 9/1993 | Anderson et al. |
| 5,245,367 A | 9/1993 | Miller et al. |
| 5,246,259 A | 9/1993 | Hellenkamp et al. |
| 5,263,992 A | 11/1993 | Guire et al. |
| 5,292,514 A | 3/1994 | Capecchi et al. |
| 5,293,186 A | 3/1994 | Seden et al. |
| 5,312,320 A | 5/1994 | Esperance, Jr. |
| 5,346,491 A | 9/1994 | Oertli et al. |
| 5,347,326 A | 9/1994 | Volk et al. |
| 5,349,395 A | 9/1994 | Stoyan et al. |
| 5,397,848 A | 3/1995 | Yang et al. |
| 5,401,508 A | 3/1995 | Manesis et al. |
| 5,428,412 A | 6/1995 | Stoyan et al. |
| 5,433,714 A | 7/1995 | Bloomberg et al. |
| 5,433,898 A | 7/1995 | Thakrar et al. |
| 5,434,630 A | 7/1995 | Bransome et al. |
| 5,472,436 A | 12/1995 | Fremstad et al. |
| 5,489,300 A | 2/1996 | Capecchi et al. |
| 5,496,084 A | 3/1996 | Miralles et al. |
| 5,517,260 A | 5/1996 | Glady et al. |
| 5,522,888 A | 6/1996 | Civerchia et al. |
| 5,538,301 A | 7/1996 | Yavitz et al. |
| 5,552,452 A | 9/1996 | Khadem et al. |
| 5,570,144 A | 10/1996 | Lofgren-Nisser et al. |
| 5,578,332 A | 11/1996 | Hamilton et al. |
| 5,598,233 A | 1/1997 | Haralambopoulos et al. |
| 5,612,432 A | 3/1997 | Taniguchi et al. |
| 5,628,794 A | 5/1997 | Lindstrom et al. |
| 5,632,733 A | 5/1997 | Shaw et al. |
| 5,632,773 A | 5/1997 | Graham et al. |
| 5,649,922 A | 7/1997 | Yavitz et al. |
| 5,662,706 A | 9/1997 | Legerton et al. |
| 5,671,038 A | 9/1997 | Porat et al. |
| 5,712,721 A | 1/1998 | Large et al. |

(56) References Cited

U.S. PATENT DOCUMENTS

| | | |
|---|---|---|
| 5,713,957 A | 2/1998 | Steele et al. |
| 5,716,633 A | 2/1998 | Civerchia et al. |
| 5,732,990 A | 3/1998 | Yavitz et al. |
| 5,757,458 A | 5/1998 | Miller et al. |
| 5,760,100 A | 6/1998 | Nicolson et al. |
| 5,760,870 A | 6/1998 | Payor et al. |
| 5,804,263 A | 9/1998 | Goldberg et al. |
| 5,814,329 A | 9/1998 | Shah et al. |
| 5,820,624 A | 10/1998 | Yavitz et al. |
| 5,836,313 A | 11/1998 | Perez et al. |
| 5,854,291 A | 12/1998 | Laughlin et al. |
| 5,869,533 A | 2/1999 | Holt et al. |
| 5,885,597 A | 3/1999 | Botknecht et al. |
| 5,905,561 A | 5/1999 | Lee et al. |
| 5,910,512 A | 6/1999 | Conant et al. |
| 5,923,397 A | 7/1999 | Bonafini, Jr. et al. |
| 5,929,968 A | 7/1999 | Cotie et al. |
| 5,932,205 A | 8/1999 | Wang et al. |
| 5,942,243 A | 8/1999 | Shah et al. |
| 5,953,098 A | 9/1999 | Lieberman et al. |
| 5,957,921 A | 9/1999 | Mirhashemi et al. |
| 5,962,532 A | 10/1999 | Campbell et al. |
| 5,971,541 A | 10/1999 | Danker et al. |
| 5,980,040 A | 11/1999 | Xu et al. |
| 5,986,001 A | 11/1999 | Ingenito et al. |
| 6,010,219 A | 1/2000 | Stoyan et al. |
| 6,030,974 A | 2/2000 | Schwartz et al. |
| 6,036,314 A | 3/2000 | Wolfson et al. |
| 6,036,688 A | 3/2000 | Edwards et al. |
| 6,048,855 A | 4/2000 | De Lacharriere et al. |
| 6,055,990 A | 5/2000 | Thompson et al. |
| 6,075,066 A | 6/2000 | Matsuda et al. |
| 6,090,995 A | 7/2000 | Reich et al. |
| 6,092,898 A | 7/2000 | De Juan et al. |
| 6,099,121 A | 8/2000 | Chapman et al. |
| 6,143,315 A | 11/2000 | Wang et al. |
| 6,217,171 B1 | 4/2001 | Auten et al. |
| 6,244,709 B1 | 6/2001 | Vayntraub et al. |
| 6,248,788 B1 | 6/2001 | Robbins et al. |
| 6,325,509 B1 | 12/2001 | Hodur et al. |
| 6,340,229 B1 | 1/2002 | Lieberman et al. |
| 6,361,169 B1 | 3/2002 | Tung et al. |
| 6,364,482 B1 | 4/2002 | Roffman et al. |
| 6,406,145 B1 | 6/2002 | Jubin et al. |
| 6,454,800 B2 | 9/2002 | Dalton et al. |
| 6,474,814 B1 | 11/2002 | Griffin et al. |
| 6,520,637 B2 | 2/2003 | Hodur et al. |
| 6,541,028 B1 | 4/2003 | Kuri-Harcuch et al. |
| 6,544,286 B1 | 4/2003 | Perez et al. |
| 6,551,307 B2 | 4/2003 | Peyman et al. |
| 6,568,808 B2 | 5/2003 | Campin et al. |
| 6,579,918 B1 | 6/2003 | Auten et al. |
| 6,593,370 B2 | 7/2003 | Tamura et al. |
| 6,607,522 B1 | 8/2003 | Hamblin et al. |
| 6,645,715 B1 | 11/2003 | Griffith et al. |
| 6,652,095 B2 | 11/2003 | Tung et al. |
| 6,659,607 B2 | 12/2003 | Miyamura et al. |
| 6,689,165 B2 | 2/2004 | Jacob et al. |
| 6,702,807 B2 | 3/2004 | Peyman et al. |
| 6,726,322 B2 | 4/2004 | Andino et al. |
| 6,726,684 B1 | 4/2004 | Woloszko et al. |
| 6,779,888 B2 | 8/2004 | Marmo et al. |
| 6,843,563 B2 | 1/2005 | Richardson et al. |
| 6,849,671 B2 | 2/2005 | Steffen et al. |
| 6,880,558 B2 | 4/2005 | Perez et al. |
| 6,918,904 B1 | 7/2005 | Peyman et al. |
| 6,951,894 B1 | 10/2005 | Nicolson et al. |
| 6,958,148 B1 | 10/2005 | Green et al. |
| 6,958,158 B2 | 10/2005 | Tenhuisen et al. |
| 7,004,953 B2 | 2/2006 | Pallikaris et al. |
| 7,018,039 B2 | 3/2006 | Legerton et al. |
| 7,025,455 B2 | 4/2006 | Roffman et al. |
| 7,077,839 B2 | 7/2006 | Hamblin et al. |
| 7,080,905 B2 | 7/2006 | Marmo et al. |
| 7,097,301 B2 | 8/2006 | Legerton et al. |
| 7,104,648 B2 | 9/2006 | Dahi et al. |
| 7,150,529 B2 | 12/2006 | Legerton et al. |
| 7,163,292 B2 | 1/2007 | Dahi et al. |
| 7,193,124 B2 | 3/2007 | Coffee et al. |
| 7,216,974 B2 | 5/2007 | Meyers et al. |
| 7,229,685 B2 | 6/2007 | Full et al. |
| 7,249,849 B2 | 7/2007 | Marmo et al. |
| 7,270,412 B2 | 9/2007 | Legerton et al. |
| 7,322,694 B2 | 1/2008 | Dahi et al. |
| 7,329,001 B2 | 2/2008 | Benrashid et al. |
| 7,338,160 B2 | 3/2008 | Lieberman et al. |
| 7,360,890 B2 | 4/2008 | Back et al. |
| 7,377,637 B2 | 5/2008 | Legerton et al. |
| 7,401,922 B2 | 7/2008 | Legerton et al. |
| 7,401,992 B1 | 7/2008 | Lin et al. |
| 7,404,638 B2 | 7/2008 | Miller et al. |
| 7,461,937 B2 | 12/2008 | Steffen et al. |
| 7,491,350 B2 | 2/2009 | Silvestrini et al. |
| 7,530,689 B2 | 5/2009 | Berke et al. |
| 7,537,339 B2 | 5/2009 | Legerton et al. |
| 7,543,936 B2 | 6/2009 | Legerton et al. |
| 7,559,649 B2 | 7/2009 | Cotie et al. |
| 7,585,074 B2 | 9/2009 | Dahi et al. |
| 7,594,725 B2 | 9/2009 | Legerton et al. |
| 7,628,810 B2 | 12/2009 | Christie et al. |
| 7,682,020 B2 | 3/2010 | Berke et al. |
| 7,695,135 B1 | 4/2010 | Rosenthal et al. |
| 7,699,465 B2 | 4/2010 | Dootjes et al. |
| 7,717,555 B2 | 5/2010 | Legerton et al. |
| 7,735,997 B2 | 6/2010 | Muckenhirn et al. |
| 7,748,844 B2 | 7/2010 | Lai et al. |
| 7,762,668 B2 | 7/2010 | Dai et al. |
| 7,828,432 B2 | 11/2010 | Meyers et al. |
| 7,859,769 B2 | 12/2010 | Zalevsky et al. |
| 7,976,577 B2 | 7/2011 | Silvestrini et al. |
| 7,984,988 B2 | 7/2011 | Berke et al. |
| 8,137,344 B2 | 3/2012 | Jia et al. |
| 8,201,941 B2 | 6/2012 | Choo et al. |
| 8,459,793 B2 | 6/2013 | De Juan et al. |
| 8,485,662 B2 | 7/2013 | Collins et al. |
| 8,591,025 B1 | 11/2013 | De Juan et al. |
| 8,678,584 B2 | 3/2014 | De Juan et al. |
| 8,864,306 B2 | 10/2014 | De Juan et al. |
| 8,882,757 B2 | 11/2014 | Muller et al. |
| 8,926,096 B2 | 1/2015 | De Juan et al. |
| 9,107,773 B2 | 8/2015 | De Juan et al. |
| 9,125,735 B2 | 9/2015 | De Juan et al. |
| 9,241,837 B2 | 1/2016 | De Juan et al. |
| 9,341,864 B2 | 5/2016 | De Juan et al. |
| 9,395,558 B2 | 7/2016 | De Juan et al. |
| 9,423,632 B2 | 8/2016 | De Juan et al. |
| 9,465,233 B2 | 10/2016 | De Juan et al. |
| 9,498,385 B2 | 11/2016 | De Juan et al. |
| 9,740,025 B2 | 8/2017 | De Juan et al. |
| 9,740,026 B2 | 8/2017 | De Juan et al. |
| 9,810,921 B2 | 11/2017 | De Juan et al. |
| 9,851,586 B2 | 12/2017 | De Juan et al. |
| 9,943,401 B2 | 4/2018 | De Juan et al. |
| 1,003,690 A1 | 7/2018 | De Juan et al. |
| 1,003,967 A1 | 8/2018 | De Juan et al. |
| 1,019,130 A1 | 1/2019 | De Juan et al. |
| 2001/0047203 A1 | 11/2001 | Dalton et al. |
| 2002/0095199 A1 | 7/2002 | West et al. |
| 2002/0107567 A1 | 8/2002 | Terwee et al. |
| 2002/0151972 A1 | 10/2002 | Hughes et al. |
| 2002/0164484 A1 | 11/2002 | Jiang et al. |
| 2003/0144650 A1 | 7/2003 | Smith |
| 2003/0187515 A1 | 10/2003 | Hariri et al. |
| 2004/0015163 A1 | 1/2004 | Buysse et al. |
| 2004/0037866 A1 | 2/2004 | Semertzides et al. |
| 2004/0048796 A1 | 3/2004 | Hariri et al. |
| 2004/0053442 A1 | 3/2004 | Akram et al. |
| 2004/0068933 A1 | 4/2004 | Nakamura et al. |
| 2004/0071272 A1 | 4/2004 | Mizuguchi et al. |
| 2004/0088050 A1 | 5/2004 | Norrby et al. |
| 2004/0121885 A1 | 6/2004 | Garcia-Rill et al. |
| 2004/0141150 A1 | 7/2004 | Roffman et al. |
| 2004/0143026 A1 | 7/2004 | Shah et al. |
| 2004/0166255 A1 | 8/2004 | Pierce et al. |

(56) References Cited

U.S. PATENT DOCUMENTS

| | | |
|---|---|---|
| 2004/0170666 A1 | 9/2004 | Keates et al. |
| 2004/0171878 A1 | 9/2004 | Kok et al. |
| 2004/0184158 A1 | 9/2004 | Shadduck et al. |
| 2004/0194815 A1 | 10/2004 | Deiss et al. |
| 2004/0200320 A1 | 10/2004 | Knopp et al. |
| 2004/0208362 A1 | 10/2004 | Suzuki et al. |
| 2004/0211476 A1 | 10/2004 | Hager et al. |
| 2004/0212779 A1 | 10/2004 | Dahi et al. |
| 2005/0018130 A1 | 1/2005 | Dahi et al. |
| 2005/0028723 A1 | 2/2005 | Ancel et al. |
| 2005/0033420 A1 | 2/2005 | Christie et al. |
| 2005/0107775 A1 | 5/2005 | Huang et al. |
| 2005/0191365 A1 | 9/2005 | Creasey et al. |
| 2005/0213030 A1 | 9/2005 | Meyers et al. |
| 2005/0236236 A1 | 10/2005 | Farooq et al. |
| 2005/0238692 A1 | 10/2005 | Hughes et al. |
| 2005/0245367 A1 | 11/2005 | Horvath et al. |
| 2005/0246259 A1 | 11/2005 | Lavoie et al. |
| 2005/0259221 A1 | 11/2005 | Marmo et al. |
| 2005/0288196 A1 | 12/2005 | Horn et al. |
| 2006/0010219 A1 | 1/2006 | Saito et al. |
| 2006/0013050 A1 | 1/2006 | Fukuzumi et al. |
| 2006/0030974 A1 | 2/2006 | Tsukasaki et al. |
| 2006/0034807 A1 | 2/2006 | Griffith et al. |
| 2006/0036314 A1 | 2/2006 | Perez et al. |
| 2006/0048855 A1 | 3/2006 | Honkura et al. |
| 2006/0075066 A1 | 4/2006 | Farchmin et al. |
| 2006/0077581 A1 | 4/2006 | Schwiegerling et al. |
| 2006/0083773 A1 | 4/2006 | Myung et al. |
| 2006/0099121 A1 | 5/2006 | Doona et al. |
| 2006/0100617 A1 | 5/2006 | Boukhny et al. |
| 2006/0132707 A1 | 6/2006 | Tung et al. |
| 2006/0134170 A1 | 6/2006 | Griffith et al. |
| 2006/0152673 A1 | 7/2006 | Cotie et al. |
| 2006/0197909 A1 | 9/2006 | Legerton et al. |
| 2006/0197910 A1 | 9/2006 | Legerton et al. |
| 2006/0217171 A1 | 9/2006 | Roireau et al. |
| 2006/0235514 A1 | 10/2006 | Silvestrini et al. |
| 2006/0238712 A1 | 10/2006 | Dahi et al. |
| 2006/0241751 A1* | 10/2006 | Marmo .............. A61F 9/0017 623/5.11 |
| 2006/0244709 A1 | 11/2006 | Lin et al. |
| 2006/0246113 A1 | 11/2006 | Griffith et al. |
| 2006/0248788 A1 | 11/2006 | Harris et al. |
| 2006/0250576 A1 | 11/2006 | Legerton et al. |
| 2006/0256283 A1 | 11/2006 | Legerton et al. |
| 2006/0256284 A1 | 11/2006 | Dahi et al. |
| 2006/0285071 A1 | 12/2006 | Erickson et al. |
| 2006/0285072 A1 | 12/2006 | Dahi et al. |
| 2006/0290882 A1 | 12/2006 | Meyers et al. |
| 2007/0002046 A1 | 1/2007 | Tanacs et al. |
| 2007/0013869 A1 | 1/2007 | Dahi et al. |
| 2007/0014760 A1 | 1/2007 | Peyman et al. |
| 2007/0018039 A1 | 1/2007 | Hillen et al. |
| 2007/0025455 A1 | 2/2007 | Greenwood et al. |
| 2007/0037898 A1 | 2/2007 | Phelan et al. |
| 2007/0046894 A1 | 3/2007 | Muckenhirn et al. |
| 2007/0055222 A1 | 3/2007 | Hohla et al. |
| 2007/0080905 A1 | 4/2007 | Takahara et al. |
| 2007/0097301 A1 | 5/2007 | Yang et al. |
| 2007/0104648 A1 | 5/2007 | Shull et al. |
| 2007/0106394 A1 | 5/2007 | Chen et al. |
| 2007/0129720 A1 | 6/2007 | Demarais et al. |
| 2007/0132948 A1 | 6/2007 | Evans et al. |
| 2007/0135915 A1 | 6/2007 | Klima et al. |
| 2007/0150529 A1 | 6/2007 | McCall et al. |
| 2007/0163292 A1 | 7/2007 | Weng et al. |
| 2007/0182920 A1 | 8/2007 | Back et al. |
| 2007/0193124 A1 | 8/2007 | Thompson et al. |
| 2007/0196454 A1 | 8/2007 | Stockman et al. |
| 2007/0216974 A1 | 9/2007 | Silverbrook et al. |
| 2007/0232755 A1 | 10/2007 | Matsushita et al. |
| 2007/0242216 A1 | 10/2007 | Dootjes et al. |
| 2007/0244559 A1 | 10/2007 | Shiuey et al. |
| 2007/0249849 A1 | 10/2007 | Wiebe et al. |
| 2007/0270412 A1 | 11/2007 | Bell et al. |
| 2007/0273834 A1 | 11/2007 | Legerton et al. |
| 2008/0039832 A1 | 2/2008 | Palanker et al. |
| 2008/0074611 A1 | 3/2008 | Meyers et al. |
| 2008/0100796 A1 | 5/2008 | Pruitt et al. |
| 2008/0201941 A1 | 8/2008 | Montena et al. |
| 2008/0243156 A1 | 10/2008 | John et al. |
| 2008/0287915 A1 | 11/2008 | Rosenthal et al. |
| 2008/0291391 A1 | 11/2008 | Meyers et al. |
| 2009/0033864 A1 | 2/2009 | Shone et al. |
| 2009/0096987 A1 | 4/2009 | Lai et al. |
| 2009/0161826 A1 | 6/2009 | Gertner et al. |
| 2009/0161827 A1 | 6/2009 | Gertner et al. |
| 2009/0182312 A1 | 7/2009 | Gertner et al. |
| 2009/0209954 A1 | 8/2009 | Muller et al. |
| 2009/0216217 A1 | 8/2009 | Odrich et al. |
| 2009/0237612 A1 | 9/2009 | Cotie et al. |
| 2009/0244477 A1 | 10/2009 | Pugh et al. |
| 2009/0303434 A1 | 12/2009 | Tung et al. |
| 2009/0303442 A1 | 12/2009 | Choo et al. |
| 2010/0036488 A1 | 2/2010 | De Juan et al. |
| 2010/0060849 A1 | 3/2010 | Hibino et al. |
| 2010/0128224 A1 | 5/2010 | Legerton et al. |
| 2010/0145447 A1 | 6/2010 | Jia et al. |
| 2010/0157250 A1 | 6/2010 | Berke et al. |
| 2010/0185192 A1 | 7/2010 | Muller et al. |
| 2010/0191178 A1 | 7/2010 | Ross et al. |
| 2010/0208196 A1 | 8/2010 | Benrashid et al. |
| 2010/0271589 A1 | 10/2010 | Legerton et al. |
| 2011/0034854 A1 | 2/2011 | Neuberger et al. |
| 2011/0071631 A1 | 3/2011 | Rosenthal et al. |
| 2011/0081000 A1 | 4/2011 | Gertner et al. |
| 2011/0081001 A1 | 4/2011 | Gertner et al. |
| 2011/0190742 A1 | 8/2011 | Anisimov |
| 2011/0208300 A1 | 8/2011 | De Juan, Jr. et al. |
| 2012/0105804 A1 | 5/2012 | Legerton et al. |
| 2012/0113386 A1 | 5/2012 | Back et al. |
| 2012/0169994 A1 | 7/2012 | Matsushita et al. |
| 2012/0310133 A1 | 12/2012 | De Juan, Jr. et al. |
| 2012/0327362 A1 | 12/2012 | Doraiswamy et al. |
| 2013/0025606 A1 | 1/2013 | De Juan, Jr. et al. |
| 2013/0066283 A1 | 3/2013 | Alster et al. |
| 2013/0070200 A1 | 3/2013 | De Juan, Jr. et al. |
| 2013/0077044 A1 | 3/2013 | De Juan, Jr. et al. |
| 2013/0201442 A1 | 8/2013 | Back et al. |
| 2013/0201443 A1 | 8/2013 | Back et al. |
| 2013/0201454 A1 | 8/2013 | Back et al. |
| 2013/0208236 A1 | 8/2013 | McCabe et al. |
| 2013/0208237 A1 | 8/2013 | Hawke et al. |
| 2013/0222761 A1 | 8/2013 | Hansen et al. |
| 2013/0242255 A1 | 9/2013 | Caldarise et al. |
| 2013/0258276 A1 | 10/2013 | Hansen et al. |
| 2013/0278890 A1 | 10/2013 | De Juan, Jr. et al. |
| 2013/0293832 A1 | 11/2013 | De Juan, Jr. et al. |
| 2014/0028979 A1 | 1/2014 | De Juan, Jr. et al. |
| 2014/0043588 A1 | 2/2014 | Grant et al. |
| 2014/0069438 A1 | 3/2014 | De Juan, Jr. et al. |
| 2014/0069439 A1 | 3/2014 | De Juan, Jr. et al. |
| 2014/0155800 A1 | 6/2014 | De Juan et al. |
| 2014/0251347 A1 | 9/2014 | De Juan et al. |
| 2014/0362338 A1 | 12/2014 | De Juan, Jr. et al. |
| 2015/0055081 A1 | 2/2015 | De Juan et al. |
| 2015/0077701 A1 | 3/2015 | De Juan et al. |
| 2016/0067109 A1 | 3/2016 | De Juan et al. |
| 2016/0170233 A1 | 6/2016 | De Juan et al. |
| 2016/0180233 A1 | 6/2016 | Britt et al. |
| 2016/0223835 A1 | 8/2016 | De Juan et al. |
| 2016/0334640 A1 | 11/2016 | De Juan et al. |
| 2016/0370603 A1 | 12/2016 | De Juan et al. |
| 2017/0023800 A1 | 1/2017 | De Juan et al. |
| 2017/0038604 A1 | 2/2017 | De Juan et al. |
| 2017/0131566 A1 | 5/2017 | De Juan et al. |
| 2017/0315380 A1 | 11/2017 | De Juan et al. |
| 2017/0315381 A1 | 11/2017 | De Juan et al. |
| 2017/0340481 A1 | 11/2017 | Daxer |
| 2018/0000639 A1 | 1/2018 | Alster et al. |
| 2018/0011341 A1 | 1/2018 | De Juan et al. |

(56) References Cited

U.S. PATENT DOCUMENTS

| | | |
|---|---|---|
| 2018/0321511 A1 | 11/2018 | De Juan et al. |
| 2018/0344521 A1 | 12/2018 | Daxer |
| 2019/0353930 A1 | 11/2019 | De Juan, Jr. et al. |

FOREIGN PATENT DOCUMENTS

| | | |
|---|---|---|
| DE | 3143839 A1 | 5/1983 |
| EP | 0042679 A2 | 12/1981 |
| EP | 0378512 A2 | 7/1990 |
| EP | 0378512 A3 | 5/1991 |
| EP | 0434205 A2 | 6/1991 |
| EP | 0574352 A1 | 12/1993 |
| EP | 0590772 A1 | 4/1994 |
| EP | 0378512 B1 | 2/1995 |
| EP | 0638416 A1 | 2/1995 |
| EP | 0683416 A1 | 11/1995 |
| EP | 0590772 B1 | 4/1998 |
| EP | 0985157 A1 | 3/2000 |
| EP | 0985157 B1 | 10/2004 |
| EP | 1629317 A2 | 3/2006 |
| EP | 1664907 A1 | 6/2006 |
| EP | 1496388 B1 | 4/2016 |
| FR | 2330025 A1 | 5/1977 |
| GB | 2107895 A | 5/1983 |
| JP | S55101125 U | 7/1980 |
| JP | 2661909 B2 | 10/1997 |
| JP | H11151263 A | 6/1999 |
| JP | H11249048 A | 9/1999 |
| JP | 2003107411 A | 4/2003 |
| JP | 2004504105 A | 2/2004 |
| JP | 2004510199 A | 4/2004 |
| JP | 2009098457 A | 5/2009 |
| JP | 5278453 B2 | 9/2013 |
| JP | 5727456 B2 | 6/2015 |
| JP | 5727457 B2 | 6/2015 |
| JP | 5943931 B2 | 7/2016 |
| WO | WO-9014083 A1 | 11/1990 |
| WO | WO-9207617 A1 | 5/1992 |
| WO | WO-9307840 A1 | 4/1993 |
| WO | WO-9405225 A1 | 3/1994 |
| WO | WO-9429756 A2 | 12/1994 |
| WO | WO-9513764 A1 | 5/1995 |
| WO | WO-9515134 A1 | 6/1995 |
| WO | WO-9627816 A1 | 9/1996 |
| WO | WO-9719381 A1 | 5/1997 |
| WO | WO-9803267 A1 | 1/1998 |
| WO | WO-9854603 A1 | 12/1998 |
| WO | WO-9930560 A1 | 6/1999 |
| WO | WO-9943354 A2 | 9/1999 |
| WO | WO-9946631 A1 | 9/1999 |
| WO | WO-9943354 A3 | 11/1999 |
| WO | WO-0009042 A1 | 2/2000 |
| WO | WO-0168082 A1 | 9/2001 |
| WO | WO-0206883 A2 | 1/2002 |
| WO | WO-0210841 A1 | 2/2002 |
| WO | WO-02068008 A1 | 9/2002 |
| WO | WO-03097759 A1 | 11/2003 |
| WO | WO-2004068196 A1 | 8/2004 |
| WO | WO-2004097502 A1 | 11/2004 |
| WO | WO-2004109368 A2 | 12/2004 |
| WO | WO-2005079290 A2 | 9/2005 |
| WO | WO-2005116729 A2 | 12/2005 |
| WO | WO-2006026666 A2 | 3/2006 |
| WO | WO-2006026666 A3 | 7/2006 |
| WO | WO-2006113149 A2 | 10/2006 |
| WO | WO-2006121591 A1 | 11/2006 |
| WO | WO-2006134649 A1 | 12/2006 |
| WO | WO-2007002231 A1 | 1/2007 |
| WO | WO-2007044513 A1 | 4/2007 |
| WO | WO-2007053297 A2 | 5/2007 |
| WO | WO-2007053297 A3 | 10/2007 |
| WO | WO-2009065061 A1 | 5/2009 |
| WO | WO-2006113149 A3 | 6/2009 |
| WO | WO-2009073213 A1 | 6/2009 |
| WO | WO-2009145842 A2 | 12/2009 |
| WO | WO-2009146151 A2 | 12/2009 |
| WO | WO-2010051172 A1 | 5/2010 |
| WO | WO-2010144317 A1 | 12/2010 |
| WO | WO-2011004800 A1 | 1/2011 |
| WO | WO-2011050327 A1 | 4/2011 |
| WO | WO-2011050365 A1 | 4/2011 |
| WO | WO-2012061160 A1 | 5/2012 |
| WO | WO-2012149056 A1 | 11/2012 |
| WO | WO-2013184239 A1 | 12/2013 |
| WO | WO-2014043221 A1 | 3/2014 |
| WO | WO-2014210186 A2 | 12/2014 |
| WO | WO-2015069927 A1 | 5/2015 |
| WO | WO-2015073718 A1 | 5/2015 |
| WO | WO-2015116559 A1 | 8/2015 |

OTHER PUBLICATIONS

AU2012249773 Examination Report dated Jun. 23, 2016.
Bausch & Lomb Boston® Materials & Solutions Product Guide (38 pages) (2009).
Bissen-Miyajima et al. Role of the endothelial pump in flap adhesion laser in situ keratomileusis. J Cataract Refract Surg 30(9):1989-1992 (2004).
CA2816031 Examination Report dated Aug. 31, 2017.
CA2916885 Examination Report dated Jan. 24, 2017.
EP10825787.4 Office Action dated Aug. 12, 2014.
EP10825787.4 Search Report dated Jun. 18, 2013.
EP10825813.8 Examination Search Report dated Feb. 20, 2017.
EP17183160.5 Extended Search Report dated Sep. 12, 2017.
JP2011502997 English translation of Japanese Office Action dated Jun. 14, 2013.
JP2011502997 Office Action dated Jun. 14, 2013.
JP2011502997 Office Action dated Mar. 3, 2014.
Muller et al. Architecture of human corneal nerves. Invest Ophthalmol Vis Sci. 38:985-994 (1997).
PCT/US2009/002166 International Search Report and Written Opinion dated Nov. 19, 2009.
PCT/US2009/002166 International Preliminary Report on Patentability dated Oct. 5, 2010.
PCT/US2010/053854 International Search Report and Written Opinion dated Mar. 1, 2011.
PCT/US2010/053854 International Preliminary Report on Patentability dated Apr. 24, 2012.
PCT/US2010/053975 International Search Report and Written Opinion dated Feb. 11, 2011.
PCT/US2010/053975 International Preliminary Report on Patentability dated Apr. 24, 2012.
PCT/US2011/57755 International Search Report dated Feb. 7, 2012.
PCT/US2012/035050 International Search Report and Written Opinion dated Oct. 3, 2012.
PCT/US2013/033567 International Search Report dated Mar. 4, 2014.
PCT/US2013/037219 International Search Report and Written Opinion dated Jul. 22, 2013.
PCT/US2013/059244 International Search Report and Written Opinion dated Nov. 18, 2013.
PCT/US2014/044136 International Search Report and Written Opinion dated Jan. 16, 2015.
PCT/US2014/064391 International Search Report and Written Opinion dated Jan. 26, 2015.
PCT/US2014/065543 International Preliminary Report in Patentability dated May 17, 2016.
PCT/US2014/065543 International Search Report and Written Opinion dated dated Feb. 25, 2015.
PCT/US2015/013006 International Search Report and Written Opinion dated Apr. 2, 2015.
Schimmelpfenning et al. A technique for controlled sensory denervation of the rabbit cornea, Database accession No. NLM7129102. Graefe's Archive for Clinical and Experimental Opthalmology 218(6):287-293 (1987). (Abstract only).
Sorbara et al. Metrics of the normal cornea: anterior segment imaging with the Visante OCT. Clin Exp Optom 93(3):150-156 (2010).

(56) References Cited

OTHER PUBLICATIONS

SynergEyes® Inc. Product Overview of CLEARKONE® and SYNERGEYES® PS retrieved from the Internet http:/US7www.synergeyes.comUS7index.html on May 29, 2012 (5 pages).
SynergEyes Inc. SynergEyes® A. package insert P/N 70008 Rev. 1 (12 pages).
SynergEyes Inc. SynergEyes® A Practitioner Training retrieved from the Internet< http:/www.fitsynergeyes.com/syn_asynergeyesA_presentation.pdf> (52 pgs).
U.S. Appl. No. 12/384,659 Office Action dated Jan. 21, 2016.
U.S. Appl. No. 12/384,659 Office Action dated May 30, 2017.
U.S. Appl. No. 12/384,659 Office Action dated Nov. 4, 2016.
U.S. Appl. No. 12/897,131 Office Action dated Jan. 24, 2013.
U.S. Appl. No. 12/897,131 Office Action dated Jul. 5, 2012.
U.S. Appl. No. 12/897,131 Office Action dated Sep. 9, 2014.
U.S. Appl. No. 13/456,168 Notice of Allowance dated May 30, 2014.
U.S. Appl. No. 13/456,168 Office Action dated Sep. 12, 2013.
U.S. Appl. No. 13/503,841 Office Action dated Jun. 27, 2014.
U.S. Appl. No. 13/503,841 Office Action dated Jun. 9, 2016.
U.S. Appl. No. 13/503,841 Office Action dated Mar. 1, 2017.
U.S. Appl. No. 13/503,841 Office Action dated Nov. 16, 2015.
U.S. Appl. No. 13/503,841 Office Action dated Nov. 26, 2014.
U.S. Appl. No. 13/503,842 Notice of Allowance dated Jul. 11, 2016.
U.S. Appl. No. 13/503,842 Office Action dated Apr. 3, 2014.
U.S. Appl. No. 13/503,842 Office Action dated Aug. 13, 2014.
U.S. Appl. No. 13/503,842 Office Action dated Nov. 25, 2015.
U.S. Appl. No. 13/555,056 Office Action dated Mar. 28, 2014.
U.S. Appl. No. 13/555,056 Office Action dated Sep. 5, 2014.
U.S. Appl. No. 13/615,111 Notice of Allowance dated Apr. 23, 2013.
U.S. Appl. No. 13/715,917 Notice of Allowance dated Aug. 1, 2013.
U.S. Appl. No. 13/865,780 Notice of Allowance dated Mar. 28, 2016.
U.S. Appl. No. 13/865,780 Office Action dated Nov. 6, 2015.
U.S. Appl. No. 13/885,135 Notice of Allowance dated Mar. 16, 2016.
U.S. Appl. No. 13/885,135 Office Action dated Jun. 11, 2015.
U.S. Appl. No. 13/885,135 Office Action dated Nov. 18, 2014.
U.S. Appl. No. 13/894,176 Notice of Allowance dated Feb. 26, 2014.
U.S. Appl. No. 13/894,176 Office Action dated Aug. 5, 2013.
U.S. Appl. No. 13/928,077 Notice of Allowance dated Jan. 15, 2014.
U.S. Appl. No. 13/928,077 Office Action dated Oct. 22, 2013.
U.S. Appl. No. 14/061,311 Office Action dated Apr. 21, 2016.
U.S. Appl. No. 14/061,311 Office Action dated Mar. 9, 2017.
U.S. Appl. No. 14/173,516 Office Action dated Apr. 3, 2019.
U.S. Appl. No. 14/173,516 Office Action dated Feb. 8, 2017.
U.S. Appl. No. 14/286,605 Office Action dated Dec. 18, 2014.
U.S. Appl. No. 14/468,075 Office Action dated Apr. 1, 2016.
U.S. Appl. No. 14/468,075 Office Action dated Nov. 5, 2015.
U.S. Appl. No. 14/468,075 Office Action dated Nov. 7, 2016.
U.S. Appl. No. 14/532,707 Notice of Allowance dated Jun. 8, 2016.
U.S. Appl. No. 14/532,707 Office Action dated Feb. 25, 2016.
U.S. Appl. No. 14/532,732 Office Action dated Apr. 11, 2016.
U.S. Appl. No. 14/532,732 Office Action dated Oct. 3, 2016.
U.S. Appl. No. 14/539,698 Notice of Allowance dated Jan. 21, 2016.
U.S. Appl. No. 14/539,698 Office Action dated Oct. 9, 2015.
U.S. Appl. No. 14/793,965 Office Action dated Dec. 31, 2015.
U.S. Appl. No. 14/966,918 Office Action dated Nov. 18, 2016.
U.S. Appl. No. 15/096,442 Office Action dated Dec. 28, 2016.
U.S. Appl. No. 15/184,922 Office Action dated Jun. 2, 2017.
U.S. Appl. No. 15/184,922 Office Action dated Mar. 30, 2018.
U.S. Appl. No. 15/209,511 Office Action dated Apr. 30, 2018.
U.S. Appl. No. 15/209,511 Office Action dated Jan. 3, 2019.
U.S. Appl. No. 15/221,942 Office Action dated Feb. 1, 2018.
U.S. Appl. No. 15/253,183 Office Action dated Nov. 3, 2017.
U.S. Appl. No. 15/289,793 Office Action dated Jan. 22, 2019.
U.S. Appl. No. 15/652,855 Office Action dated Aug. 9, 2018.
U.S. Appl. No. 15/652,855 Office Action dated Mar. 1, 2019.
U.S. Appl. No. 15/654,344 Office Action dated Mar. 22, 2019.
U.S. Appl. No. 15/695,889 Office Action dated Sep. 18, 2018.
U.S. Appl. No. 15/807,985 Office Action dated Feb. 5, 2019.
U.S. Appl. No. 15/695,889 Office Action dated Jun. 13, 2019.
U.S. Appl. No. 15/209,511 Office Action dated Aug. 5, 2019.
U.S. Appl. No. 15/684,010 Office Action dated Aug. 12, 2019.

* cited by examiner

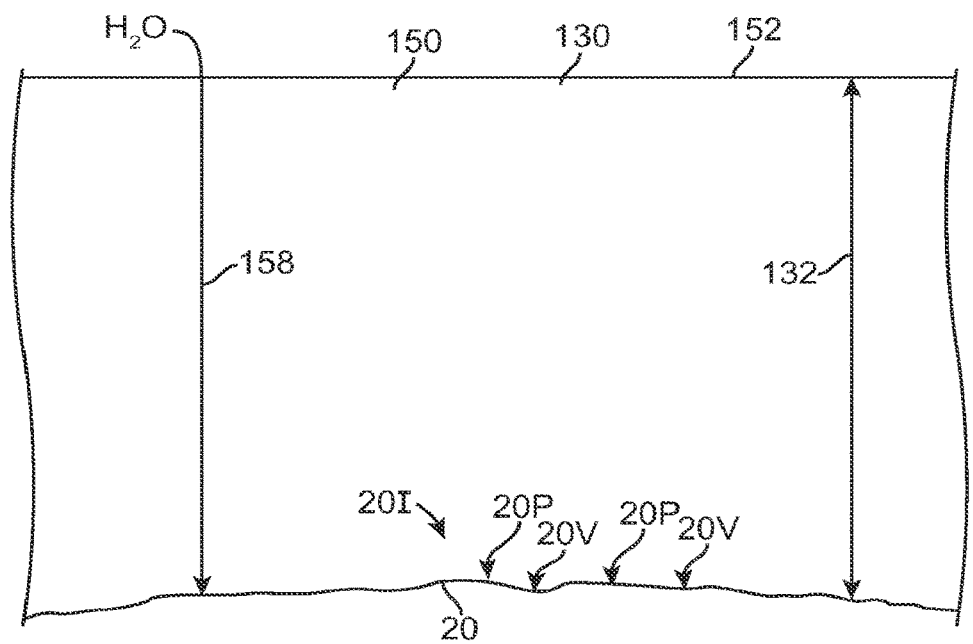
FIG. 1C1
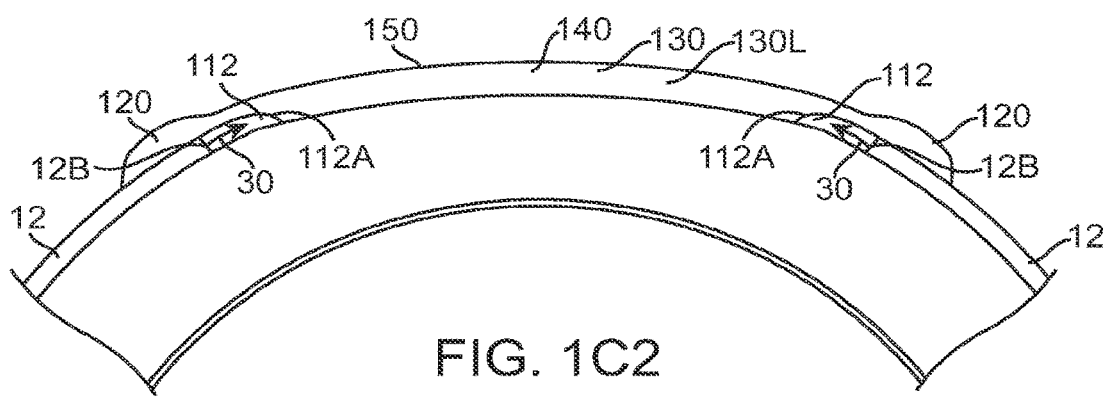
FIG. 1C2

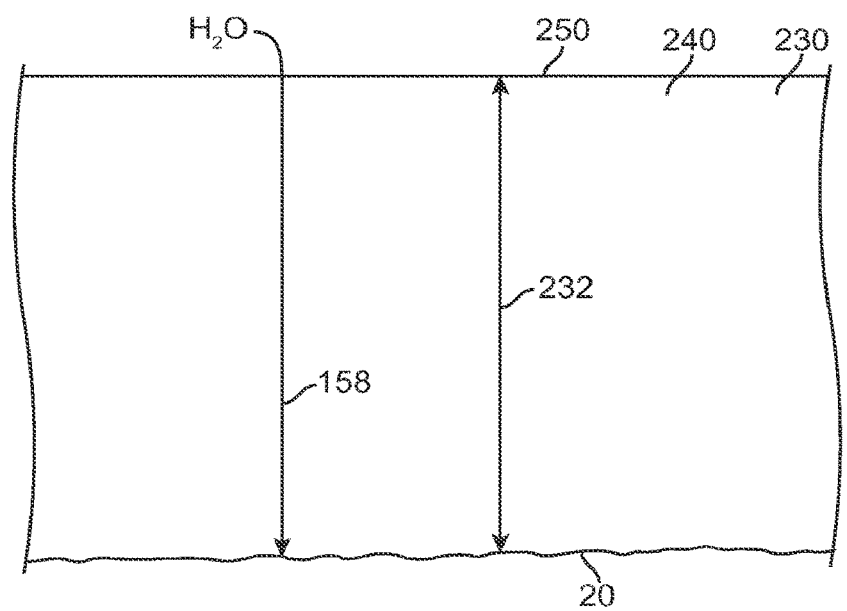
FIG. 2B1
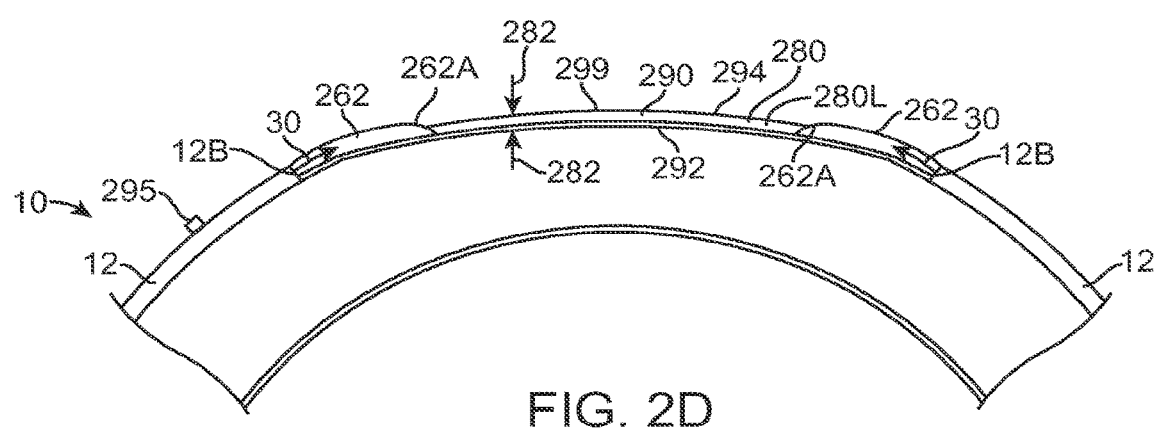
FIG. 2D

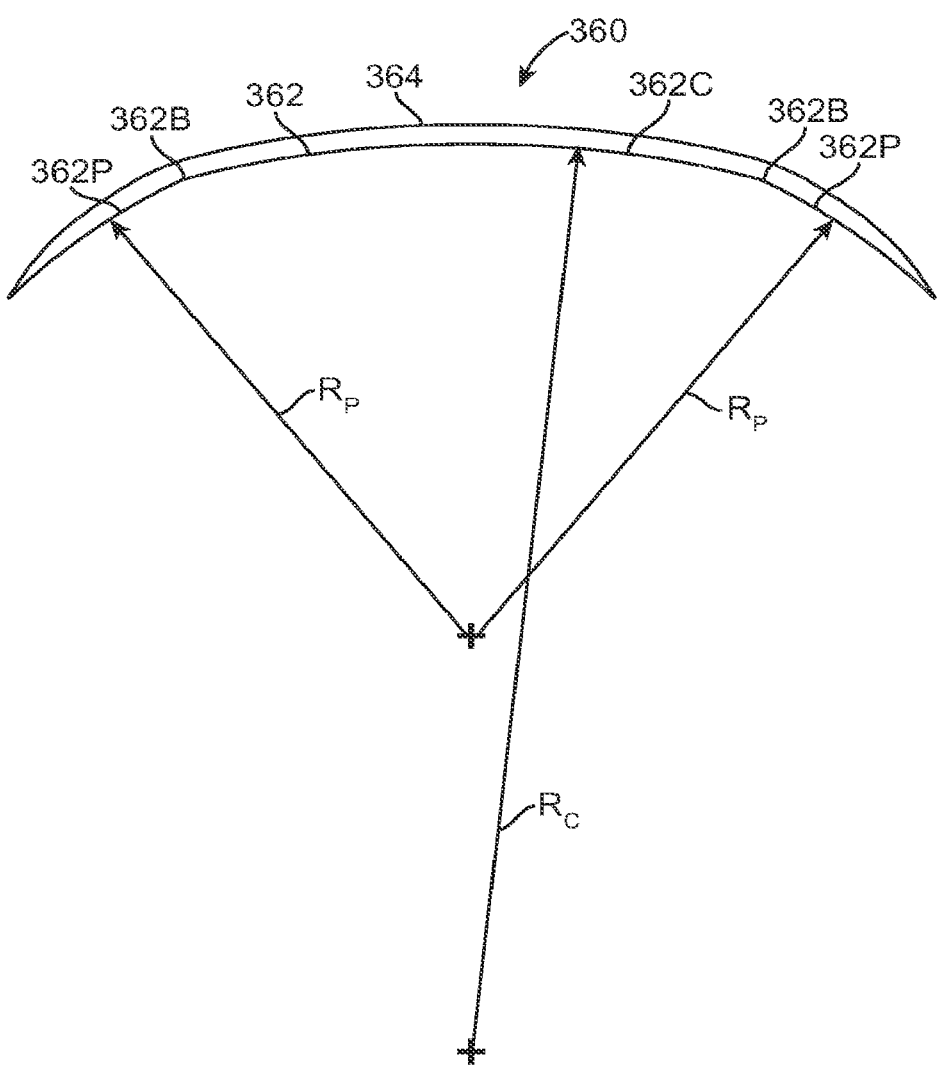
FIG. 3B1

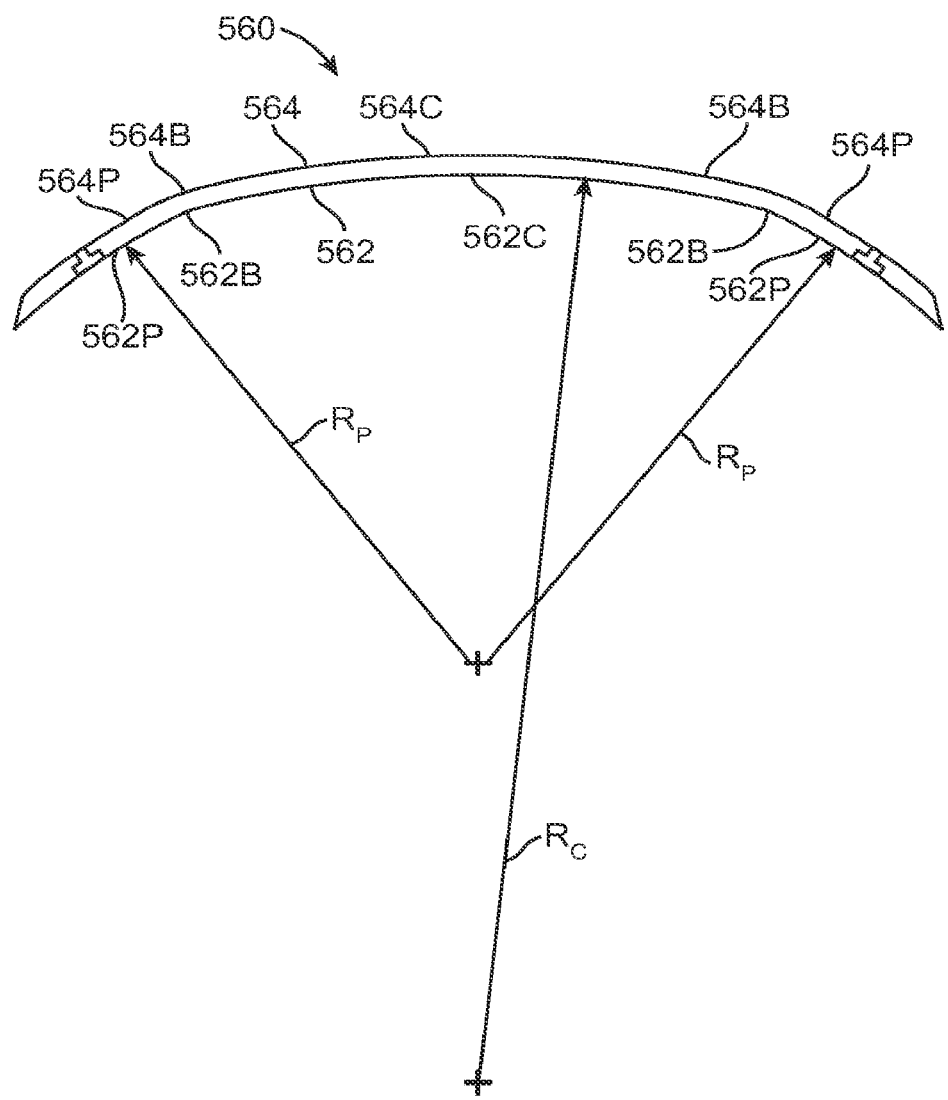
FIG. 5B1

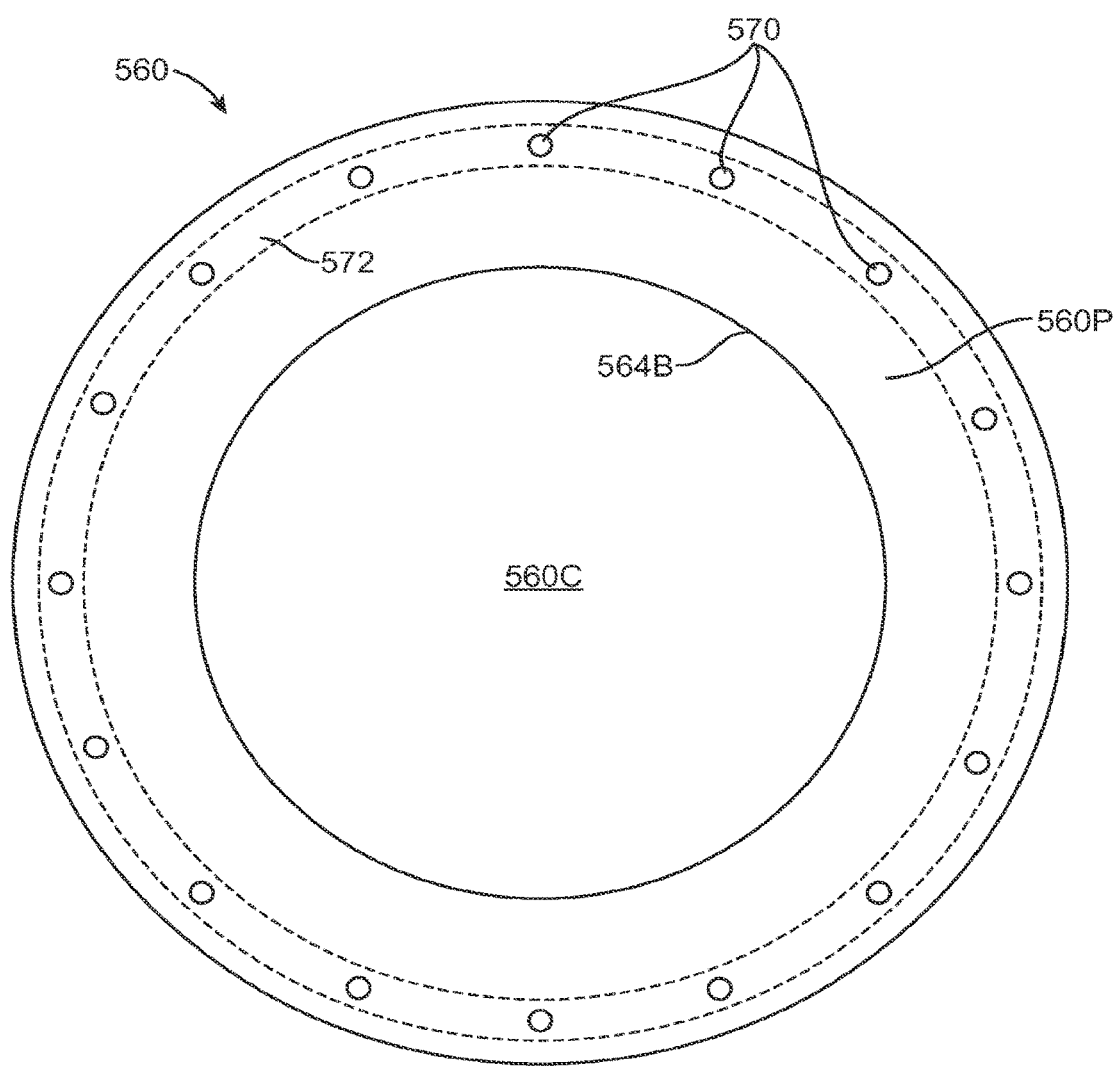
FIG. 5B2

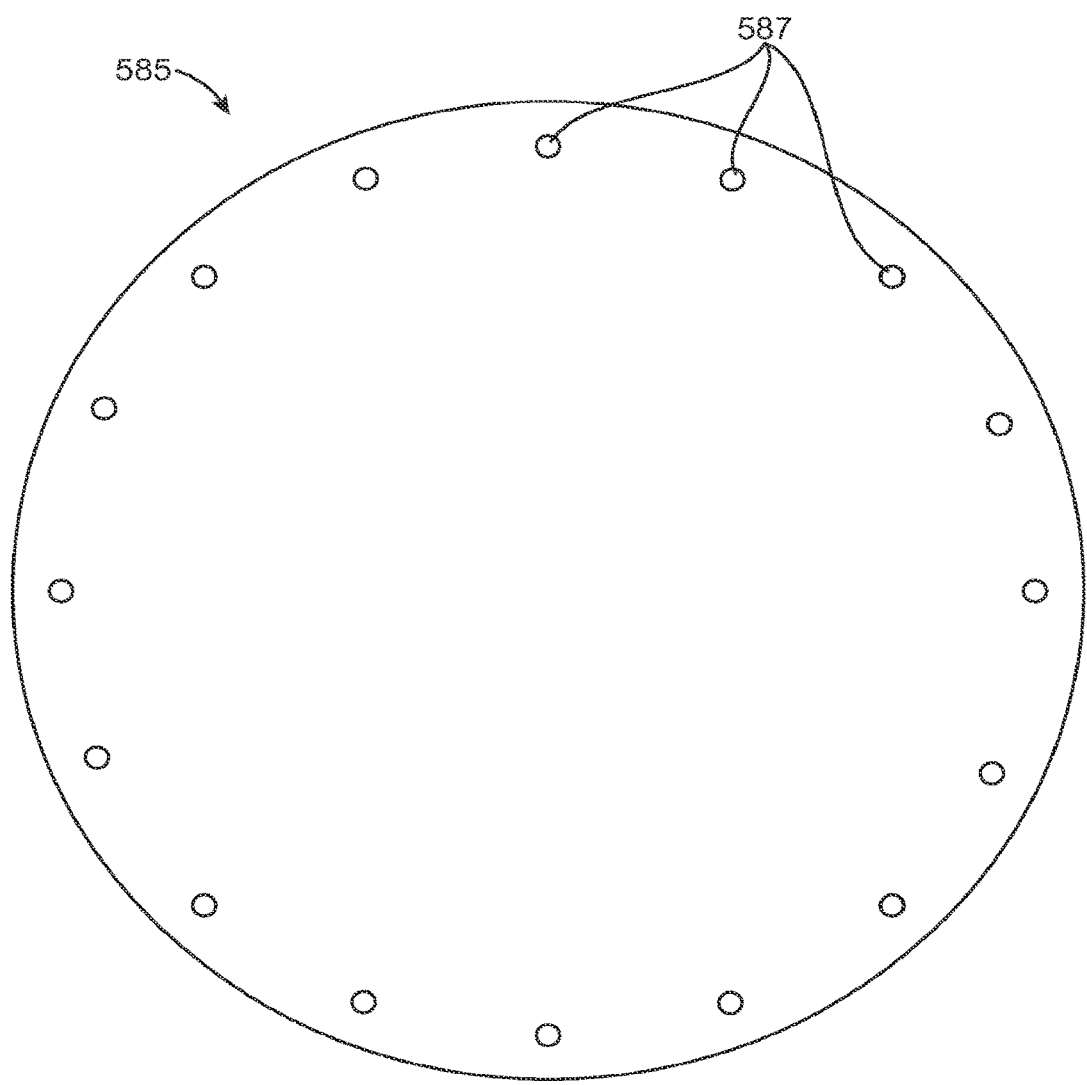
FIG. 5B3

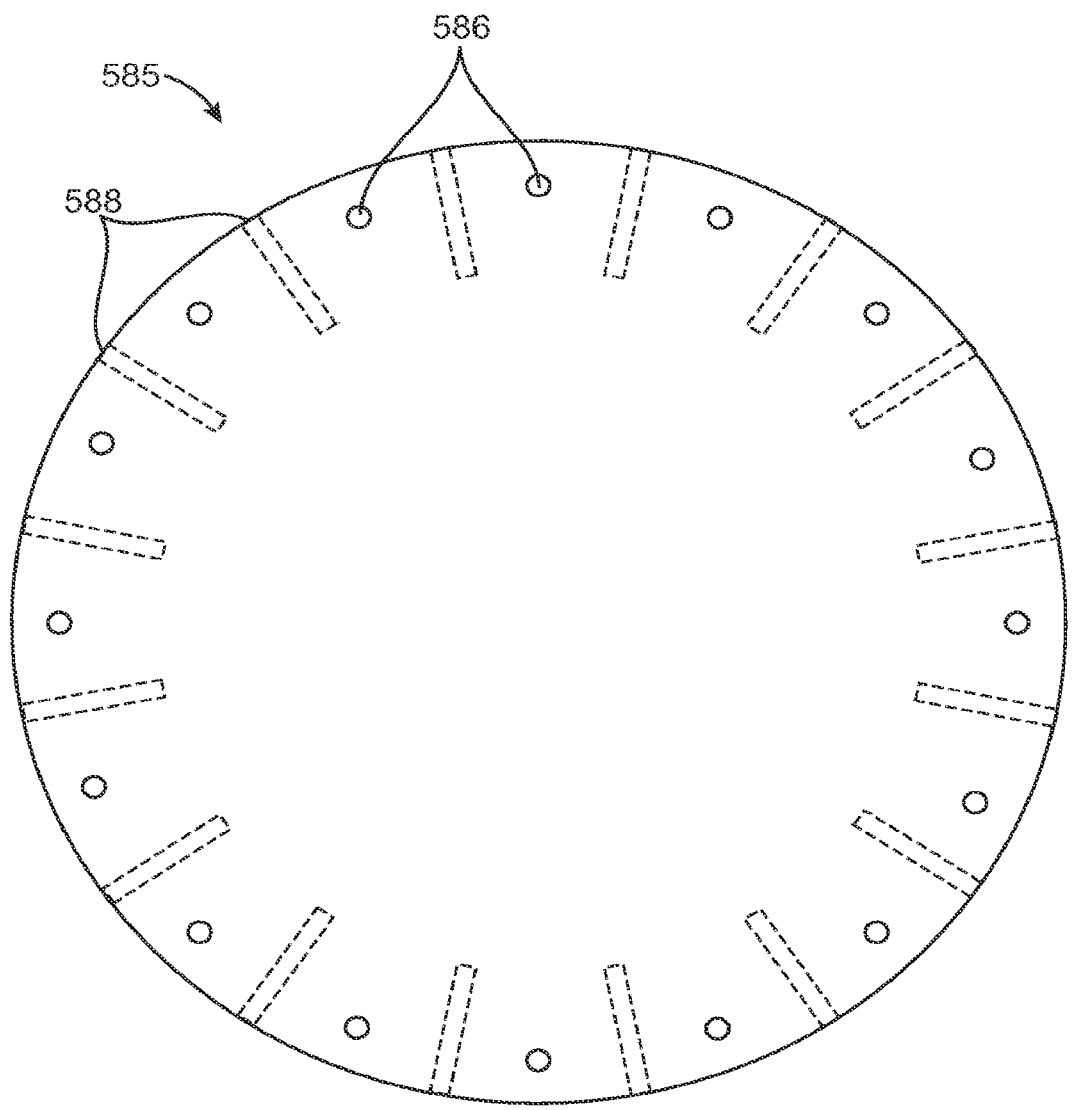
FIG. 5B4

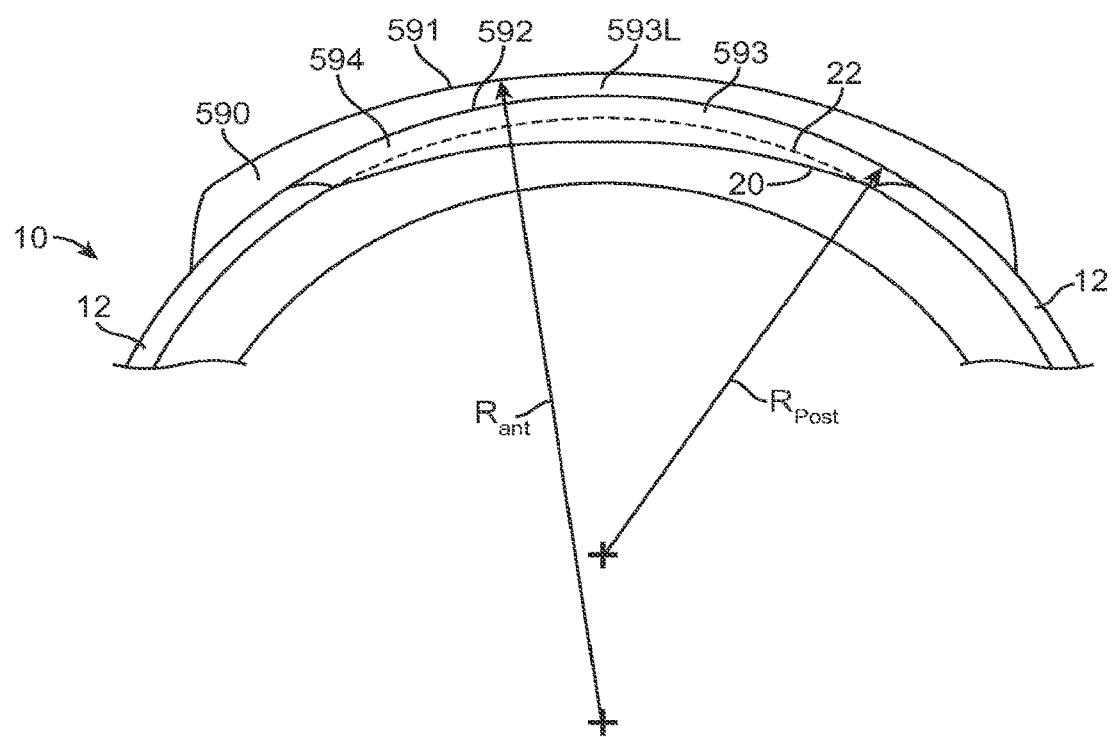
FIG. 5B5

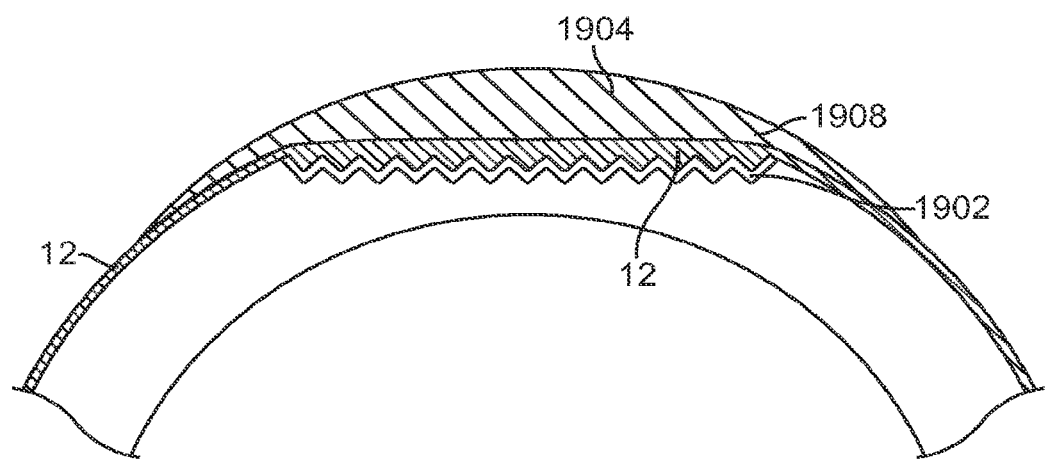
FIG. 19B1

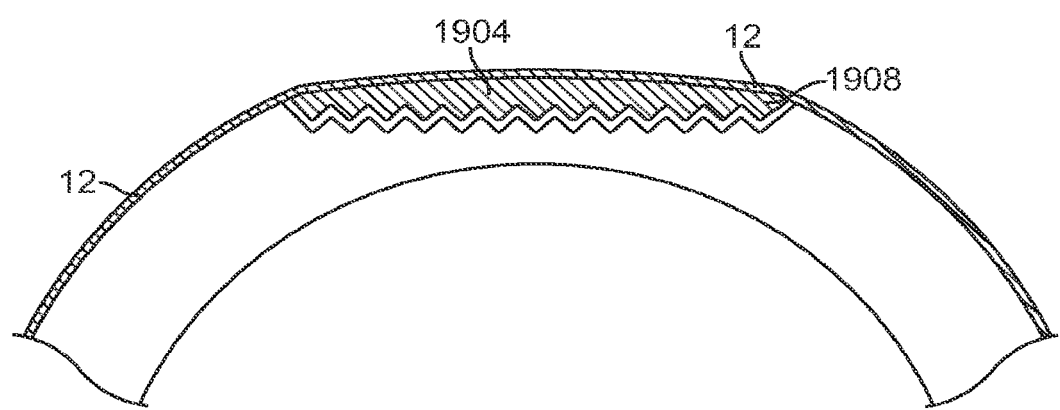
FIG. 19B2

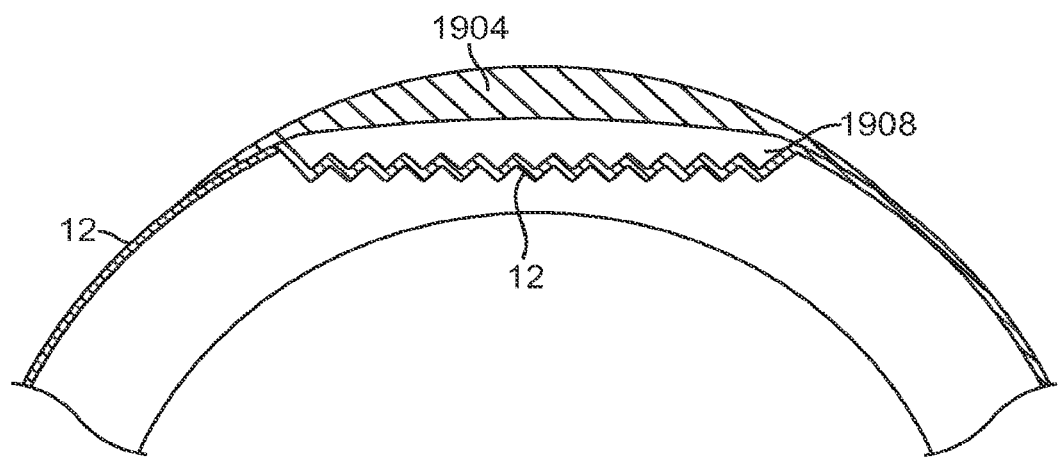
FIG. 19B3

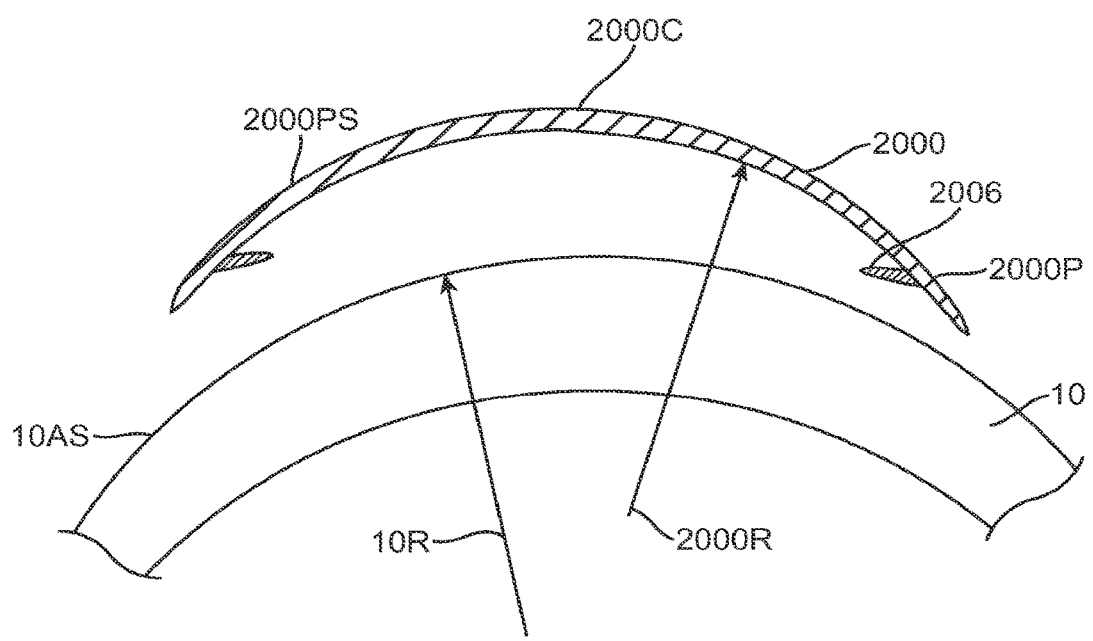
FIG. 20E1

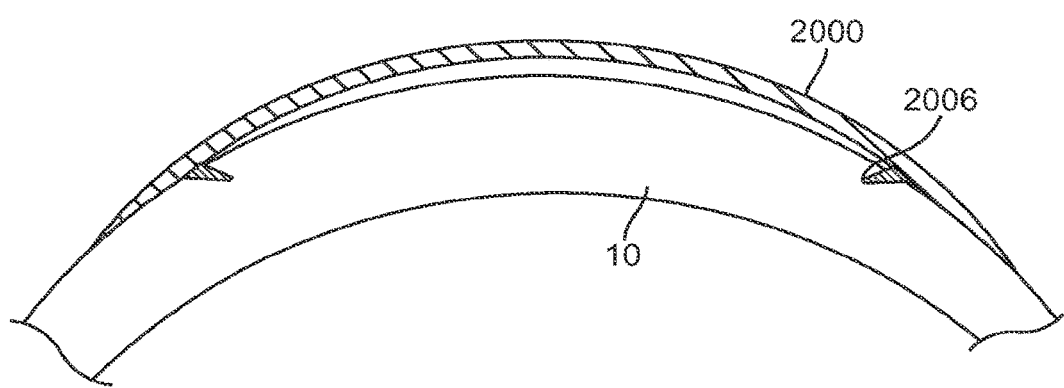
FIG. 20E2

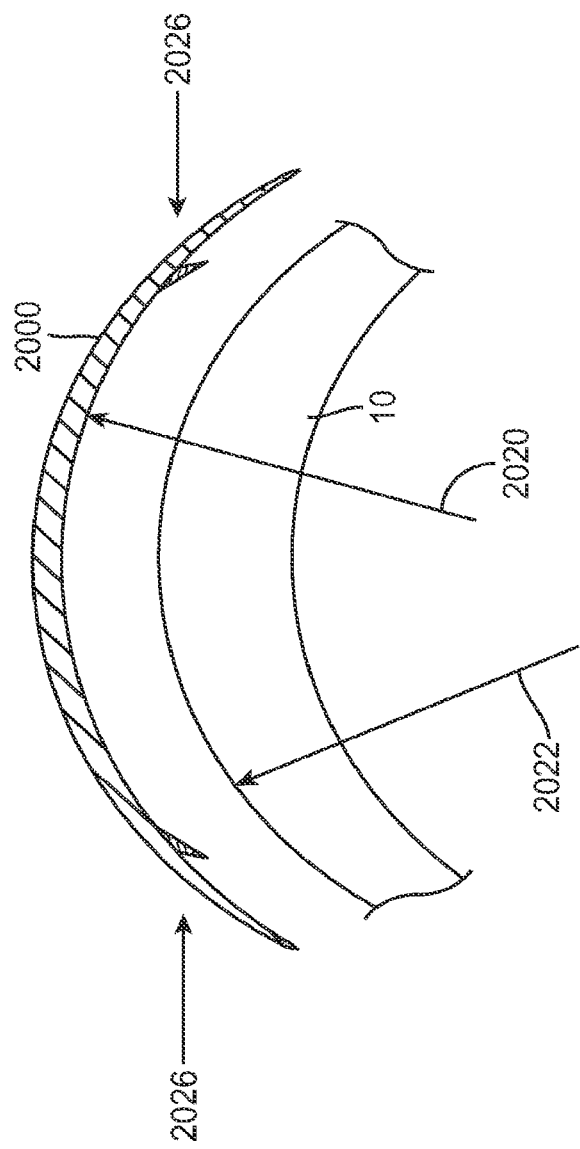

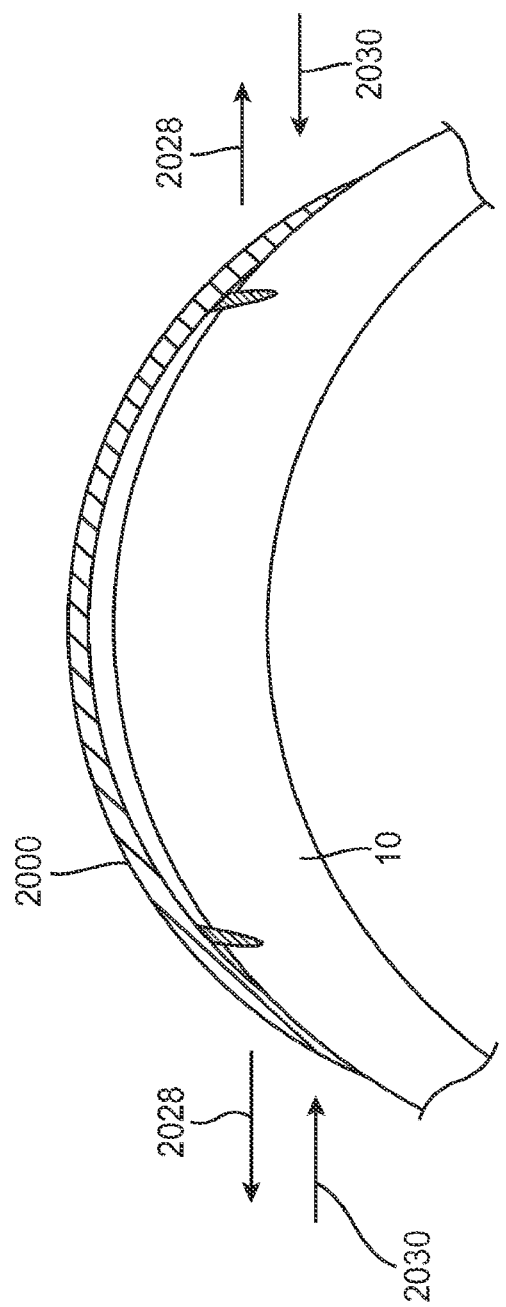
FIG. 20H2

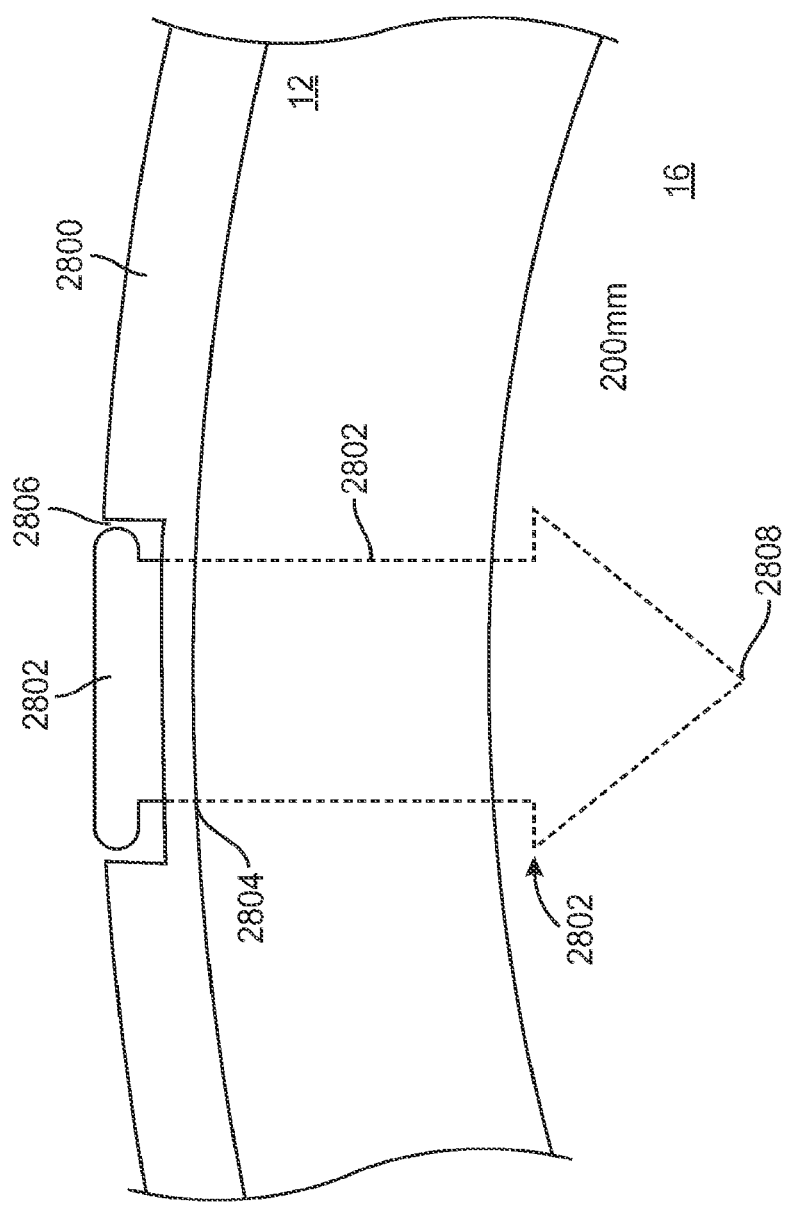

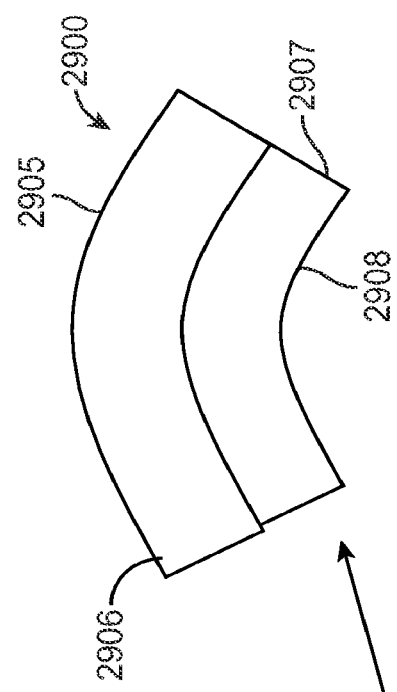
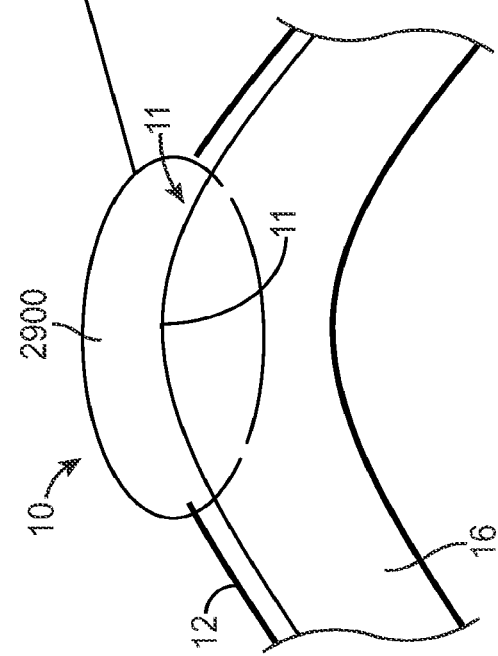
FIG. 29A-5
FIG. 29A-4

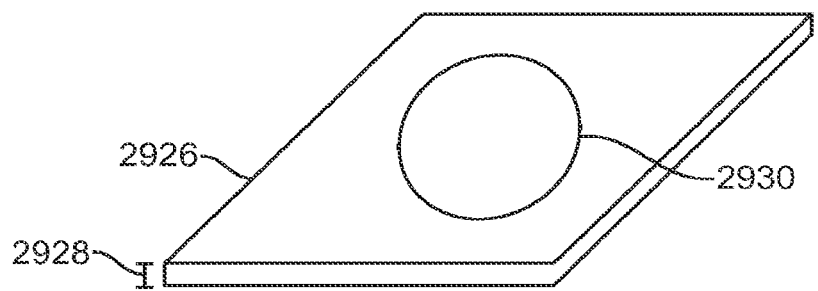
FIG. 29C1
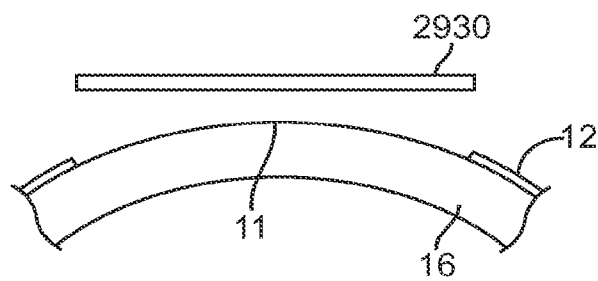
FIG. 29C2
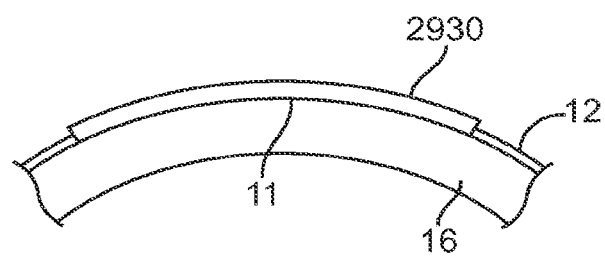
FIG. 29C3

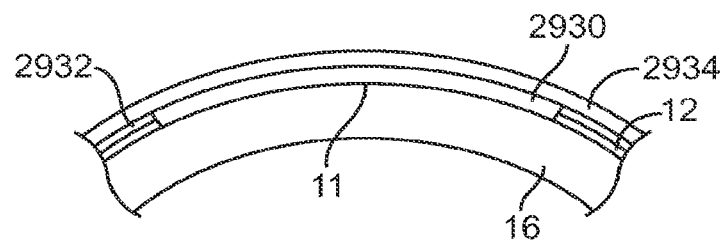
FIG. 29C4
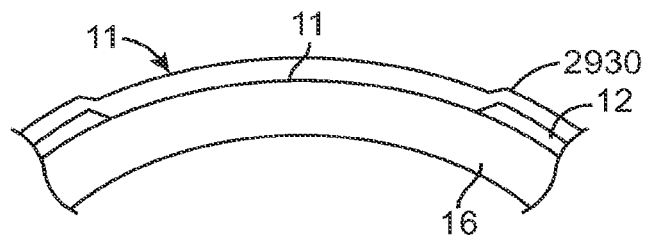
FIG. 29C5
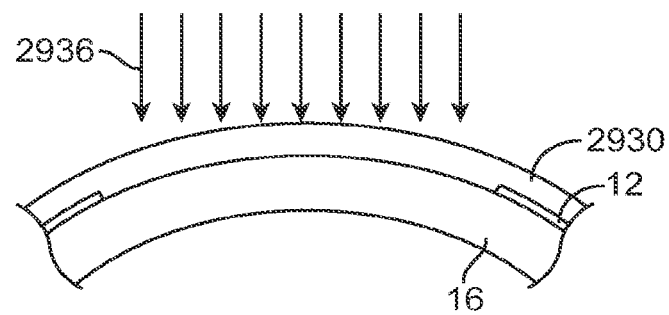
FIG. 29C6

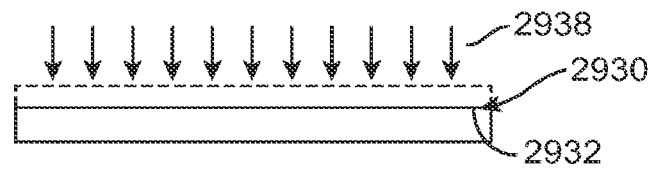
FIG. 29C7
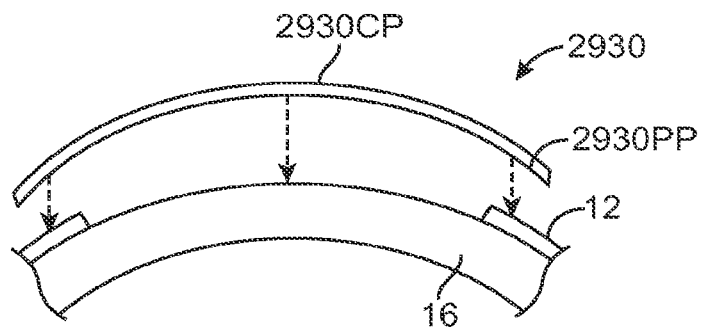
FIG. 29C8-1
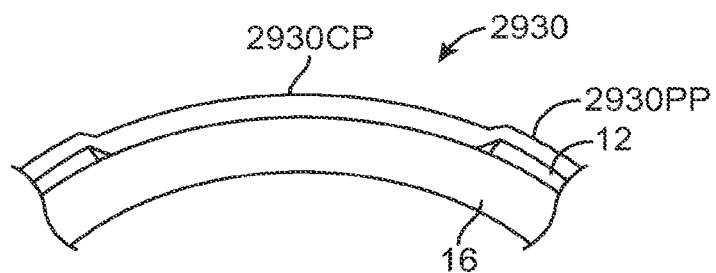
FIG. 29C8-2

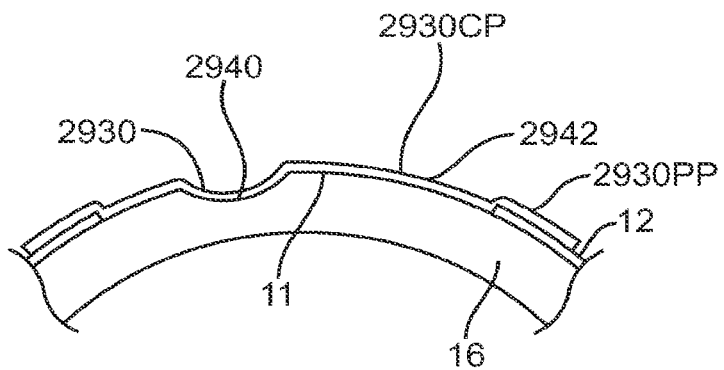
FIG. 29C8-3
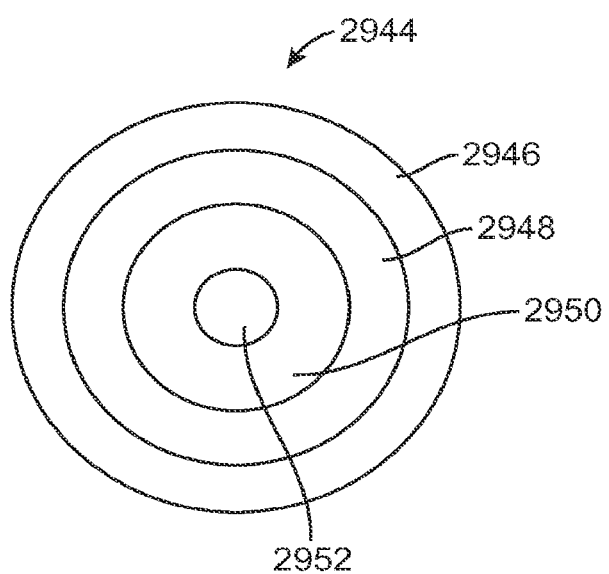
FIG. 29D

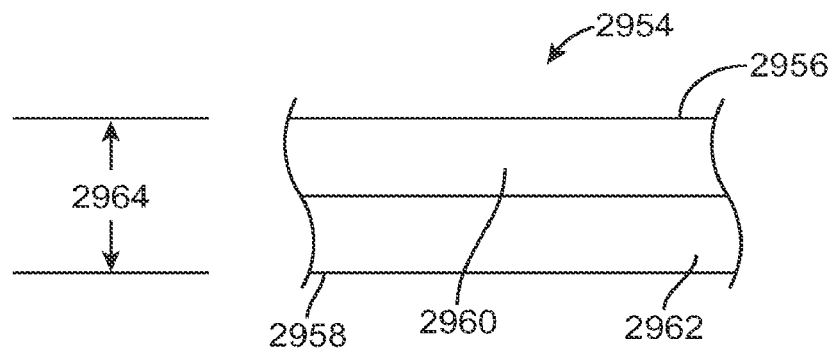
FIG. 29E1
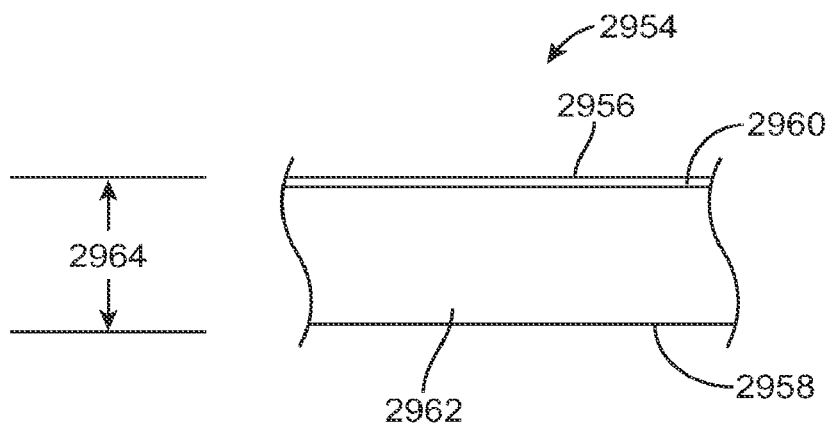
FIG. 29E2
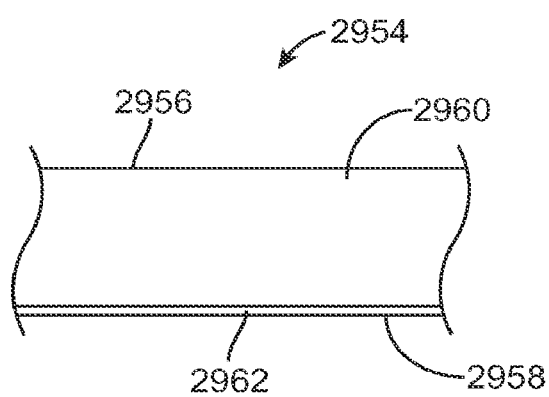
FIG. 29E3

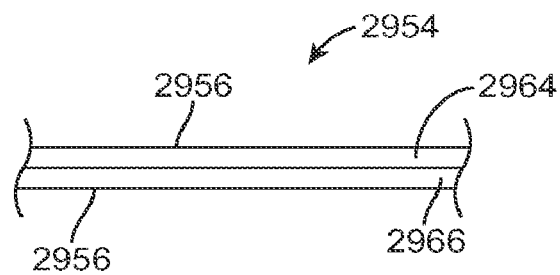
FIG. 29E4
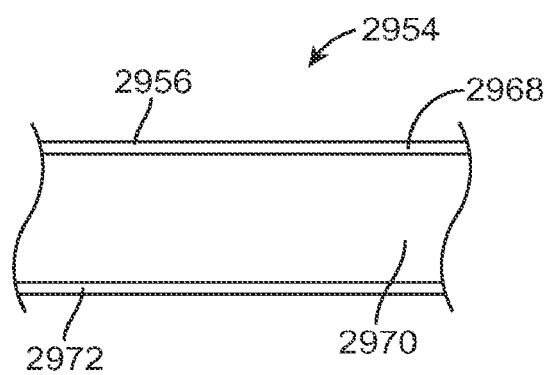
FIG. 29E5
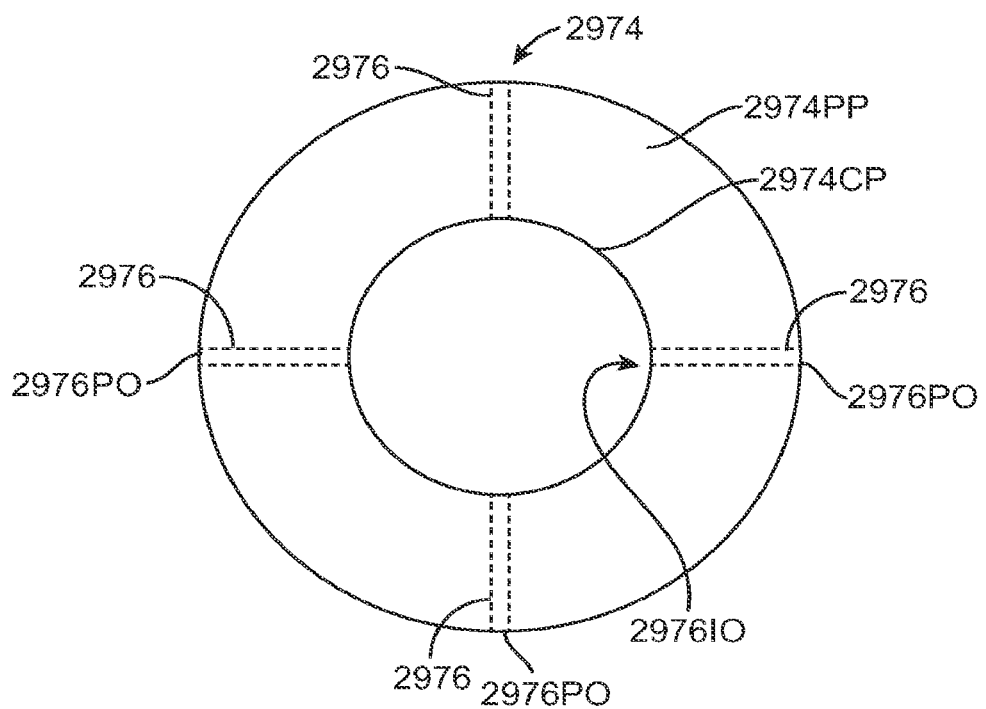
FIG. 29F1

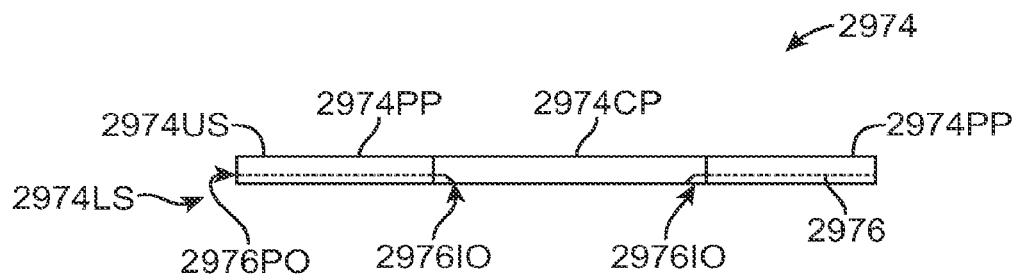
FIG. 29F2
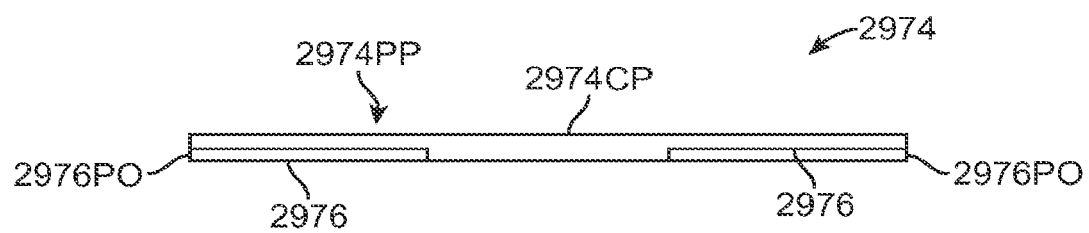
FIG. 29F3
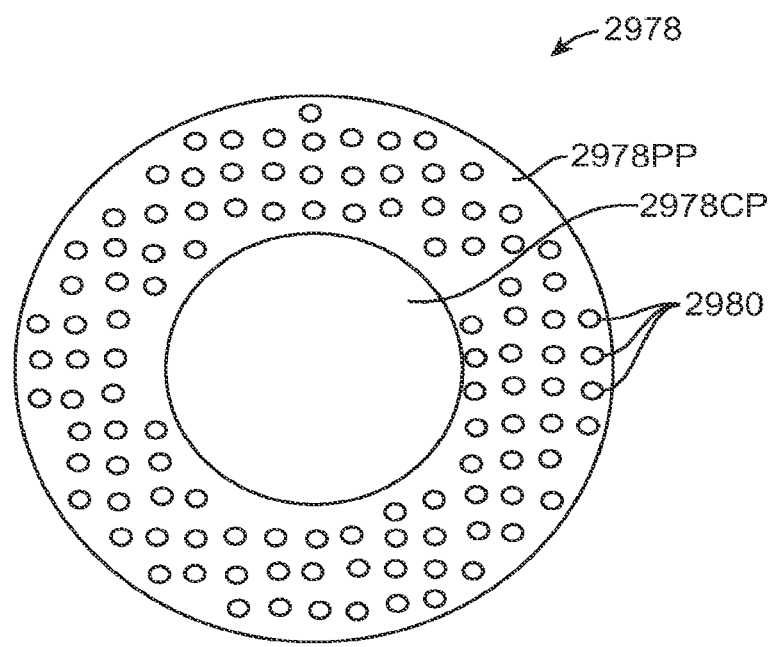
FIG. 29G

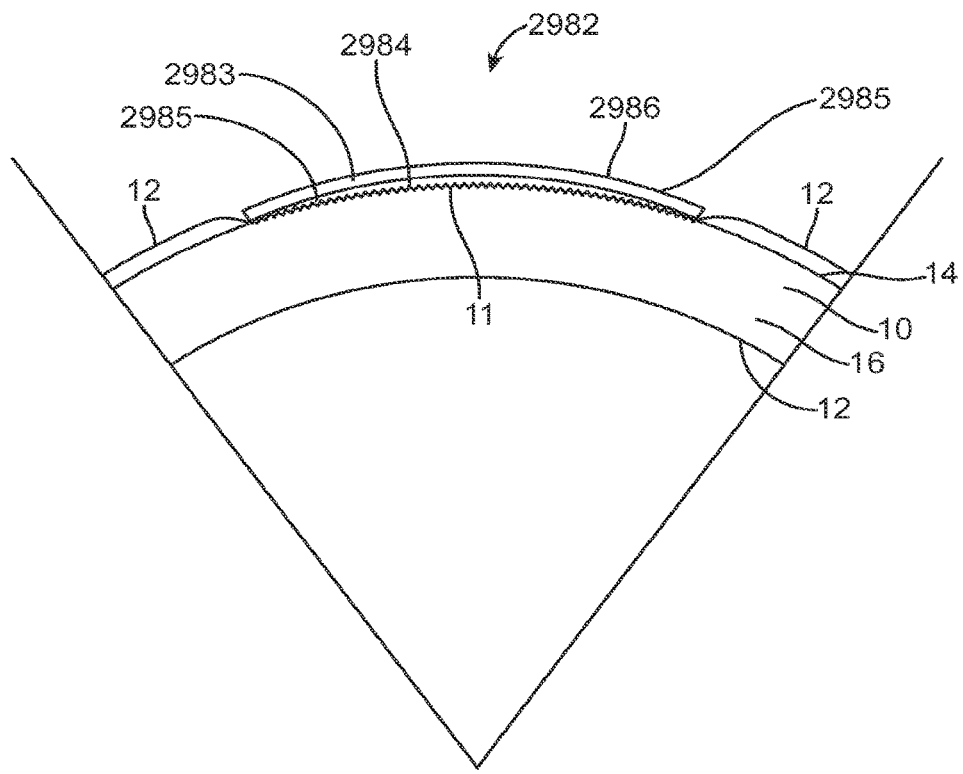
FIG. 29H
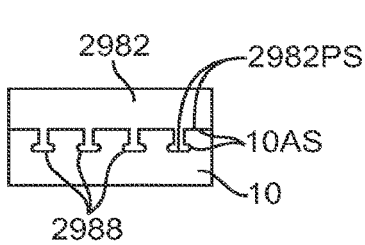
FIG. 29H1
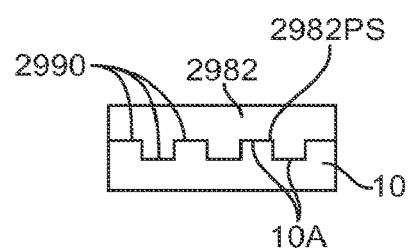
FIG. 29H2

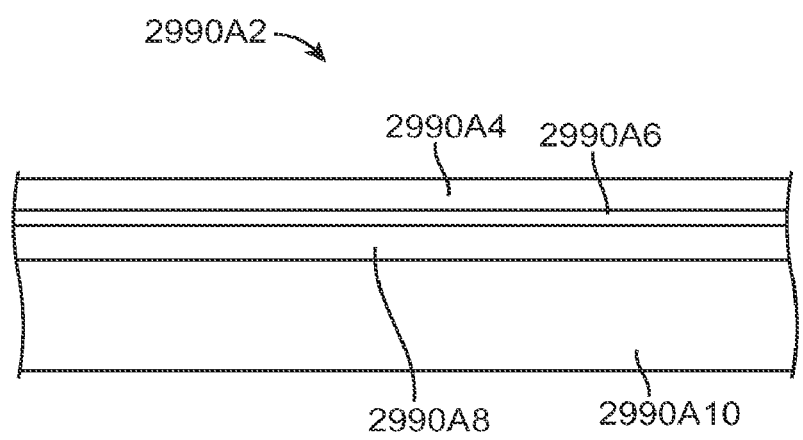
FIG. 29H3

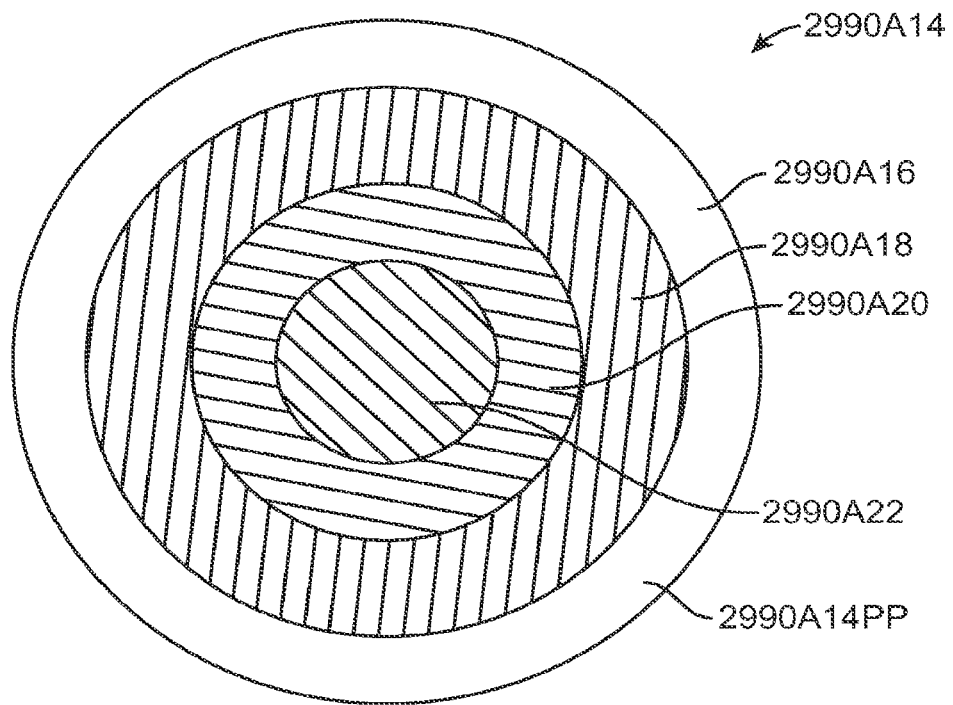
FIG. 29J1
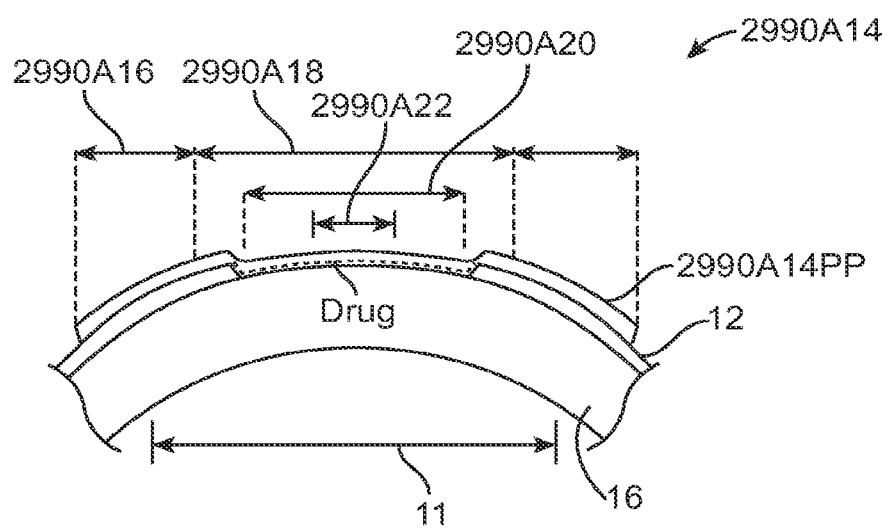
FIG. 29J2

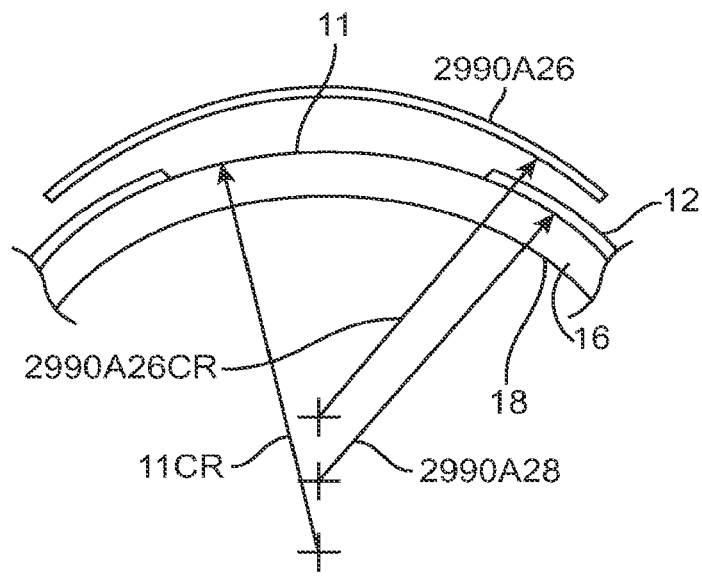
FIG. 29K1
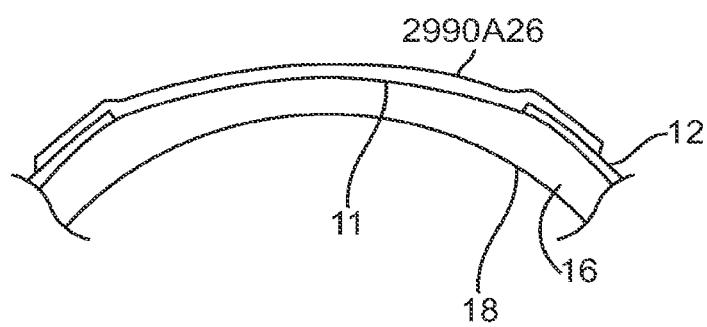
FIG. 29K2

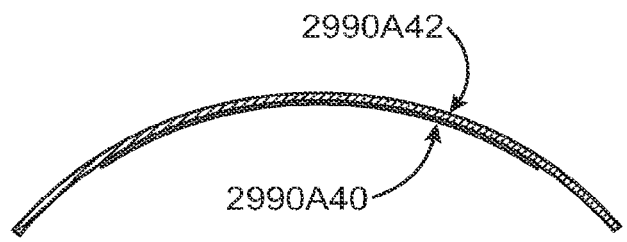
FIG. 29M1A
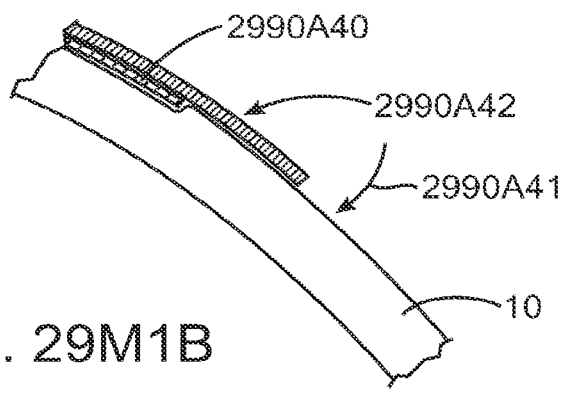
FIG. 29M1B
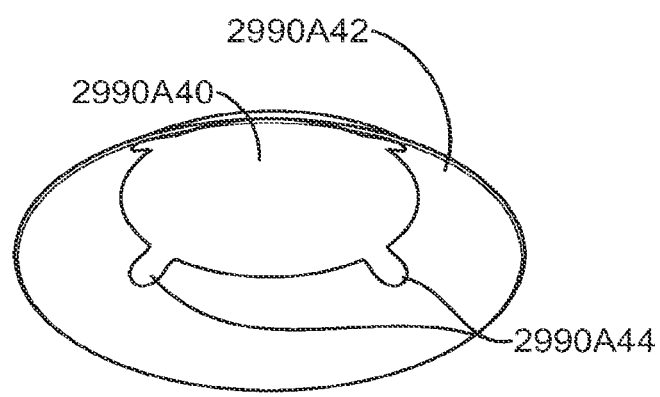
FIG. 29M1C

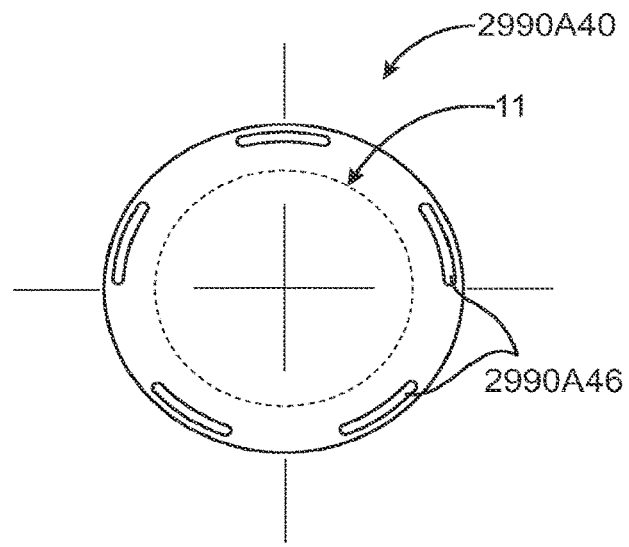
FIG. 29M1D
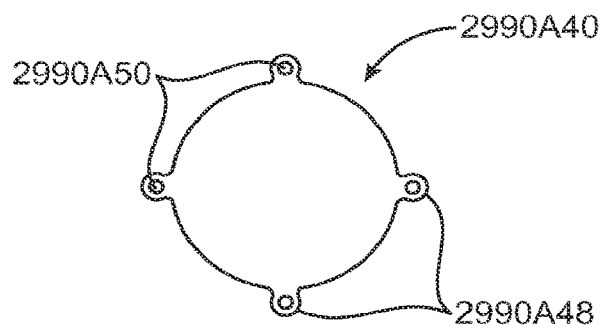
FIG. 29M1E
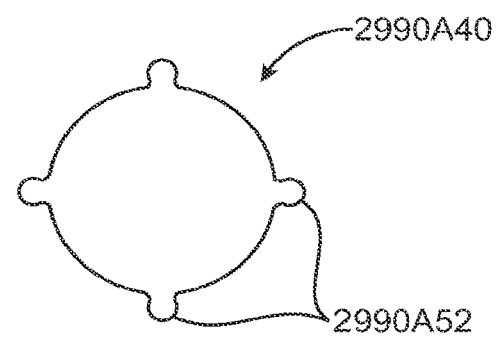
FIG. 29M1F

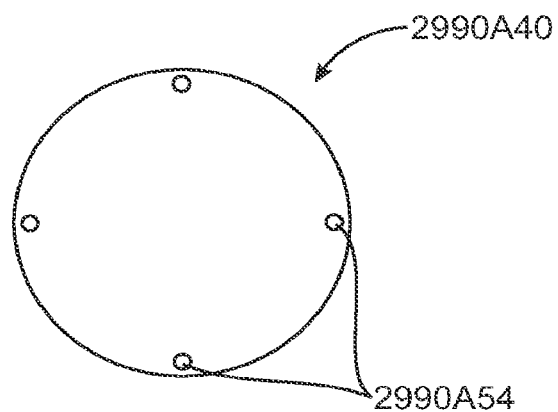
FIG. 29M1G
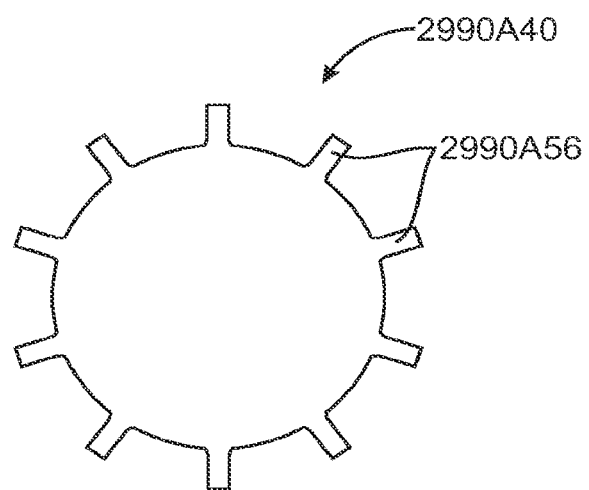
FIG. 29M1H

PRESSED TOGETHER, AFTER HEATING, AND FLOW OF POLYCARBONATE

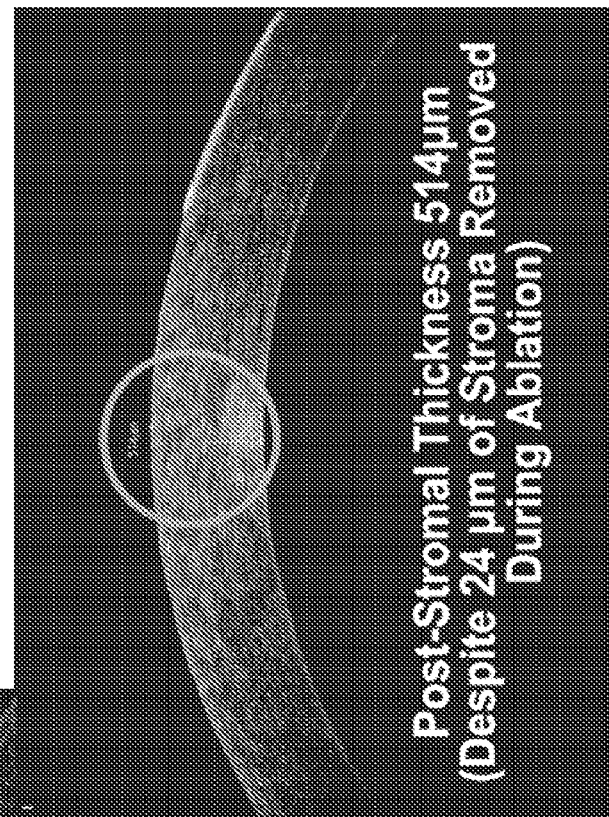
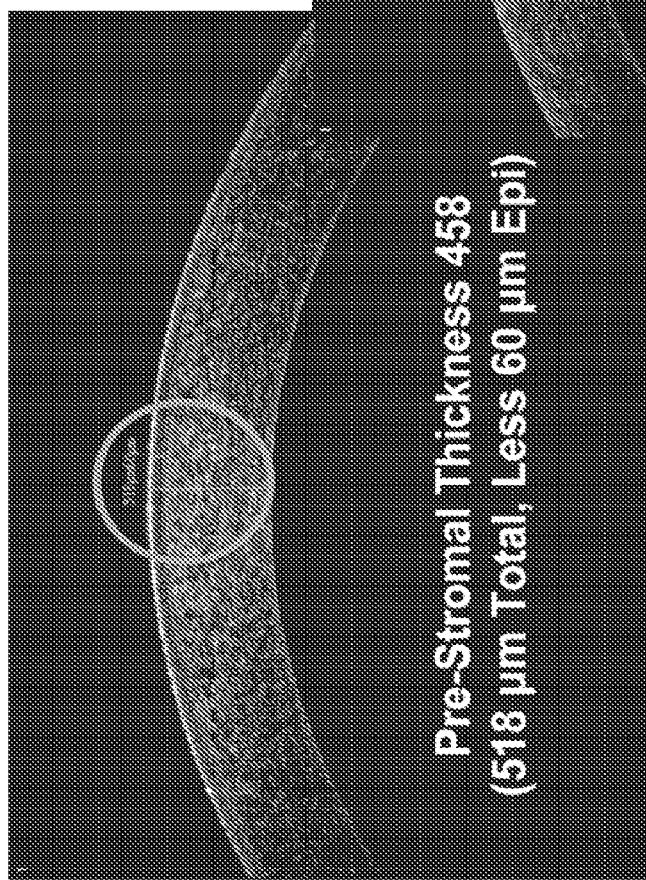
FIG. 34A
FIG. 34B

Updated Results (3 pts, 6 eyes)

| | Pt 1 OD | Pt 1 OS | Pt 2 OD | Pt 2 OS | Pt 3 OD | Pt 3 OS |
|---|---|---|---|---|---|---|
| Ref | -7.5-2.25x12 | -6-2.5x5 | -1.25 | -1.25 | -5.75-1x20 | -5.5-1.5x165 |
| VA -Pre | 20/25 | 20/25 | 20/20 | 20/20 | 20/25 | 20/25 |
| Ablation depth | 72μ | 64μ | 24μ | 24μ | 50μ | 53μ |
| Over refraction on RGP | -9 | -9 | -2 | -3.5 | -6.5 | -6.5 |
| Over refraction on BL | +1.25 | +1.25 | -1 | +1.25 | +1.0 | +0.75 |
| VA-post +BL | 20/50 | 20/50 | 20/40 | 20/40 | 20/40 | 20/40 |
| VA – post + RGP | 20/50 | 20/50 | 20/50 | 20/40 | 20/40 | 20/40 |
| Pentacam Pre Thickness (μ) | | | 524 | 531 | 448 | 451 |
| Pentacam PostThickness (μ) | | | 537 | 538 | 412 | 411 |
| Delta (post-pre)(μ) | | | 13 | 7 | -36 | -40 |
| OCT Pre-Epi Thickness (μ) | 47 | 62 | 60 | 65 | 56 | 56 |
| OCT Pre-Stromal Thickness (μ) | 468 | 452 | 458 | 453 | 406 | 428 |
| OCT Post-Stromal Thickness (μ) | 466 | 453 | 514 | 514 | 410 | 423 |
| Delta (Stroma post-Stroma preμ) | -2 | -1 | 56 | 61 | 4 | -5 |
| Edema OCT based | 70 | 65 | 80 | 85 | 54 | 48 |
| Edema Pentacam based | | | 97 | 96 | 70 | 69 |

FIG. 35

Post-PRK: Clinical Results (1 Day)

|  | P+.1 OD | P+.1 OS | P+.2 OD | P+.2 OS | P+.3 OS |
|---|---|---|---|---|---|
| Ref pre op | -6.5-2.5x20 | -5.5-3x160 | +1x90 | +0.75x90 | -12-3.5x160 |
| VA pre op | 20/25 | 20/25 | 20/15 | 20/15 | 20/40 |
| Pa pre op | 497 | 508 | 539 | 539 | 508 |
| Pa baseline | 469 | 494 | 574 | NA Descemet folds | |
| Ablation depth | 124 μ | 120 μ | 9 μ | 7 μ | 121 μ |
| Pa Glycerin 1 | 560 (0:30) | 471 (0:40) | 561 (0:20) | | |
| Pa Glycerin 2 | | | 666 (5:30) | | |
| VA w/BL | 20/100 | 20/40 | 20/22 | | |
| VA wo/BL | 20/50 | 20/66 | 20/40 | | |
| VA wo/BL+Gly 1 | 20/33 (1) | 20/40 (1) | 20/28 (1:30) | | |
| VA wo/BL+Gly 2 | 20/66 (5:30) | 20/100 (5:30) | 20/40 (5:25) | | |
| VA + RGB + Healon | 20/33 (add -1D) | 20/40 (add -1D) | 20/50 (add +2.5D) | | |
| Edema ( epi=60μ) | 156 | 166 | 104 | | |
| Baseline Pa@PRK day- Pa@1st day | | 76 | 17 | | |

FIG. 36

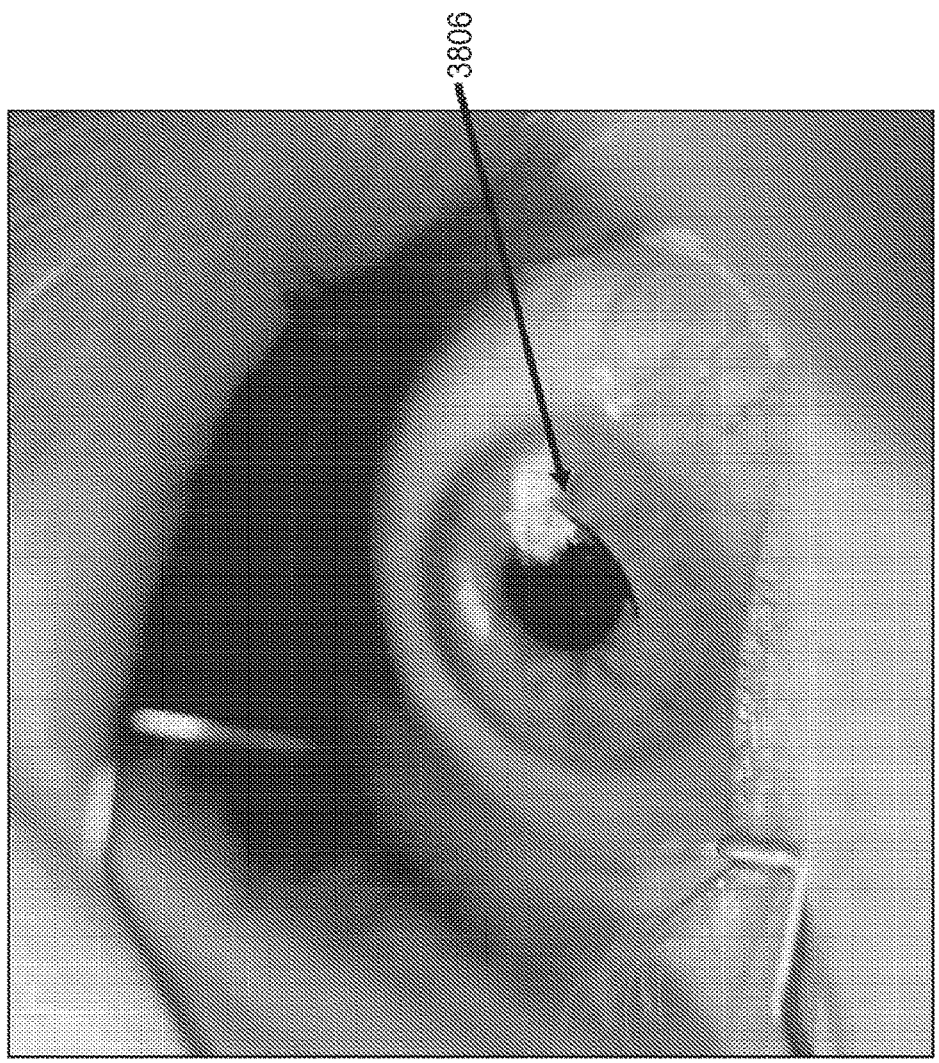
FIG. 38A — Fibrin on Epi: Initial Placement

Fibrin Lens w/BCL @ 15 Mins

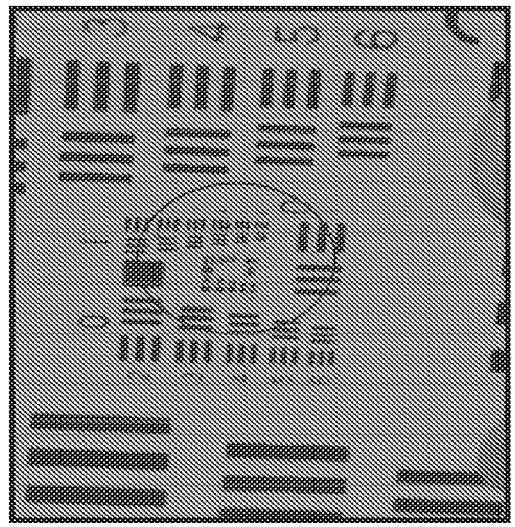
FIG. 39C Cast Formulation
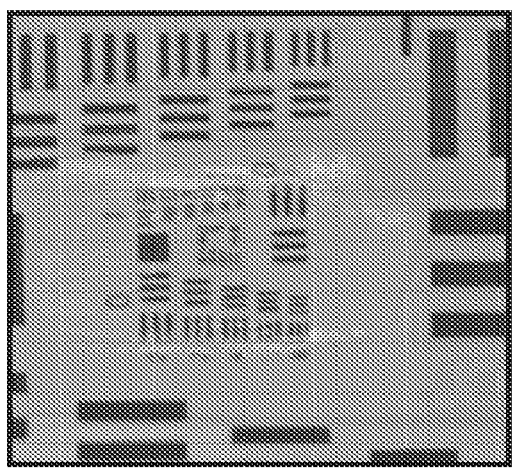
FIG. 39B Custom Formulation
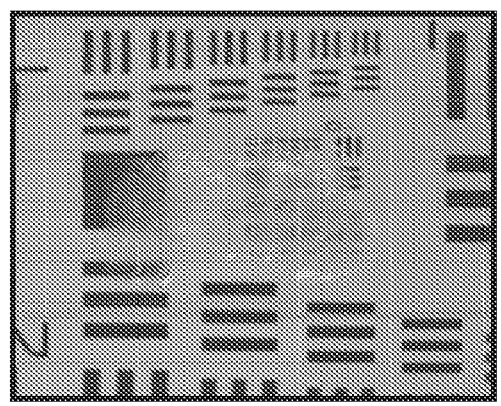
FIG. 39A Standard Formulation

THERAPEUTIC DEVICE FOR PAIN MANAGEMENT AND VISION

CROSS-REFERENCES TO RELATED APPLICATIONS

The present application is a Continuation of U.S. application Ser. No. 12/384,659, filed on Apr. 6, 2009, now allowed, which claims priority to U.S. Application Nos. 61/042,594 filed on Apr. 4, 2008; 61/050,147 filed on May 2, 2008; 61/191,915 filed on Sep. 11, 2008; 61/119,712 filed on Dec. 3, 2008; and 61/211,815 filed on Apr. 3, 2009; the full disclosures of which are incorporated herein by reference.

BACKGROUND OF THE INVENTION

The present invention is generally directed to visual rehabilitation and treatment of pain for patients with epithelial defects on the cornea of the eye. Although specific reference is made to epithelial defects following photorefractive keratectomy, embodiments of the present invention can be used to treat epithelial defects from other causes, for example corneal abrasions, trauma, keratoconus, penetrating keratoplasty and dystrophies.

The eye includes several tissues that allow patients to see. The cornea of the eye is an anterior tissue of the eye that is clear in healthy eyes and refracts light so as to form an image on the retina. The retina is a posterior tissue of the eye that senses light from the image formed thereon and transmits signals from the image to the brain. The cornea includes an outer layer of tissue, the epithelium, which protects the underlying tissues of the cornea, such as Bowman's membrane, the stroma and nerve fibers that extend into the stroma and Bowman's. The healthy eye includes a tear film disposed over the epithelium. The tear film can smooth small irregularities of the epithelium so as to provide an optically smooth surface. The tear film is shaped substantially by the shape of the underlying epithelium, stroma, and Bowman's membrane, if present. The tear film comprises a liquid that is mostly water and does include additional components, such as mucoids and lipids. The many nerve fibers of the cornea provide sensation to promote blinking that can cover the cornea with the tear film. The never fibers also sense pain so that one will normally avoid trauma to the cornea and also avoid direct contact of an object to the cornea so as to protect this important tissue.

In the healthy cornea, the proper amount of hydration of the cornea, sometimes referred to as dehydration of the cornea, is maintained such that the cornea remains clear. The cornea includes a posterior endothelial layer that pumps water from the cornea into the adjacent anterior chamber. The epithelium minimizes flow of water from the tear liquid into the cornea, such that the corneal stroma can be maintained with the proper amount of hydration with endothelial pumping. The endothelial pumping of water from the cornea to maintain the proper hydration and thickness of the eye is often referred to as deturgescence.

In patients with epithelial defects, the barrier function of the epithelium is compromised, such that water can enter the cornea through the epithelial defect so as to cause swelling of the corneal stroma. As a result, excessive hydration of the cornea may occur in eyes with epithelial defects. In some instances, excessive hydration that swells the corneal stroma can result in light scattering, or haze, such that an image seen by a patient is degraded. The scattering of light by the corneal stroma can be seen with a slit lamp examination to diagnose the patient, and is sometimes referred to as corneal haze. In addition to potentially causing excess hydration of the cornea, an epithelial defect can expose the nerve fibers of the cornea such that the patient feels pain.

Several known techniques exist to treat corneal epithelial defects, including bandage therapeutic lenses, non-steroidal anti-inflammatories (hereinafter NSAIDS), steroids, antibiotics and analgesics. These known techniques may be somewhat effective in reducing symptoms associated with the epithelial defect. However, many of these known techniques may not provide a barrier to water entry into the corneal stroma, such that the cornea may swell with water and may affect patient vision in at least some instances. For example, a bandage therapeutic lens may be placed over the epithelial defect to cover and protect the corneal tissues under the defect, such as the corneal stroma and nerve fibers. However, in at least some instances the bandage therapeutic lens may not prevent water of the tear from leaking through the epithelial defect into the stroma. Also, a bandage therapeutic lens may slide over the epithelial defect when positioned on the eye in at least some instances, potentially decreasing the therapeutic benefit of the therapeutic lens when the lens slides along the delicate underlying tissue, for example when a patient blinks.

Work in relation to embodiments of the present invention suggests that at least some of the known therapeutic bandage lenses used to treat epithelial defects may actually contribute to corneal edema and pain in at least some instances. At least some of the current bandage lenses may provide less oxygen than would be ideal, and decreased oxygen to the cornea may be related pain and corneal edema in at least some instances. Also, in at least some instances, bandage lenses may be fit loosely on the cornea, such that water can go around the bandage lens and may penetrate the stroma through the epithelial defect.

Although analgesics such as lidocaine may reduce pain, the overuse of these treatments can delay regeneration of the epithelial tissue over the defect, such that the defect may last longer. Consequently many people with epithelial defects may feel pain and have degraded vision while the epithelial defect heals.

Many people elect to undergo laser vision correction surgery to treat refractive error of the eye, such as near sightedness. With one form of this surgery known as photorefractive keratectomy (hereinafter "PRK"), a large area of the epithelium is removed, for example a 6 mm area. Following ablation of the underlying tissues such as the corneal stroma and/or Bowman's membrane, the epithelium grows back over the ablation to cover the area where the epithelium was removed. This re-growth of the epithelium can take three to four days, and at least some of the patients who undergo this surgery may feel pain. In addition, the epithelium may be somewhat irregular while growing back over the corneal stroma, and the irregularities may degrade patient vision in at least some instances. Further, work in relation to embodiments of the present invention suggests that anterior stromal edema, ablated surface irregularities and necrotic cells in the ablated surface area may decrease vision in some instances. Therefore, improved treatment of epithelial defects may result in improved patient comfort and vision following PRK, and possibly other surgeries that remove the corneal epithelium.

In light of the above, it would be desirable to provide improved treatments for epithelial defects of the cornea. Ideally, these treatments would avoid at least some of the deficiencies of known techniques while providing improved patient comfort and/or vision while the epithelial defect heals.

SUMMARY OF THE INVENTION

The present invention is generally directed to visual rehabilitation and treatment of pain for patients with epithelial defects on the cornea of the eye. Although specific reference is made to epithelial defects following photorefractive keratectomy, embodiments of the present invention can be used to treat epithelial defects from other causes, for example corneal abrasions, trauma, keratoconus and corneal dystrophies. Embodiments of the present invention can provide patients having epithelial defects with improved hydration of the cornea and improved vision with decreased pain.

Embodiments of the present invention provide a therapeutic covering for the treatment of an epithelial defect of a cornea of an eye, in which the cornea comprises a stroma and/or Bowman's membrane. The covering may comprise a layer of a therapeutic material positionable over the stroma and/or Bowman's membrane of the eye. The layer can be positionable over the eye to reduce pain, for functional vision through the layer, to inhibit and/or minimize swelling of the cornea, and/or so as to decrease light scatter of the cornea. The layer can be configured to reduce pain in many ways, for example by covering exposed nerve fibers and/or by adhering to the stroma and/or Bowman's so as to inhibit, in some embodiments minimize, rubbing of the layer on the stroma and/or Bowman's membrane where nerve fibers may be located. The layer may be configured for positioning on the eye with mechanical resistance sufficient to resist a blink of the eyelid, and this resistance may decrease pain by inhibiting motion of the covering over corneal nerve fibers. The layer can be configured for functional vision through the layer in many ways, for example configured to contact the stroma and/or Bowman's membrane for a plurality of days so as to inhibit and/or minimize, swelling of the cornea and/or so as to inhibit and/or minimize light scatter from an anterior surface of the cornea. The layer may comprise an index of refraction so as to inhibit and/or minimize light scatter from the anterior surface of the stroma and/or Bowman's membrane. The layer can be configured to inhibit and/or minimize swelling of the cornea in many ways, for example with a hyperosmotic solution, a hydrophobic liquid and/or a matrix material that inhibits and/or minimizes water flow from the tear liquid to the stroma and/or Bowman's membrane. The layer may be configured to inhibit and/or minimize swelling of the cornea for a plurality of days when positioned on the eye, and the layer may restore deturgescence of the cornea. In some embodiments, the layer is configured to inhibit and/or minimize swelling of the cornea so as to inhibit and/or minimize light scatter from the stroma and/or Bowman's membrane. The layer may comprise an index of refraction to inhibit and/or minimize light scatter from an anterior surface of the stroma and/or Bowman's membrane. The layer may be configured for the eye to view through for a plurality of days when positioned on the eye. The layer can be configured to adhere to the stroma and/or Bowman's membrane. The layer may comprise a curved anterior surface that corresponds to the anterior surface of the stroma and/or Bowman's membrane to within about +/−1 D, for example with post-PRK patients, such that the lens with the curved anterior surface comprises a lens to correct vision of the patient when the epithelium regenerates. The layer of therapeutic material can be positioned on the eye in many ways, for example with a covering that is placed on the eye or with a spray that is cured to adhere the layer to the exposed surface of the stroma and/or Bowman's membrane. In many embodiments a thin layer sprayed on the corneal surface may comprise a curved anterior surface of the therapeutic layer that corrects patient vision. In some embodiments, a therapeutic lens disposed over the layer of therapeutic material may comprise a curved anterior surface that corrects patient vision.

The therapeutic covering may comprise oxygen permeability sufficient to restore deturgescence of the cornea, for example with an oxygen permeability Dk parameter of 80 or more, such that the epithelial and endothelial cell layers have oxygen for epithelial regeneration and endothelial pumping to restore deturgescence, respectively. The covering may comprise a hydrophobic water barrier layer disposed between a hydrophilic lower surface to contact the cornea and a hydrophilic upper surface to contact the tear film. An outer portion of the covering may be configured to form a seal with the epithelium such that the covering can be adhered to the cornea with endothelial suction of the covering onto the epithelial defect. As the endothelial suction may not immediately adhere the covering to the cornea, the covering may be held in place with another mechanism initially. For example, a contact lens may be placed over the covering to hold the covering against the epithelial defect, and the contact lens removed after the covering is adhered to the cornea with endothelial suction, for example removed after one hour or less.

In a first aspect, embodiments of the present invention provide a therapeutic covering for treating an epithelial defect of a cornea of an eye, in which the cornea comprises a stroma and/or a Bowman's membrane. The covering comprises a layer of a water impermeable material positionable over the stroma and/or Bowman's membrane of the eye to inhibit swelling of the cornea.

In many embodiments, the layer is configured to inhibit swelling of the cornea for a plurality of days cornea when positioned on the eye. For example, the layer can be configured to minimize swelling of the cornea for the plurality of days.

In many embodiments, the layer is configured to conform to irregularities of the cornea to inhibit the swelling.

In many embodiments, a hydrophobic material is disposed along a lower surface of the layer to adhere to the cornea, and a hydrophilic material is disposed along an upper surface to contact a tear liquid of the eye. The hydrophobic surface may help the layer stick to the cornea and inhibit sliding, and the hydrophilic surface can form a smooth tear film for vision and may allow a contact lens placed over the covering to slide when the covering sticks to the epithelium.

In many embodiments, the layer is configured for the eye to view through the layer for a plurality of days when positioned on the eye.

In many embodiments, the layer is configured to adhere to the stroma and/or Bowman's membrane for a plurality of days. The therapeutic covering can be configured to separate from the epithelium such that the epithelium remains on the Bowman's and/or stroma. The layer may be configured to separate from the epithelium with a removal agent.

In many embodiments, the layer is configured to provide functional vision for the eye. For example, the layer can be configured to enhance the optical properties of the cornea.

In another aspect embodiments, of the present invention provide a therapeutic covering for treating an epithelial defect of a cornea of an eye, in which the cornea comprises a stroma and/or a Bowman's membrane. The covering comprises at least one layer of a therapeutic material positionable over the stroma and/or Bowman's membrane of the eye to inhibit water flow to the stroma and/or Bowman's membrane.

In many embodiments, an epithelium and a tear liquid are disposed over the stroma and/or Bowman's membrane, and the at least one layer is configured to inhibit water flow from the tear liquid of the eye to the stroma and/or Bowman's membrane. For example, the at least one layer can be configured to decrease swelling of the cornea to within about 5% of a thickness of the cornea without the epithelial defect, and the at least one layer is configured to decrease swelling of the cornea to within about 2.5% of a thickness of the cornea without the epithelial defect.

In many embodiments, the at least one layer comprises at least one of a solid, an adhesive, a gel, a low adhesion gel or a liquid.

In many embodiments, the at least one layer comprises a lower surface configured to adhere to the stroma and/or Bowman's membrane. The lower surface may comprise a hydrophobic material to adhere to the cornea. For example, the lower surface may be configured to adhere to the epithelium with the hydrophobic material.

In many embodiments, the at least one layer comprises a hydrophilic upper surface configured to contact the tear liquid of the eye, which can provide a smooth tear film over the covering eye so that the patient can see clearly.

In many embodiments, an anterior refracting surface disposed on the at least one layer to correct vision of the eye.

In many embodiments, the therapeutic material comprises a bio-compatible material configured to detach the lower surface from the epithelium when the epithelium regenerates.

In many embodiments, the at least one layer comprises a lens. The lens may comprise an upper surface, in which the upper surface is curved and configured to contact the tear liquid. The upper surface may comprise a curvature so as to corresponds to a curvature of an ablated profile of the stroma and/or Bowman's membrane to within about +/−1 Diopter. The at least one layer may comprise a lower surface configured to contact the stroma and/or Bowman's membrane, in which a thickness of the at least one layer from the lower surface to the upper surface is uniform to within about +/−10 microns so as to correspond to the curvature of the ablated profile.

In many embodiments, the therapeutic material comprises an optically clear material configured to transmit light.

In another aspect, embodiments of the present invention provide a therapeutic covering system for treating an epithelial defect of a cornea of an eye, in which the cornea comprises a stroma and/or Bowman's membrane. The covering system comprises a layer of a therapeutic material configured to contact the stroma and/or Bowman's membrane of the eye to decrease light scatter from the cornea. A therapeutic lens is configured for placement over the layer, and the therapeutic lens comprises an anterior surface to correct patient vision and a posterior surface to fit against the epithelium.

In many embodiments, the posterior surface comprises a radius of curvature that corresponds to the radius of curvature of the cornea where the lens fits against the epithelium so as to fit the lens against the epithelium.

In another aspect, embodiments of the present invention provide a therapeutic covering for a cornea of an eye of a patient. A first portion comprising a lens is configured for positioning on the eye. At least a second portion is configured to conform to irregularities of the epithelium to adhere to the first portion to cornea to inhibit motion.

In many embodiments, the at least the second portion is configured with a lower hydrophobic surface so as to adhere the first lens portion to the cornea with mechanical resistance sufficient to resist a blink of the eyelid.

In another aspect, embodiments of the present invention provide a therapeutic device to treat a cornea of a patient having an epithelium with a defect. A covering comprises at least one region adapted to conform to the shape of cornea so as to decrease swelling of the cornea.

In many embodiments, the covering is configured to at least one of deturgesce or minimize swelling of the cornea when the covering is placed on the cornea over the epithelial defect. The covering may comprises a thickness of no more than about 200 microns and a width of at least about 5 mm to conform to the cornea.

In many embodiments, the covering comprises at least one of a hydrophobic layer or an upper hydrophobic surface extending along at least a inner portion of the covering to inhibit water flow through the covering. The at least one of the hydrophobic layer or the upper hydrophobic surface may comprise at least one of silicone, elastomer, silicone elastomer, silicone hydrogel or polyurethane.

In many embodiments, the covering comprises at least one of a lower hydrophilic layer or a hydrophilic surface extending along at least a inner portion of the covering to inhibit sliding of the covering along the cornea.

In many embodiments, the at least one of the lower hydrophilic layer or the lower hydrophilic surface comprises at least one of hydrogel, 2-hydroxyethylmethacrylate (HEMA), methacrylic acid (MA), methyl methacrylate (MMA), N,N-dimethylacrylamide (DMA); N-vinyl pyrrolidone (NVP), phosphorylcholine (PC), poly vinyl alcohol (PVA) or polyvinyl pyrrolidone (PVP), tris-(trimethylsiloxysilyl) propylvinyl carbamate (TPVC); N-carboxyvinyl ester (NCVE); silicone hydrogel, poly[dimethylsiloxyl] di [silylbutanol] bis[vinyl carbamate] (PBVC); silicate, plasma treated silicone hydrogel, plasma coating producing glassy islands, 25 nm plasma coating with high refractive index, fibrin, or bioglue.

In many embodiments, the covering comprises an oxygen Dk parameter of at least about 80.

In many embodiments, the covering comprises a thickness within a range from about 25 to about 100 microns and a an oxygen Dk parameter of at least about 80.

In many embodiments, the oxygen permeability Dk parameter comprise at least about 350 or more to inhibit swelling when the covering is worn for a plurality of days.

In many embodiments, the covering comprises an upper optical surface extending along at least an inner portion of the covering. The covering may comprise a inner portion adapted to conform to an ablated surface contour of the cornea. The inner portion may be adapted to conform to an aberration ablated into the cornea to correct an aberration of the eye.

In many embodiments, the covering comprises at least a inner portion having a substantially uniform thickness extending from a lower surface to an upper surface such that the covering has an optical power within a range from about −5 D to about +5 D along at least the inner portion of the covering. The range is from about −1 D to about +1 D to decrease a thickness of the inner portion, which may improve oxygen permeability.

In many embodiments, the covering comprises a lower curved surface extending along at least an outer portion of the covering, in which the lower curved surface is shaped to fit the cornea away from the epithelial defect. The outer portion may be adapted to form a seal with an unablated portion of the cornea. The outer portion may comprise a covering radius of curvature and may be configured to stretch when the peripheral portion of the covering is placed against a peripheral portion of cornea away from live epithelial defect. For example, the covering radius of curvature can be less than a radius of curvature of the cornea.

In many embodiments, the inner portion comprises a soft material and a thickness of no more than about 200 microns such that the inner portion conforms to an ablated surface contour of the cornea when the outer portion forms a seal with the unablated portion of the cornea.

In many embodiments, the covering comprises a lower flat surface and an upper optical surface opposite the lower flat surface, and the covering is adapted to conform to a curved surface of the cornea.

In many embodiments, the covering comprises a inner portion and an outer portion, and the inner portion comprises a lower hydrophilic surface sized to contact an exposed stromal tissue under an epithelial defect and wherein the outer portion comprises a hydrophobic lower surface sized to contact the epithelium. The inner portion can be adapted to conform to a surface profile of the exposed stromal tissue and inhibit sliding along the exposed surface. The outer portion can be adapted to form a seal when the outer portion contacts the epithelium.

In many embodiments, a contact lens is configured to hold the covering against an epithelial defect when the epithelial defect heals, and the covering is adapted to conform to a curved surface contour of the cornea when the contact lens retains the covering against the epithelial detect.

In another aspect, embodiments of the present invention provide a method of treating a cornea of an eye of a patient. A covering is placed on the cornea, and the covering is adhered to the cornea to reduce swelling of the cornea.

In many embodiments, a speculum is placed against the eyelids to expose the eye such that the cornea dries, and the covering is placed on the cornea when the speculum is positioned against the eyelids. An exposed stromal tissue of the cornea can be ablated with a laser beam to correct vision of the eye. At least a portion of the covering can be placed against the exposed stromal tissue of the dried cornea, and the portion of the covering placed against the exposed stromal tissue may comprises an amount of hydration that corresponds to less than physiological hydration when the covering is placed against the exposed stromal tissue.

In many embodiments, the covering forms a seal between the cornea and at least a portion of the covering to decrease water flow into the cornea.

In many embodiments, the covering comprises an outer periphery, and the epithelium grows over at least a portion of the outer periphery. For example, the covering may grow over the portion to form the seal. The covering may be placed on the epithelium such that the epithelium is disposed under the outer periphery when the epithelium grows over the outer periphery.

In many embodiments, the covering is placed over an epithelial defect of the cornea, and the covering is removed when the epithelial defect is healed. The epithelium remains on the cornea and separates from the covering when the covering is removed. For example, water can be provided to the eye to loosen the covering from the epithelium when the covering is removed.

In many embodiments, the covering comprises a lower surface that is hydrophilic to inhibit sliding.

In many embodiments, the covering may comprise a substantially water impermeable material to at least one of deturgesce or inhibit swelling of the cornea when the seal is formed.

In many embodiments, the cornea comprises an epithelial defect, and the covering comprises at least one of a lower surface or a lower material configured to suck down against the stroma and adhere to the stroma when the seal is formed. The at least one of the lower surface or lower material can be configured to adhere substantially less to the epithelium than to the stroma. The at least one of the lower surface or the lower material may comprises a hydrophilic lower surface to contact the stroma and wherein the hydrophilic lower surface comprises less adherence to the epithelium than to the stroma when the epithelium covers the defect.

In many embodiments, the covering comprises a substantially oxygen permeable material.

In many embodiments, the cornea comprises an epithelial defect when the covering is placed on the cornea, the covering is removed when epithelial defect is healed.

In many embodiments, the cornea is measured to determine a characteristic of the covering. The covering can be selected from among a plurality of coverings in response to the characteristic such that the seal is formed when the covering is placed on the cornea. The cornea can be measured to determine a curvature of the cornea and the characteristic may comprise a radius of curvature of a lower surface of the covering.

In many embodiments, the covering comprises an optical power within a range from about −5 D to about −5 D. The range may be from about −1 D to about +1 D to decrease a thickness of the covering.

In another aspect, embodiments of the present invention provide a method of treating an eye of a patient following PRK, in which the eye has a cornea comprising an epithelium and a detect of the epithelium. A contact lens is placed over the eye to form a seal with an unablated region of the epithelium such that swelling of the cornea is at decreased. The contact lens is removed when the defect of the epithelium is healed.

In many embodiments, the contact lens comprises at least one of a surface or a material to inhibit water flow through the contact lens and deturgesce the cornea when the seal is formed. The contact lens may comprises at least an inner portion comprising hydrophilic surface to adhere the contact lens to ablated stroma when the seal is formed and to release the contact lens from the epithelium when the epithelium regenerates and covers the epithelial defect.

In another aspect, embodiments provide therapeutic covering to treat an eye having a cornea with an epithelial defect. An inner portion comprises a lens. An outer portion is configured to conform to irregularities of the cornea the eye to retain the inner portion comprising the lens over the epithelial defect.

In many embodiments, the irregularities comprise art epithelial defect. The irregularities may comprise a stromal defect.

In many embodiments, a water impermeable layer extends across the inner portion and the outer potion to adhere the inner portion and the outer portion to the cornea with water suction.

In many embodiments, the inner portion may comprise rigidity to retain optical smoothness of a front surface of the lens when the lens is placed over the epithelial defect.

In many embodiments, the inner portion comprises a first rigidity to retain optical smoothness of a front surface of the lens when the lens is placed over the epithelial defect, and the outer portion comprises a second rigidity to conform to the cornea and seal the epithelial defect, in which the first rigidity is greater than the second rigidity.

In many embodiments, the inner portion is configured to comprise a first inner configuration prior to placement on the eye and a second inner configuration after placement on the eye, in which the second inner configuration substantially similar to the first inner configuration to retain optical properties of the lens.

In many embodiments, the outer portion is configured to comprise a first outer configuration prior to placement on the eye and a second outer configuration after placement on the eye, in which the second outer configuration is substantially different from the first outer configuration such that the second configuration conforms to the epithelium to seal the outer portion against the epithelium with endothelial suction.

In many embodiments, the inner portion and the outer portion each comprise a hydrophobic layer to inhibit water and an upper hydrophilic layer and a lower hydrophilic layer, in which the hydrophobic layer is disposed between the upper hydrophilic layer and the lower hydrophilic layer.

In many embodiments, the outer portion comprise an oxygen permeability Dk parameter of at least about 200. For example, the outer portion may comprise an oxygen permeability Dk parameter of at least about 350, at least about 400, and in specific embodiments at least about 500.

In many embodiments, the inner portion may comprise an oxygen permeability Dk parameter of at least about 100. For example, the outer portion comprise an oxygen permeability Dk parameter of at least about 200, at least about, 350, at least about 400, and in specific embodiments at least about 500.

In many embodiments, the inner portion comprises a hardness parameter within a range from about 30 Shore A to about 94M on a known Rockwell scale.

In many embodiments, outer portion comprises a Shore A durometer hardness parameter within a range from about 20 to about 80.

In many embodiments, the hydrophobic layer of the inner portion and the hydrophobic layer of the outer portion comprise silicone having a Dk of at least about 200.

In many embodiments, the inner portion comprises a thickness of no more than about 200 um, and the outer portion comprises a peripheral thickness of no more than about 100 um and extends toward the central portion with an increase in thickness.

In many embodiments, the outer portion comprises a radius of curvature along a lower surface. The outer portion can be configured to conform to an outer boundary of the epithelial defect. The outer portion of the covering can be configured to conform to a first curvature of the cornea outside an ablation zone and conform to a second curvature of the cornea within the ablation zone such that the cornea is sealed over the ablation zone.

In many embodiments, the inner portion comprises a first piece of material and the outer portion comprises a second piece of material adhered to the first piece.

In many embodiments, the inner portion and the outer portion comprise a similar material, and the inner portion comprises a first thickness and the outer portion comprises a second thickness less than the first thickness, such that the inner portion is configured to retain art optical front surface when placed on the cornea and the outer portion is configured to conform to the irregularities of the cornea.

In many embodiments, the inner portion comprises a first hardness and the outer portion comprises a second hardness, in which the first hardness is greater than the second hardness such that the inner portion is configured to retain an optical front surface when positioned on irregularities of the cornea. The irregularities of the cornea may comprise irregularities of a stroma. The irregularities of the cornea may comprise irregularities of an epithelium.

In another aspect, embodiments provide method of treating an eye having a cornea with an epithelial defect. A therapeutic covering is placed on the cornea of the eye, and swelling of the cornea decreases when the covering is adhered to the cornea.

In many embodiments, the covering is adhered to the cornea with water suction. For example, the endothelium can pumps water from the cornea so as to suck the covering onto the cornea.

In many embodiments, the epithelial defect comprises an epithelial defect following ablation of an optical zone with PRK surgery to correct vision, and within the optical zone the cornea comprises a first swelling of no more than about 5% from a baseline value before the PRK surgery to a first day after the PRK surgery.

In many embodiments, at the first day the patient is capable of at least about 20/30 vision with the covering over the optical zone.

In many embodiments, the first swelling at the first day comprises no more than about 2% such that patient is capable of at least about 20/30 vision with the covering over the optical zone.

In many embodiments, the swelling of the cornea is minimized such that the cornea is substantially restored to a preoperative amount of hydration.

In many embodiments, the covering comprises an inner portion and an outer portion, in which the outer portion conforms to the cornea to seal the cornea, and the inner portion comprising a lens. The lens may comprise a shape, and the outer portion may be more rigid than the inner portion such that the shape of the lens is substantially retained when the epithelium regenerates to close the defect and the cornea is sealed.

In many embodiments, the epithelial defect comprises an area of corneal tissue, and the covering is removed when the epithelial defect is healed with an epithelial layer over the area of corneal tissue. The covering can be separated from the epithelial layer when the covering is removed such that the epithelial layer remains over the area.

In many embodiments, a contact lens is placed over the covering to adhere the covering to the cornea. The contact lens can be removed from the covering when the covering is adhered to the cornea. For example, the contact lens is removed from the covering no more than about one hour after the contact lens is positioned on the covering.

In another aspect, embodiments provide a method of treating an eye having a cornea with an epithelial defect. A therapeutic covering is placed on the cornea, and the therapeutic covering corrects optical aberrations of the eye when the covering is adhered to the cornea.

In many embodiments, the optical aberrations correspond to irregularities of the cornea. The optical aberrations may correspond to irregularities of the stroma, the epithelium or Bowman's membrane.

BRIEF DESCRIPTION OF THE DRAWINGS

FIG. 1C1 shows optical smoothing of a corneal surface and barrier protection with the therapeutic lens as in FIG. 1C;

FIG. 1C2 shows regeneration of the epithelial layer with centripetal advancement of the epithelial layer under the therapeutic lens;

FIG. 2B1 shows optical smoothing of a corneal surface with the therapeutic lens as in FIG. 2B;

FIG. 2D shows regeneration of the epithelial layer with centripetal advancement of the epithelial layer as the therapeutic lens sloughs off the cornea;

FIG. 3B1 shows detail of the lens used to mold the therapeutic lens as in FIG. 3B;

FIG. 5B1 shows detail of therapeutic lens as in FIG. 5B;

FIG. 5B2 shows a plan view of the therapeutic lens as in FIG. 5B;

FIG. 5B3 shows peripheral apertures through a therapeutic lens to adhere the lens to the periphery of the epithelium, according to embodiments of the present invention;

FIG. 5B4 shows peripheral apertures through a therapeutic lens to adhere the lens to the periphery of the epithelium and surface channels on the underside of the lens to release material from the under the lens as the epithelial layer migrates centripetally, according to embodiments of the present invention;

FIG. 5B5 shows retention of the filler material with a therapeutic lens to retain the filler material, in which the therapeutic lens has a posterior curvature to fit the curvature of the unablated peripheral cornea and an anterior curvature to provide optical correction, according to embodiments of the present invention;

FIG. 19B1 shows epithelial growth over at least one layer of a therapeutic covering as in FIG. 19A;

FIG. 19B2 shows epithelial growth over at least one layer of a therapeutic covering as in FIG. 19A;

FIG. 19B3 shows epithelial growth under the therapeutic covering as in FIG. 19A;

FIG. 20E1 shows detail of the therapeutic lens as in FIG. 20A with a centrally inclined peripheral tack and removal of the centrally inclined peripheral tack;

FIG. 20E2 shows detail of the therapeutic lens as in FIG. 20A with a centrally inclined peripheral tack and removal of the centrally inclined peripheral tack;

FIGS. 20H, 20H1 and 20H2 show a method of application of a therapeutic lens as in FIGS. 20F and 20G;

FIG. 28A1 shows a tack for use with the lens as in FIG. 28A;

FIG. 28B-1 shows a protrusion comprising a tip and a barb for use with lenses as in FIGS. 28A and 28B;

FIG. 28B-2 shows a protrusion comprising a tack with a tip and a barb for use with lenses as in FIGS. 28A and 28B;

FIG. 28B-3 shows a protrusion comprising a tip and an expanded cross section for use with lenses as in FIGS. 28A and 28B;

FIG. 28B-4 shows a protrusion comprising a tip and an expanded cross section for use with a lenses as in FIGS. 28A and 28B;

FIG. 28M-1 shows a channel extending normal to the lower surface of a lens as in FIG. 28M;

FIG. 28M-2 shows inclined channel in a lens as in FIG. 28M;

FIG. 29A-1 shows a thin covering at least one of sealed or adhered onto the cornea with physiologic pressure from endothelial pumping;

FIG. 29A-2 shows a thin covering as in FIG. 29A-1 sized to extend beyond an epithelial debridement area;

FIG. 29A-3 shows a thin covering as in FIG. 29A-2 size to fit an epithelial debridement area;

FIGS. 29A-4 and 29A-5 show a thin covering comprising a hydrophobic portion to decrease water flow and a hydrophilic portion to contact ablated stroma;

FIG. 29A-5 shows a thin covering as in FIG. 29A-4 comprising an upper hydrophobic portion and a lower hydrophilic portion;

FIG. 29B-1 shows a silicone flap covering comprising peripheral portion and a central portion;

FIG. 29B-2 shows a flap covering as in FIG. 29B-1 contacting a stromal tissue surface;

FIG. 29C shows a curved covering comprising a curved central portion adapted to conform to the cornea and a curved peripheral portion to seal against the cornea and placement of the covering on the cornea;

Figure 28A:
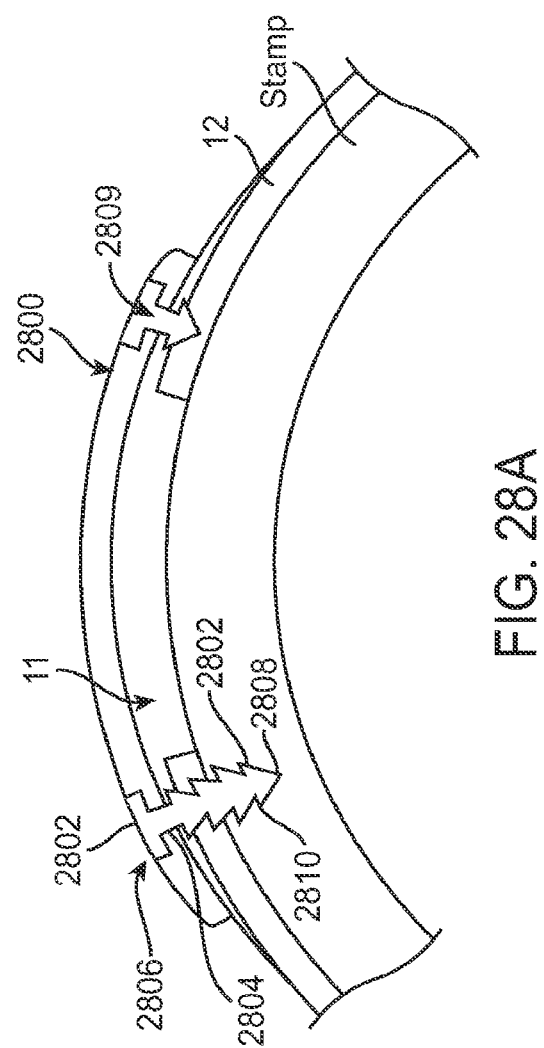
FIG. 28A shows a lens adhered to the cornea with protrusions comprising peripheral tacks, according to embodiments of the present invention.
Figure 28B:
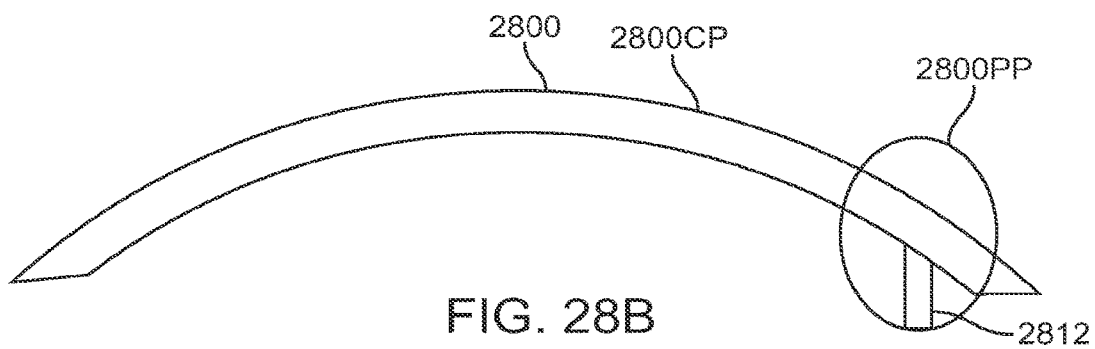
FIG. 28B shows a lens with protrusions to adhere the lens to the cornea, according to embodiments of the present invention.
Figures 1, 28B:
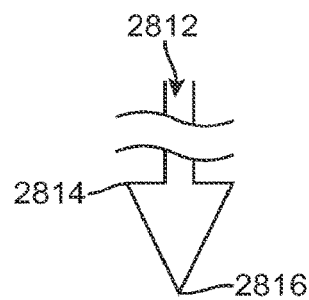
Figures 2, 28B:
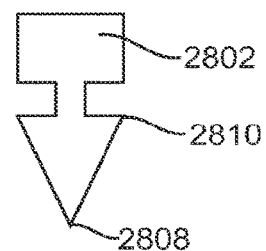
Figures 3, 28B:
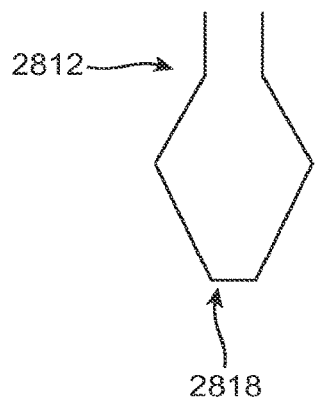
Figures 4, 28B:
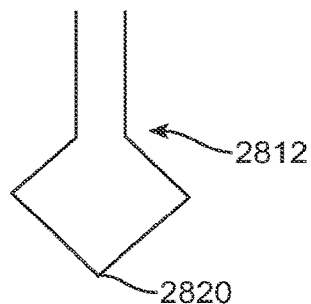
Figure 29A:
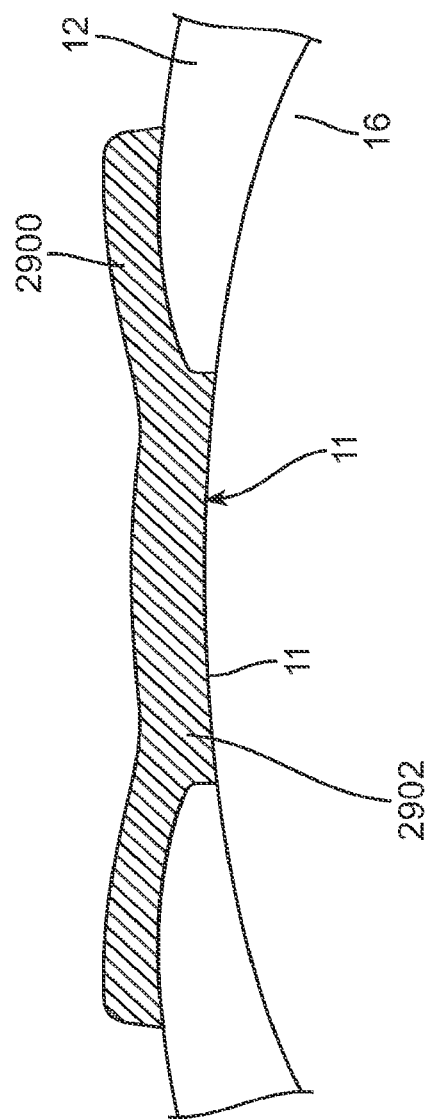
FIG. 29A shows a covering sucked down onto the cornea with pumping action from endothelial cells.
Figures 1, 29A:
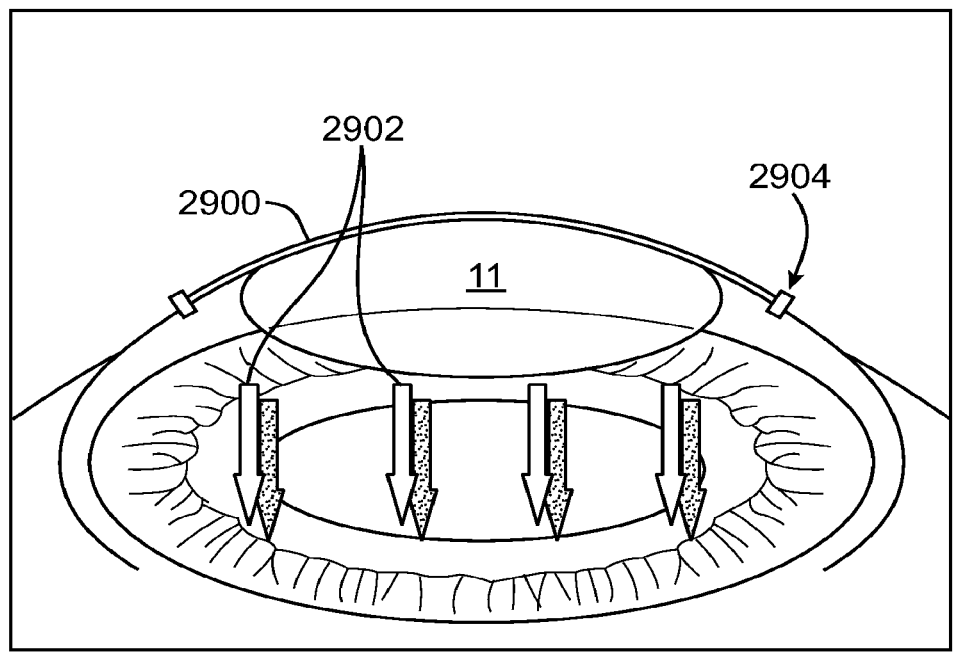
Figures 3, 29A:
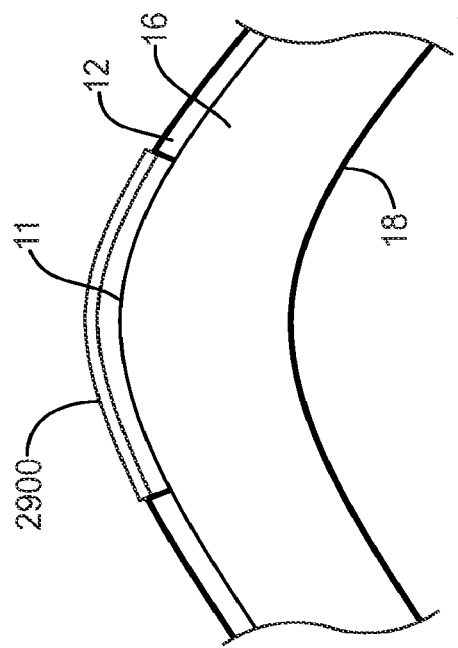
Figures 2, 29A:
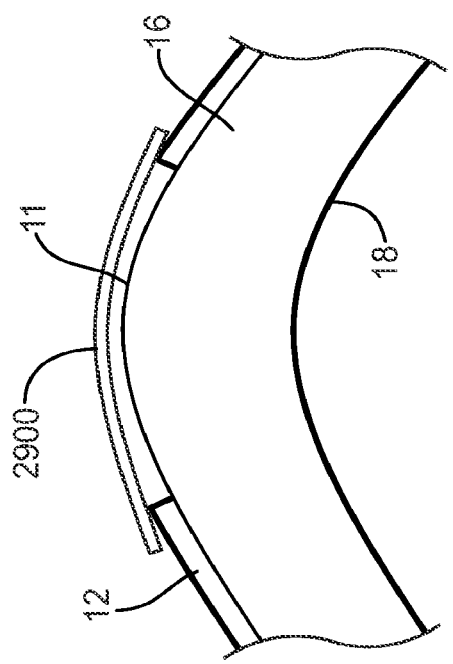
Figures 1, 29B:
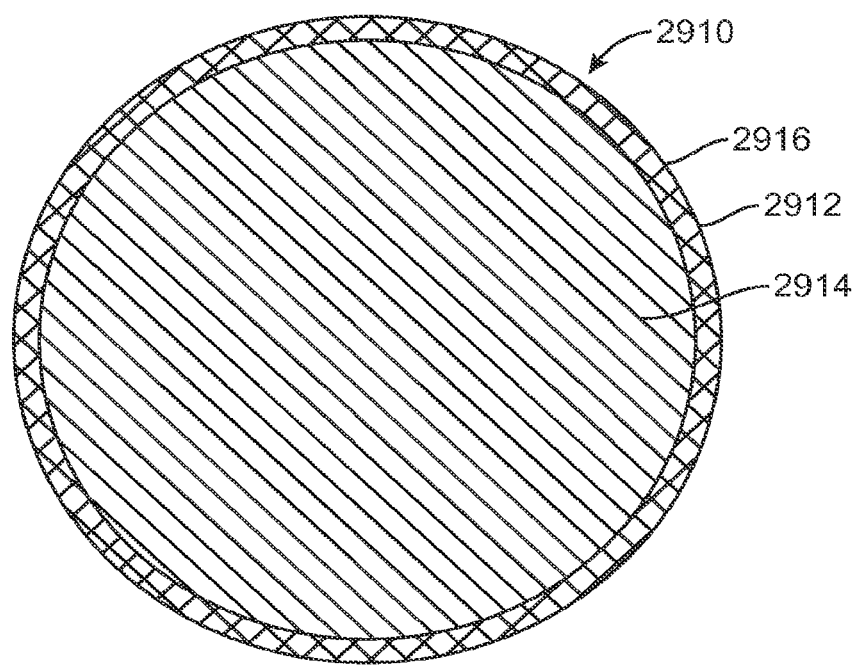
Figures 2, 29B:
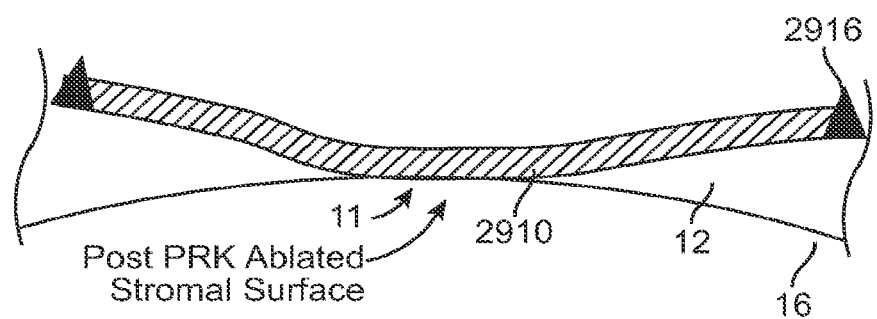
Figure 29C:
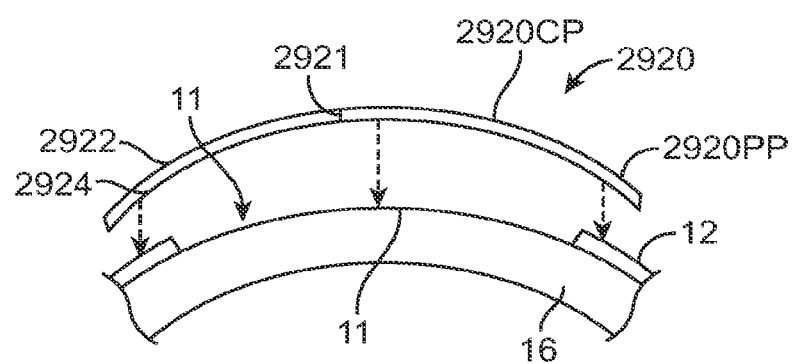
Figure 29I:
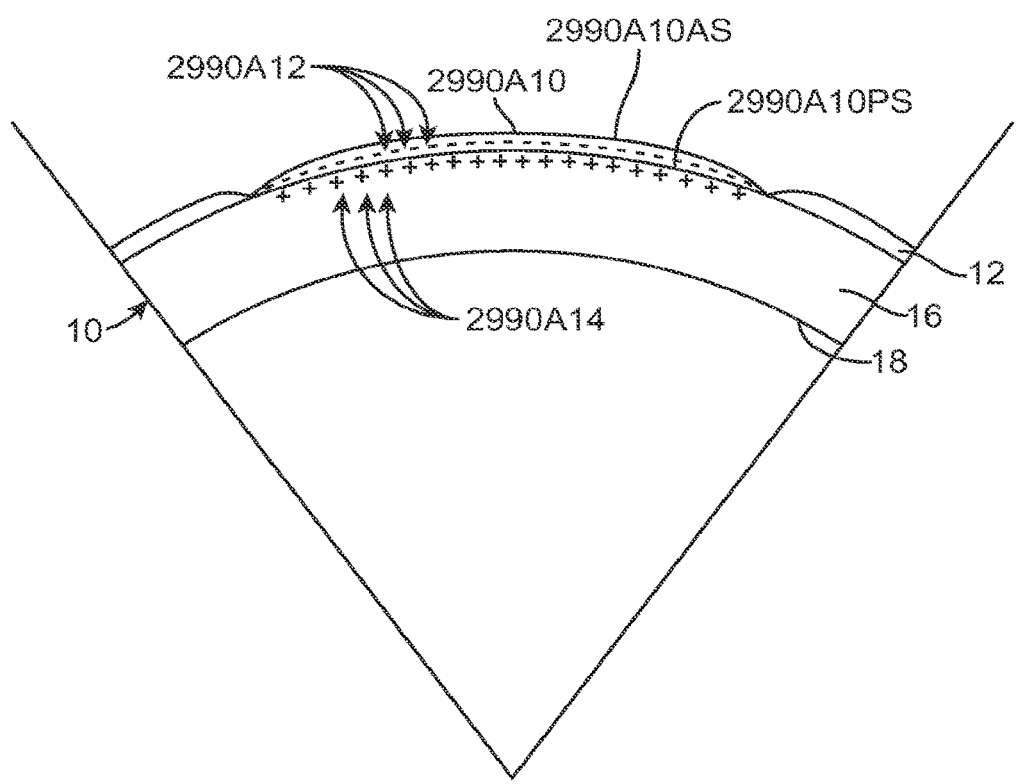

FIGS. 29C1 to 29C4 show a method covering an ablated cornea with a covering, according to embodiments of the present invention;

FIG. 29C5 shows a covering for use with the method as in FIGS. 29C1-29C4 with the covering sized to extend beyond the debrided area, according to embodiments of the present invention;

FIG. 29C6 shows in situ ablation of a covering to correct vision of a patient after ablation of the stroma to correct vision, according to embodiments of the present invention;

FIG. 29C7 shows ablation of a covering prior to placement on the cornea;

FIG. 29C8-1 shows a curved covering adapted to conform to the cornea and placement of the covering on a debrided and ablated cornea;

FIG. 29C8-2 shows the covering of FIG. 29C8-1 conforming to the ablated surface contour;

FIG. 29C8-3 shows the covering of FIG. 29C8-1 conforming to wavefront aberrations ablated into a corneal surface to correct aberrations of the eye;

FIG. 29D shows an erodible covering, according to embodiments of the present invention;

FIG. 29E1 shows a covering with a hydrophobic layer and a hydrophilic layer, according to embodiments of the present invention;

FIG. 29E2 shows a covering with a hydrophobic upper layer and a hydrophilic lower layer with the lower layer thicker than the hydrophobic layer, according to embodiments of the present invention;

FIG. 29E3 shows a covering with a hydrophobic upper layer and a hydrophilic lower layer with the upper layer thicker than the hydrophobic layer, according to embodiments of the present invention;

FIG. 29E4 shows a covering with a hydrophobic upper mono layer opposite a hydrophilic lower mono layer, according to embodiments of the present invention;

FIG. 29E5 shows a covering with a hydrophilic upper layer, hydrophobic inner layer and a hydrophilic lower layer, according to embodiments of the present invention;

FIGS. 29F1 and 29F2 show a covering with inner channels to pass tear liquid front an outer opening to an inner portion, according to embodiments of the present invention;

FIG. 29F3 shows a covering with lower surface channels to pass tear liquid from an outer opening to an inner portion, according to embodiments of the present invention;

FIG. 29G shows a covering comprising an inner portion and a peripheral portion, in which with holes extend from an upper surface to a lower surface to pass liquid to remove the covering, according to embodiments of the present invention;

FIG. 29H shows a covering with a rough lower surface and a smooth upper surface, according to embodiments of the present invention;

FIG. 29H1 shows a covering with interlocking structures, according to embodiments of the present invention;

FIG. 29H2 shows a covering with nano structures, according to embodiments of the present invention;

FIG. 29H3 shows an amniotic membrane suitable for incorporation with a therapeutic covering, according to embodiments of the present invention;

FIG. 29I shows a covering with charge to retain the covering on the cornea;

FIG. 29J1 shows a covering comprising a plurality of zones configured to release a drug for each of one, two and three days, according to embodiments of the present invention;

FIG. 29J2 shows the covering of FIG. 29J1 on a cornea two days after ablation.

Figure 1A:
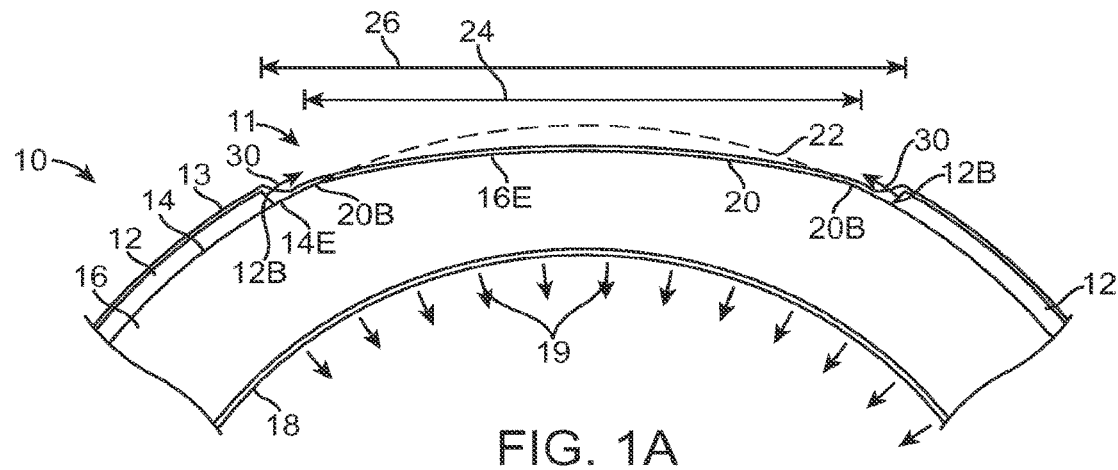
FIG. 1A shows an eye with an epithelial defect following refractive surgery, according to embodiments of the present invention.
Figure 1B:
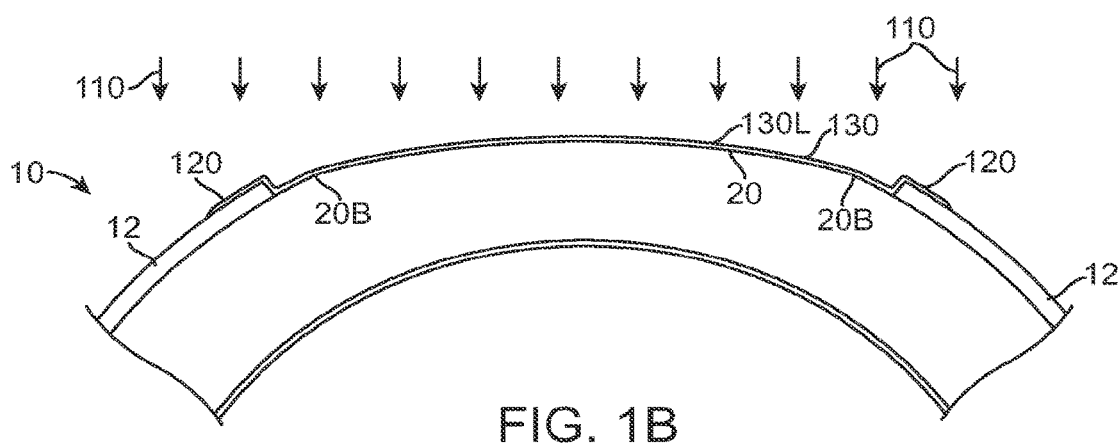
FIG. 1B shows application of a therapeutic filler material to an eye, according to embodiments of the present invention.
Figure 1C:
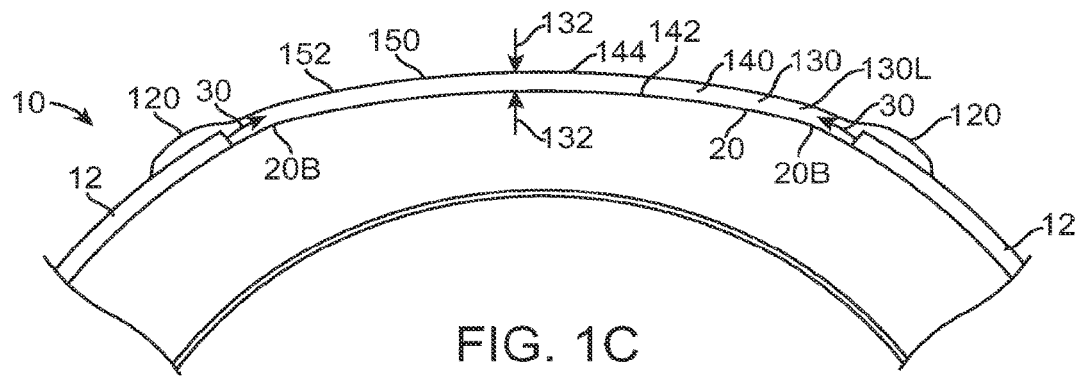
FIG. 1C shows a therapeutic lens comprising the cured filler material as in FIG. 1B.
Figure 29L:
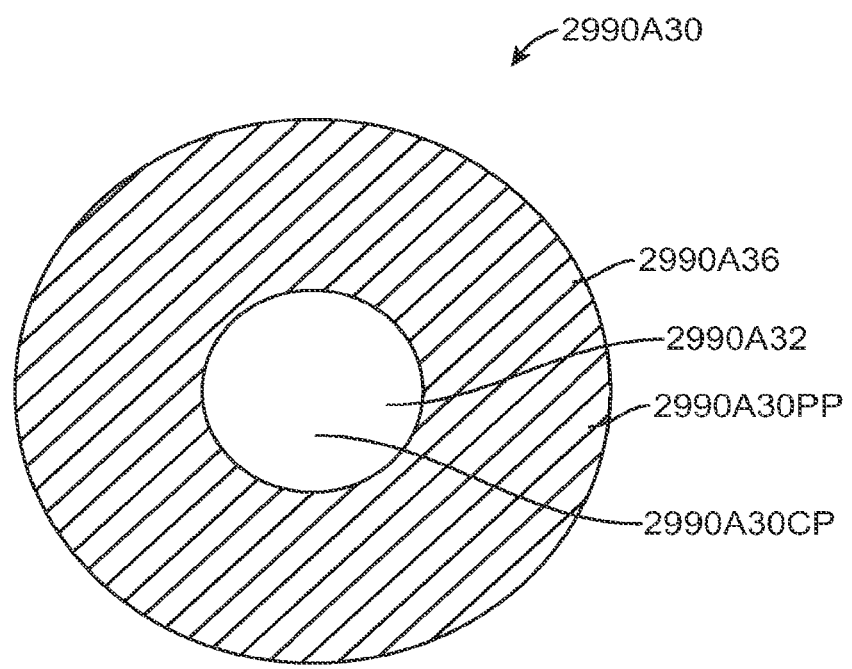

FIG. 29K1 shows a covering configured for a tight fit with a cornea, according to embodiments of the present invention;

FIG. 29K2 shows the covering of FIG. 29K1 placed on the cornea with the tight fit such that the covering conforms to the ablated stroma;

FIG. 29L shows a covering with a light transmitting central portion and a non-light transmitting peripheral portion, according to embodiments of the present invention;

FIG. 29M1A shows a covering comprising structures to inhibit or minimize motion of the covering on the cornea and a bandage lens positioned over the covering, according to embodiments of the present invention;

FIG. 29M1B shows a cross sectional view of the covering and bandage lens of FIG. 29M1A placed on a cornea;

FIG. 29M1C shows an isometric view of the covering comprising structures and bandage lens of FIG. 29M1A;

FIG. 29M1D shows a covering comprising aperture structures to inhibit or minimize motion of the covering on the cornea, in which the aperture structures are positioned away from the epithelial defect when the covering is placed on the cornea following PRK;

FIG. 29M1E shows covering comprising protruding aperture structures to inhibit or minimize motion of the covering on the cornea, in which the aperture structures are positioned away from the epithelial defect when the covering is placed on the cornea following PRK;

FIG. 29M1F shows a plan view of the covering of FIGS. 29M1A to 29M1C.

Figure 29N:
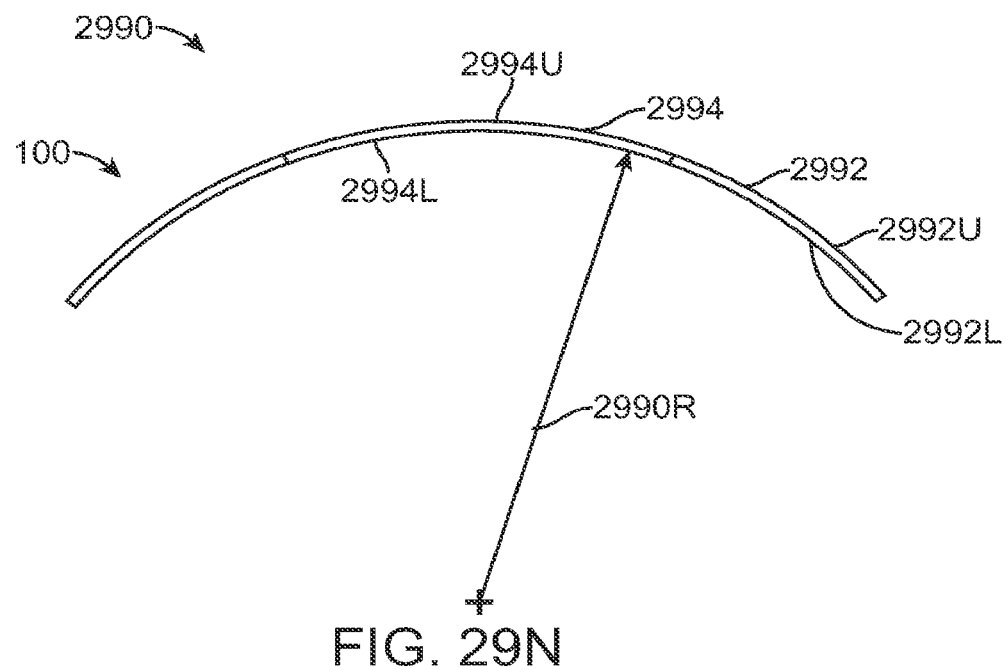
Figures 1, 29N:
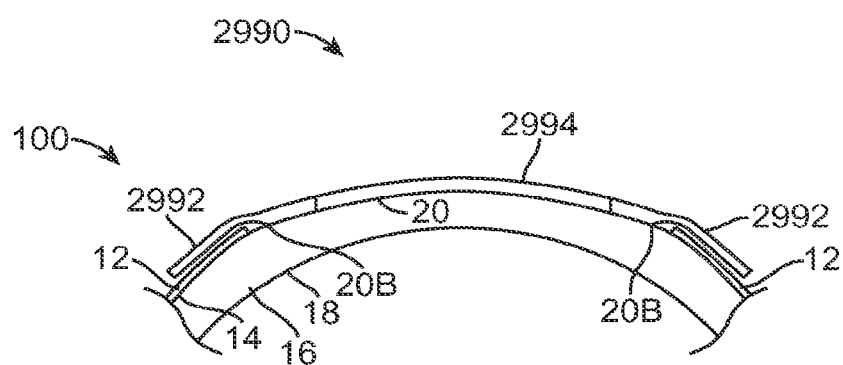
Figures 2, 29N:
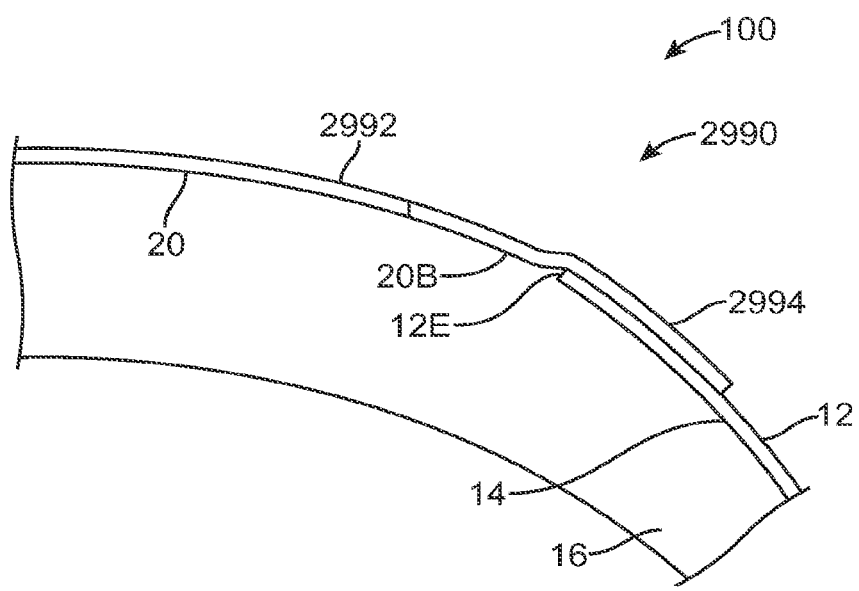
Figures 3, 29N:
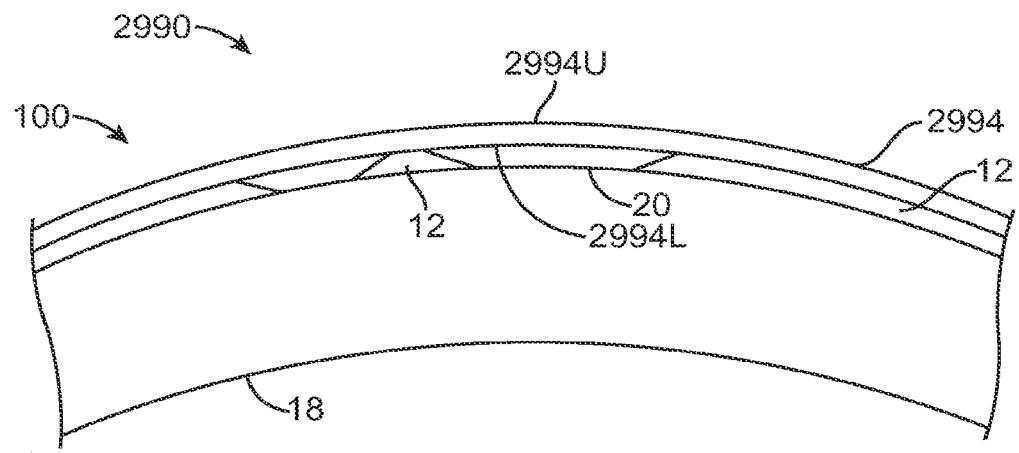
Figure 29O:
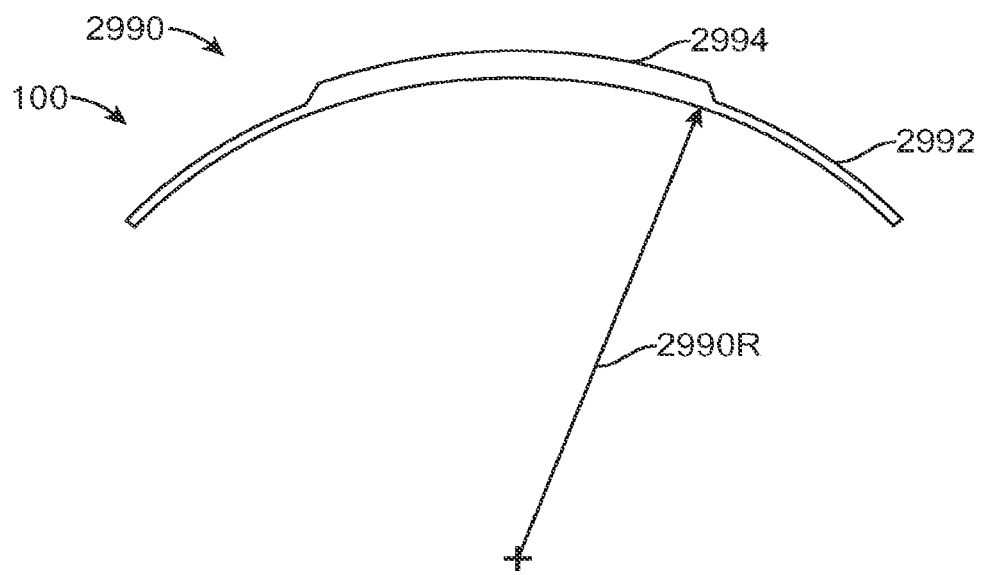
Figure 29P:
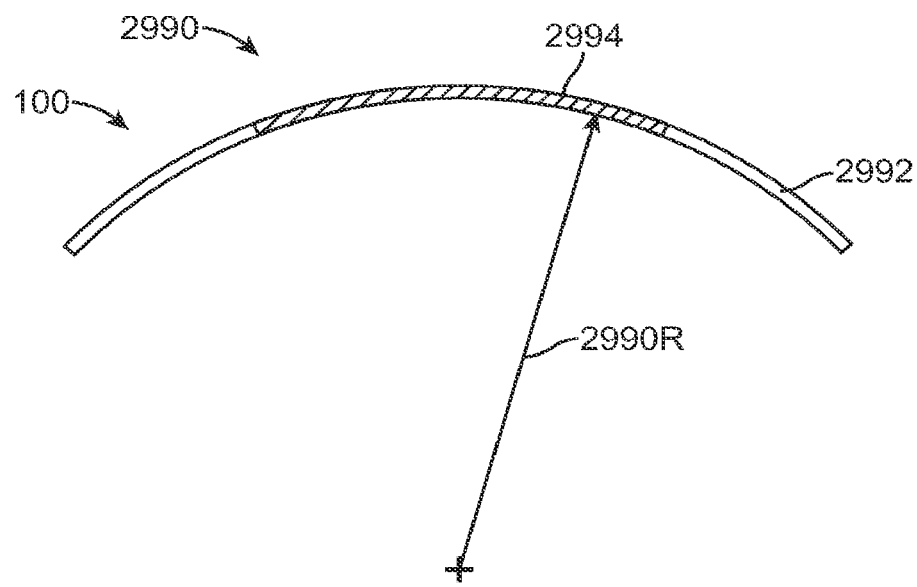
Figure 29Q:
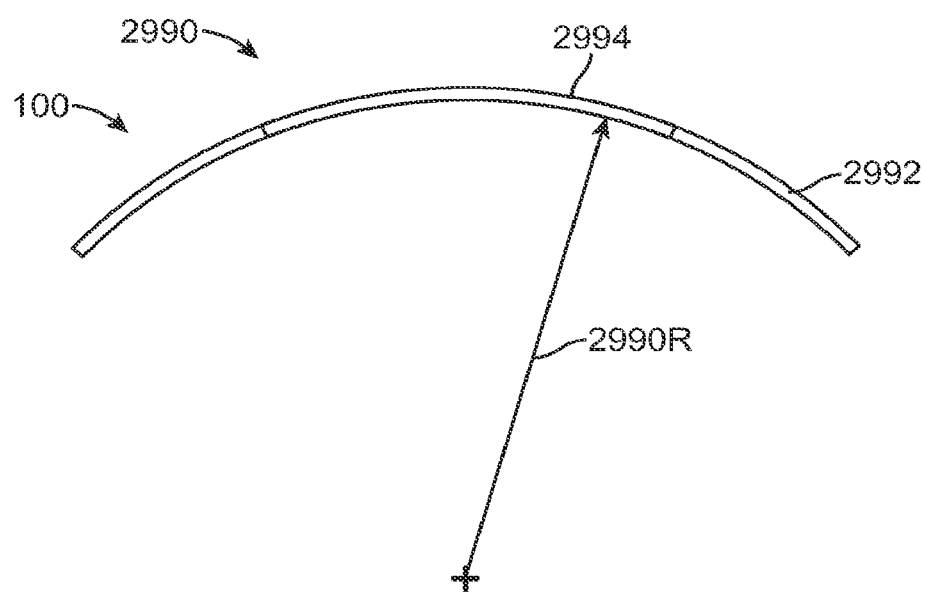
Figure 29R:
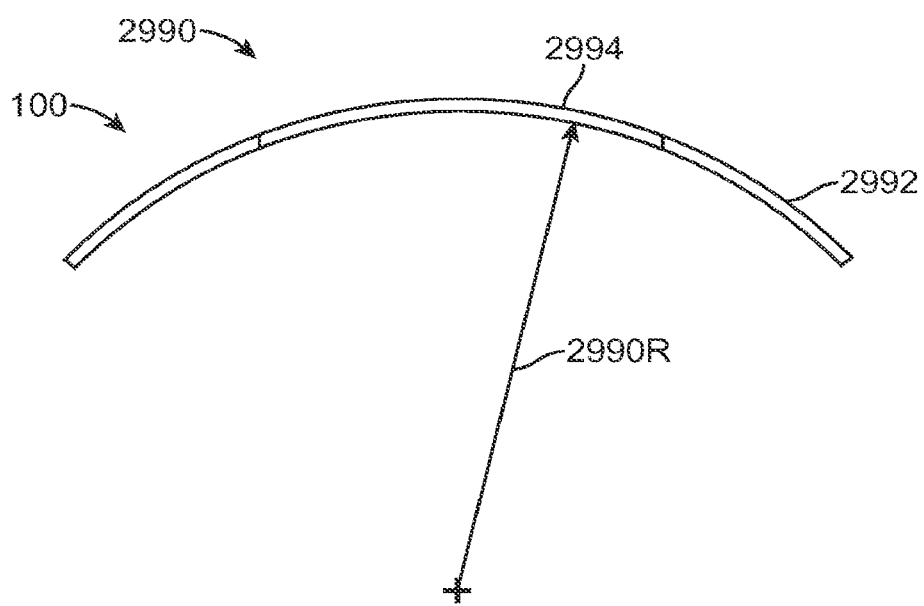
Figure 30A:
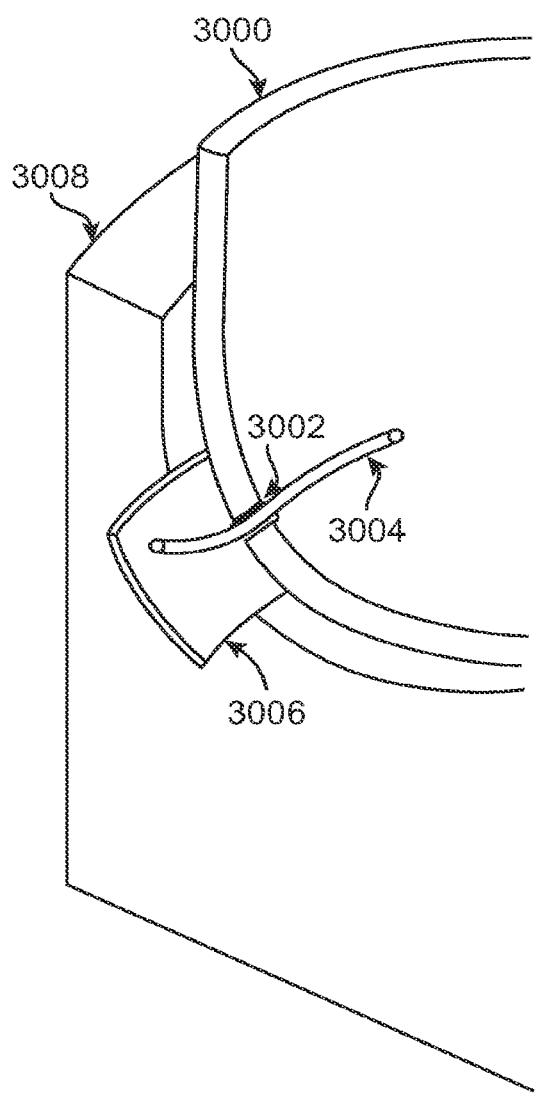
Figure 30B:
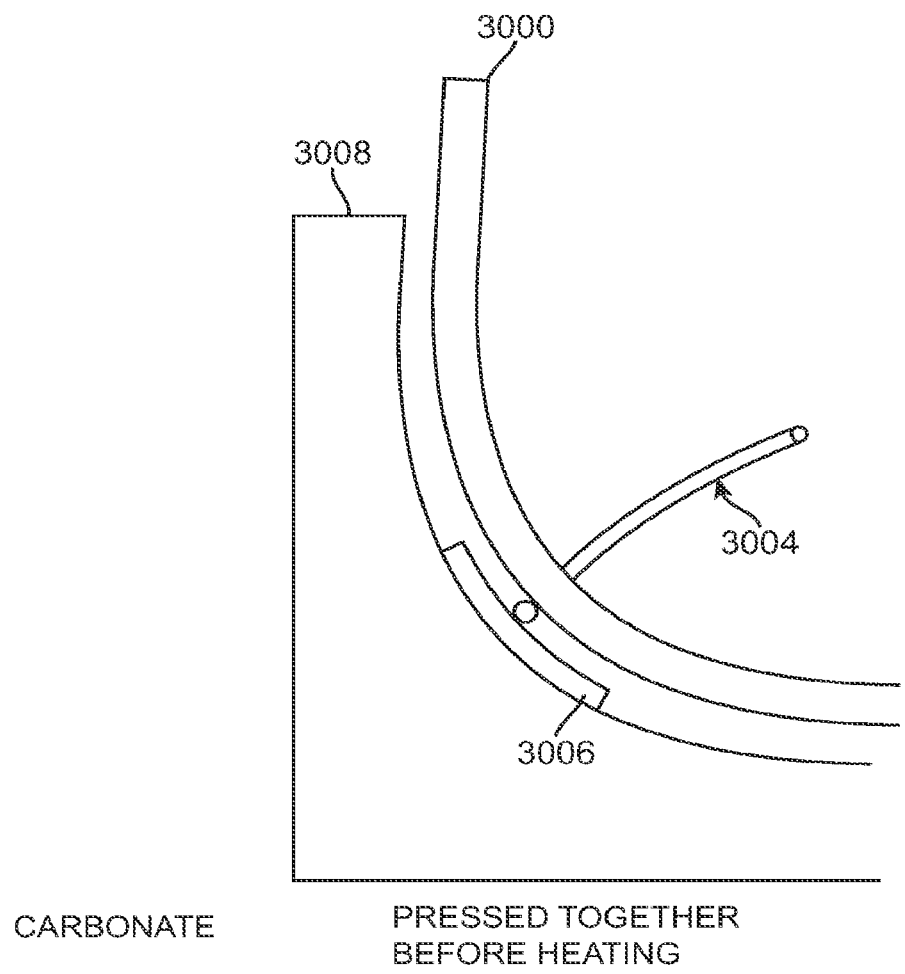
Figure 30C:
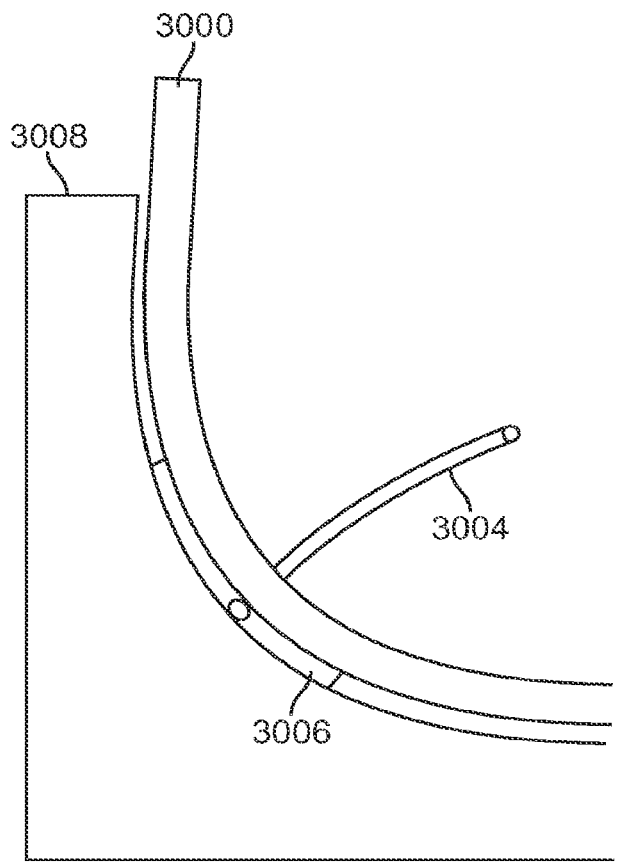
Figure 30D:
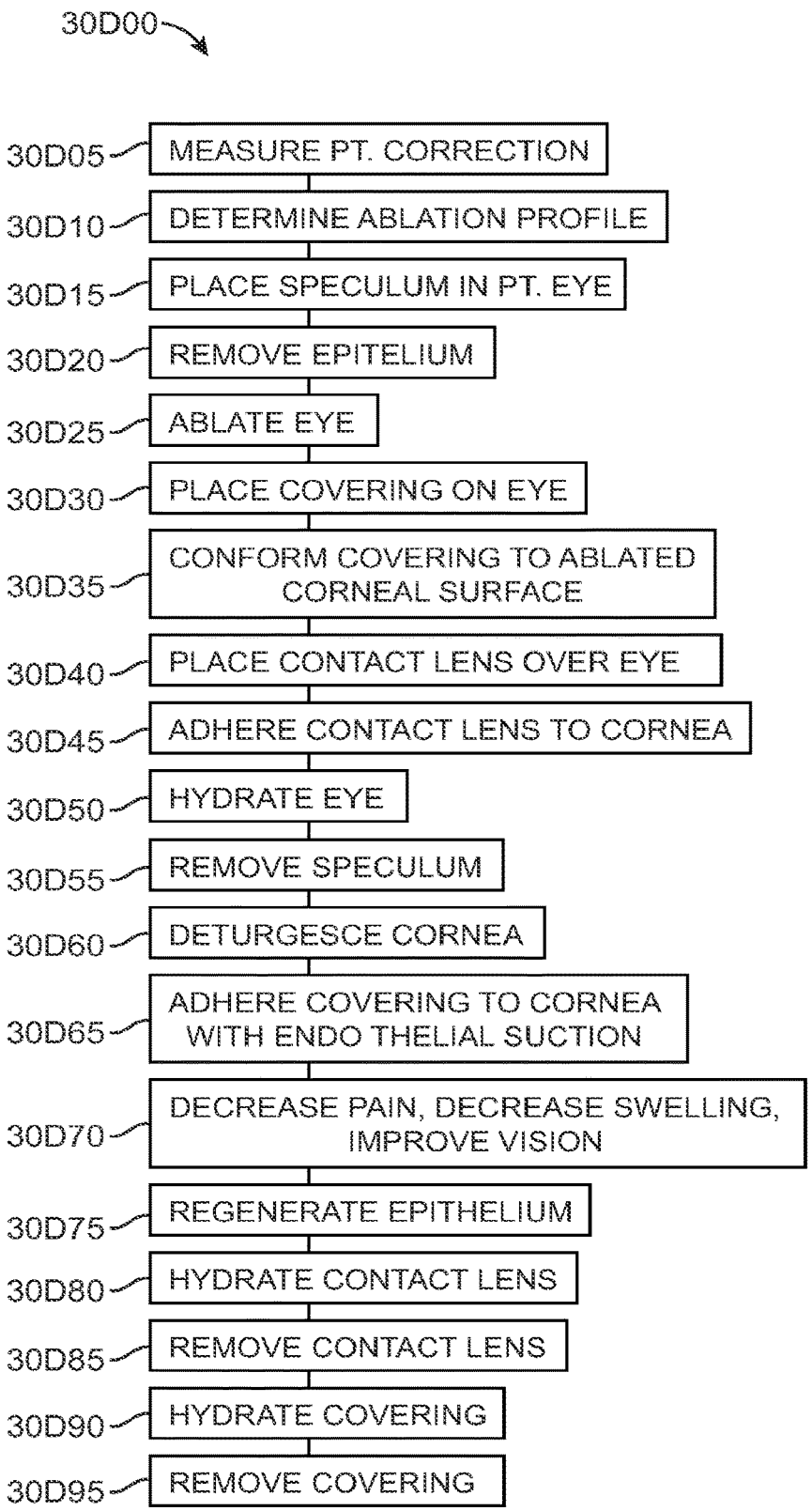
Figure 31B:
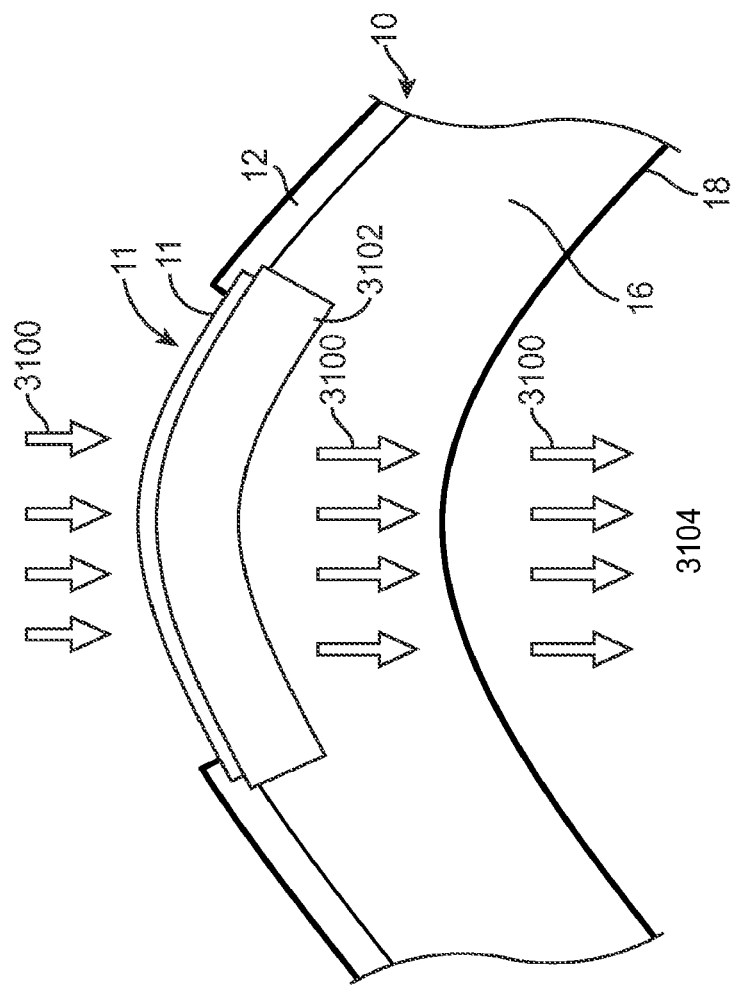
Figure 31A:
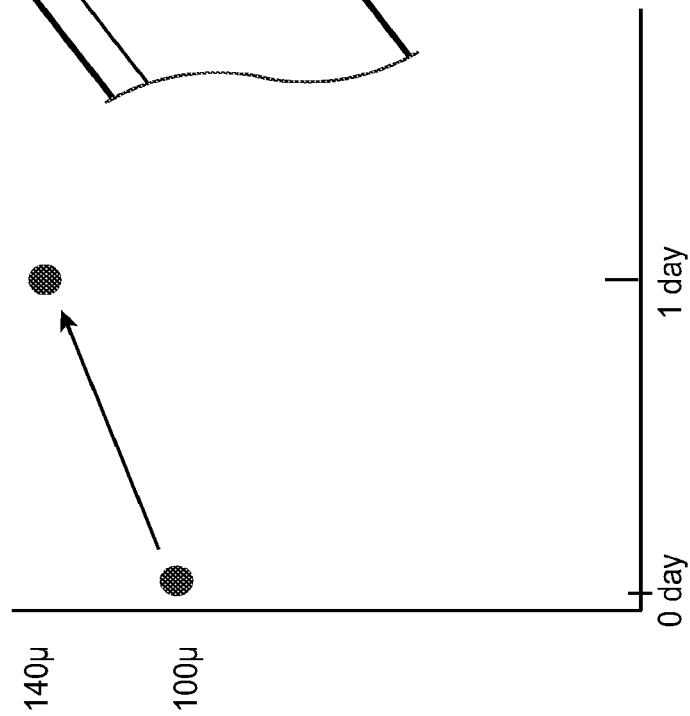
Figure 32A:
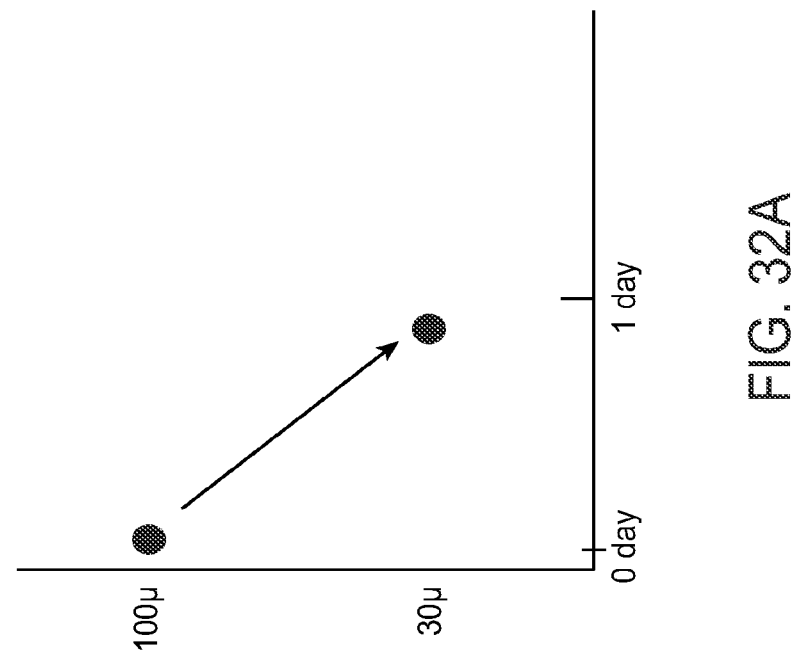
Figure 32B:
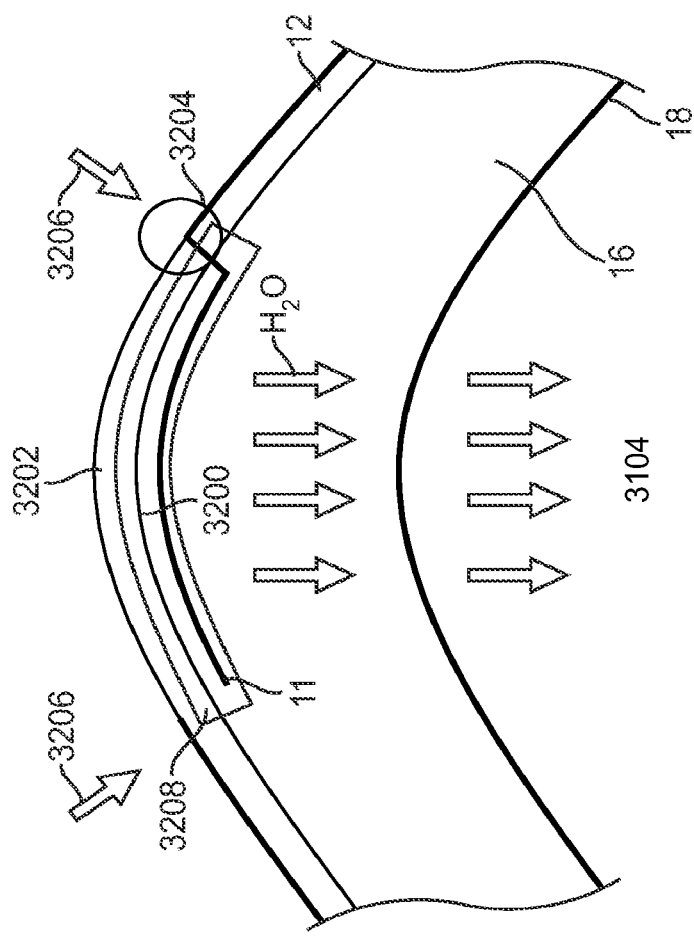
Figures 33A, 33B:
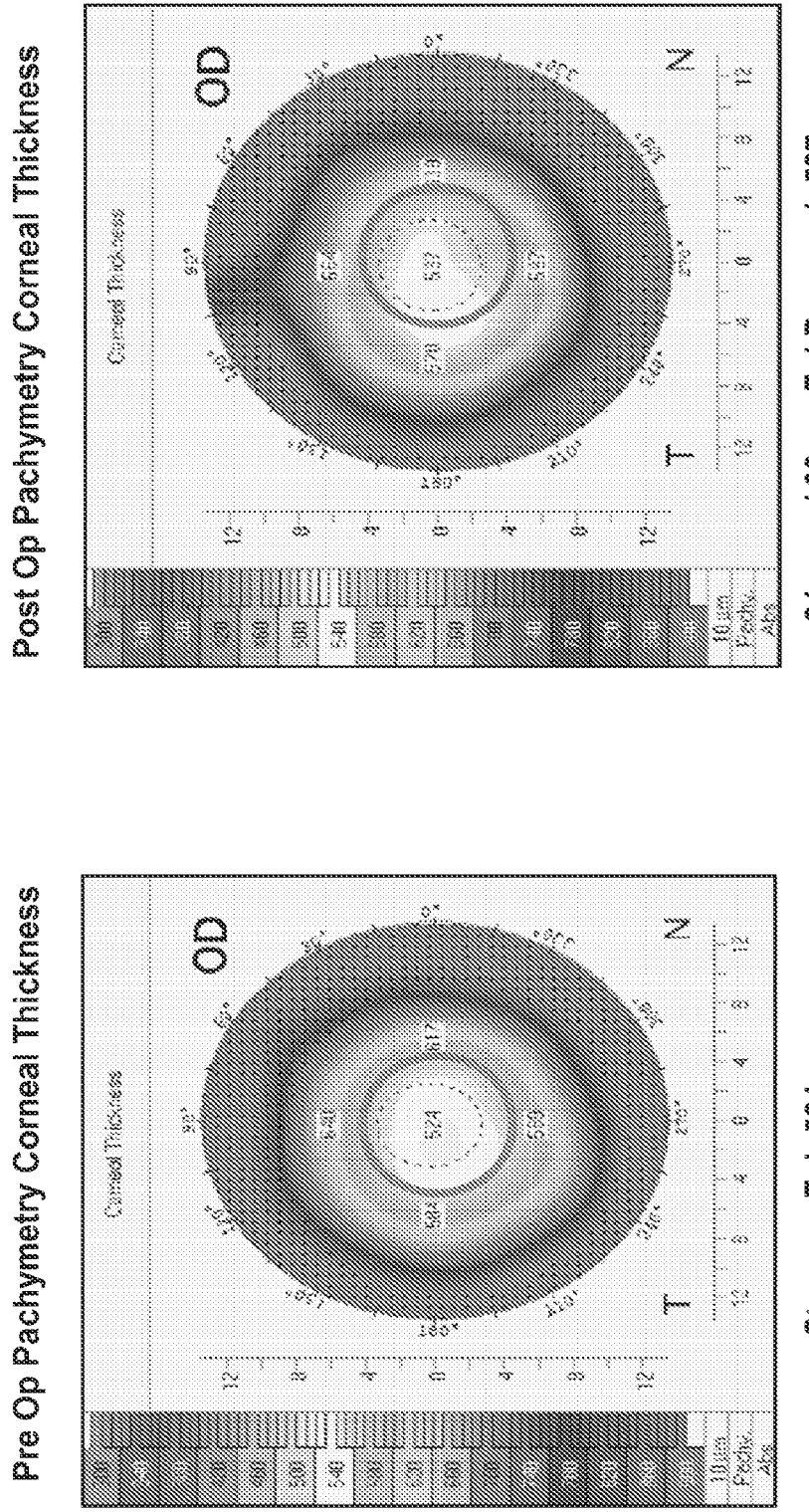
Figure 37:
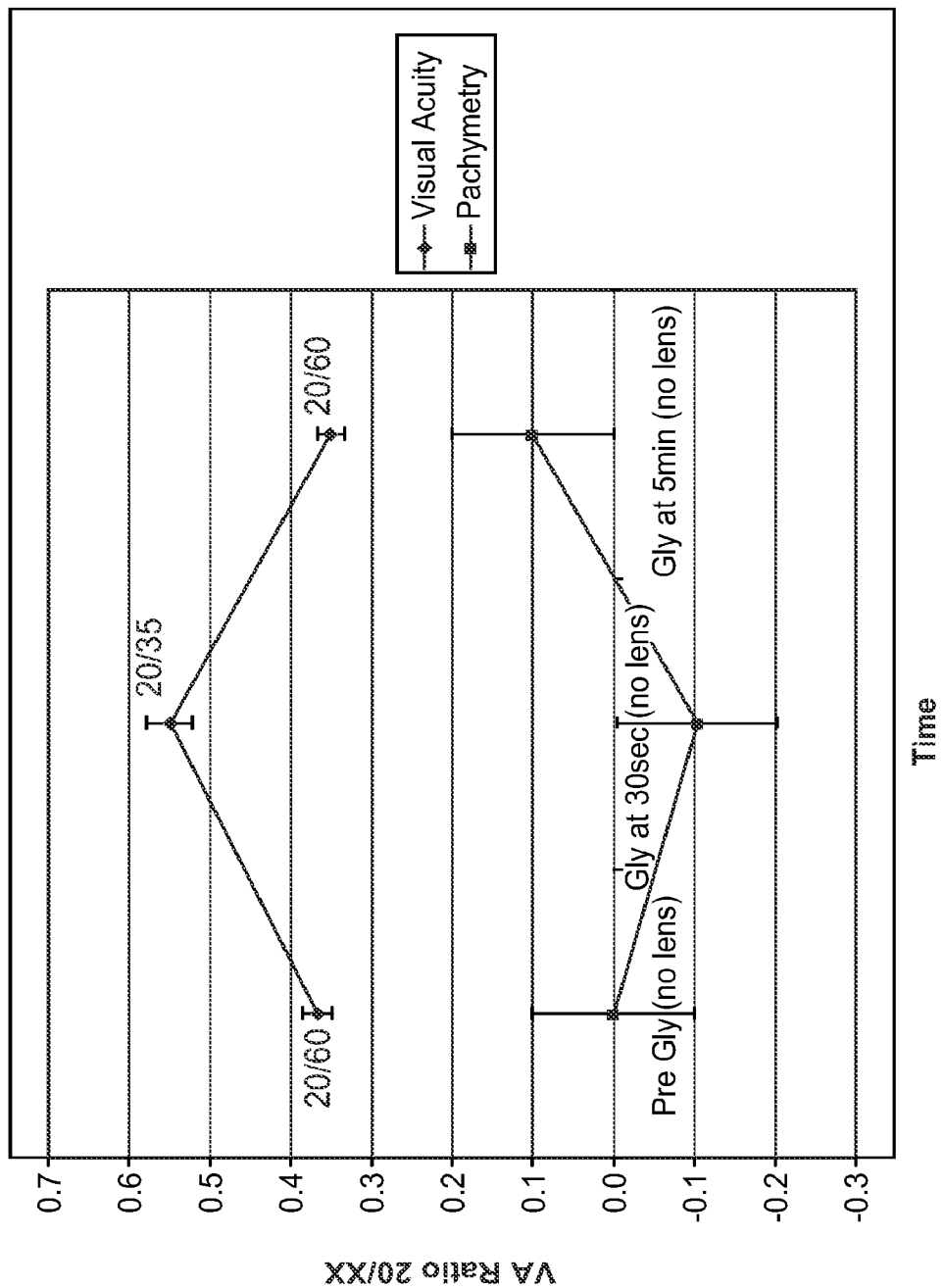
Figure 38B:
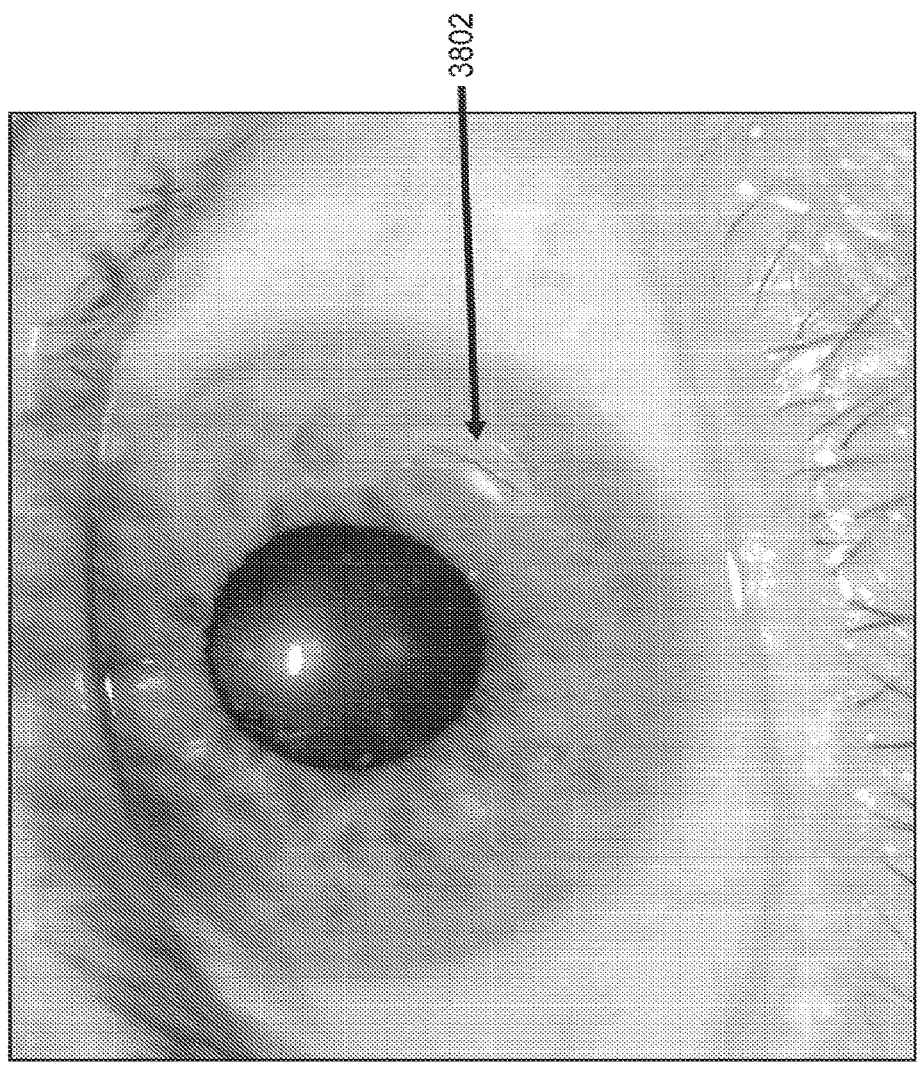
Figure 38C:
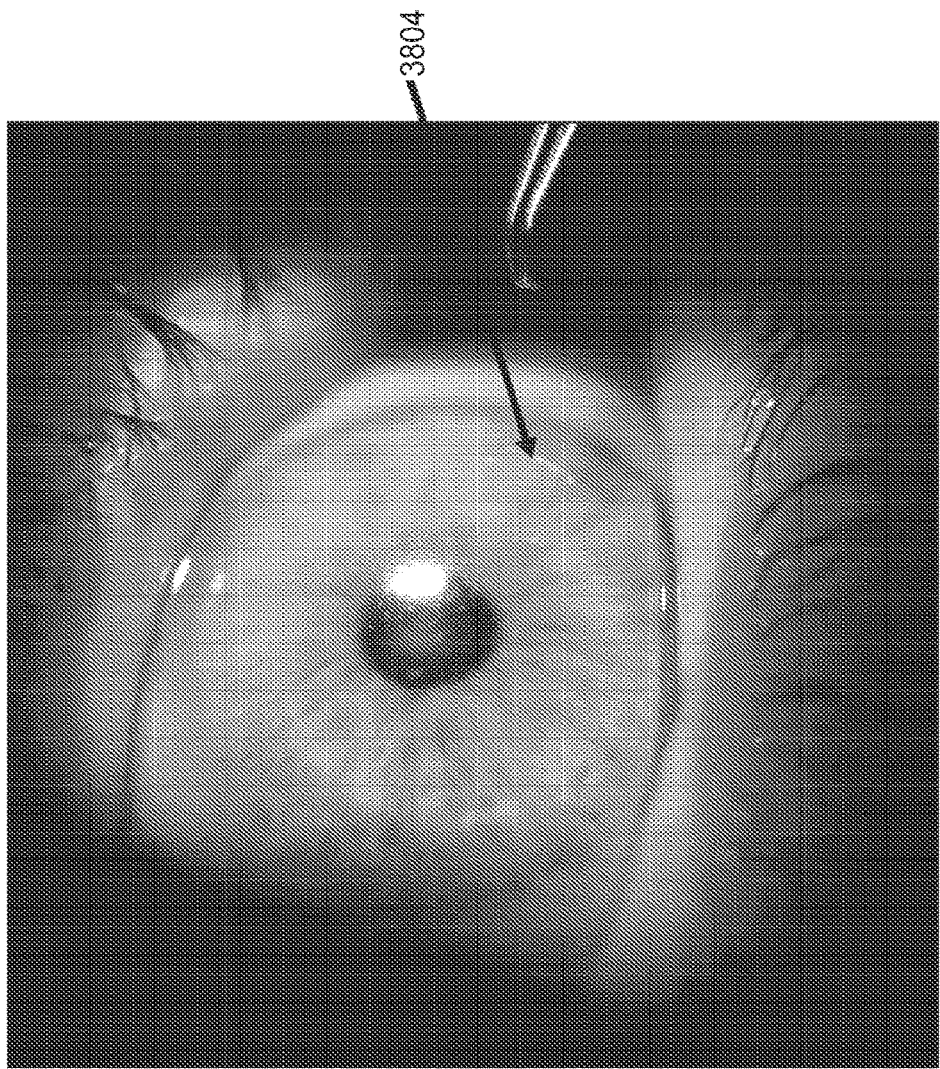
Figure 38D:
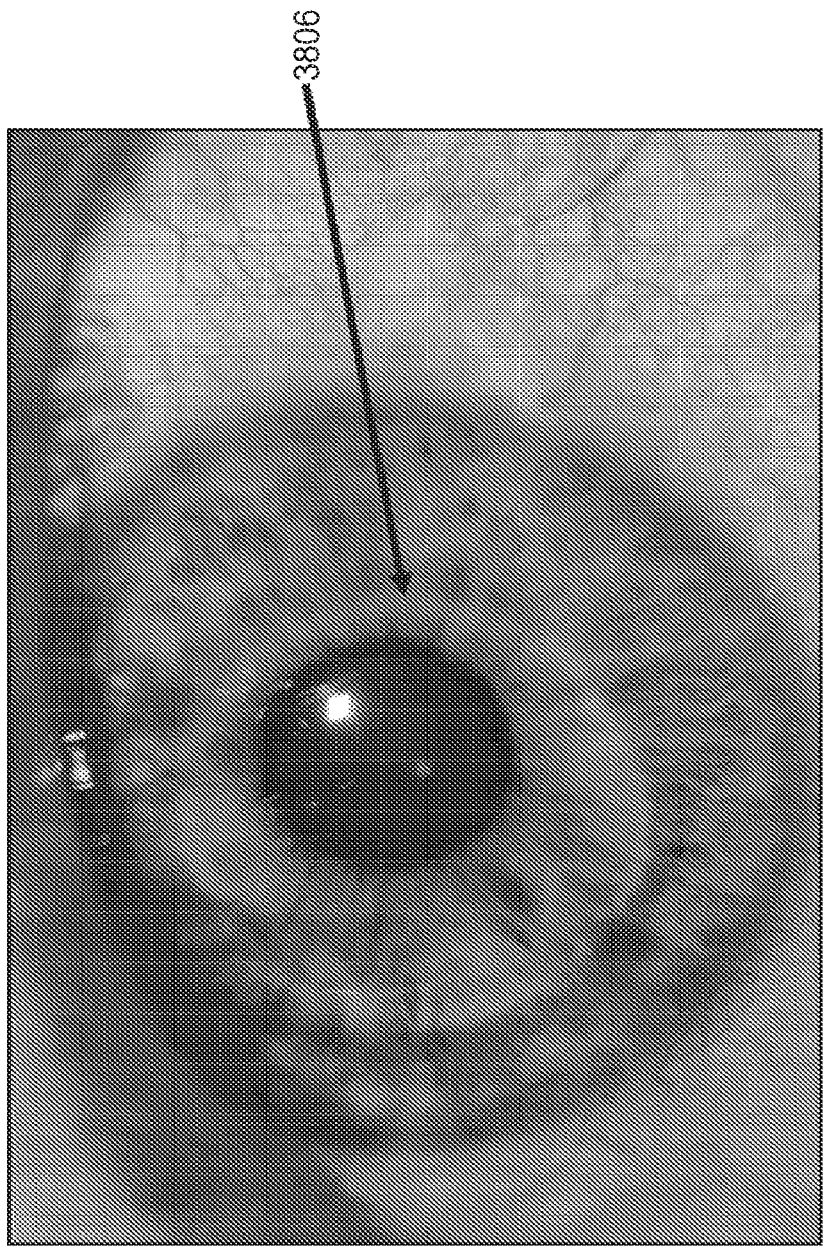
Figures 1, 2, 38E:
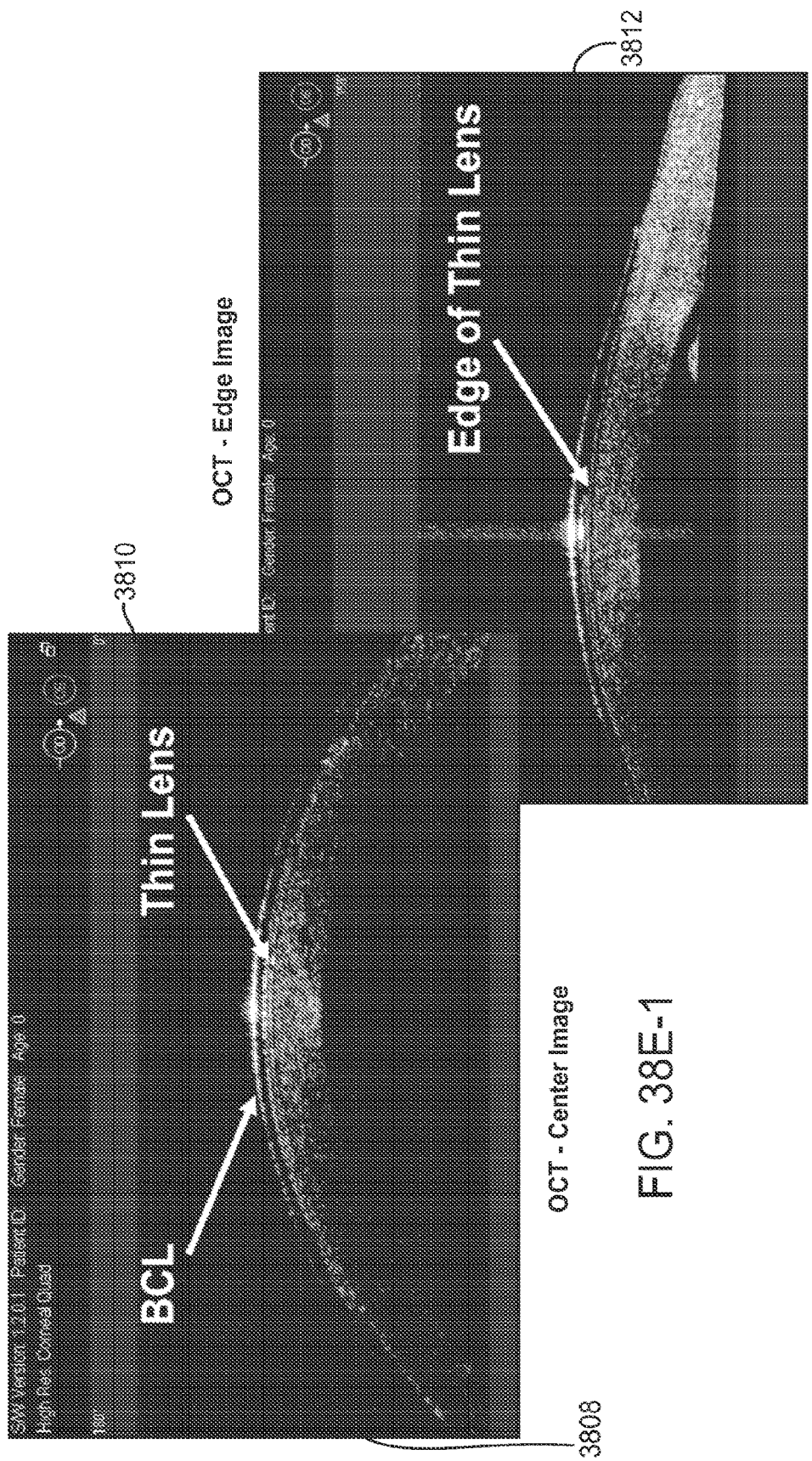
Figure 40:
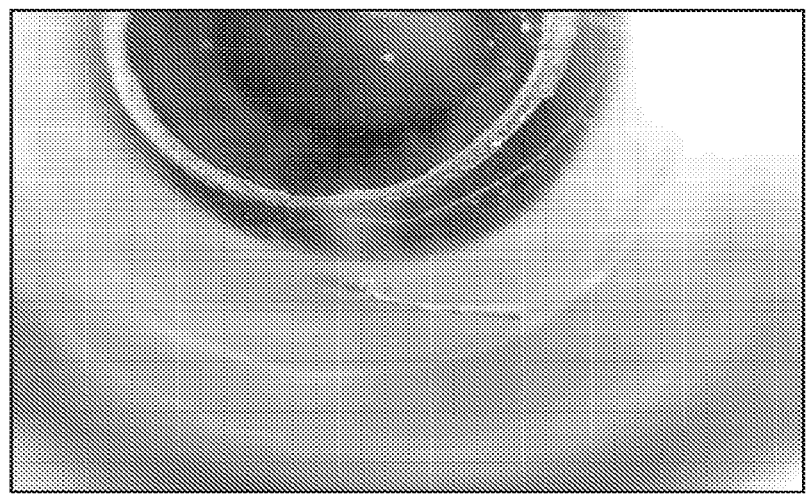
Figure 41A:
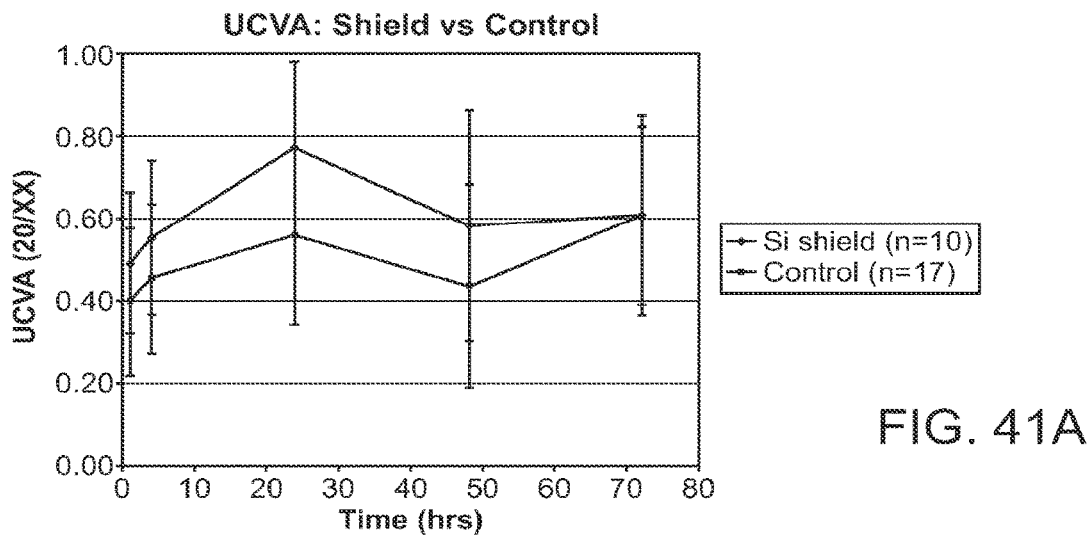
Figure 41B:
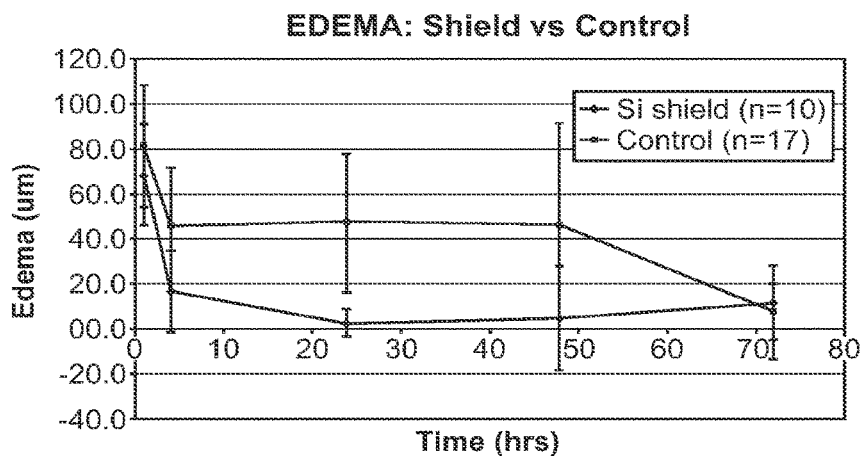
Figure 41C:
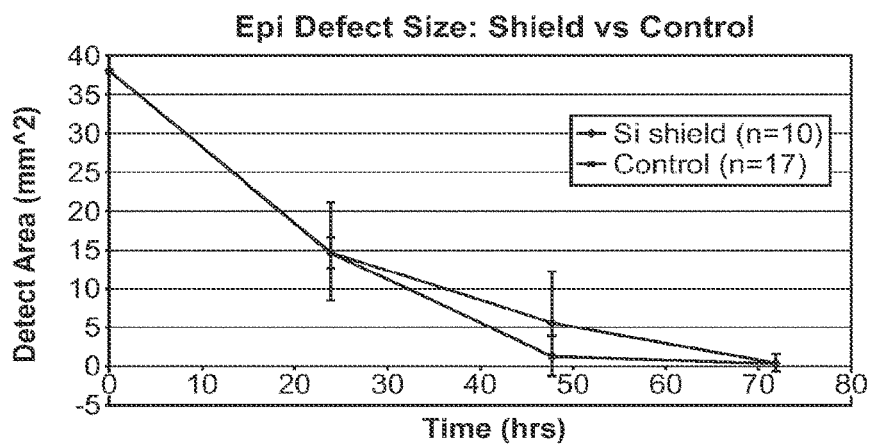
Figure 42:
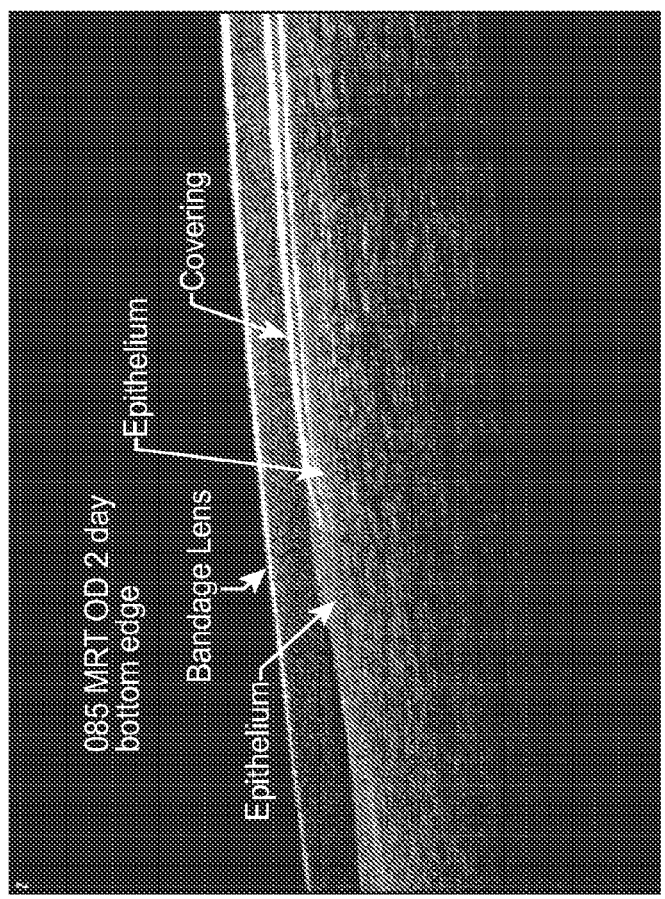

FIG. 29M1G shows a covering comprising aperture structures to inhibit or minimize motion of the covering on the cornea, in which the aperture structures are positioned away from the epithelial defect when the covering is placed on the cornea following PRK;

FIG. 29M1H shows covering comprising protruding radially elongate structures to inhibit or minimize motion of the covering on the cornea, in which the protruding radially elongate structures are positioned away from the epithelial defect when the covering is placed on the cornea following PRK;

FIG. 29N shows a therapeutic covering comprising an outer portion configured to conform to the cornea so as to seal the covering over the cornea and an non-conforming inner portion configured to retain an optical shape and smooth the cornea for vision, according to embodiments;

FIG. 29N-1 shows the therapeutic covering as in FIG. 29N adhered to a cornea after PRK with endothelial suction:

FIG. 29N-2 shows the outer portion therapeutic covering as in FIGS. 29N and 29N-1 conforming to the cornea over the undebrided epithelium and over the edge of the ablation;

FIG. 29N-3 shows the inner portion of the therapeutic covering as in FIGS. 29N and 29N-1 with an optical surface disposed over regenerating corneal epithelium;

FIG. 29O shows a therapeutic covering as in FIG. 29N comprising a covering molded with a homogeneous material, in which the outer portion comprises a thickness configured to conform with the cornea and in which the inner portion comprises thickness configured to retain the optical shape;

FIG. 29P shows a therapeutic covering as in FIG. 29N comprising a covering molded with a first outer material and a second inner material, in which the outer portion comprises a first hardness configured to conform with the cornea and in which the inner portion comprises second hardness configured to retain the optical shape;

FIG. 29Q shows a therapeutic covering as in FIG. 29N comprising a first outer portion composed of a first material affixed to a second inner portion composed of a second material, in which the outer portion comprises a first hardness configured to conform with the cornea and in which the inner portion comprises second hardness configured to retain the optical shape;

FIG. 29R shows a covering comprising an annular configuration with an inner portion comprising an optic zone composed of a hydrophobic material configured for placement over the epithelial defect, and an outer annular portion comprising a hydrophilic material configured to contact the epithelium;

FIGS. 30A to 30C show a method of forming an annular band with protrusions to attach a contact lens to the cornea, according to embodiments of the present invention;

FIG. 30D shows a method of treating a PRK patient with a therapeutic covering, according to embodiments of the present invention;

FIG. 31A shows measured corneal edema immediately following PRK surgery and one day post-op with PRK patients;

FIG. 31B shows a model for corneal swelling with PRK patients as in FIG. 31A, according to embodiments of the present invention;

FIG. 32A shows measured corneal edema immediately following LASIK surgery and one day post-op with LASIK patients;

FIG. 32B shows a model for corneal swelling with LASIK patients as in FIG. 31A, according to embodiments of the present invention;

FIGS. 33A and 33B show pre-op and post-op pachymetry measurements on patients with a Pentacam™ to determine corneal edema at one day post-op;

FIGS. 34A and 34B show pre-op and post-op pachymetry measurements on patients with a OCT to determine corneal edema at one day post-op;

FIG. 35 shows loss of visual acuity and cornea edema with PRK patients the day of surgery;

FIG. 36 shows loss of visual acuity and cornea edema with PRK patients one day after surgery;

FIG. 37 shows decrease in corneal edema and increase in visual acuity in response to glycerin applied to patient eyes to reduce swelling;

FIG. 38A-38D show clinical pictures a flat covering on a human cornea with the covering conforming to the curved cornea of the patient and a contact lens placed over the covering;

FIGS. 38E-1 and 38E-2 show OCT images of the covering of FIGS. 38A-38D with a contact lens placed over the cornea and the covering conforming to the cornea;

FIGS. 39A to 39C show optical images through casting of a U.S. Air Force resolution target and improvements in optical characteristics of the castings in response to improvements to the casting materials and process; and FIG. 40 show an annular band made with the method of FIGS. 30A to 30C placed over a contact lens to adhere the contact lens to the cornea;

FIGS. 41A, 41B and 41C shows uncorrected visual acuity, corneal edema, and epithelial defect area over time for patient for treat with a therapeutic covering as described above, and control patients receiving a therapeutic hydrogel bandage lens;

FIG. 42 shows an optical coherence tomography image of a therapeutic covering adhered to an eye so as to remodel the epithelium, in accordance with embodiments.

Figure 42A:
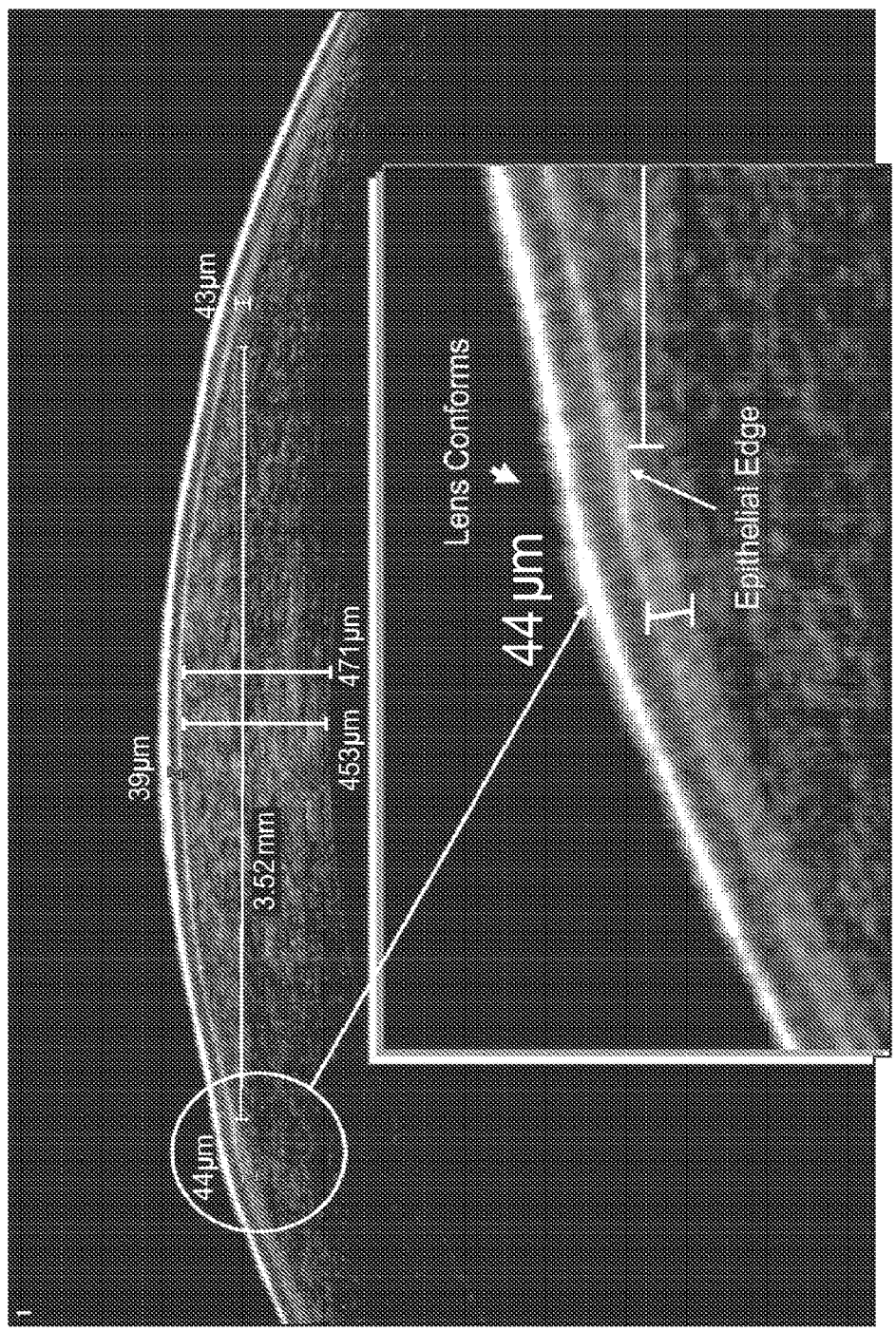
Figure 43:
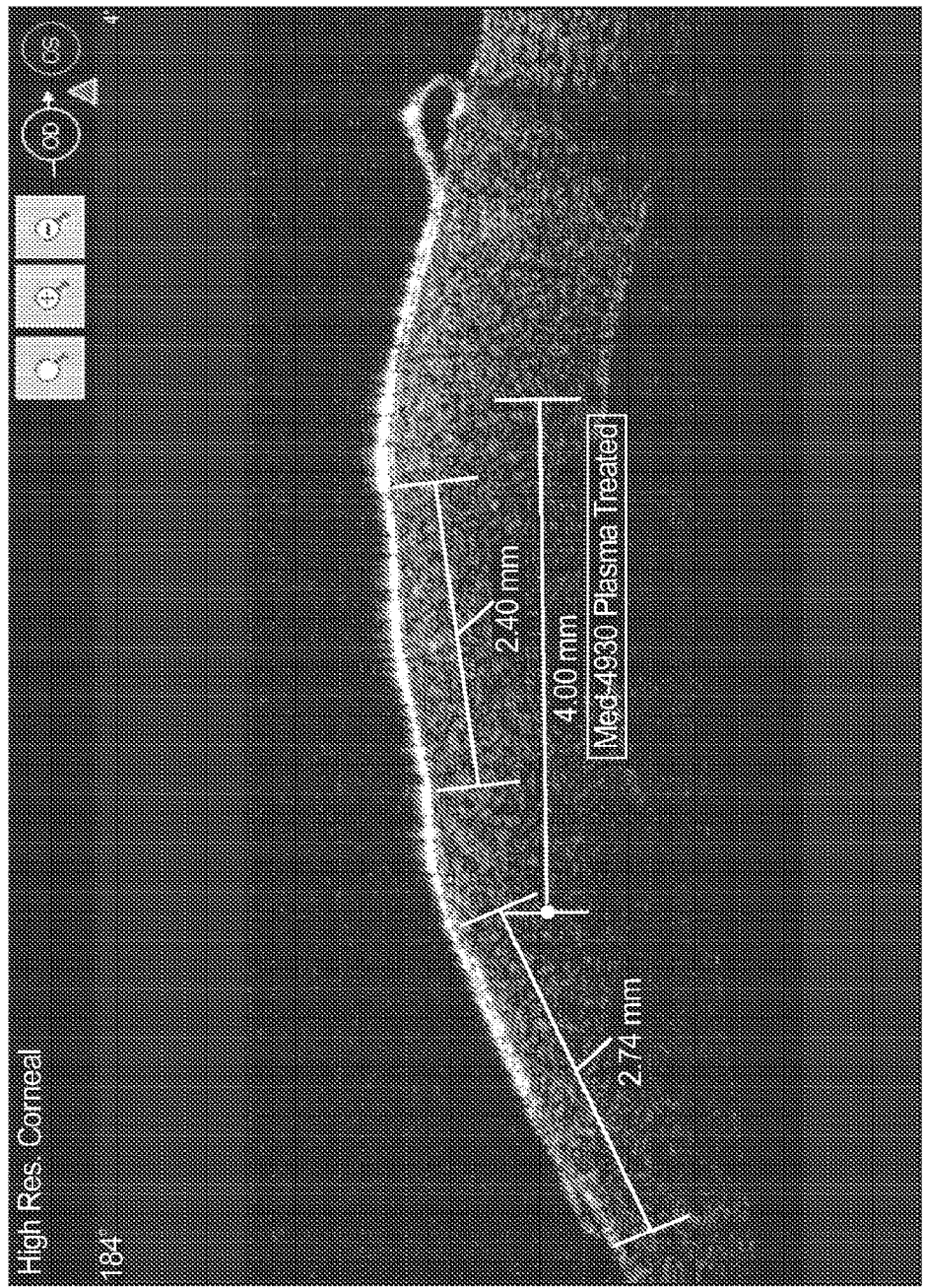

FIG. 42A shows an optical coherence tomography image of a therapeutic covering conforming to an epithelial layer of a PRK patient at 24 hours post-op, in accordance with embodiments; and FIG. 43 shows an optical coherence tomography image of a therapeutic covering conforming to a porcine eye, in accordance with embodiments.

DETAILED DESCRIPTION OF THE INVENTION

Embodiments of the present invention provide a therapeutic cover for the treatment of an epithelial defect. The cover may comprise a layer of therapeutic material positionable over the stroma and/or Bowman's membrane. A person or ordinary skill in the art may refer to Bowman's membrane as "Bowman's". The cover may minimize water flow into the stroma and/or Bowman's membrane, such that corneal deturgescence can be restored and can decrease light scattering when the epithelium regenerates. The layer of therapeutic material can cover and protect nerve fibers so as to decrease pain felt by the patient. The layer may comprise an index of refraction to inhibit or minimize light scatter from an anterior surface of the stroma and/or Bowman's membrane, for example with an index of refraction that matches the index of refraction of the anterior surface of the stroma and/or Bowman's membrane. The cover may comprise a curved anterior surface that corresponds to the anterior surface of the stroma and/or Bowman's membrane, for example with post-PRK patients, such that the curved anterior surface comprises a lens to correct vision of the patient when the epithelium regenerates. The lens on the anterior surface of the layer may correspond to the optical power of the anterior surface of the stroma and/or Bowman's to within about +/−1 Diopter. The layer of therapeutic filler material may comprise a solid, an adhesive, a gel, a low adhesion gel, and/or a liquid with therapeutic properties. The layer of therapeutic material can be positioned on the eye in many ways, for example with a spray that is cured to adhere the layer to the exposed surface of the stroma and/or Bowman's membrane. In many embodiments a thin layer sprayed on the corneal surface may comprise the curved anterior surface of the therapeutic lens that corrects patient vision. In additional embodiments, a therapeutic lens disposed over the layer of therapeutic material may comprise the curved anterior surface of the therapeutic lens that corrects patient vision, and the therapeutic lens may comprise a posterior surface with a curvature that fits the curvature of the epithelium.

The therapeutic covering as described herein can be used with many corneal surgeries. For example, the therapeutic covering can be used with surgery of the cornea where an incision is made, and the covering used to shape the cornea when the cornea heals, for example with penetrating keratoplasty, also referred to as PKP.

As used herein, a lens encompasses at least one light transmitting body with two opposite surfaces with optical properties suitable for forming images. A therapeutic contact lens encompasses a lens that can be worn on the cornea of the eye. In many embodiments the lens may comprise little or no refractive power when placed on the cornea.

As used herein the stroma and/or (the) Bowman's encompasses: the Bowman's membrane or the stroma, or both. For example, the ablations and coverings described herein can be used to cover one of Bowman's membrane or the stroma following laser ablation, or both. With PRK, for example, both the stroma and Bowman's can be ablated, such that the ablated surface includes an exposed surface of Bowman's membrane and an exposed stromal surface such that the covering contacts both the stroma and Bowman's membrane. In some instances, Bowman's membrane may be ablated such that the coverings described herein may cover mostly stromal tissue, for example with a deep PRK ablation of about 150 um. With a very shallow PRK ablation, for example to about five microns, the ablated surface in a human cornea may comprise Bowman's membrane without exposed stromal tissue.

A tie layer encompasses a layer that can be optically clear, and adhere the lens, itself or other "layer" to the cornea, for example to at least one of the stroma, the epithelium or the conjunctiva.

Work in relation to embodiments suggests that edema can be caused by both a decreased water barrier function and decreased oxygenation of the cornea. The thin lens covering can provide pain management both mechanically and metabolically. From a mechanical standpoint, the thin lens covering can provide a barrier against rubbing between the debrided zone and the inside of the eye lid. The thin lens covering may also comprise a barrier sealed against the epithelium so as to inhibit or minimize water entering the debrided area. From a metabolic standpoint, the thin lens covering comprises oxygen permeability so as to provide the amounts of oxygenation helpful for corneal epithelium healing. The oxygenation can also be sufficient for increased endothelial pumping and associated metabolism that may occur in response to the epithelial defect. For epithelial re-growth of the debrided epithelium, the oxygen requirement of the epithelium growing over the defect can be much higher than for intact epithelium. Without adequate oxygenation, the epithelium may shift the metabolic pathway away from producing the carbon dioxide to producing lactic acid. The lactic acid can cause hyperosmosis in the epithelial and stromal layers and draw water into these layers which, in turn, may cause the cornea to swell. The decreased oxygen of the cornea may also cause nerve activation manifested by pain, for example nerve activation due to increase swelling. Embodiments can provide a therapeutic covering with a high oxygen permeability, for example a Dk of at least about 350. In at least some embodiments the Dk of the covering comprises a value of 400 or more, for example a Dk of at least about 500. This increased permeability can decrease swelling associated with the metabolically active epithelium when the epithelium regenerates over the debrided cornea.

The therapeutic material and/or layer as described herein may comprise permeability to water no more than about 50% more than a healthy cornea, or about 1.5 times the permeability of the cornea, for example about no more than 25% more than a healthy cornea, or 1.25 times the permeability of the healthy cornea, such as the cornea prior to ablation. The permeability of the cornea, for example the permeability of the corneal epithelium, can be expressed as a quantity of water per unit area of the cornea per unit time. The permeability of the cornea to water may comprise the permeability of the corneal epithelium to water.

The therapeutic device may be used as a drug delivery platform. At least one of the therapeutic materials or the therapeutic lens may comprise a therapeutic agent. The therapeutic agent may comprise at least one of an analgesic, an anti-inflammatory, an antibiotic, a non-steroidal anti-inflammatory, a steroid or an epithelial growth factor to enhance epithelialization. The analgesic may comprise at least one of gabapentin, proparacaine, lidocaine, or tetracaine or a derivative thereof. The antibiotic may comprise one of or a combination of, doxycycline (4-(dimethyl-amino)-1,4,4a,5,5a,6,11,12a-octahydro-3,5,10,12,12a-pentahydroxy-6-methyl-1,11-dioxo-2-naphthacenecarboxamide monohydrate, C22H24N2O8H2O), aminoglycosides (e.g., streptomycin, amikacin, gentamicin, tobramycin), cephalosporins (e.g., beta lactams including penicillin), tetracyclines, acyclorvir, amantadine, polymyxin B, amphotericin B, amoxicillin, ampicillin, atovaquone, azithromycin, azithromycin, bacitracin, cefazolin, cefepime, cefotaxime, cefotetan, cefpodoxime, ceftazidime, ceftizoxime, ceftriaxone, cefuroxime, cephalexin, chloramphenicol, clotimazole, ciprofloxacin, clarithromycin, clindamycin, dapsone, dicloxacillin, erythromycin, fluconazole, foscarnet, ganciclovir, gatifloxacin, griseofulvin, isoniazid, itraconazole, ketoconazole, metronidazole, nafcillin, neomycin, nitrofurantoin, nystatin, pentamidine, rifampin, rifamycin, valacyclovir, vancomycin, or derivatives thereof. The non-steroidal anti-inflammatory may comprises at least one of diclofenac, nepafenac, or suprofen or a derivative thereof. Other agents may also be added, such as NSAIDS, vitamins, minerals, cytokines, growth factors, etc. Examples of the above include, but are not limited to, colchicine, naproxen sodium (ANAPROX® and ANAPROX DS®, (Roche); flurbiprofen (ANSAID®, Pharmacia Pfizer); diclofenac sodium and misoprostil (ARTHROTEC®, Searle Monsanto); valdecoxib (BEXTRA®, Pfizer); diclofenac potassium (CATAFLAM®, Novartis); celecoxib (CELEBREX®, Searle Monsanto); sulindac (CLINORIL®, Merck); oxaprozin (DAYPRO®, Pharmacia Pfizer); salsalate (DISALCID®, 3M); salicylate (DOLOBID®, Merck); naproxen sodium (EC NAPROSYN®, Roche); piroxicam (FELDENE®, Pfizer); indomethacin (INDOCIN®, Merck); etodolac (LODINE®, Wyeth); meloxicam (MOBIC®, Boehringer Ingelheim); ibuprofen (MOTRIN®, Pharmacia Pfizer); naproxen (NAPRELAN®, Elan); naproxen (NAPROSYN®, Roche); ketoprofen (ORUDIS®, ORUVAIL®, Wyeth); nabumetone (RELAFEN®, SmithKline); tolmetin sodium (TOLECTIN®, McNeil); choline magnesium trisalicylate (TRILISATE®, Purdue Fredrick); rofecoxib (VIOXX®, Merck), vitamins A, B (thiamine), B6 (pyridoxine), B12 (cobalamine), C (ascorbic acid), D1, D2 (ergocalciferol), D3 (cholcalciferol), E, K (phytonadione), K1 (phytylmenaquinone), K2 (multiprenylmenaquinone); carotenoids such as lutein and zeaxanthin; macrominerals and trace minerals including, but not limited to, calcium, magnesium, iron, iodine, zinc, copper, chromium, selenium, manganese, molybdenum, fluoride, boron, etc. Commercially available supplements are also included such as high potency zinc (commercially available as OCUVITE® PRESERVISION®, Bausch & Lomb, Rochester N.Y.), or high potency antioxidants (zinc, lutein, zeaxanthin) (commercially available as ICAPS® Dietary Supplement, Alcon, Fort Worth Tex.). The steroid include, but are not limited to, one of triamcinolone (Aristocort®; Kenalog®), betamethasone (Celestone®), budesonide, cortisone, dexamethasone (Decadron-LA®; Decadron® phosphate; Maxidex® and Tobradex® (Alcon)), hydrocortisone, methylprednisolone (Depo-Medrol®, Solu-Medrol®), prednisolone (prednisolone acetate, e.g., Pred Forte® (Allergan); Econopred and Econopred Plus® (Alcon); AK-Tate® (Akorn); Fred Mild® (Allergan); prednisone sodium phosphate (Inflamase Mild and Inflamase Forte® (Ciba); Metreton® (Schering); AK-Pred® (Akorn)), fluorometholone (fluorometholone acetate (Flarex® (Alcon); Eflone®), fluorometholone alcohol (FML® and FML-Mild®, (Allergan); Fluor OP®)), rimexolone (Vexol® (Alcon)), medrysone alcohol (H MS® (Allergan)); lotoprednol etabonatc (Lotemax® and Alrex® (Bausch & Lomb), 11-desoxycortisol, and anacortave acetate (Alcon)) or a derivative thereof. The growth factor may comprise at least one of fibroblast growth factor, fibronectin, or arginine glycine aspartic acid (RGD) comprising peptide sequence or a derivative thereof.

In some embodiments, an analgesic therapeutic agent may comprise an anesthetic therapeutic agent configured for delivery to the cornea at an amount so as to have an analgesic effect and reduce pain, for example without numbing the cornea.

Other types of therapeutic agents may be used as the therapeutic agent or in combination with the above mentioned therapeutic agents. These may include mitomycin C (MMC) 0.02%, topical interferon alpha 2b (IFN-alpha), or a miotic alpha-blocker drug such as Dapiprazole 0.5% for treating haze; nerve growth factor (NGF) in combination with docosahexaenoic acid (DHA) for treating dry eye; ketorolac tromethamine 0.4% ophthalmic solution, 0.1% indomethacin. Topical amethocaine, and 10 tablets of co-dydramol (10 mg dihydrocodeine, and 500 mg paracetamol per tablet for treating pain; timolol maleate 0.5% and dorzolamide 2 to relieve intraocular pressure; and flurbiprofen sodium 0.03% (Ocufen) and diclofenac sodium 0.1% (Decrol) for treating myopic regression and/or pain.

FIG. 1A shows a cornea 10 of an eye with an epithelial defect 11 following refractive surgery, for example PRK, suitable for incorporation of embodiments of the present invention. Cornea 10 includes an epithelium 12 disposed over a stroma 16. A tear liquid 13 covers the anterior surface of epithelium 12. In at least humans, primates and some birds, a Bowman's membrane 14 is disposed between epithelium 12 and stroma 16. Bowman's membrane 14 comprises an acellular collagenous tissue with a thickness of about 5 to 10 microns. In some animals, Bowman's membrane may be absent and the epithelium may be disposed adjacent to the stromal layer. An endothelium 18 is disposed under stroma 16. Endothelium 18 comprises a layer of cells that pump water from cornea 10 as indicated by arrows 19. Tear liquid 13 also covers surfaces of the cornea that are exposed by the epithelial defect, such as an exposed surface of Bowman's membrane 14E and an exposed stromal surface 16E.

In a normal healthy eye, epithelium 12 is disposed across cornea 10 and is a protective layer. Epithelium 12 covers nerves of the cornea and minimizes the flow of water from the tear film of the eye to into the stroma. Epithelium 12 in most human patients can be about 40 to 60 microns thick, for example about 50 microns. When epithelium 12 is intact, endothelium 18 can pump water from stroma 16 and maintain hydration in the cornea at a proper level. The mechanism by which the stroma of the cornea remains properly hydrated can be referred to as deturgescence. Deturgescence of the cornea can be important because excess hydration of the cornea can result in swelling of the cornea and light scattering, or haze, that can degrade vision. The total thickness of normal cornea 10 from endothelium 18 to tear liquid 13 in most human patients can be from about 400 to 600 microns. A healthy cornea with normal hydration comprises about 80 to 85% water. Edema of the cornea due to swelling of the cornea, for example with additional water can increase, the thickness of the cornea.

With refractive surgery, for example PRK, the epithelium can be removed to ablate a refractive correction into Bowman's membrane 14 and/or stroma 16. An initial profile 22 of the anterior surface of stroma and/or Bowman's membrane is ablated to an ablated profile 20 to correct the patient's vision. The profile of tissue removed to correct vision is described in U.S. Pat. No. 5,163,934, entitled "Photorefractive keratectomy", the disclosure of which may be suitable for combination in accordance with some embodiments of the present invention described herein. Ablated profile 20 generally comprises an optical zone that extends across the cornea to correct refractive error of the eye and may correct aberrations of the eye, for example wavefront aberrations. Ablated profile 20 is bounded by boundary 20B that may circumscribe the ablated profile. The epithelium grows centripetally from circumscribing boundary 12B toward the center of ablated profile 20 to cover the exposed stroma, as indicated by arrows 30.

FIG. 1B shows application of a therapeutic tiller material 130 to an eye to form a protective coating to the eye while the epithelium regenerates. Filler material 130 can be applied to the eye in many ways, for example with an aerosol spray 110 comprising small particles directed toward the anterior exposed surface of cornea 10. Although an aerosol spray is shown, filler material 130 can be formed in many ways, for example by application of a drop of liquid that spreads on the eye, for example with surface tension and/or a therapeutic lens mold. Filler material 130 may comprise a two component system with a polymer component and a cross-linker component. The two components may be applied separately, for example by separate application, or simultaneously, for example with a mixed aerosol spray. Filler material 130 can be applied over ablated profile 20. Filler material 130 can be applied over epithelium 20 with a peripheral flap 120 that can facilitate removal of filler material 130 when epithelium 12 regenerates centripetally as shown by arrows 30, as shown in FIG. 1C.

The therapeutic filler material can be applied in many ways. The therapeutic filler material can be applied as a spray onto the cornea post PRK, with a layer thin enough to match PRK contour find thick enough to smooth roughness of the post ablation contour at the interface of the filler material and stroma and/or Bowman's membrane. The filler material can be applied with an inkjet deposition process, for example with separate cartridges for each component of two component system. Microparticles of the filler material can be applied, for example microparticles of collagen. The filler material can build up over time with deposition to make the therapeutic layer and/or lens. The shape of the layer can be customized based shape on an intended shape, for example a customized lens shape with computer controlled deposition profile. Application of material to the eye is described in U.S. Pub No. 2004/0170666 in the name of Keates, the disclosure of which may be suitable for combination with some embodiments of the present invention described herein. Known electrospray aerosol generators can be used to generate nanoparticles. For example a known electrospray generator is available from TSI that is capable of generating 3 nm particles with a density as high as $10^7$ particles per $cm^3$.

FIG. 1C shows a therapeutic lens 150 comprising a layer 130L of filler material 130 as in FIG. 1B, in which the filler material has been cured to form a tie layer 140. Lens 150 comprises an optical surface 152 that is smooth to improve patient vision. Tie layer 140 comprises a lower surface 142, or posterior surface, that is adhered to the stroma and/or Bowman's along ablated profile 20. This adherence of tie layer 140 allows tie layer 140 to remain on the cornea when the epithelium regenerates, so as to provide a therapeutic barrier.

FIG. 1C1 shows optical smoothing of a corneal surface and barrier protection with therapeutic lens 150 comprising optical surface 152. Filler material 130 and/or tie layer 140 comprise a thickness 132. Thickness 132 can be sufficient to inhibit or minimize passive transport of water, for example by diffusion, from the tear film near the anterior surface through filler material 130 and/or the layer 140 to ablated profile 20 as indicated by arrow 158. Optical surface 152 corresponds to abated surface 20 over an optically useful portion of ablated surface 20, for example at least about a central 3 mm of ablated surface 20.

The permeability to water of filter material 130 and/or tie layer 140 may be no more than about 50% more than the pumping capacity of the endothelial layer. For example, the permeability of the filler material and/or tie layer may be no more than about 50% more than the permeability of the intact epithelium.

Optical surface 152 comprises an anterior surface of layer 130L and/or tie layer 140 and is sufficiently smooth to provide functional vision while the epithelium regenerates, for example a visual acuity of 20/40 or better for driving, for example 20/25 or better. Filler material 130 and/or tie layer 140 comprises thickness 132 extending from ablated surface 20 to optical surface 152 that is sufficient to smooth irregularities 20I of ablated profile 20. Irregularities 20I can include peaks 20P and valleys 20V. Such irregularities may be caused by the ablation of tissue and may be present prior to ablation for example with naturally occurring roughness of Bowman's membrane and/or roughness of an exposed surface of the cornea following debridement of the corneal epithelium.

Anterior optical surface 152 comprises a profile, for example a curvature profile, that corresponds to ablated profile 20 so as to correct vision of the patient, for example with an anterior surface profile that corresponds to a refractive and/or wavefront ablation profile. Thickness 132 can be substantially uniform such that the profile of anterior optical surface 152 corresponds to ablated profile 20 and smoothes irregularities 20I. For example, thickness 132 can be within a range from about 1 micron to about 200 microns, as noted above, and thickness 132 can vary from a mean value by no more than about +/−10 microns over an optically useful portion of the layer, such that the anterior surface of therapeutic layer 130 and/or tie layer 140 corresponds to ablated profile 20. An optically useful portion of the layer may comprise a distance that is no more than about 3 mm across, for example about 2 mm across.

Filler material 130 comprising layer 130L and/or tie layer 140 may comprise an index of refraction close to the index of refraction of the cornea so as to inhibit or minimize the optical effect of these irregularities. Cornea 10 may comprise an index of refraction of about 1.376 to about 1.377. The tear liquid has an index of refraction of no more than about 1.34, for example no more than about 1.337. Work in relation to embodiments of the present invention indicates that this difference in the index of refraction of about 0.04 may be sufficient to degrade patient vision with irregularities 20I at the interface of the tear film and stroma when the tear film covers ablated profile 20. The difference between the index of refraction of the material in contact with the cornea can be minimized so as to improve patient vision. Filler material 130 comprising layer 130L and/or tie layer 140 may comprise an index of refraction that is close to the index of refraction of the cornea from about 1.34 to about 1.42, for example from about 1.36 to about 1.40, such that vision is improved. The index of refraction of the filler material and/or tie layer may be from about 1.37 to about 1.39 so as to substantially match the index of refraction of the cornea.

Thickness 132 and filler material 130 can be selected to inhibit or minimize the permeability of water to within the above amounts and to smooth ablated profile 20. The thickness of layer 130L of filler material 130 and/or tie layer 140 can be from about 1 micron to about 200 microns, for example from about 2 microns to about 50 microns. Filler material 130 can cure to form tie layer 140 so as to inhibit or minimize permeability of water and may comprise known adhesives such as a fibrin based adhesive, a polyethylene glycol based adhesive, an albumin based adhesive, a cyanoacrylate based adhesive, and/or modified proteins with activated functional groups and a multi-arm branched prepolymer based adhesive. Many of these known adhesives are commercially available as Tisseal™, Coseal™, Durascal™, Bioglue™, ArterX™, Neomend™, Dermabond™, Histocryl™ and OcuSeal™. Many known adhesives may comprise a two component system with a protein and/or polymer component and a cure components, such as a fibrin based adhesive, a polyethylene glycol based adhesive, an albumin based adhesive, many of which may comprise a cure component with gluteraldehyde. A two component system may comprise a cross-linker and a branched prepolymer. The hydration of many of these materials can be adjusted prior to curing so as to provide an index of refraction within the above ranges and/or that matches the index of refraction of cornea.

The adhesive may comprise a two component system. A first component may comprise protein and/or a prepolymer component. The protein may comprise, for example, fibrinogen, and the prepolymer may comprise, for example polyethylene glycol. A second component may comprise a catalyst and/or a cross-linker, for example glutaraldehyde. The therapeutic layer may be soaked in the protein and/or prepolymer, and the catalyst and/or cross-linker may be applied to the exposed tissue of the eve, for example the stroma and/or Bowman's. The therapeutic layer can then be positioned on the exposed tissue such that the first component reacts with the second component so as to adhere the therapeutic layer to the exposed tissue. In some embodiments, the therapeutic layer may be soaked in the catalyst and/or cross-linker, and the protein and/or pre-polymer applied to the exposed tissue, for example the stroma and/or Bowman's. The therapeutic layer can then be placed on the eye. At least one of the first component or the second component may comprise a photosensitizer for tissue welding and/or photoactivated curing.

Layer 130L comprising filler material 130 may comprise photosensitizers for curing filler material 130 with light to form tie layer 140. Photosensitizers can include ultraviolet (hereinafter "UV") or blue light photosensitizer such as riboflavin, IR photosensitizer such as indocyanine green, visible light photosensitizers such as Janus green, rose Bengal and methylene blue, known protein crosslinking agents such as heterobifunctional with at least one photoactivated group. The photosensitizers can be used to cure the therapeutic material. The photosensitizer can be used to adhere and/or to weld therapeutic material to the tissue. U.S. Pat. Nos. 5,552,452; 6,607,522 and 7,077,839 describe tissue welding and/or adhesion, the disclosures of which may be suitable for combination with in accordance with some embodiments of the present invention described herein.

Layer 130 comprising therapeutic material 130 may include the following materials that may be cured to form tie layer 140: A) Collagen based, such as porcine and/or bovine collagen based, human recombinant, such as Fibrogen, collagen combined with polymer such as Neoglycopolymer-crosslinked biopolymer matrix as described by US Pub. No 2007/002046 in the name of Griffith, biosynthetic matrix as described by US Pub. Nos. 2006/0246113; 2006/013050 and 2006/0134170 in the name of Griffith, collagen hydrogels as described in U.S. Pat. Nos. 4,983,181; 5,522,888 and 5,716,633 in the name of Civerchia, collagen hydrogels for promoting epithelial growth as described in U.S. Pat. Nos. 5,213,720 and 5,114,627, collagen combined with PEA hydrogel as layers as described in U.S. Pat. No. 5,836,313 in the name of Perez, collagen combined with acrylate as described in U.S. Pat. No. 4,452,925 in the name of Kuzma, collagen-based tissue such as amniotic membrane as described in U.S. Pat. Nos. 6,143,315 and 5,932,205 in the name of Wang, optically clear material such as US20030187515 and US20040048796 in the name of Hariri; B) Biopolymer based, for example with known biopolymers such as hyaluronic acid and carboxymethylcellulose; C) Synthetic polymer based as described in U.S. Pat. No. 5,713,957, such as acrylate, silicone polymer based, silicone plastic as described in U.S. Pat. No. 4,612,912, porous hydroxyethyl methacrylate (HEMA) hydrogel as described in U.S. Pat. No. 5,244,799 in the name of Anderson and U.S. Pat. No. 5,401,508, HEA hydrogel as described in U.S. Pat. No. 4,452,776; bioadhesives and/or mucoadhesive compositions as described in U.S. Pat. Nos. 5,814,329; 5,942,243; and U.S. Pub No. 2004/0143026; crosslinked gels comprising polyalkyleneimines as described in U.S. Pub. No. 2007/0196454, the disclosures of which U.S. patents and publications may be suitable for combination with some embodiments of the present invention described herein.

The above therapeutic materials, for example collagen based filler materials, can be stabilized by soaking in riboflavin followed by photocatalyzed crosslinking to form the tie layer, for example with UV or blue light.

The therapeutic layer may comprise tissue from a donor cornea, and the donor cornea may comprise a human donor cornea, also referred to as an allograft. The donor tissue may comprise homologous donor tissue, and in some embodiments may comprise autologous donor tissue. Known methods of preparing a donor cornea can be used. The donor cornea may comprise an artificial human cornea capable of innervation when placed on the cornea. In some embodiments, the donor cornea may comprise a xenograft, for example porcine or bovine cornea.

Layer 130 may comprise a therapeutic agent. The therapeutic agent may comprise at least one of an analgesic, an anti-inflammatory, an antibiotic, a non-steroidal anti-inflammatory, a steroid or an epithelial growth factor to enhance epithelialization. The analgesic may comprise at least one of gabapentin, proparacaine, lidocaine, or tetracaine or a derivative thereof. The antibiotic may comprise tobramycin or a derivative thereof. The non-steroidal anti-inflammatory may comprises at least one of diclofenac, nepafenac, or suprofen or a derivative thereof. The steroid may comprise at least one of fluorometholone, dexamethasone or prednisolone or a derivative thereof. The growth factor may comprise at least one of fibroblast growth factor, fibronectin, or arginine glycine aspartic acid (RGD) comprising peptide sequence or a derivative thereof.

In some embodiments, an analgesic therapeutic agent may comprise an anesthetic therapeutic agent configured for delivery to the cornea at an amount so as to have an analgesic effect and reduce pain, for example without numbing the cornea.

Collagen Based Materials

The therapeutic layer may comprise many collagen based materials. The therapeutic layer may comprise human recombinant material, for example fibrogen. The therapeutic layer material may comprise collagen plus a polymer, for example a neoglycopolymer-crosslinked biopolymer matrix, a biosynthetic matrix, collagen hydrogel, for example collagen with poly ether amide (PEA) hydrogel and collagen with acrylate. Collagen based materials that may be used in accordance with some embodiments of the present invention are described in the following US patents and patent applications: U.S. Pat. Nos. 4,452,925; 4,983,181; 5,213,720; 5,522,888; 5,114,627; 5,716,633; 5,836,313; 6,645,715; 2006/0034807; US2006/013050; US2006/0134170; 2006/0246113; and 2007/002046, the disclosures of which may be suitable for combination in accordance with some embodiments of the present invention described herein. In some embodiments, homologous tissue from a human cell line may be used, for example a human fibroblast cell line, and cross-linked with a cross-linker. The therapeutic layer may comprise known human or mammal-derived amniotic membrane, such as AmbioDry2™ from IOP Inc. of Costa Mesa, Calif., EpiFix™ from Surgical Biologies of Kennesaw Ga., AcelaGraft™ from Oasis of Glendoar, Calif., and AmnioGraft™ from Bio-Tissue of Miami, Fla., a solution comprising amniotic membrane tissue repair and growth factors, or ground up amniotic membrane. The therapeutic material may comprise an optically clear material, for example as described in US20030187515, US20040048796, the disclosures of which may be suitable for combination in accordance with some embodiments of the present invention described herein.

The above donor and collagen based materials can be stabilized and/or solidified by soaking in a photosensitizer, for example riboflavin, and exposed to light so as to induce photocatalyzed crosslinking, for example with UV or blue light.

II. C. Synthetic

The therapeutic layer lens material may comprise a known synthetic material, for example porous hydroxyethyl methacrylate (HEMA) hydrogel, hydrogel, silicone, for example hydrated silicone and derivatives thereof.

Adhesion of Therapeutic Layer to Bowman's Membrane and/or the Corneal Stroma

The adhesive can hold the therapeutic layer in place on the cornea as the epithelium grows over the anterior surface of the therapeutic layer. The adhesive can be applied in many ways.

Glue

In many embodiments, the adhesive comprises an adhesive glue. The adhesive glue may comprise many known surgical sealants. The adhesive may comprise a synthetic adhesive, a natural or biologically derived adhesive, a hybrid adhesive, and/or a recombinant adhesive. The synthetic adhesive may comprise, for example, poly-lysine, cyanoacrylate, and/or polyethylene glycol. The natural or biologically derived adhesive may comprise, for example, known fibrin adhesive. The hybrid adhesive may comprise, for example, albumin with glutaraldehyde, and/or modified proteins with activated functional groups, such as such as succinylated collagen. The recombinant adhesive may comprise recombinant fibrin bio-derived from plasma and/or poly-lysine.

In specific embodiments, the adhesive may comprise a fibrin and/or fibrinogen adhesive, commercially available as Tisseal™. The adhesive may comprise a two part component. For example, the fibrinogen component can be placed on cornea, the therapeutic layer soaked in thrombin, then applied to cornea so as to form fibrinogen and covalently bond the therapeutic layer to the exposed Bowman's and/or stroma, for example with a collagen or collagen based therapeutic layer.

The optical clarity of the fibrin adhesive may be modulated by altering the fibrin structure (solid phase) within the fibrin gel, for example when the adhesive is sprayed onto the eye to form a layer with a thickness from about 5 to 100 microns. This may be accomplished by altering the gelation time (thrombin concentration between 1-1000 units/mL) or by altering the ionic strength of the liquid phase of the gel. A more opaque ("coarse") gel is created by lower ionic strength and slower gelation times (low thrombin concentration). A clear or "fine" gel can be made by increasing the ionic strength or decreasing the gelation lime (almost instantaneous at a high thrombin concentration, while several minutes at a low thrombin concentration). As gelation time usually is preferably consistent for a given medical application, it may be more convenient to alter the ionic strength of the liquid phase by increasing or decreasing the salt concentration (as an example, if using sodium chloride, the concentrations range between 0-500 mM). For example, lyophilized thrombin may be reconstituted in a low ionic strength buffer with the requisite calcium chloride (required for covalent crosslinking of the resultant gel by the transamidation reaction of Factor XIII) in order to create a more opaque gel. To create an optically clear gel, a higher salt concentration buffer system (e.g., saline at twice or more physiological concentration) with calcium chloride can be used. Other ways of altering the ionic strength can be by use of compatible salts and buffers such as potassium chloride, calcium chloride, tris buffer, carbonate buffer, and the like. Alternately or in combination, sugar-based solutions can be used such as dextrose. Dextran solutions can also be used to alter the ionic strength. The buffer/salt solution can be used in either the fibrinogen component or the thrombin component, though it is most convenient to reconstitute and dilute the thrombin component in order to attain the desired gel time. The above can be used to spray an optically clear and optically transmissive layer on the eye such that a patient has functional vision of 20/40 or better, for example 20/25 or better.

The adhesive may comprise polyethylene glycol (PEG) based adhesive, for example commercially available under the trade names Coseal™ and Duraseal™. The PEG components may be placed on cornea, the therapeutic layer soaked in catalyst, for example a higher pH solution, and the therapeutic layer then applied to cornea.

Albumin based glue is commercially available and can be obtained commercially under the trade name Bioglue™

Cyanoacrylate is commercially available and can be obtained commercially with the trade name Dermabond™ and Histocryl™. Commercially available methylmethacrylate can be obtained and may be used.

The glue may comprise BSA-GTA know as Bioglue™, available from Cryolife; BSA-GTA glue known as Artex™, commercially available from Tenaxis Medical; polysaccharide multi-arm glue known as OcuSeal™, commercially available from Hyperbranch Medical; and PEG-based glue known as ProPEG™ and NeoMend™.

Many of the above adhesive glues, for example fibrinogen and/or PEG based glues can be disposed as a dry material on the therapeutic layer, such that moisture from the cornea cures the glue when the adhesive is placed on the cornea.

The therapeutic covering comprising the layer may comprise at least one of a synthetic adhesive, a natural and/or biologically derived adhesive, a recombinant adhesive or a hybrid adhesive or derivatives thereof. The synthetic adhesive may comprise, for example, a least one of a polylysine adhesive, a cyanoacrylate adhesive or a polyethylene glycol adhesive or derivative thereof. The natural and/or biologically derived adhesive may comprise, for example, at least one of a fibrin adhesive or an RPG adhesive or derivatives thereof. The recombinant adhesive may comprise, for example, at least one of a fibrin adhesive, a polylysine adhesive, a biologically derived adhesive from plasma or an RPG adhesive or derivatives thereof. The hybrid adhesive may comprise, for example an albumin with glutaraldehyde adhesive.

Tissue Welding

Optical tissue welding can be used to adhere the therapeutic layer to the stroma and/or Bowman's. A light sensitive material comprising a photo sensitizer may be disposed in the therapeutic layer, in the cornea, and or between the cornea and therapeutic layer, for example within an indentation of the therapeutic layer. Light is applied to the therapeutic layer, for example with a laser beam. The applied light interacts with the photo sensitive material and welds the tissue. Although light welding is shown, other welding such as thermal and electrosurgical welding may be used in some embodiments.

Many photosensitizers may be used and wavelengths of light may be used to initiate photo-chemical reactions and/or chemical bonding with an appropriate flux of the light energy. The corneal therapeutic layer material described above may be combined with the photosensitizer to adhere the therapeutic layer to the stroma and/or Bowman's, for example to form a covalent bond with the stroma and/or Bowman's. In some embodiments, UV or blue light may be used, for example with riboflavin as a photosensitizer with an appropriate flux of the light energy distributed over an area. Infrared (IR) light may be used with indocyanine green photosensitizer. Visible light and visible light photosensitizers, for example Janus green, rose Bengal and/or methylene blue may be used. Examples of known photo-sensitizers are described in U.S. Pat. Nos. 5,552,452; 6,607,522; and 7,077,839, the disclosures of which and may be suitable for combination in accordance with some embodiments of the present invention described herein.

Table 1 shows examples of photosensitizers and laser sources that may be used.

TABLE 1

| Photosensitizer Laser Source Wavelength |
| --- |
| Riboflavin-5-phosphate Argon 488-514 nm |
| Rose Bengal Krypton Red 600-670 nm |
| Porphyrins Argon/Krypton/488-514 |
| Tunable Dye Lasers 546, 600-670 nm |

Table 1 is merely an example of some of the electromagnetic radiation wavelength that may be used to achieve photo-activation, which may generally have a wavelength from about 10 nm to about 700 nm and will be within the visual, infra red or ultra violet spectra. The radiation may be supplied in the form of a monochromatic laser beam or other form of electromagnetic radiation source. The choice of energy source can be made in conjunction with the choice of photosensitizer employed in the composition. For example, an argon laser may be particularly suitable for use with flavins such as riboflavin-5-phosphate, i.e., flavins are optimally excited at wavelengths corresponding to the wavelength of the radiation emitted by the argon laser. For similar reasons, a diode laser can be suitable for use with chlorophylls such as bacteriochlorophyll A.

There are at least two major types of sensitized photo-oxidative processes, for example Type I and Type II. The sensitizer in its ground state can first absorb light energy to form $S_x$ and $T_x$ which may comprise sensitizer molecules in their excited singlet and triplet states, respectively. Both Type I and Type II reactions can then proceed via the triplet state because it has a much longer lifetime than the singlet state.

In many Type I reactions, the sensitizer triplet $T^\char`\^$ can then directly bind to the substrate to produce substrate free radicals or radical anions. The substrate radicals then can undergo further reactions, including that with molecular oxygen to form the superoxide anion $O_{2-}$. The superoxide anion then can react in numerous ways. For example, the superoxide anion can further react to generate hydrogen peroxide ($H_2O_2$) and the hydroxyl radical (OH*).

In Type II reactions, the sensitizer triplet may react first with molecular oxygen to produce singlet oxygen ($^1O_2$). The singlet oxygen can then oxidize the substrate to form photo-oxidation products. Direct electron transfer from triplet to oxygen can also occur to yield superoxide anions, but in some instances much less efficiently.

Photosensitizers can then cause oxidative damage to susceptible amino acid residues, for example histidine, tryptophan, tyrosine, cysteine, and methionine. They may cause non-disulfide covalent cross-links in susceptible proteins. This process can be oxygen dependent and may be mediated by singlet oxygen rather than by superoxide anions, hydrogen peroxide, or hydroxyl radicals. Natural collagen can be devoid of disulfide bridges. Embodiments of the present invention enable one to produce non-disulfide covalent cross-links within collagen when exposed to light to adhere an onlay to the stroma and/or Bowman's membrane.

In at least some embodiments of the present invention, water soluble photosensitizers that have high quantum efficiency for singlet oxygen production can be selected. These photosensitizers may include rose bengal (excited by the argon laser), riboflavin-5-phosphate (argon laser), porphyrins (argon/krypton) and methylene blue (krypton laser). The photosensitizer can then be mixed with a protein solder, applied to the wound, and exposed to the appropriate laser. An 18% fibrinogen solution may have the right consistency for ease of application and dissolved all photosensitizers without problem. Welded fibrinogen may resorb in vivo (Oz and Chuck et al., 1989), and may be a good substrate for an organic glue in embodiments where resorbtion is used such that the onlay is temporarily adhered with the adhesive, for example prior to integration and/or re-epithelialization. Other proteins that may be used in accordance with embodiments of the present invention include albumin, collagen, myoglobin, glutathione, acid soluble collagen, $/3_H$ crystalline β crystalline and lysine, at various concentrations and in combinations with each other and with various photosensitizers and salts. For a more complete list of formulations, see Table 2, which shows protein and photosensitizer combinations that may be used.

TABLE 2

Protein and photosensitizer combinations.
PROTEIN/PHOTOSENSITIZER MIXTURES

Saline + Fluorescein isothiocyanate
Saline + Fluorescein isothiocyanate + HC03
25% Albumin + Fluorescein isothiocyanate
25% Albumin + Fluorescein isothiocyanate (1 1) + HA (1:1)
25% Albumin + Fluorescein isothiocyanate (1 1) + HC03**
25% Albumin + Fluorescein isothiocyanate (1 1) + HC03 + HA (1:1)
25% Albumin + Fluorescein isothiocyanate (10:1) + HC03
25% Albumin + Fluorescein isothiocyanate (10:1) + HC03 + HA
25% Albumin + Fluorescein isothiocyanate (1 1) + HC03 + 20% ETOH
25% Albumin + Fluorescein isothiocyanate (1 1) + HC03 + 50% ETOH
25% Albumin + Fluorescein
25% Albumin + Fluorescein + HA
Zyplast (collagen) + 10% Fluorescein
Zyplast + Saline + HC03 + Fluorescein isothiocyanate
Zyplast + Saline + HC03 + Fluorescein isothiocyanate + HA
35% Albumin + Fluorescein
35% Albumin + Fluorescein + HA
35% Albumin + Fluorescein isothiocyanate (1 1) +
HC03 + 20% ETOH
35% Albumin + Fluorescein isothiocyanate (1 1) +
HC03 + 10% ETOH
35% Albumin + Red # 40**
35% Albumin + Yellow #6
50% Albumin (fatty acid, globulin free) +
Fluorescein isothiocyanate (1:1) + Saline + HC03
50% Albumin + Fluorescein isothiocyanate (1 1) + HC03 + 10% ETOH
50% Albumin + 10% ETOH
44% Myoglobin + Saline
44% Myoglobin + Saline + HA
10% Myoglobin + Saline
10% Myoglobin + Saline + HA
1% Myoglobin + Saline 1% Myoglobin + Saline + HA
5 uM Myoglobin (1:1 with Albumin) + 25% Albumin 10 uM Myoglobin (2:1 with Albumin) +
25% Albumin
5 mm Glutathione + Saline + Fluorescein isothiocyanate + HC03 + HA 50 mm Glutathione +
Saline + Fluorescein isothiocyanate + HC03 + HA
5 mm Glutathione (1:1) + 35% Albumin +
Fluorescein isothiocyanate + HC03
5 mm Glutathione + 35% Albumin + Fluorescein isothiocyanate + HC03 + HA
55 mg Glutathione (70:1) + 35% Albumin +
Fluorescein isothiocyanate + HC03
50 mm Glutathione + 35' Albumin + Fluorescein isothiocyanate + HC03 50 mm Glutathione +
35' Albumin + Fluorescein isothiocyanate + HC03 ■ HA
HA + Saline + fluorescein isothiocyanate + HC03
Rose Bengal (2 mM) + 35% Albumin Rose Bengal (0.2 mM) + 35% Albumin Rose Bengal
(0.02 mM) + 35% Albumin Rose Bengal (20 uM) + 35% Albumin** Rose Bengal (2 uM) +
35% Albumin Rose Bengal (8 mM) Rose Bengal (1 mM)
Methylene Blue (500 uM) + 35% Albumin + Argon Laser
Methylene Blue (500 uM) + 35% Albumin + Krypton Laser
Methylene Blue (50 uM) + 35% Albumin + Krypton Laser
Methylene Blue (5 uM) + 35% Albumin + Krypton Laser
2% Collagen (from Calf Tendon, dissolved in acetic acid) + Rose Bengal (1:1) (Ph adjusted
to 9 with NaOH)
3.8% Fibrinogen + De-ionized H20 + Rose Bengal (Ph adjusted)
BH Crystalline + De I H20 + RB + NaOH BL Crystalline + De I H20 + RB + NaOH
Collagen (1.7%) + Riboflavin-5-Phosphate (R5P) (Ph adjusted)
Collagen (1.7%) + (R5P) (Ph adjusted) + Glutathione (70:1)
3.8% Fibrinogen + R5P
3.8% Fibrinogen + R5P + Glutathione (70:1)
18% Fibrinogen + R5P (1:1)
18% Fibrinogen + R5P (10:1)**
18% Fibrinogen + R5P (10:1) + Na Azide
18% Fibrinogen + Fluorescein isothiocyanate + HC03**
18% Fibrinogen + Fluorescein isothiocyanate + HC03 + R5P (10:1)
Lysine + 18% Fibrinogen + R5P (10:1) Lysine + De I H20 + R5P (10:1)

Table 2 shows examples of photosensitizers that may be used and empirical experiments can be performed on a suitable number of animals and/or patients to determine appropriate characteristics to adhere and/or cure the onlay on the exposed surface of the stroma and/or Bowman's membrane. The photosensitizers of Table 2 can be combined with many of the onlay materials described and/or adhesives described herein to form a material suitable for adhesion to the stroma and/or Bowman's membrane.

Adhesion of a therapeutic layer can be used to hold the therapeutic layer in place while an adhesive sets. A photosensitizer may be disposed under the therapeutic layer and tack welded with laser and/or other light to weld the therapeutic layer to the tissue. In some embodiments, an additional adhesive may be employed, for example delivered with a deliver tool near the periphery of the therapeutic layer. The tack welds can hold the therapeutic layer in place while the adhesive sets. In some embodiments, an annular track of adhesive may be disposed on the therapeutic layer as described above, and used with tack welding of the therapeutic layer with light.

Protein Cross-Linking Agents

Many protein cross-linking agents may be used, for example adhesives as described above. In some embodiments, a heterobifunctional with a photoactivated group and a cross-linking group can be employed so as to cross-link the layer to the Bowman's membrane and/or stroma with covalent bonds in response to photo activation with an appropriate flux. In some embodiments, the cross-linking agent may crosslink the therapeutic layer to Bowman's membrane and/or the stroma without photoactivation.

FIG. 1C2 shows regeneration of the epithelial layer with centripetal advancement of the epithelial layer under therapeutic lens 150. Regenerated epithelium 112 comprises a leading edge 112A that advances centripetally as shown by arrows 30. Filler material 130 and/or tie layer 140 comprise peripheral flap 120 that allows the epithelium to advance centripetally under and dislodge a peripheral portion of the filler material and/or tie layer while a central portion of the filler material and/or tie layer remains adhered to the cornea. This adherence of a central portion of the filler material and/or tie layer while the peripheral portion is dislodged allows the filler material and/or tie layer to inhibit or minimize water transport into the cornea and provide good vision through the adhered portion. The epithelium continues to regenerate centripetally and dislodge filler material 130 and/or tie layer 140 with leading edge 112A near the center of ablated profile 20. When the epithelium substantially covers the cornea so as to provide a natural barrier to water and natural smoothing of most of ablated profile 20, therapeutic lens 150 can be completely dislodged from the cornea, for example when the epithelial defect is no more than about 1 mm across.

Figure 2A:
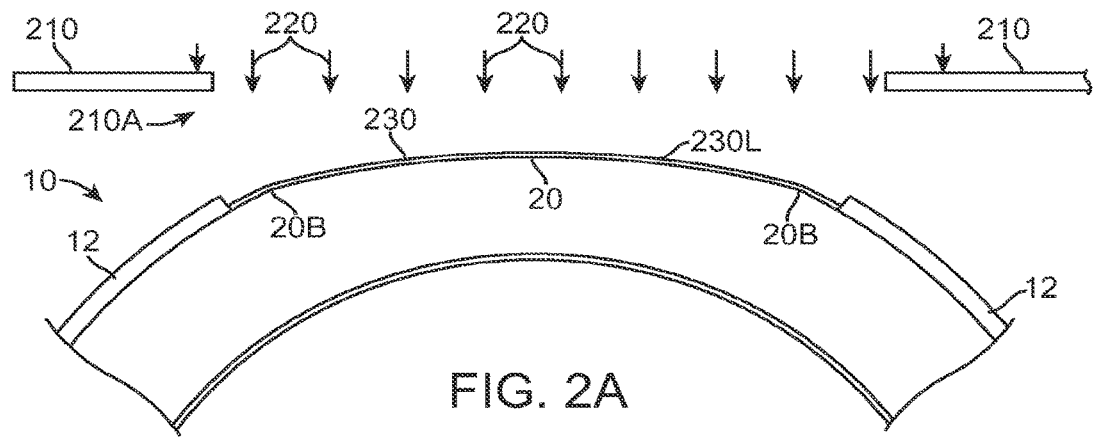
FIG. 2A shows application of a therapeutic filler material to an eye, according to embodiments of the present invention.

FIG. 2A shows application of a therapeutic filler material 230 to an eye with an aperture 210A disposed in a blocking material 210 so as to form a protective coating to the eye when the epithelium regenerates. Aperture 210A can be shaped so as to apply filler material 230 to the eye over the exposed corneal surface and/or Bowman's membrane. A layer 230L of filler material forms over the exposed corneal surface, and/or Bowman's membrane. Filler material 230 can be applied to the eye in many ways, for example as described above, and with aperture 210A disposed between the cornea and source of aerosol, for example with an aerosol spray 220 comprising small particles directed toward the anterior exposed surface of cornea 10. Although an aerosol spray is shown, filler material 230 can be formed in many ways as described above. Filler material 230 may comprise a two component system, as described above. Filler material 230 can be applied over ablated profile 20 so as to inhibit or minimize deposition of the filler material on the epithelium, as this may allow the epithelium 12 to regenerate over the cured filler material.

Figure 2B:
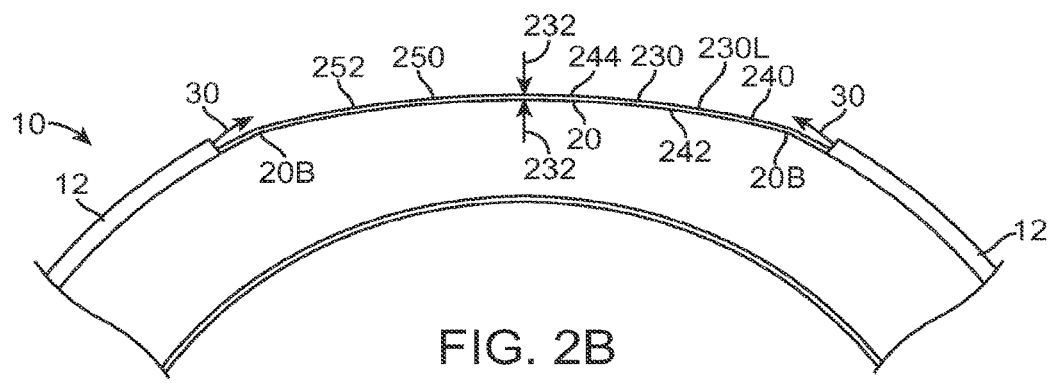
FIG. 2B shows a therapeutic lens comprising the cured filler material as in FIG. 2A.

FIG. 2B shows a therapeutic lens 250 comprising a layer 230L of filler material 230 as in FIG. 2A, in which the filler material has been cured to form a tie layer 240. Lens 250 comprises an optical surface 252 that is smooth to improve patient vision as described above. Optical surface 252 corresponds to ablated surface 20 over an optically useful portion of ablated surface 20, for example at least about a central 3 mm of ablated surface 20. Tie layer 240 comprises a lower surface 242, or posterior surface, and an upper surface 244, or anterior surface. Lower surface 242 is adhered to the stroma and or Bowman's along ablated profile 20. This adherence of tie layer 240 allows tie layer 240 to remain on the cornea when the epithelium regenerates, so as to provide a therapeutic barrier and therapeutic optical surface.

FIG. 2B1 shows optical smoothing of a corneal surface and barrier protection with therapeutic lens 250 comprising optical surface 252. Filler material 230 and/or tie layer 240 comprise a thickness 232. Thickness 232 can be sufficient to inhibit or minimize transport of water from the anterior surface near the tear film through filler material 230 and/or tie layer 240 to the stromal ablated profile 20 as indicated by arrow 258. Optical surface 252 corresponds to ablated surface 20 over an optically useful portion of ablated surface 20, for example a central 3 mm of ablated surface 20.

The permeability and optical properties of fillet material 230 and/or tie layer 240 can be similar to filler layer 130 and/or tie layer 140 described above.

Optical surface 252 can be sufficiently smooth to provide functional vision while the epithelium regenerates, similar to optical surface 152 described above.

Filler material 230 and/or tie layer 240 may comprise an index of refraction similar to filler layer 130 and/or tie layer 140 described above.

Thickness 232 and filler material 230 can be selected to inhibit or minimize the permeability of water to within the above ranges and to smooth ablated profile 20, as described above. Work in relation to embodiments of the present invention suggest that epithelium 12 can grow over filler material 230 and/or tie layer 240 when the thickness is within a range from about 1 um to about 100 microns, for example from about 2 microns to 50 microns. As the irregularities of the cornea can be small, a thickness of about 1 um can provide optical smoothing and provide a barrier. In some embodiments, thickness 232 can be within a range from about 3 microns to about 25 microns, for example from about 4 microns to about 10 microns, and provide a therapeutic barrier and therapeutic optical surface. Filler material 230 can cure to form tie layer 240 so as to inhibit or minimize permeability of water may comprise materials similar to filler material 130 described above. Filler material 230 may comprise at least one of a silicone oil or a perfluorocarbon based oil.

Figure 2C:
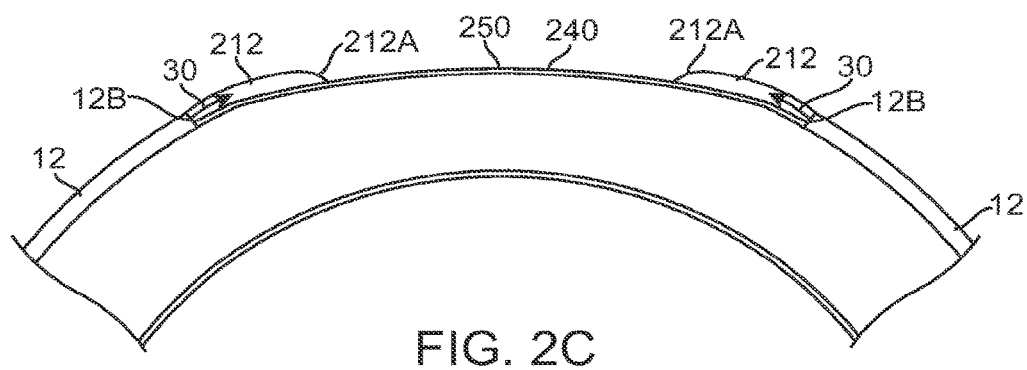
FIG. 2C shows regeneration of the epithelial layer with centripetal advancement of the epithelial layer over the therapeutic lens as in FIG. 2B.

FIG. 2C shows regeneration of the epithelial layer with centripetal advancement of the epithelial layer over therapeutic lens 250. Regenerated epithelium 212 comprises a leading edge 212A that advances centripetally (as shown by arrows 30) over lens 250. Filler material 230 and/or tie layer 240 can be disposed within boundary 12B so as to allow the epithelium to advance centripetally over the filler material and/or tie layer while the filler material and/or tie layer remains adhered to the cornea. This adherence of the filler material and/or tie layer allows the filler material and/or tie layer to inhibit or minimize water transport into the cornea and provide good vision when the epithelium advances centripetally. The epithelium continues to regenerate centripetally and cover filler material 230 and/or tie layer 240 centrally with leading edge 212A near the center of ablated profile 20, when the epithelium substantially covers the cornea so as to provide a natural barrier to water and natural smoothing of ablated profile 20. In many embodiments, filler material 230 and/or tie layer 240 may comprise a biodegradable material that erodes when the epithelium is disposed over the filler material and/or tie layer. The biodegradable filler material and/or tie layer may comprise at least one of collagen, fibrin or degradable polyesters such as polylactic acid, polyglycolic acid and polycaprolactones. In some embodiments, filler material 230 and/or tie layer 240 may comprise an implantable material that remains in the cornea after the epithelium covers the implantable material. The implantable material may comprise many of the materials described above with reference to filler material 130 an/or tie layer 140. The implantable material may comprise known implantable materials, for example perfluorocarbons, polyethylene, polypropylene.

FIG. 2D shows a therapeutic lens 299 and regeneration of the epithelial layer with centripetal advancement of the epithelial layer as a portion 295 of therapeutic lens 299 sloughs off the cornea. Therapeutic lens 299 comprises an anterior optical surface, similar to optical surfaces 152 and 252 described above. A layer 280L of filler material 280, similar to layer 130L, layer 230L, filler material 130 and filler material 230, can be applied to the cornea and cured to form a tie layer 290, similar to tie layer 140 and tie layer 240 as described above. Tie layer 290 comprises a lower surface 292, or posterior surface, and an upper surface 294, or anterior surface. Regenerated epithelium 262 comprises a leading edge 262A, for example a leading edge circumscribing the adhered portion of the lens, that advances centripetally and dislodges and/or fractures filler material 280 and/or tie layer 290, such that portion 295 sloughs from lens 299 as the epithelium advances centripetally. As the epithelium continues to advance additional portions can slough from layer 280L and/or tie layer 290. A thickness 282 of filler material 280 can be similar to thickness 132 and thickness 232, described above. Filler material 290 may comprise filler materials similar to filler material 230 described above.

Figure 3A:
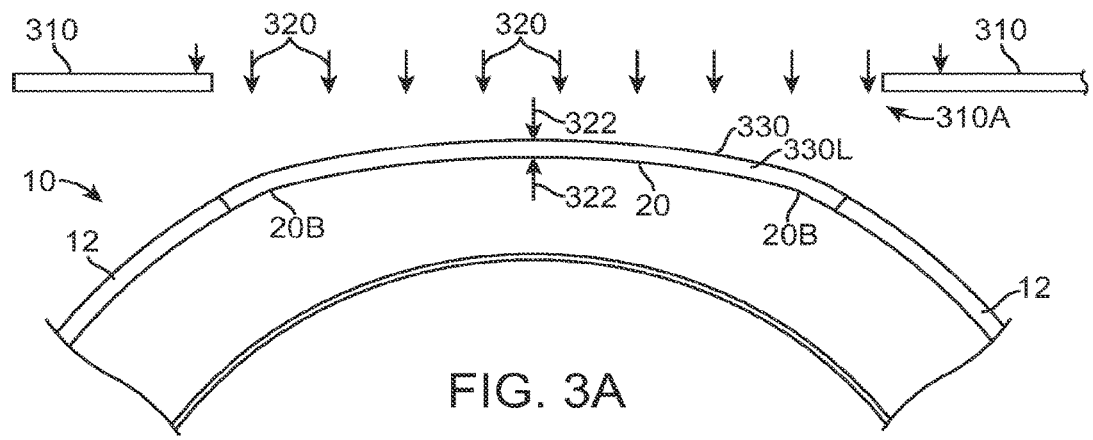
FIG. 3A shows application of a therapeutic filler material to an eye, according to embodiments of the present invention.

FIG. 3A shows application of a therapeutic filler material 330 to an eye. Filler material 330 can be applied to the eye in many ways, for example with a drop of liquid applied to the eye from a syringe such that the drop spreads over and covers the epithelial defect of the eye. Filler material 330 can be applied to the eye with an aperture 310A disposed in a blocking material 310 so as to form a protective coating to the eye while the epithelium regenerates. Aperture 310A can be shaped so as to apply filler material 330 to the eye over the exposed corneal surface and/or Bowman's membrane. Filler material 330 can be applied to the eye in many ways with aperture 310 disposed between the cornea and source of aerosol, for example with an aerosol spray 320 comprising small particles directed toward the anterior exposed surface of cornea 10. Although an aerosol spray is shown, filler material 330 can be applied to form layer 330L in many ways. Filler material 330 may comprise a two component system, as described above. Filler material 330 may be applied to ablated profile 20 so as to inhibit or minimize deposition on the epithelium. Filler material 330 may comprise the filler materials described above.

Figure 3B:
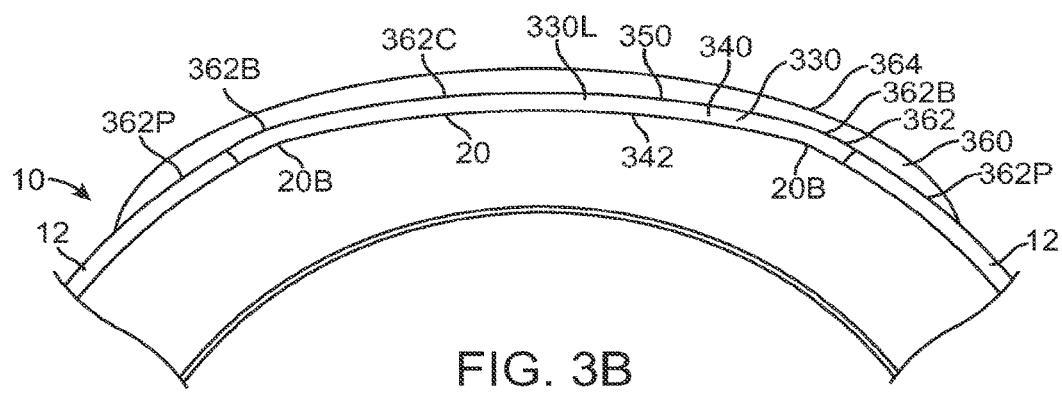
FIG. 3B shows molding the filler material as in FIG. 3A with a lens to form a therapeutic lens in situ on the cornea.

FIG. 3B shows molding the filler material 330 as in FIG. 3A with mold comprising a lens 360 to form a therapeutic lens 350 in situ on the cornea. Therapeutic lens 360 may comprise known therapeutic lens materials such as low water content silicone material, for example no more than about 25% water content, high water content silicone material, for example at least about 25% water content, polymethylmethacrylate (hereinafter "PMMA"), hydrogel material, or other materials, either singly and in various combinations (i.e. "copolymers"): HEMA 2-hydroxyethylmethacrylate; MA methacrylic acid; MMA methyl methacrylate; NVP N-vinyl pyrrolidone; PC phosphorylcholine; PVA poly vinyl alcohol; PVP polyvinyl pyrrolidone and a hard therapeutic lens, for example comprising PMMA or one or more of the following materials, either singly or in combination, gas permeable therapeutic lens are harder/stiffer and are silicone based, but have greater oxygen permeability than the soft lenses and include these singly and in copolymer: DMA N,N-dimethylacrylamide; HEMA 2-hydroxyethylmethacrylate; MA methacrylic acid; NVP N-vinyl pyrrolidone; TPVC tris(trimethylsiloxysilyl) propylvinyl carbamate, NCVE N-carboxyvinyl ester; PBVC poly [dimethylsiloxyl] di [silylbutanol] bis[vinyl carbamate]; PVP polyvinyl pyrrolidone. The therapeutic lens comprising a hard lens material may reduce lens pressure on the wound, for example when the patient blinks. Lens 360 comprises a lower surface 362, or posterior surface, and an upper surface 364, or anterior surface. Lower surface 362 is shaped to fit on the cornea and form therapeutic lens 350 with a desired shape. Lower surface 362 comprises a peripheral portion 362P shaped to fit over the unablated cornea, for example with a radius of curvature that corresponds to the radius of curvature of the cornea. Lower surface 362 comprises a central portion 362C shaped to correspond to the ablated profile 20, for example with a radius of curvature that corresponds to the intended post ablation curvature of the cornea, such as a curvature within about +/−1 D of the intended optical power of the curvature of ablated profile 20. With wavefront ablations that ablate a wavefront shape on the eye, the curvature of the wavefront ablation can comprise the lower order corrections of the wavefront ablated profile such as sphere and/or cylinder.

Filler material 330 can be cured to form tie layer 340, similar to the curing of tie layers described above. Tie layer 340 comprises a lower surface 342, or posterior surface, and an upper surface 344, or anterior surface. Lower surface 342 is adhered to the stroma and or Bowman's along ablated profile 20. This adherence of tie layer 340 can allow layer 340 to remain on the cornea when the epithelium regenerates, so as to provide a therapeutic barrier and therapeutic optical surface as described above.

FIG. 3B1 shows detail of the lens 360 used to mold the therapeutic lens 350 as in FIG. 3B. Peripheral portion 362P of lower surface 362 comprises a peripheral radius of curvature Rp that corresponds to the pre-operative radius of curvature of the cornea. Work in relation to embodiments of the present invention indicates that most human patients can be fit with Rp within about 2 D of the curvature of the cornea, based on keratometer readings, for example with curvatures corresponding to corneal powers of about 42 D, 44 D and 46 D. Patients can be fit with Rc within about 1 D, for example about 0.5 D, of the curvature of the cornea, based on keratometer readings, for example with curvatures corresponding to post ablation corneal powers from about 35 D to about 50 D in about 0.5 D increments. In the exemplary embodiment, 3 values of Rp can be selected and 32 values of Rc can be selected, such that a kit comprising about 96 lens can be used to select a lens for the patient. Central portion 362C of lower surface 362 comprises a central radius of curvature 362C that corresponds to the intended post operative curvature of the stroma and/or Bowman's membrane. A circumscribing boundary 362B, for example an annular boundary, extends around central portion 362C along peripheral portion 362P.

Therapeutic lens 350 can be molded in situ on the cornea with the mold comprising therapeutic lens 360 position over the cornea. Peripheral portion 362P is aligned with the unablated periphery of the epithelium. Central portion 362C is aligned with ablated profile 20. Filler material 330 is configured to form tie layer 340. Tie layer 340 comprises a lower surface 342 configured to adhere to the stromal tissue exposed with ablated profile 20 and Bowman's membrane near boundary 20B. Tie layer 340 comprises an upper surface 344. Upper surface 344 can be configured for removal of the mold comprising therapeutic lens 360. In some embodiments, the mold comprising therapeutic lens 360 may comprise a high water content therapeutic lens, a PTFE coating and known low adhesion and/or low friction surfaces, for example a polished surface, such that therapeutic lens 360 can be removed from tie layer 340 when tie layer 340 is adhered to the anterior stroma and/or Bowman's membrane that defines ablated profile 360.

Figure 3C:
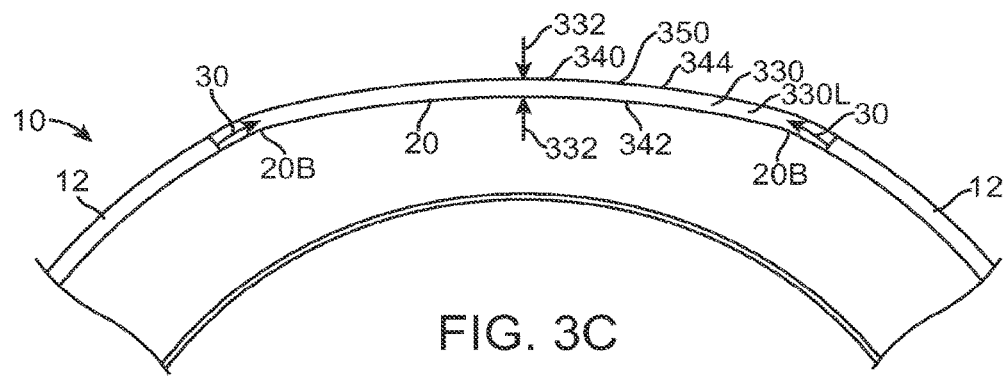
FIG. 3C shows a therapeutic lens comprising the cured filler material as in FIGS. 3A and 3B.

FIG. 3C shows therapeutic lens 350 comprising tie layer 340 with the mold comprising therapeutic lens 360 removed. Therapeutic lens 350 may comprises a thickness 332 for optical smoothing, to inhibit or minimize water transport into the cornea and to protect tissue the anterior stroma and/or Bowman's membrane, as described above. Tie layer 340 may comprise materials and thicknesses as described above.

Figure 3D:
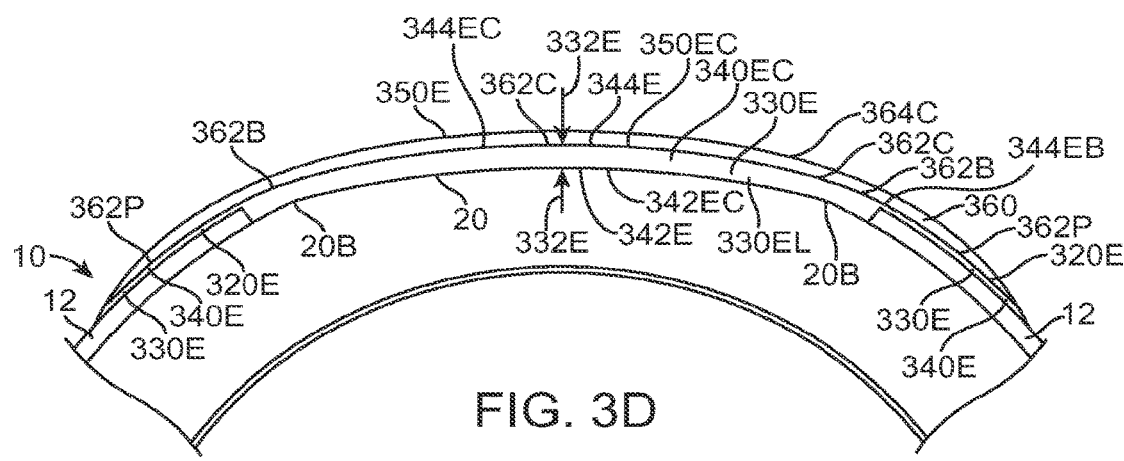
FIG. 3D shows molding of the therapeutic lens with a lie layer formed over the epithelial layer, according to embodiments of the present invention.

FIG. 3D shows molding of the therapeutic lens 350E with a tie layer 340E comprising a flap 320E formed over the epithelial layer. Lens 350E can be formed with the mold comprising therapeutic lens 360. Filler material 330E, similar to material 330, can be applied over the peripheral epithelium as described above. The mold comprising therapeutic lens 360 can be positioned over the filler material, such that filler material 330E is disposed over the intact epithelium 12. Filler material 330E can be cured to form tie layer 340E comprising flap 320E. The layer 340E comprises a lower surface 342E, or posterior surface, an upper surface 344E, or anterior surface. Lower surface 342E comprises a peripheral portion 342EP and a central portion 342EC. Upper surface 344E comprises a peripheral portion 344EP and a central portion 344EC. A circumscribing boundary 344EB extends around central portion 344EC between the central portion and peripheral portion. Central lower surface 342EC is adhered to the anterior stroma and/or Bowman's having ablated profile 20. The central upper surface may comprise an anterior optical surface as described above. Thickness 332E is sufficient to provide optical smoothing, minimize water transport from the tear to the stroma and protect the stroma and/or Bowman's membrane as described above.

Filler material 330E can be cured to form tie layer 340E, as described above. Tie layer 340E comprises a lower surface 342E, or posterior surface, and an upper surface 344E, or anterior surface. Lower surface 342E is adhered to the stroma and or Bowman's along ablated profile 20. This adherence of tie layer 340E can allows to layer 340E to remain on the cornea when the epithelium regenerates, so as to provide a therapeutic barrier, a therapeutic optical surface and decreased pain, as described above.

Figure 3E:
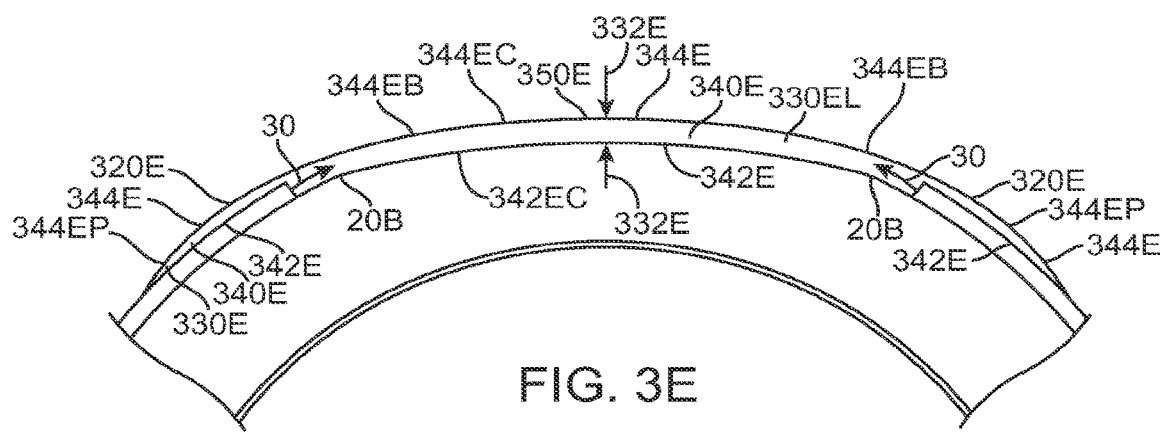
FIG. 3E shows a cured therapeutic lens molded over the corneal epithelium and the stroma.

FIG. 3E shows therapeutic lens 350E with the mold comprising therapeutic lens 360 removed. The epithelium can grow under flap 320E with centripetal advancement of the epithelium as described above.

In situ molding on the cornea may comprise the steps of placing a filler material on the cornea, placing a mold on the cornea, curing the filler material to form a tie layer, and removing the mold. In situ molding is described in U.S. Pat. Nos. 5,163,596 and 6,055,990 in the name of Thompson, U.S. Pat. No. 4,983,181; 4,994,081 5,114,627; and 5,213, 720 in the name of Civerchia, the disclosures of which may be suitable for combination in accordance with some embodiments of the present invention described herein. The filler material cured to form the tie layer may be ablated. U.S. Pat. Nos. 4,923,467; 5,156,622; 5,196,027 and 6,702, 807 describe ablation, the disclosures of which may be suitable for combination in accordance with some embodiments of the present invention described herein.

Figure 3F:
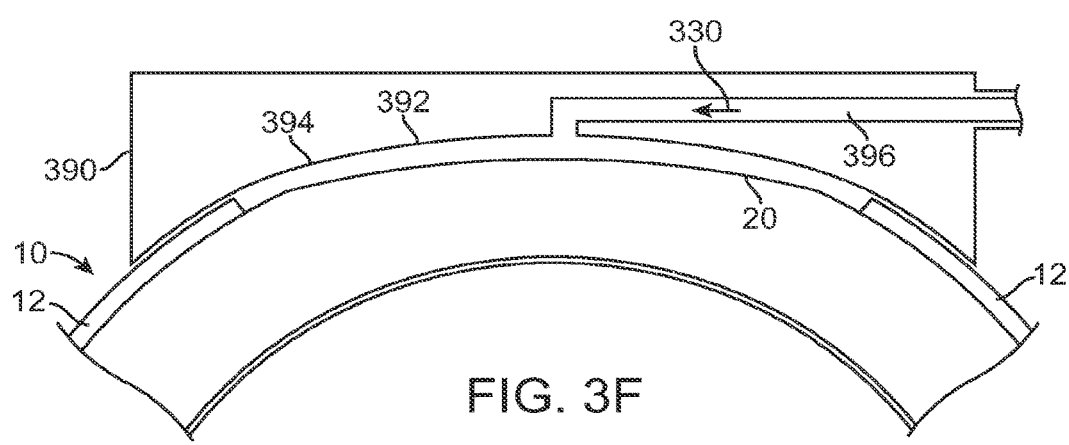
FIG. 3F shows a mold with channels to inject the therapeutic filler material and form the therapeutic lens in situ, according to embodiments of the present invention.

FIG. 3F shows a mold 390 with at least one channel 396 to inject the therapeutic filler material 330 and form the therapeutic lens in situ. Lens 392 may comprise a therapeutic lens shaping surface 392. Surface 392 may comprise a non-adhesive and/or low friction coating, as described above. Although at least one channel 396 is shown to inject material centrally, the at least one channel may be disposed to inject material peripherally, and may comprise multiple channels.

Figure 4A:
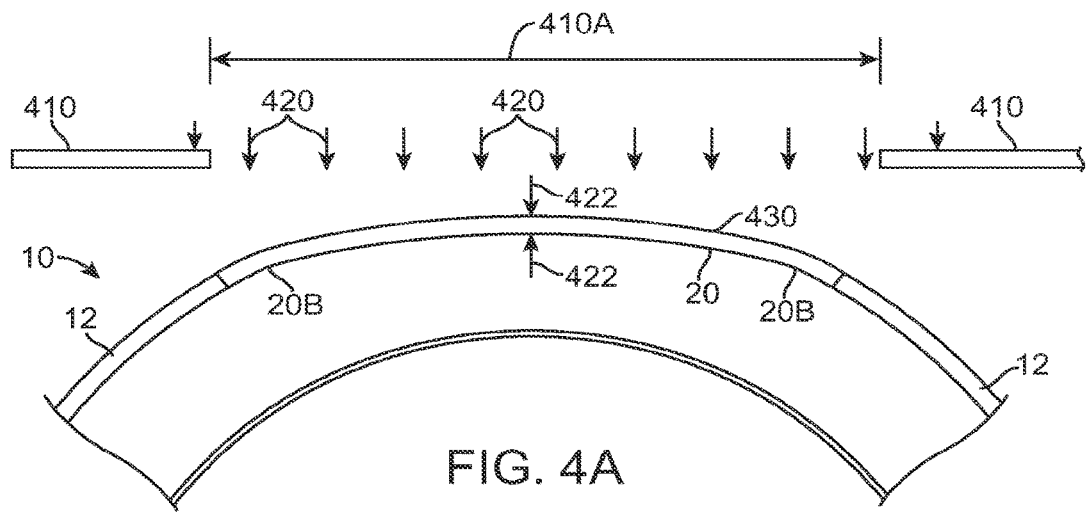
FIG. 4A shows application of a therapeutic filler material to an eye, according to embodiments of the present invention.

FIG. 4A shows application of a therapeutic filler material 430 to an eye with an aperture 410A disposed in a blocking material 410 so as to form a protective coating to the eye while the epithelium regenerates. Filler material 430 may comprise the filler material, as described above. Aperture 410A can be shaped so as to apply filler material 430 to the eye over the exposed corneal surface and/or Bowman's membrane. Filler material 430 can be applied to the eye in many ways with aperture 410 disposed between the cornea and source of aerosol, for example with an aerosol spray 420 comprising small particles directed toward the anterior exposed surface of cornea 10. Although an aerosol spray is shown, filler material 430 can be applied in many ways, as described above. Filler material 430 may comprise a two component system, as described above. Filler material 430 can be applied over ablated profile 20 so as to inhibit or minimize deposition on the epithelium. In some embodiments, filler material 430 can be applied over the epithelium, for example to form a flap as described above.

Figure 4B:
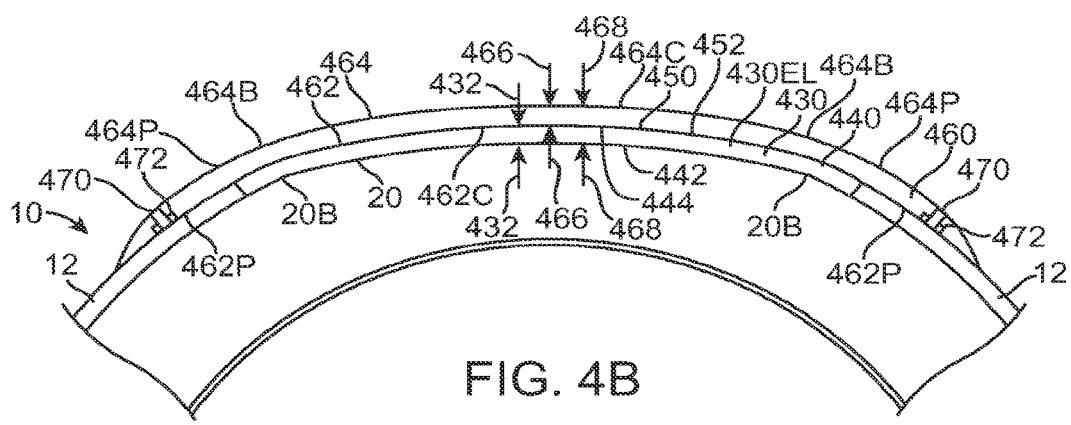
FIG. 4B shows molding the filler material as in FIG. 4A with a therapeutic lens to form a therapeutic lens in situ on the cornea.

FIG. 4B shows molding filler material 430 as in FIG. 4A with a mold comprising a therapeutic lens 460 to form a layer 430L of therapeutic material 430. Layer 430L comprises a thickness 532. Layer 430L may comprise a therapeutic lens 450 formed in situ on the cornea. Therapeutic lens 460 may comprise known therapeutic lens materials such as low water content silicone material, for example about 25% water content, high water content silicone material, for example about 25% water content, polymethylmethacrylate (hereinafter "PMMA"), hydrogel material, and a hard therapeutic lens material such as PMMA. The therapeutic lens comprising a hard lens material may reduce lens pressure on the wound, for example when the patient blinks. Therapeutic lens 460 comprises a lower surface 462, or posterior surface, and an upper surface 464, or posterior surface. Lens 460 comprises a thickness 466. Upper surface 464 comprises a central portion 464C over the ablated profile 20 and a peripheral portion 464P. A boundary 464B extends around central portion 464C between the central portion and peripheral portion 464P. Upper surface 464 comprises an anterior surface of the therapeutic lens and can be separated from the ablated surface with ablated profile 20 with a distance 468. Central portion 464C comprises a radius of curvature that corresponds to the radius of curvature of ablated profile 20 of the stroma so as to provide optical correction for the patient. Lower surface 462 can be shaped to fit on the cornea and form therapeutic lens 450 with a desired shape. Lower surface 462 comprises a peripheral portion 462P shaped to fit over the unablated cornea, for example with a radius of curvature that corresponds to the radius of curvature of the cornea, as described above. Lower surface 462 comprises a central portion 462C that may be shaped to correspond to the ablated profile 20, for example with a radius of curvature that corresponds to the intended post ablation curvature of the cornea such as live intended curvature of ablated profile 20, as described above. With wavefront ablations that ablate a wavefront shape on the eye, the curvature of the wavefront lens can correspond to the lower order corrections of the wavefront ablated profile such as sphere and/or cylinder.

Filler material 430 can be cured to form tie layer 440, as described above. Tie layer 440 comprises a lower surface 442, or posterior surface, and an upper surface 444, or anterior surface. Lower surface 442 is adhered to the stroma and or Bowman's along ablated profile 20. This adherence of tie layer 440 can allow layer 440 to remain on the cornea when the epithelium regenerates, so as to provide a therapeutic barrier, a therapeutic optical surface and/or protection of nerve fibers and the stroma and/or Bowman's membrane as described above.

Therapeutic lens 460 may comprise peripheral structures to adhere the therapeutic lens to the epithelium. The peripheral structures may comprise many shapes including apertures 470 to apply an adhesive to the epithelium through the aperture of the lens. The peripheral structures may comprise a circumferential annular channel 472 in fluid communication with the apertures, so as allows the adhesive to spread around the periphery of the therapeutic lens. This spreading of the adhesive can provide improved adhesion of the adhesive to therapeutic lens 460 and improved adhesion of the adhesive material to the cornea. Therapeutic lens 460 may comprise additional structures to adhere the lens to the adhesive to the lens, for example roughening of the lens with serrations, castellation, and the like.

Figure 4C:
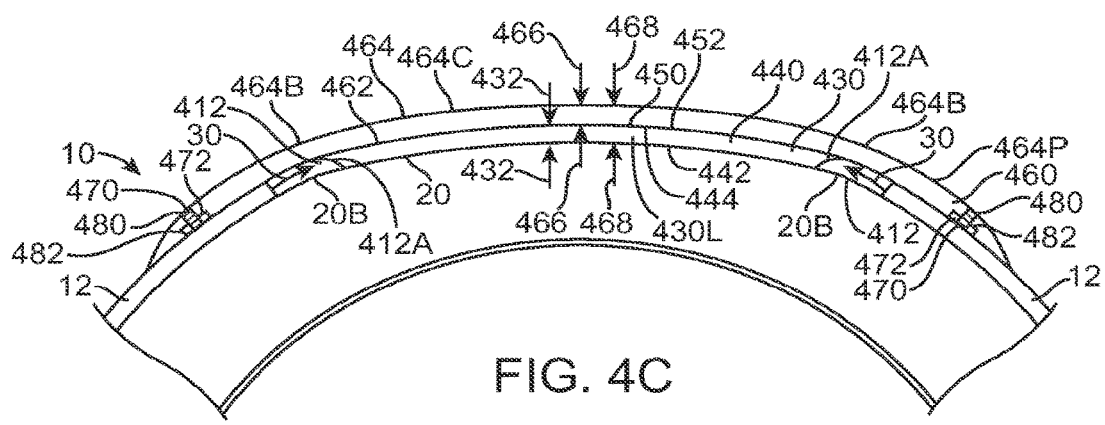
FIG. 4C shows a therapeutic lens comprising the cured filler material as in FIGS. 4A and 4B, with peripheral adhesion of the therapeutic lens to the epithelium.

FIG. 4C shows a therapeutic lens comprising the cured filler material and therapeutic lens as in FIGS. 4A and 4B, with peripheral adhesion of the therapeutic lens to the epithelium. Filler material 430 can comprise filler material as described above and can be cured to form the tie layer as described above. An adhesive 480 is disposed in aperture 470. Adhesive 480 comprises a portion 482 that extends into channel 472 to adhere to the epithelium and/or lens 560. Adhesive 480 may comprise the adhesives and/or tie layer materials described above, or acrylates, such as cyanoacrylate. Adhesive 480 may comprise at least one of a synthetic adhesive, a biologically derived adhesive, a hybrid adhesive or a recombinant adhesive, as described herein.

Therapeutic lens 460 may comprise a therapeutic agent. The therapeutic agent may comprise at least one of an analgesic, an anti-inflammatory, an antibiotic, a non-steroidal anti-inflammatory, a steroid or an epithelial growth factor to enhance epithelialization. The analgesic may comprise at least one of gabapentin, proparacaine, lidocaine, or tetracaine or a derivative thereof. The antibiotic may comprise tobramycin or a derivative thereof. The non-steroidal anti-inflammatory may comprises at least one of diclofenac, nepafenac, or suprofen or a derivative thereof. The steroid may comprise at least one of fluorometholone, dexamethasone or prednisolone or a derivative thereof. The growth factor may comprise at least one of fibroblast growth factor, fibronectin, or arginine glycine aspartic acid (RGD) comprising peptide sequence or a derivative thereof.

In some embodiments, an analgesic therapeutic agent may comprise an anesthetic therapeutic agent configured for delivery to the cornea at an amount so as to have an analgesic effect and reduce pain, for example without numbing the cornea.

Regenerated epithelium 412 under therapeutic lens 460 can displace cured therapeutic filler material 430 comprising the tie layer disposed under the therapeutic lens. The regenerated epithelium 412 advances centripetally with a leading edge 412A that displaces the cured therapeutic filler material. The therapeutic lens may comprise channels to pass, for example to extrude, the therapeutic filler material from under the therapeutic lens. The therapeutic lens can be removed when the epithelium is substantially regenerated or may be released from the cornea. Work in relation to embodiments of the present invention suggests that the epithelium regenerates naturally such that an adhesive applied to the epithelium may slough off in about one day to one week. The therapeutic lens may separate from the adhesive so as to release the therapeutic lens from the cornea, for example with therapeutic lenses having a water content from about 20% to about 80%.

Figure 5A:
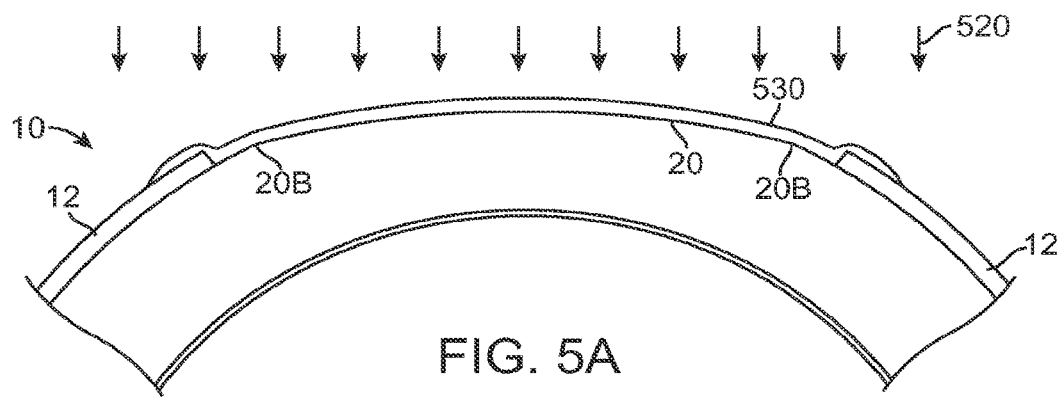
FIG. 5A shows application of a therapeutic filler material to an eye, according to embodiments of the present invention.

FIG. 5A shows application of a therapeutic filler material 530 to an eye. Filler material 530 can be applied to the eye in many ways, for example with an aperture as described above. An aerosol spray 520 comprising small particles directed toward the anterior exposed surface of cornea 10. Although an aerosol spray is shown, filler material 530 can be applied in many ways, as described above. Filler material 530 may comprise the filler materials as described above, for example a two part system. Filler material 530 can be applied over ablated profile 20 so as to inhibit or minimize deposition on the epithelium. In some embodiments, filler material 530 may be applied over the epithelium, as described above.

Figure 5B:
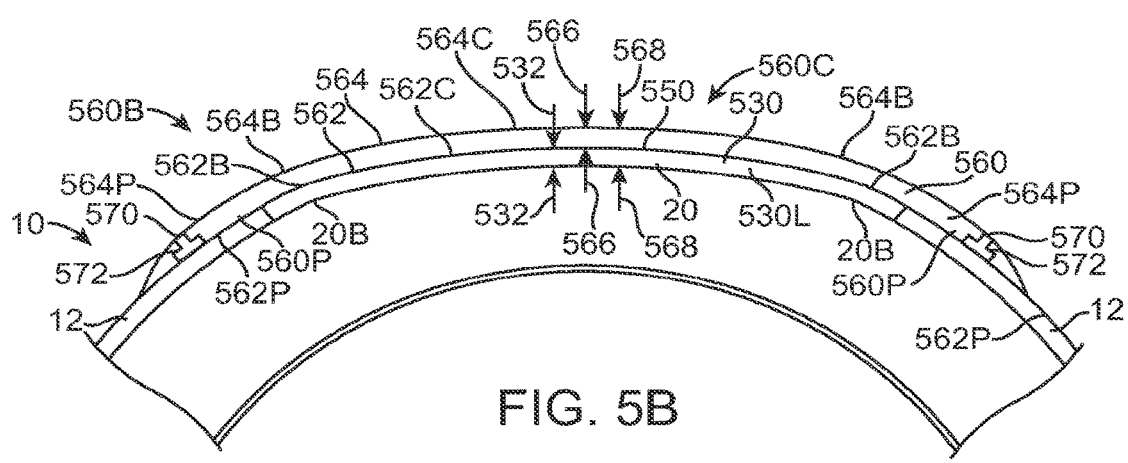
FIG. 5B shows retention of the filler material as in FIG. 5A with a therapeutic lens to provide a therapeutic lens shaped in situ on the cornea.

FIG. 5B shows a therapeutic lens comprising a therapeutic lens 560 and a layer 530L of a therapeutic filler material 530. Filler material 530 can be retained with a therapeutic lens 560. The therapeutic lens may comprise therapeutic lens 560 and therapeutic layer 530L. Layer 530L comprises a thickness 532. Layer 530L may be shaped in situ to form a therapeutic lens 550 shaped in situ on the cornea. Lens 560 comprises a lower surface 562, or posterior surface, and an upper surface 564, or anterior surface. Lens 560 comprises a thickness 566. Upper surface 564 comprises a central portion 564C over the ablated profile 20 and a peripheral portion 564P. A boundary 564B extends around central portion 564C between the central portion and peripheral portion 564P. Upper surface 564 can be separated from the ablated surface with ablated profile 20 with a distance 568. Upper surface 564 comprises an anterior surface of the therapeutic lens and can be separated from the ablated surface with ablated profile 20 with a distance 568. Central portion 564C comprises a radius of curvature that corresponds to the radius of curvature of ablated profile 20 of the stroma so as to provide optical correction for the patient. Lower surface 562 can be shaped to fit on the cornea and form therapeutic lens 550 with a desired shape as described above. Lower surface 562 comprises a peripheral portion 562P shaped to fit over the unablated cornea, for example with a radius of curvature that corresponds to the radius of curvature of the cornea as described above. Lower surface 562 comprises a central portion 562C that may be shaped to correspond to the ablated profile 20, for example with a radius of curvature that corresponds to the intended post ablation curvature of the cornea such as the intended curvature of ablated profile 20. With wavefront ablations that ablate a wavefront shape on the eye, the curvature of the ablated profile in the stroma and/or Bowman's can correspond to the lower order corrections of the wavefront ablation such as sphere and cylinder.

Therapeutic lens 560 may comprise peripheral structures to adhere the therapeutic lens to the epithelium. The peripheral structures may comprise many shapes including apertures 570 to apply an adhesive to the epithelium through the aperture of the lens. The peripheral structures may comprise a circumferential annular channel 572 in fluid communication with the apertures, so as to allow the adhesive to spread around the periphery of the therapeutic lens. This spreading of the adhesive can provide improved adhesion of the adhesive to therapeutic lens 560 and improved adhesion of the adhesive material to the cornea. Therapeutic lens 560 may comprise additional structures to adhere the adhesive to the lens, for example roughening of the lens with serrations, castellations, and the like.

Filler material 530 may comprise many materials having an index of refraction and barrier properties that minimize water transport from the tear, and protect the cornea as described above. In addition to or in combination with filler materials that can form a tie layer, as described above, filler material 530 may comprise many therapeutic liquids, many hydrated solid materials, for example gels with low adhesion, and/or visco-elastic materials. A hydrated solid material with low adhesion may comprise hyaluronic acid. Filler material 530 may comprise a sticky-highly viscous low adhesion gel-like solution, for example a muco-adhesive and/or bioadhesive as described in U.S. Pat. Nos. 5,814,329 and 5,942,243 and US Pub No. 2004/0143026. Filler material 530 may comprise a liquid such as a hyperosmotic index matching solution and/or a hydrophobic solution such as silicone oil, dextran sulfate and/or glycerin. Filler material 530 may comprise a viscoelastic hyaluronic acid commercially available as Heal-On™, commercially available from Advanced Medical Optics. Filler material 530 may comprise a pseudoplastic material, in which viscosity decreases with increasing rate of shear, also termed shear thinning. The pseudoplastic material may comprise known pseudoplastic materials, for example complex solutions. Filler material 530 may comprise methylcellulose. The therapeutic lens may comprise many materials, as described above, and may comprise a hard lens material that may reduce, or even minimize, lens pressure on the wound, for example when the patient blinks. A soft lens material may also at least partially reduce pressure on the wound when the patient blinks.

Filler material 530 may be injected under the lens when the lens is positioned and/or adhered to the cornea. In many embodiments, filler material 530 may comprise a viscoelastic or pseudoplastic material that will flow under low shear, for example when the epithelium advances and displaces filler material 530. Such a material may also be retained, for example under the lens when the lens is adhered to the cornea, so as to provide therapeutic relief when the epithelium regenerates.

Filler material 530 may comprise a therapeutic agent. Although many filler materials may be used for delivery of a therapeutic agent, the therapeutic agent be combined with filler material 530 comprising a sticky-highly viscous low adhesion gel-like solution, for example a muco-adhesive and/or bioadhesive as described in U.S. Pat. Nos. 5,814,329 and 5,942,243 and US Pub No. 2004/0143026. The therapeutic agent may comprise at least one of an analgesic, an anti-inflammatory, an antibiotic, a non-steroidal anti-inflammatory, a steroid or an epithelial growth factor to enhance epithelialization. The analgesic may comprise at least one of gabapentin, proparacaine, lidocaine, or tetracaine or a derivative thereof. The antibiotic may comprise tobramycin or a derivative thereof. The non-steroidal anti-inflammatory may comprises at least one of diclofenac, nepafenac, or suprofen or a derivative thereof. The steroid may comprise at least one of fluorometholone, dexamethasone or prednisolone or a derivative thereof. The growth factor may comprise at least one of fibroblast growth factor, fibronectin, or arginine glycine aspartic acid (RGD) comprising peptide sequence or a derivative thereof.

In some embodiments, an analgesic therapeutic agent may comprise an anesthetic therapeutic agent configured for delivery to the cornea at an amount so as to have an analgesic effect and reduce pain, for example without numbing the cornea.

FIG. 5B1 shows detail of therapeutic lens 560 used to form therapeutic layer 530L as in FIG. 5B. Peripheral portion 562P of lower surface 562 comprises a peripheral radius of curvature Rp that corresponds to the pre-operative radius of curvature of the cornea. Central portion 562C of lower surface 562 comprises a central radius of curvature Rc that may correspond to the intended post operative curvature of the cornea. The anterior upper surface 564C may comprise a radius of curvature to correct vision of the patient.

FIG. 5B2 shows a plan view of the therapeutic lens 560 as in FIG. 5B. Therapeutic lens 560 comprises central portion 560C, circumferential annular portion 560P, apertures 570 and circumferential annular channel 572.

FIG. 5B3 shows peripheral apertures 587 through a therapeutic lens 585 to adhere the lens to the periphery of the epithelium with an adhesive, as described above.

FIG. 5B4 shows peripheral apertures 586 through a therapeutic lens 585 to adhere the lens to the periphery of the epithelium, and surface channels 588 on the lower side, or posterior side, of the lens to release material from the under the lens as the epithelial layer migrates centripetally as described above. Work in relation to embodiments of the present invention suggests that the epithelium can displace the therapeutic filler material, for example the tie layer and/or the gel, such that the filler material may pass through the channels as the epithelium advances centripetally.

FIG. 5B5 shows a therapeutic lens comprising a therapeutic lens 590 and a filler material 593. Therapeutic lens 590 can retain a filler material 593 in the shape of a therapeutic layer 594 that may comprise lens 593L. Filler material 593 may comprise filler materials as described above and can be cured to form a tie layer as described above. Therapeutic lens 590 comprises a posterior surface 592 with posterior radius of curvature $R_{post}$ to fit the curvature of the unablated peripheral cornea, as described above. Therapeutic lens 590 comprises an anterior radius of curvature $R_{ant}$ to provide optical correction for the patient, as described above. The anterior radius of curvature may correspond to ablated profile 20 so as to correct patient vision, for example in response to an intended ablation profile. Therapeutic lens 590 may comprise an index of refraction, as described above. Therapeutic layer 594 can smooth irregularities of the cornea to improve patient vision, protect underlying corneal tissue, and filler material 593 may comprise a material that minimizes water transport from the tear, as described above. Therapeutic lens 590 may comprise peripheral structures to adhere the therapeutic lens to the cornea as described above.

Figure 5C:
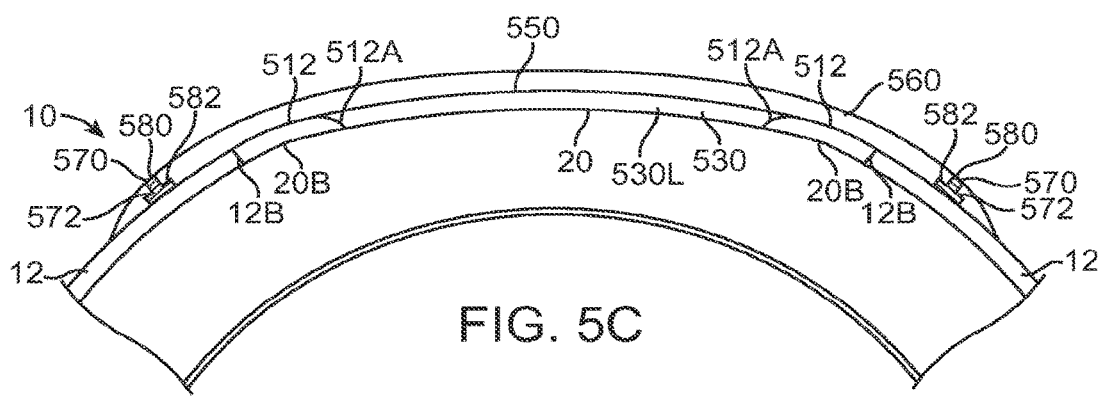
FIG. 5C shows epithelial regeneration under the therapeutic lens that displaces the therapeutic filler material under the therapeutic lens.

FIG. 5C shows regenerated epithelium 512 under therapeutic lens 560 that displaces therapeutic filler material 530 disposed under the therapeutic lens. The regenerated epithelium 512 advances centripetally with a leading edge 512 A that displaces the therapeutic filler material as described above. As described above, the therapeutic lens may comprise channels to pass, for example to extrude, the therapeutic filler material from under the therapeutic lens.

The therapeutic lens comprising the cured filler material as in FIGS. 5A and 5B, can include peripheral adhesion of the therapeutic lens to the epithelium. An adhesive 580 can be disposed in aperture 580. Adhesive 580 comprises a portion 582 that extends into channel 572 to adhere to the epithelium and/or lens 560. Adhesive 580 may comprise an adhesive as described above.

Figure 6A:
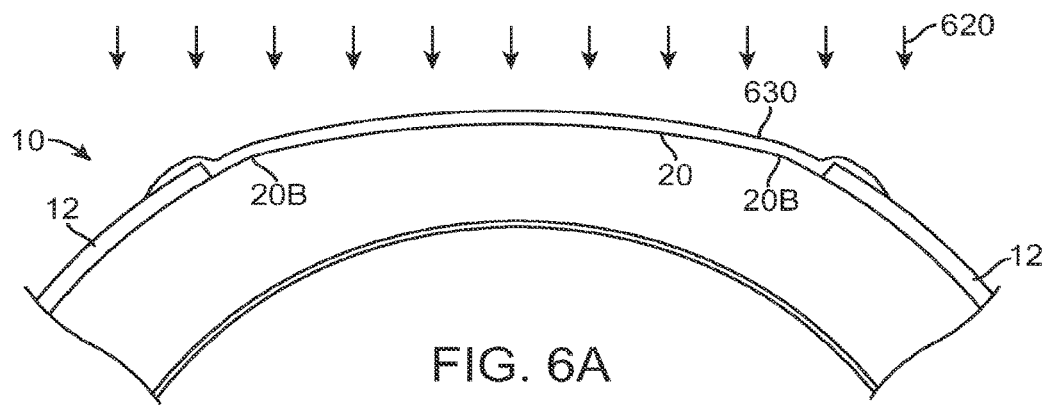
FIG. 6A shows application of a therapeutic filler material to an eye, according to embodiments of the present invention.

FIG. 6A shows application of a therapeutic filler material 630 to an eye. Filler material 630 can be applied to the eye in many ways, for example with an aperture as described above. An aerosol spray 620 comprising small particles directed toward the anterior exposed surface of cornea 10. Although an aerosol spray is shown, filler material 630 can be applied in many ways as described above. Filler material 630 may comprise a filler material as described above, which can be cured to form a tie layer, as described above, for example a two part adhesive, as described above. Filler material 630 can be applied over ablated profile 20 so as to inhibit or minimize deposition on the epithelium as described above. In some embodiments, filler material 630 may be applied over the epithelium, as described above.

Figure 6B:
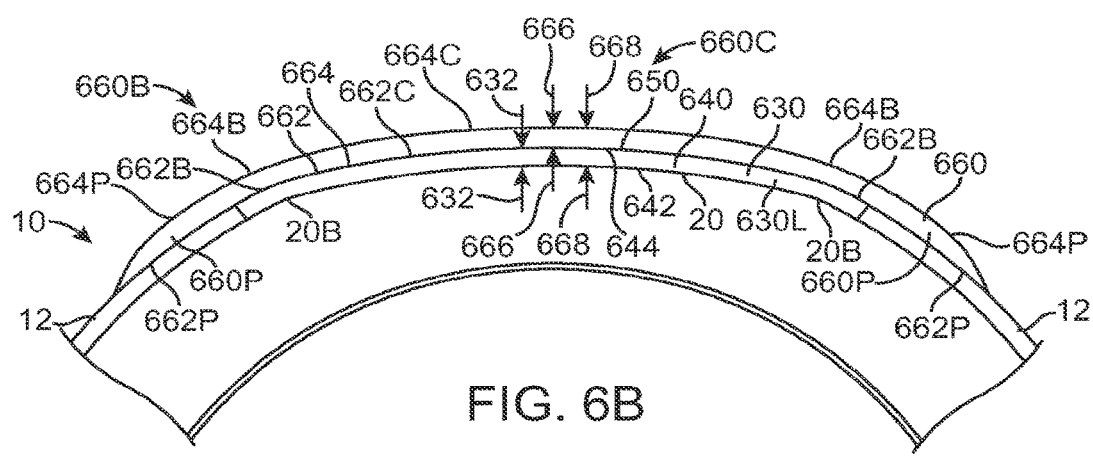
FIG. 6B shows molding the filler material as in FIG. 6A with a therapeutic lens to form a therapeutic lens in situ on the cornea.

FIG. 6B shows a therapeutic lens comprising a therapeutic lens 660 and a layer 630L of filler material 630 cured to form a tie layer 640. Layer 630L comprises a thickness 632. Filler material 630 may comprise a filler material as described above. Therapeutic lens 660 may comprise therapeutic lens material as described above. A mold comprising therapeutic lens 660 may form a therapeutic lens 650 in situ on the cornea. Lens 660 comprises a lower surface 662, or posterior surface, and an upper surface 664, or anterior surface. Lens 660 comprises a thickness 666. Upper surface 664 comprises a central portion 664C over the ablated profile 20 and a peripheral portion 664P. A boundary 664B extends around central portion 664C between the central portion and peripheral portion 664P. Upper surface 664 can be separated from the ablated surface with ablated profile 20 with a distance 668. Upper surface 464 comprises an anterior surface of the therapeutic lens. Central portion 664C comprises a radius of curvature that corresponds to the radius of curvature of ablated profile 20 of the stroma so as to provide optical correction for the patient. Lower surface 662 can be shaped to fit on the cornea and form therapeutic lens 650 with a desired shape. Lower surface 662 comprises a peripheral portion 662P shaped to fit over the unablated cornea, for example with a radius of curvature that corresponds to the radius of curvature of the cornea. Lower surface 662 comprises a central portion 662C that may be shaped to correspond to the ablated profile 20, for example with a radius of curvature that corresponds to the intended post ablation curvature of the cornea such as the intended curvature of ablated profile 20. With wavefront ablations that ablate a complex shape on the eye, the curvature of the complex lens can correspond to the lower order corrections of the wavefront ablation such as sphere, cylinder and axis.

Filler material 630 can be cured to form tie layer 640. Tie layer 640 comprises a lower surface 642, or posterior surface, and an upper surface 644, or anterior surface. Lower surface 642 is adhered to the stroma and or Bowman's along ablated profile 20. Upper surface 644 of tie layer 640 is adhered to the lower surface 662 of therapeutic lens 660. This adherence of tie layer 640 can allows tie layer 640 to remain on the cornea when the epithelium regenerates, so as to provide a therapeutic barrier and therapeutic optical surface as described above.

Figure 6C:
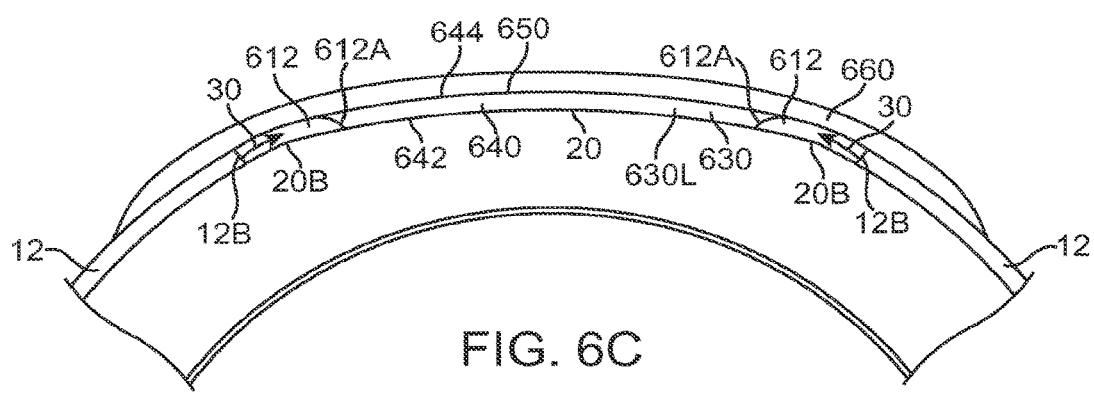
FIG. 6C shows the therapeutic lens comprising the cured filler material as in FIGS. 6A and 6B, with therapeutic lens and adhered to the cornea with the cured filler material.

FIG. 6C shows the therapeutic lens with regenerated epithelium 612 disposed under therapeutic lens 660, such that regenerated epithelium 612 displaces therapeutic filler material 630 disposed under the therapeutic lens. The regenerated epithelium 612 advances centripetally with a leading edge 612A that displaces the cured therapeutic filler material comprising tie layer 640. As described above, the therapeutic lens may comprise channels to pass, for example to extrude, the cured therapeutic filler material from under the therapeutic lens, for example radially extending surface channels on the disposed on the lower surface as described above with reference to FIG. 5B4.

Figure 7A:
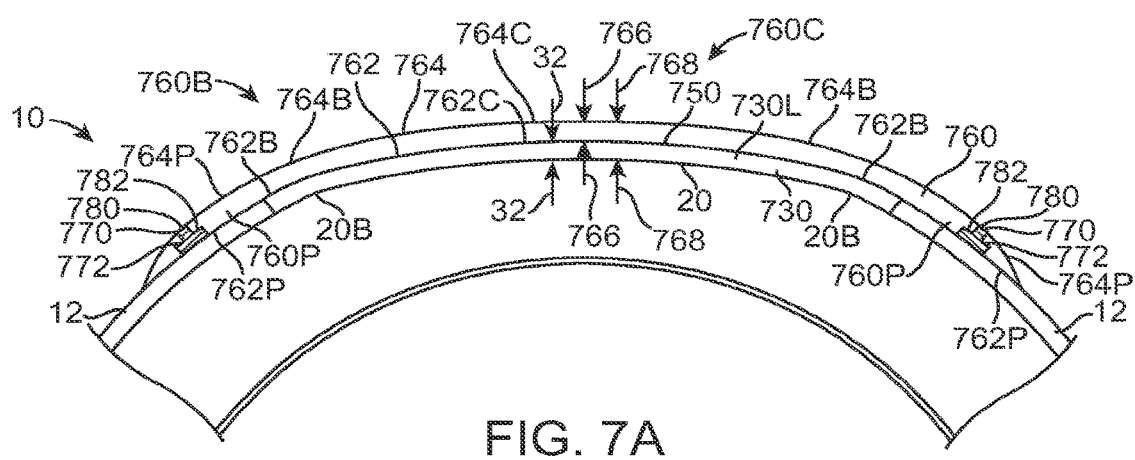
FIG. 7A shows a therapeutic lens adhered to the corneal epithelium with a liquid disposed between the cornea and the therapeutic lens.

FIG. 7A shows a therapeutic lens comprising a therapeutic lens 760 adhered to the corneal epithelium with a tear liquid 730 disposed between the cornea and the therapeutic lens. Work in relation to embodiments of the present invention suggest that adhering the therapeutic lens to the cornea can reduce motion of the leas so as to inhibit or minimize sliding of the lens over the corneal tissues, so as to provide improved epithelial healing and/or decreased pain to the patient. The therapeutic lens may comprise many therapeutic lens materials as described above, and may comprise a hard lens material, for example PMMA, so as to reduce lens pressure on the wound, for example when the patient blinks. Lens 760 comprises a lower surface 762, or posterior surface, and an upper surface 764, or posterior surface, lens 760 comprises a thickness 766. Upper surface 764 comprises a central portion 764C over the ablated profile 20 and a peripheral portion 764P. A boundary 764B extends around central portion 764C between the central portion and peripheral portion 764P. Upper surface 564 comprises an anterior surface of the therapeutic lens. Upper surface 764 can be separated from the ablated surface with ablated profile 20 with a distance 768. Central portion 764C may comprises a radius of curvature that corresponds to the radius of curvature of ablated profile 20 of the stroma so as to provide optical correction for the patient. Central portion 764C may comprises a radius of curvature that corresponds to the radius of curvature of the intended ablated profile of the stroma so as to provide optical correction for the patient. Lower surface 762 can be shaped to fit on the cornea and form therapeutic lens 750 with a desired shape. Lower surface 762 comprises a peripheral portion 762P shaped to fit over the unablated cornea, for example with a radius of curvature that corresponds to the radius of curvature of the cornea. Lower surface 762 comprises a central portion 762C that may be shaped to correspond to the ablated profile 20, for example with a radius of curvature that corresponds to the intended post ablation curvature of the cornea such as the intended curvature of ablated profile 20. With wavefront ablations that ablate a complex shape on the eye, the curvature of the wavefront ablated profile can correspond to the lower order corrections of the wavefront ablation such as sphere and cylinder.

Therapeutic lens 760 may comprise peripheral structures to adhere the therapeutic lens to the epithelium. The peripheral structures may comprise many shapes including apertures 770 to apply an adhesive to the epithelium through the aperture of the lens. The peripheral structures may comprise a circumferential annular channel 782 in fluid communication with the apertures, so as to allow the adhesive to spread around the periphery of the therapeutic lens. This spreading of the adhesive can provide improved adhesion of the adhesive to therapeutic lens 760 and improved adhesion of the adhesive material to the cornea. Therapeutic lens 760 may comprise additional structures to adhere the lens to the adhesive to the lens, for example roughening of the lens with serrations, castellation, and as described above.

Figure 7B:
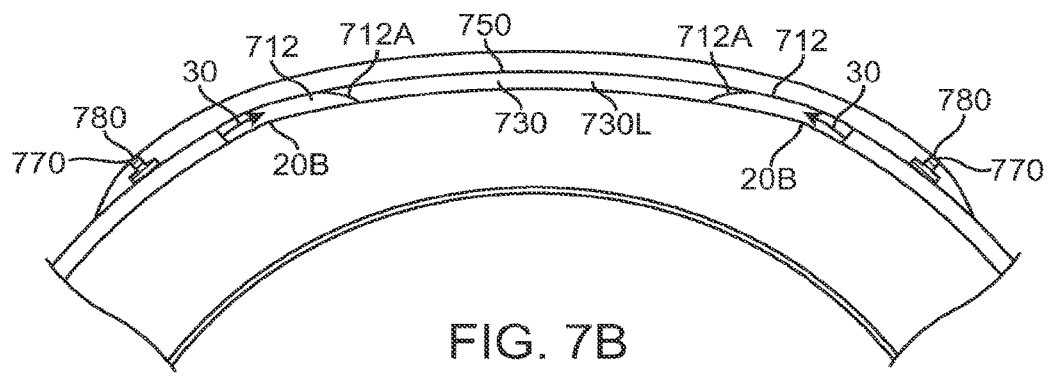
FIG. 7B shows epithelial regeneration with centripetal advancement under the therapeutic lens adhered to the cornea.

FIG. 7B shows regenerated epithelium 712 under therapeutic lens 760 that displaces therapeutic filler material 730 disposed under the therapeutic lens. The regenerated epithelium 712 advances centripetally with a leading edge 712A that displaces the therapeutic filler material. As described above, the therapeutic lens may comprise channels to pass, for example to extrude, the therapeutic filler material from under the therapeutic lens.

The therapeutic lens can be adhered to the epithelium peripherally with an adhesive 780 disposed in aperture 770. Adhesive 780 may comprises a portion 782 that extends into channel 772 to adhere to the epithelium and/or lens 60. Adhesive 780 may comprise adhesives and/or tie layer materials as described above.

Regenerated epithelium 712 under therapeutic lens 760 can displace tear liquid 730. The regenerated epithelium 712 advances centripetally with a leading edge 712A that displaces the tear liquid. The therapeutic lens may comprise channels to pass, for example to extrude, the tear liquid under the therapeutic lens.

With the molds and therapeutic lens molds described above, the eye can marked at the axis for astigmatism and the therapeutic lens may comprise an indicia to align the therapeutic lens with the mark on the cornea so as to glue the therapeutic lens to the epithelium with axis of patient and the axis of the mold comprising the therapeutic lens aligned.

Figure 8A:
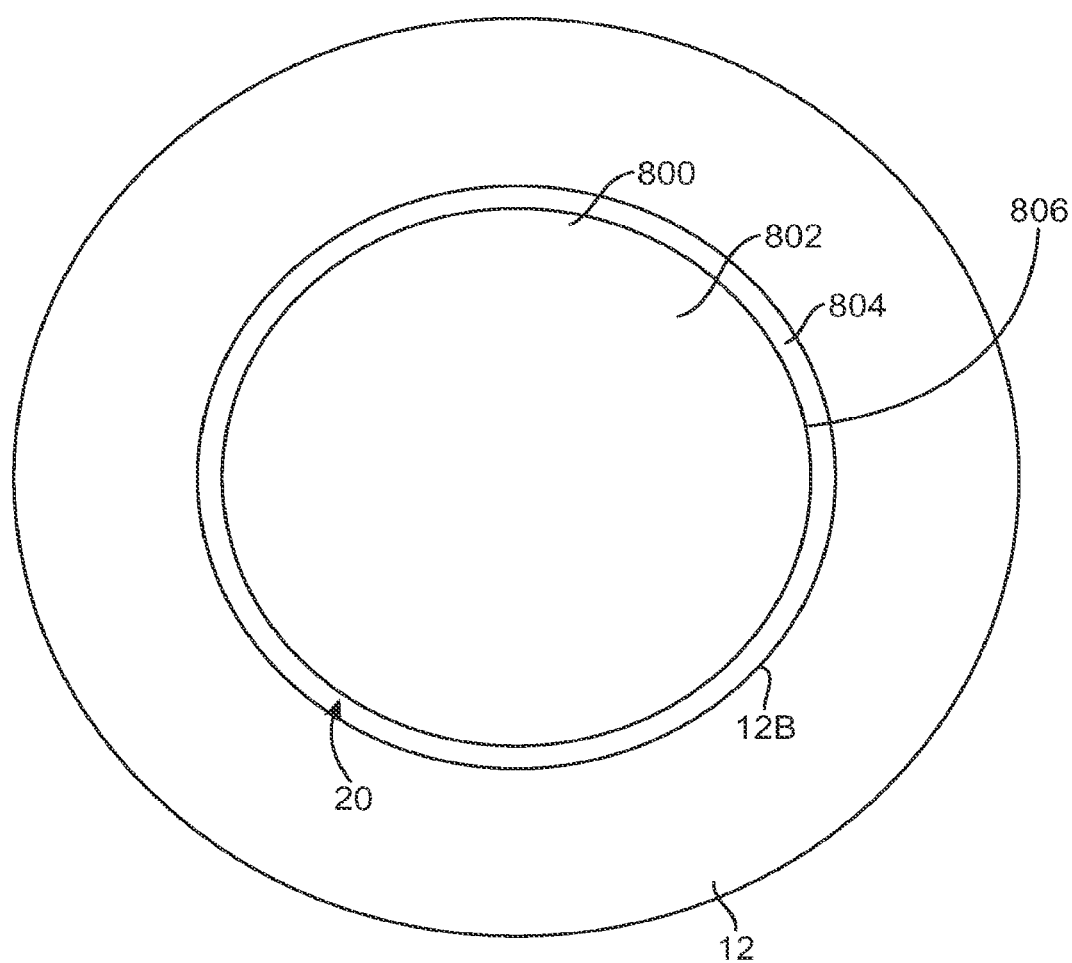
FIG. 8A shows a gap that extends from the peripheral boundary of a layer to the an inner boundary of the epithelium, according to embodiments of the present invention.

FIG. 8A shows a therapeutic covering 800 comprising a layer 802 that defines a gap 804 between the epithelium 12 and the layer that extends from the peripheral boundary of a layer to the an inner boundary of the epithelium 12B. The layer may comprise many of the layers configured to adhere to the stroma and/or Bowman's membrane as described above, and the layer can comprise the properties described above to provide therapeutic benefit such as decreased pain and improved vision. A peripheral boundary can extend circumferentially around the layer. The epithelial defect may comprises an inner boundary such that a gap extends from the peripheral boundary to the inner boundary.

Figure 8B:
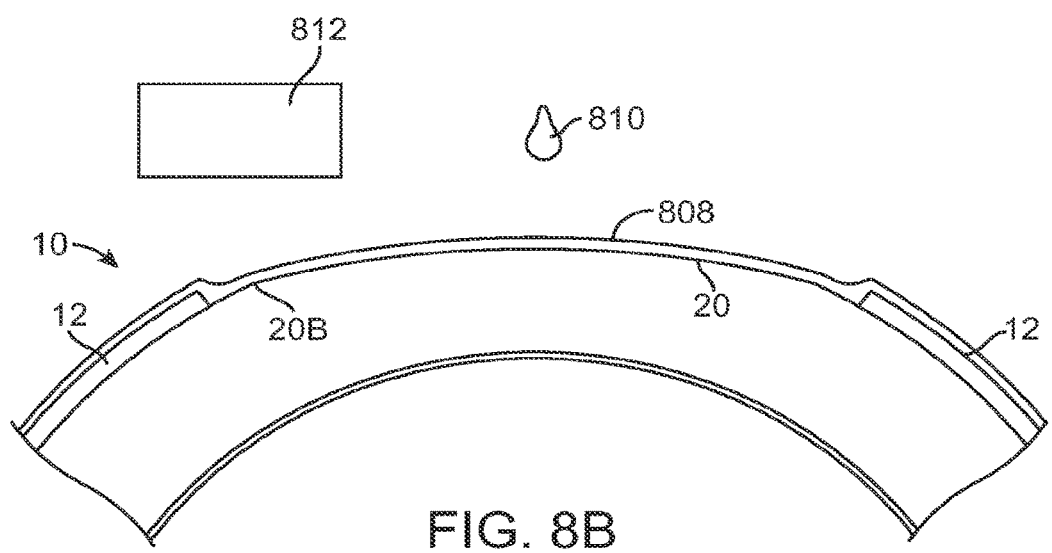
FIG. 8B shows a system and method treating a patient with a therapeutic solution, according to embodiments of the present invention.

FIG. 8B shows a system and method treating a patient. The epithelium 12 can be removed as described above to apply a refractive correction to the eye. A therapeutic layer can be applied to the eye. A drop of therapeutic liquid 810 can be applied from a bottle to the eye so as to form a uniform layer 808 over the ablated stroma 20 and/or Bowman's membrane. Although a drop of liquid is shown, the liquid can be applied to the eye with a spray, as described above. The liquid may comprise a solution with osmotic properties, index of refraction properties and/or analgesic properties as described above. The patient can be followed by a care giver and the therapeutic layer applied in response to pain of the patient at a follow up visit. In some embodiments, the uniform layer may be applied acutely following the refractive correction of the eye. The therapeutic layer may comprise a solution configured to at least one of reduce pain, provide functional vision, restore corneal deturgescence, minimize swelling of the cornea, minimize swelling of the cornea so as to inhibit or minimize light scatter from the cornea, or to inhibit or minimize light scatter from an anterior surface of the stroma and/or Bowman's membrane, and/or promote epithelial regeneration and healing, as described above. The solution may comprise at least one of an osmolarity greater than or equal to an osmolarity of the cornea, a hydrophobic solution, or an index of refraction that matches an index of refraction of the cornea. The solution may comprise at least one of glycerin, silicone oil or dextran sulfate. The solution comprises at least one of glycerin or dextran sulfate.

The therapeutic layer may comprise many therapeutic liquids, many hydrated solid materials, for example gels with low adhesion, and/or visco-elastic materials. A hydrated solid material with low adhesion may comprise hyaluronic acid. The therapeutic layer may comprise a sticky-highly viscous low adhesion gel-like solution, for example a muco-adhesive and/or bioadhesive as described in U.S. Pat. Nos. 5,814,329 and 5,942,243 and US Pub No. 2004/0143026. Filler material 530 may comprise a liquid such as a hyperosmotic index matching solution and/or a hydrophobic solution such as silicone oil, dextran sulfate and/or glycerin.

The therapeutic layer may comprise a therapeutic agent. Although many materials may be used for delivery of a therapeutic agent, the therapeutic agent be combined with filler material comprising a sticky-highly viscous low adhesion gel-like solution, for example a mucoadhesive and/or bioadhesive as described in U.S. Pat. Nos. 5,814,329 and 5,942,243 and US Pub No. 2004/0143026. The therapeutic agent may comprise at least one of an analgesic, an anti-inflammatory, an antibiotic, a non-steroidal anti-inflammatory, a steroid or an epithelial growth factor to enhance epithelialization. The analgesic may comprise at least one of gabapentin, proparacaine, lidocaine, or tetracaine or a derivative thereof. In some embodiments, the analgesic may comprise an anesthetic agent configured for delivery to the cornea at a level so as to have an analgesic effect and reduce pain, for example without numbing the cornea. The antibiotic may comprise tobramycin or a derivative thereof. The non-steroidal anti-inflammatory may comprise at least one of diclofenac, nepafenac, or suprofen or a derivative thereof. The steroid may comprise at least one of fluorometholone, dexamethasone or prednisolone or a derivative thereof. The growth factor may comprise at least one of fibroblast growth factor, fibronectin, or arginine glycine aspartic acid (RGD) comprising peptide sequence or a derivative thereof.

In some embodiments, an analgesic therapeutic agent may comprise an anesthetic therapeutic agent configured for delivery to the cornea at an amount so as to have an analgesic effect and reduce pain, for example without numbing the cornea.

The therapeutic layer described above can be applied by the physician while the patient is followed during re-epithelialization. The physician may prescribe a formulation comprising the therapeutic materials and/or agents such that the patient may apply the therapeutic materials and/or agents as directed by the physician. In some embodiments, the formulation may comprise a muco-adhesive and/or microparticles to deliver the therapeutic agent.

Figure 9A:
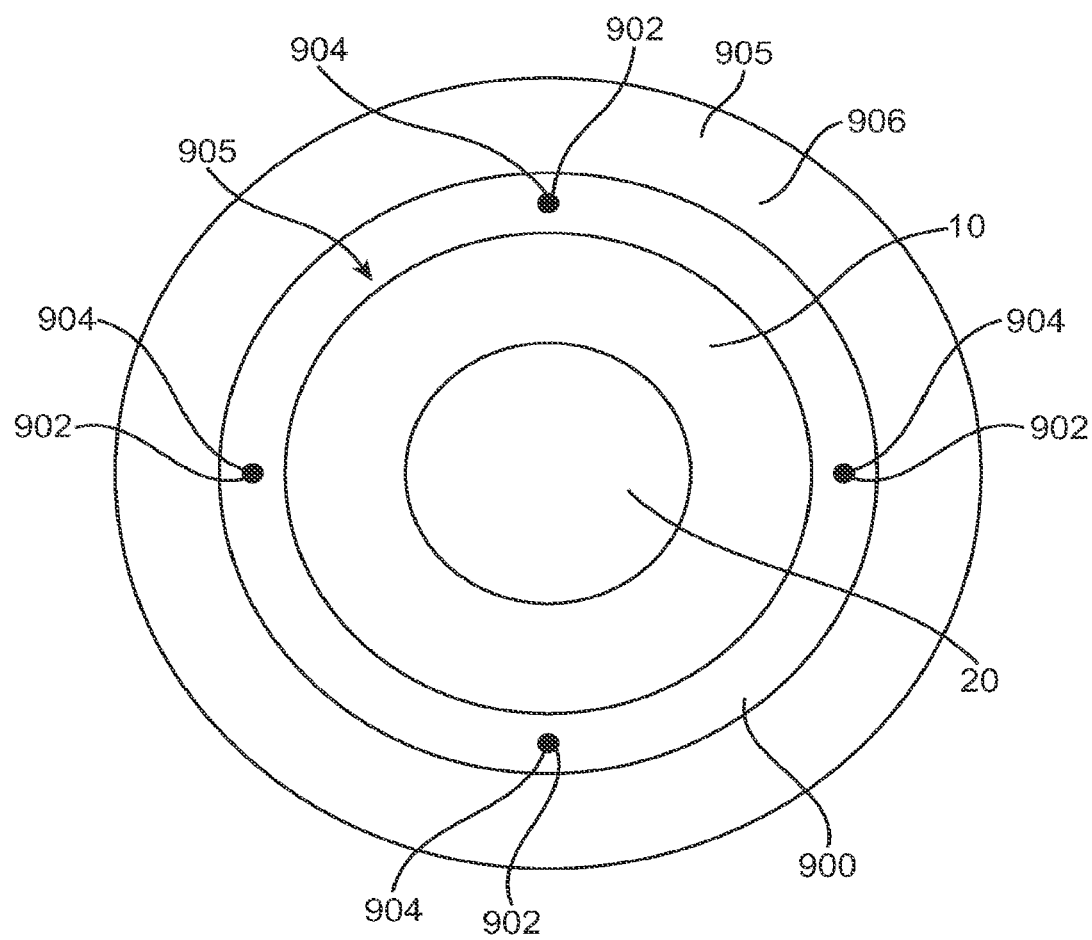
FIG. 9A shows a system and method to treat a cornea of an eye of a patient with a layer adhered to the cornea.

FIG. 9A shows a system and method to treat a cornea of an eye of a patient with a layer adhered to the cornea. The system may comprise a thin uniform layer 900 disposed over the stroma and/or Bowman's of the eye as described above. The system may comprise many of the adhesives and/or materials as described above, for example a thin layer adhered to anterior Bowman's and/or stroma as described above, for example with respect to molding and/or spraying a uniform layer of two part adhesive. The layer comprises material properties so as to protect corneal tissue to decrease pain, swelling, light scatter and increase functional vision as described above. A structure can be disposed away form a center of the lens to adhere the lens to the cornea. The lens can be configured to extend to a conjunctiva of the eye. The structure can be positioned to adhere the lens to the conjunctive. The structure may comprise an aperture 902 through the layer to receive a barb 904 to adhere the hard therapeutic lens to the conjunctiva. In some embodiments, a structure can pierce the layer, for example a barb to extend through the layer and adhere the lens to the conjunctiva 905. The structure may comprise structures including tacks, setae, and/or fibers. The structures to adhere the lens to the conjunctiva may comprise many of the structures described above. The layer may decrease pressure and/or friction on the stroma and/or Bowman's membrane when the eyelid blinks.

Figure 9B:
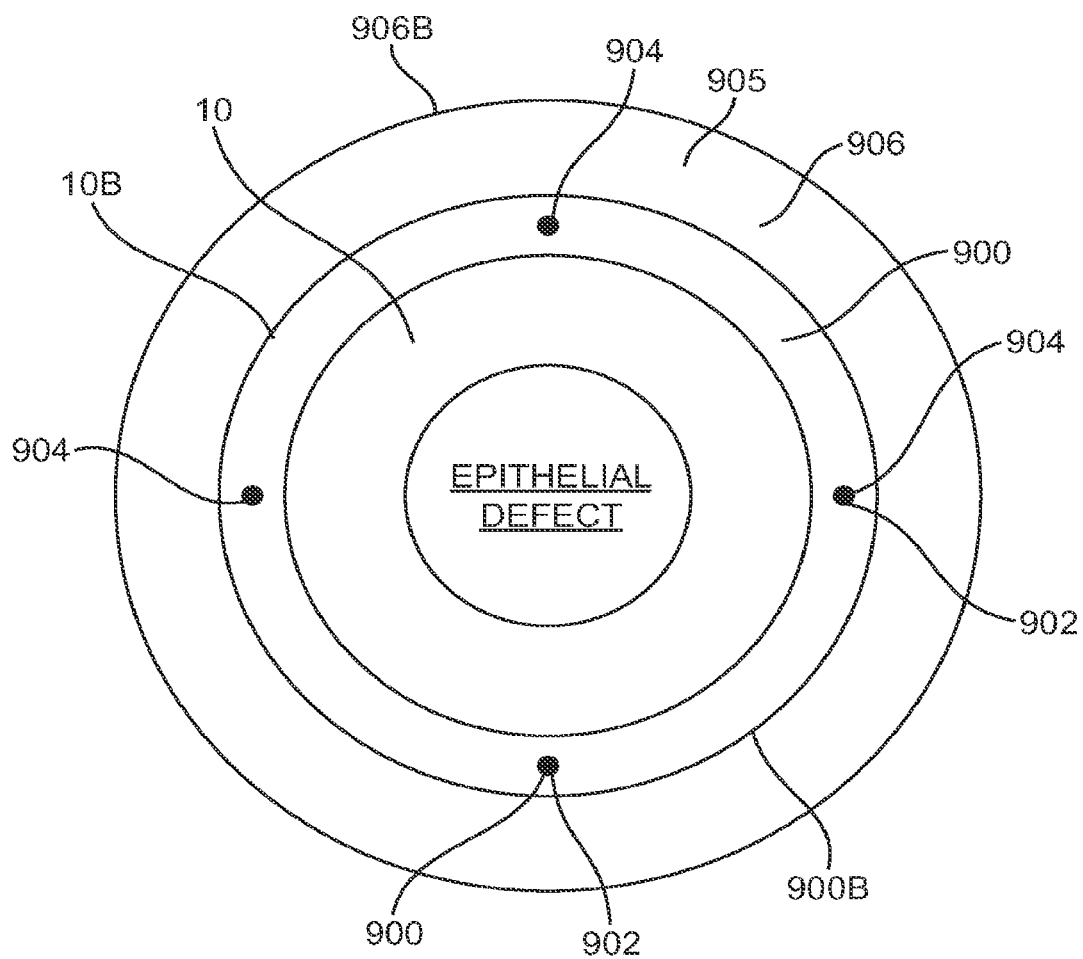
FIG. 9B shows a system and method to treat a cornea of an eye of a patient with a therapeutic lens adhered to the cornea, according to embodiments of the present invention.

FIG. 9B shows a system and method to treat a cornea of an eye of a patient. The system may comprise a hard therapeutic lens 900 disposed over the stroma and/or Bowman's membrane of the eye. The system may comprise many of the therapeutic lenses and materials as described above. The hard therapeutic lens comprises a hard material so as to protect corneal tissue under the lens when the patient blinks. A hard therapeutic lens may minimize pressure on the stroma and/or Bowman's when the eyelid blinks. A structure can be disposed away form a center of the lens to adhere the lens to the cornea. The lens can be configured to extend to a conjunctiva 905 of the eye and wherein the structure is positioned to adhere the lens to the conjunctiva. The structure may comprise an aperture 902 through the hard therapeutic lens to receive a barb 904 to adhere the hard therapeutic lens to the conjunctiva. Although a barb is shown, the aperture can receive other structures to adhere the lens to the conjunctiva including tacks, setae, fibers and/or nanostructures. The structures to adhere the lens to the conjunctive can be affixed to the hard therapeutic lens, for example glued and/or molded into to the hard therapeutic lens.

The nanostructures may comprise many structures, for example protrusions and indentations such as castellation. In some embodiments, the nanostructures may comprise setae and/or fibers with spatulas on the end, so as to increase surface area and provide charge on the nanostructure of the therapeutic layer and/or cornea, for example with Van der Waals forces. Nano structures with adhesive properties suitable for incorporation of embodiments of the present invention are described in U.S. Pat. No. 7,229,685, the disclosure of which may be suitable for combination in accordance with some embodiments of the present invention described herein. Such nano structures can be provided on the therapeutic lens, the tack, the barb and/or the cornea to adhere the therapeutic layer to the cornea. The nanostructures can be disposed on a peripheral portion of the therapeutic layer disposed away from a central vision correcting portion of the therapeutic layer.

Figure 9C:
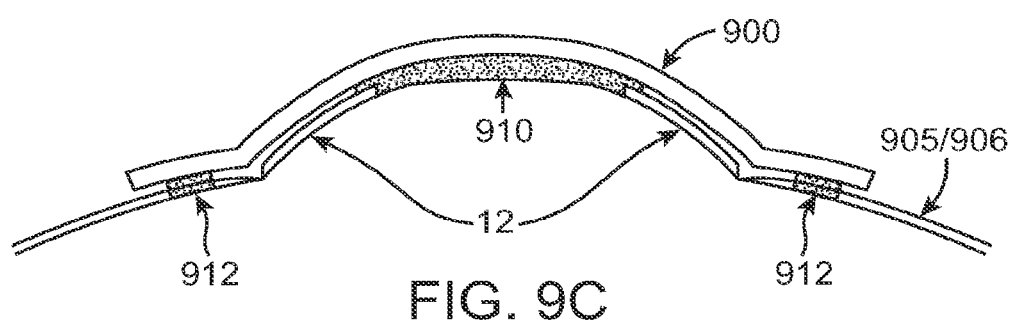
FIGS. 9C and 9D show systems and methods to treat a cornea of an eye of a patient with a therapeutic lens adhered to the conjunctiva of the cornea, according embodiments of the present invention.
Figure 9D:
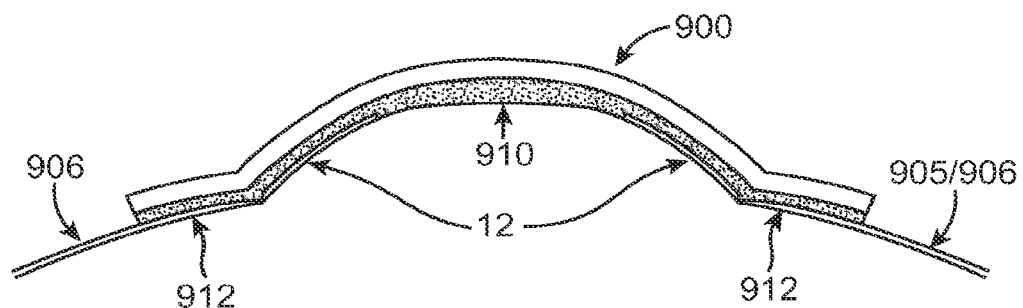

FIGS. 9C and 9D show systems and methods to treat a cornea of an eye of a patient with a therapeutic lens adhered to the conjunctiva 905 of the cornea. The conjunctiva comprises a thin membrane which sits over the sclera 906 of the eye, and the epithelial cells of the conjunctiva do not refresh as quickly such that use of the epithelial cells of the conjunctiva can prolong adhesion of the lens to the eye. A soft and/or a hard therapeutic lens 900 comprises a size, for example a diameter, to extend to the conjunctivas, for example a circumference, such that the lens covers at least, a portion of the conjunctiva, for example circumferentially around the portion of the conjunctiva. The lens can be placed following PRK. An adhesive tie layer 910 can be placed over the operated area, as described above, for example to reduce pain, improve visual acuity, etc. For example, the tie layer can extend over the cornea from conjunctiva to conjunctiva and cover the exposed stroma and/or Bowman's membrane, as shown in FIG. 9D. However, it should be noted that the tie layer may also be smaller than the exposed stroma and/or Bowman's membrane. The tie layer can be disposed in the ablated area and surrounding epithelium and can be disposed annularly around the portion of the conjunctiva 912. The tie layer may comprise a first adhesive over the debrided stroma and/or Bowman's membrane, and a second adhesive disposed over the conjunctiva. The first and second adhesive may comprise the adhesives described herein. For example the first adhesive may comprise fibrin and the second adhesive may comprise cyanoacrylate to adhere the therapeutic lens to the cornea.

The therapeutic lens may comprise a hard therapeutic lens so as to make contact with the cornea so as to allow for adhesion to the tie layer and prevention of fluid, for example tear liquid, introduction into the interface between the lens and cornea and may prevent or decrease subsequent stromal edema. The lens may comprise a lens custom fit to the patient with a first radius of curvature to fit the conjunctiva and a second radius of curvature to fit the cornea so as to inhibit or minimize a gap between the lens and cornea. Work in relation to embodiments of the present invention suggests that known hard scleral lenses may provide a gap between the cornea and hard lens so as to allow fluid to enter the epithelial defect.

Figure 10A:
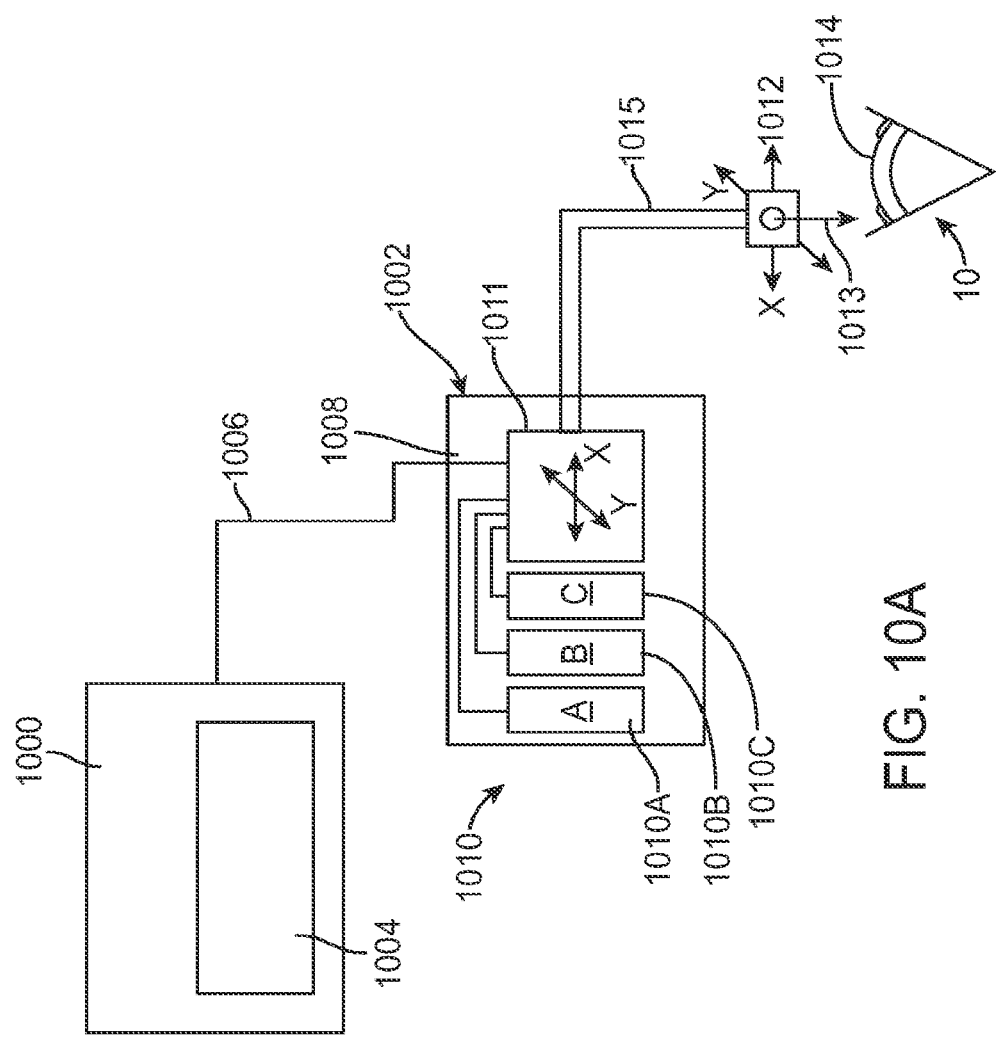
FIG. 10A shows a jet deposition system and process to form a covering comprising a therapeutic layer in situ on an exposed corneal surface, according to embodiments of the present invention.

FIG. 10A shows a jet deposition system and process to form a covering comprising a therapeutic layer in situ on an exposed corneal surface. The system may also be used to form a covering on a substrate for subsequent placement on the Bowman's membrane and/or stroma. The system comprises a processor 1000 and a jet forming device 1002 coupled to the processor to control the jet forming device in response to commands from the processor. The processor may comprise an input device such as a keyboard. Data for the deposition process can be entered with the input device. The processor comprises a tangible medium 1004 with instructions for the processor stored thereon. A control line 1006 may extend from the processor to a jet deposition apparatus 1008, similar to many known ink jet deposition apparatus. The jet deposition apparatus may comprise at least one cartridge, a drive mechanism, and a jet forming structure. The at least one cartridge 1010 may comprise three cartridges for example cartridge A 1010A, cartridge B and cartridge C. Each cartridge may comprise components for forming the therapeutic layer, for example components of the adhesives and/or materials as described above. The drive mechanism 1011 may move the jet forming structure 1012 via a support 1015, so as to control the position of the jet on the eye, such that the jet can be scanned over the eye under computer along at least two directions, for example X and Y directions along the exposed surface. The jet may comprise a pulsed jet 1013 comprising the material from one of the cartridges. A sequence of pulsed jets comprising the material from the cartridges can be sequentially applied to the exposed surface of the cornea 1014 so as to form the covering comprising the layer with the desired shape, for example the desired thickness and or diameter of the layer.

The jet may apply micro particles of collagen. The at least one cartridge may comprise a collagen cartridge similar to a cartridge for a printer. A first cartridge, for example cartridge A, and a second cartridge, for example cartridge B, may comprise components of a two component system in which the first part comprises protein and the second part curing agent. The jet deposition apparatus can build up the layer over time and sputter the therapeutic material onto the exposed surface so as to form the layer. The layer can be fabricated in situ on the eye. A third cartridge may comprise a photosensitizer. The photosensitizer can be applied with the jet to provide the photosensitizer at a level of the deposition to cure the lens and/or adhere the lens to the stroma with light activation. A light beam can be used to cure the material comprising the photo sensitizer and/or the first two components, for example the first two components from cartridge A and cartridge B, respectively. In some embodiments, the covering comprising the therapeutic layer may be fabricated on a support substrate, for example at fabrication center, similar to semiconductor processing. The therapeutic layer may comprise a customized computer based shape profile, for example a three dimensional shape profile with X-Y coordinates.

The jet may apply micro particles comprising amniotic membrane material so as to form a covering over the eye comprising amniotic membrane material.

Figure 11A:
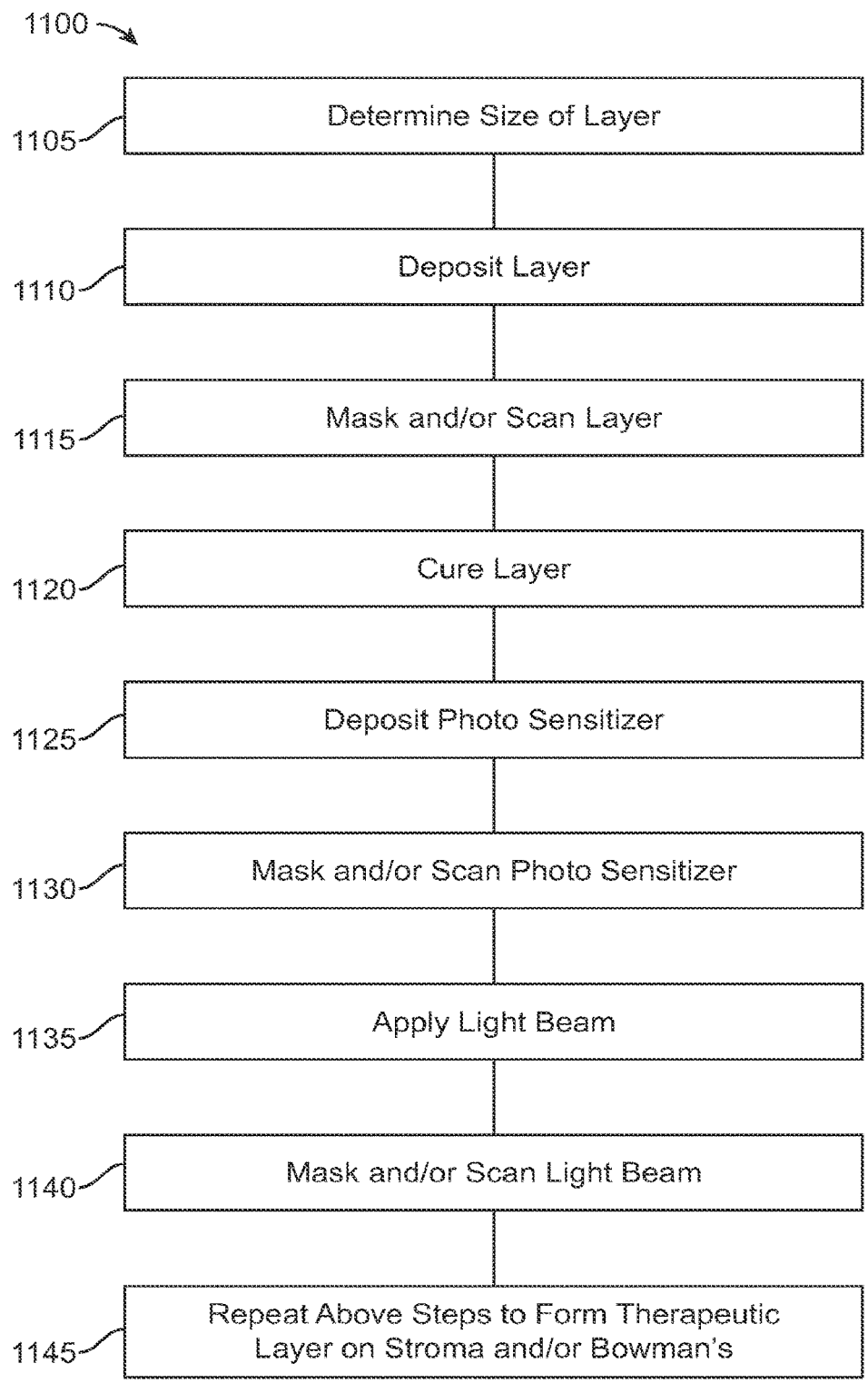
FIG. 11A shows a method of forming a covering comprising a therapeutic layer, according to embodiments of the present invention.

FIG. 11A shows a method 1100 of forming a covering comprising a therapeutic layer. A step 1105 determines a size of the covering. The covering can be sized so as to extend across the limbus and cornea, such that the covering can be tacked down and/or adhered to the conjunctiva as described above. The covering may be sized such that a gap extends between the layer and the epithelium as described above. Intermediate sizes can also be selected. A step 1110 deposits the layer. The layer can be deposit as described above. A step 1115 masks and or scans the layer during the deposition process to size the layer as described above. A step 1120 cures the layer, for example as described above. A step 1125 deposits a photosensitizer as described above. A step 1130 masks and/or scans the photosensitizer. A step 1135 applies a light beam to cure the material comprising the photosensitizer. A step 1140 masks and/or scans the light beam. A step 1145 repeats the above steps to form the therapeutic layer on the stroma and/or Bowman's membrane.

It should be appreciated that the specific steps illustrated in FIG. 11A provide a particular method of forming the layer according to one embodiment. Other steps may also be performed according to alternative embodiments. For example, alternative embodiments may perform the steps outlined above in a different order. Moreover, the individual steps illustrated in FIG. 11A may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 12A:
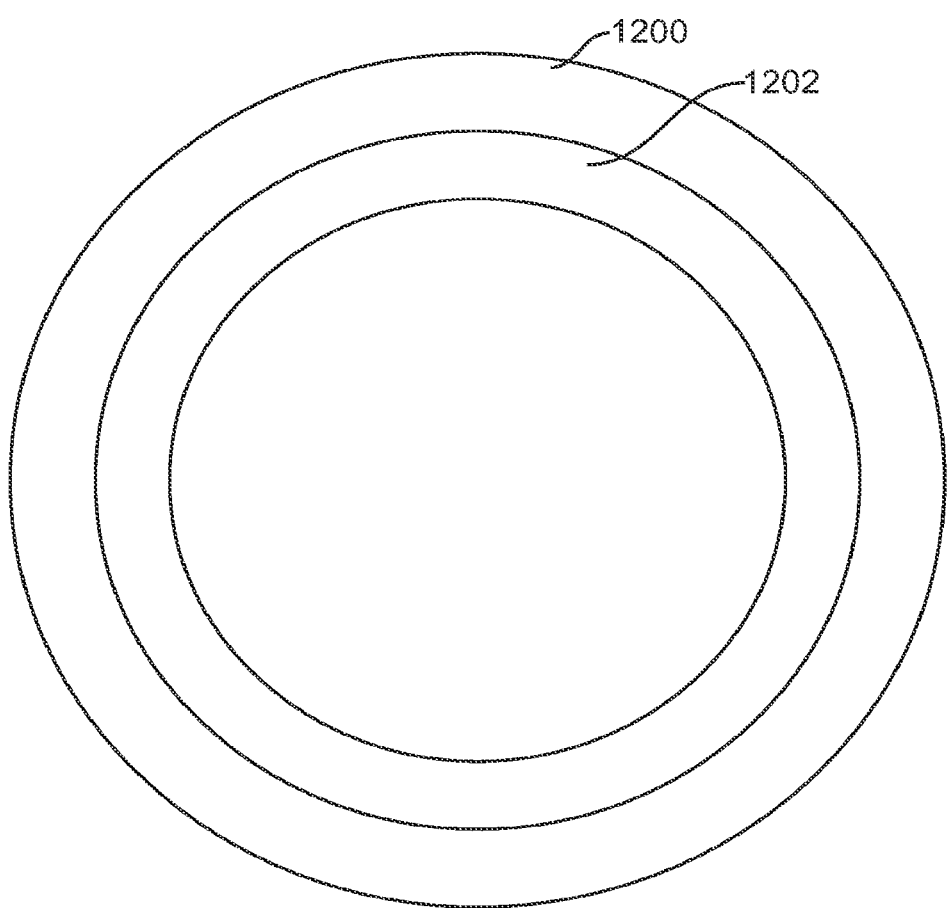
FIG. 12A shows a therapeutic lens comprising an adhesive track for welding the therapeutic lens to the cornea, according to embodiments of the present invention.

FIG. 12A shows a therapeutic lens 1200 comprising an adhesive track for welding the therapeutic lens to the cornea. The adhesive track 1202 can comprise the adhesives and/or photo sensitizers as described above, and the therapeutic lens may comprise the therapeutic lens materials as described above.

Figure 13A:
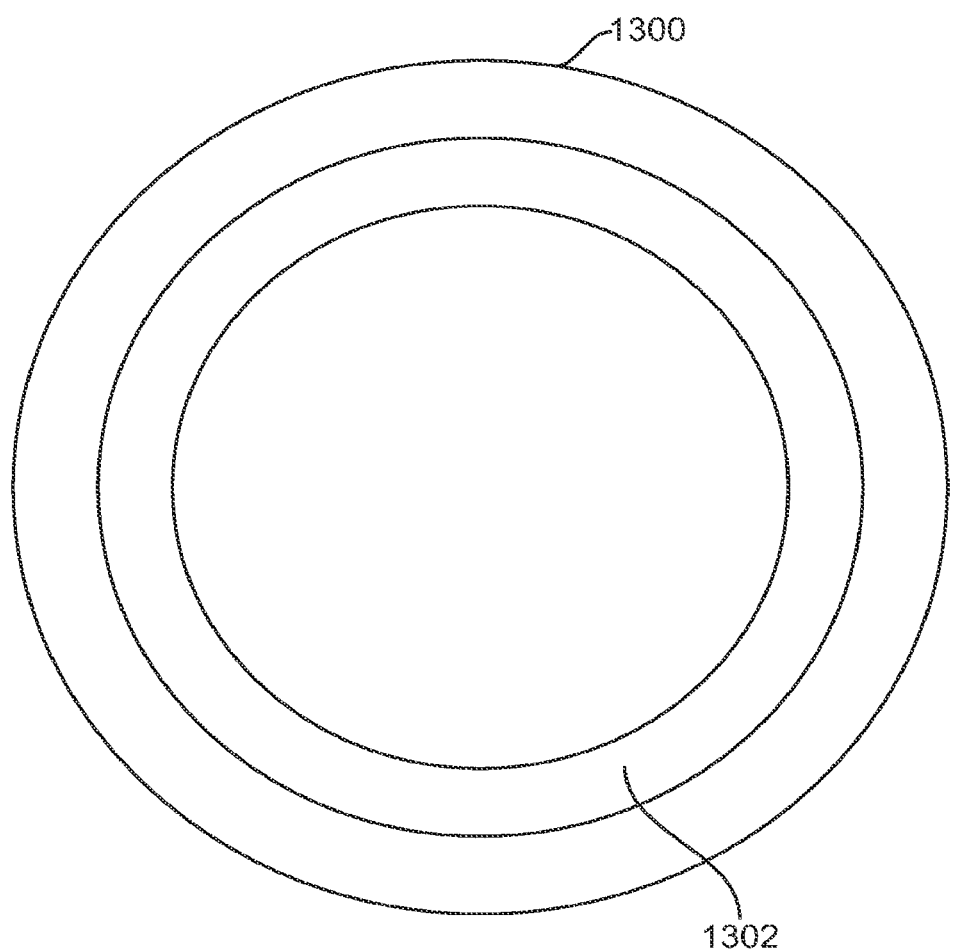
FIG. 13A shows a therapeutic lens with an adhesive, track comprising a dried water soluble adhesive, according to embodiments of the present invention.

FIG. 13A shows a therapeutic lens 1300 with an adhesive track 1302 that may comprise a dried water soluble adhesive. The water soluble adhesive may comprise many of the water soluble adhesives as described above. The dried water soluble adhesive track can be configured to adhere to the cornea, for example the epithelium, when placed on the eye. The water from the tissue of the eye hydrates the adhesive and the adhesive adheres the therapeutic lens to the eye. The water soluble adhesive may comprise at least one of a fibrin adhesive, a polyethylene glycol adhesive or an albumin adhesive.

Figure 14:
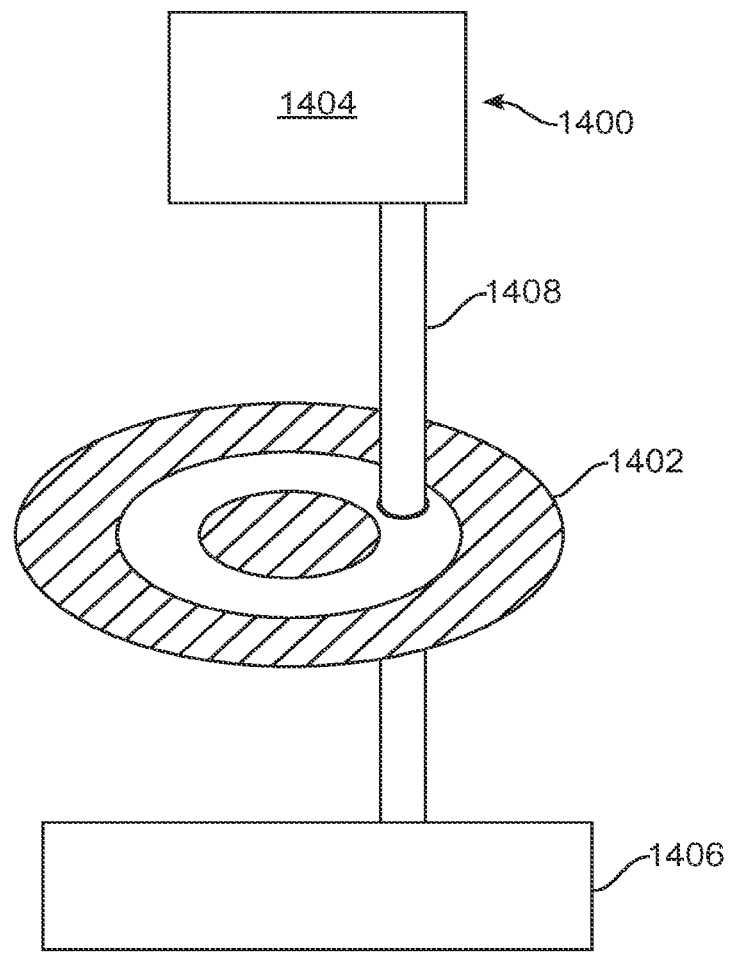
FIG. 14 shows a light beam system to irradiate material comprising a photosensitizer, according to embodiments of the present invention.

FIG. 14 shows a light beam system 1400 to irradiate material 1406 comprising a photosensitizer. The system may comprise at least one mask 1402 and/or a scanner 1404 to irradiate the material with a pattern, for example an annular pattern. The mask may comprise non-transmitting material with a light 1408 transmitting annular aperture. The scanner may comprise a known scanner. The material may comprise material with photosensitizer as described above, for example a therapeutic lens with photosensitizer.

Figure 15A:
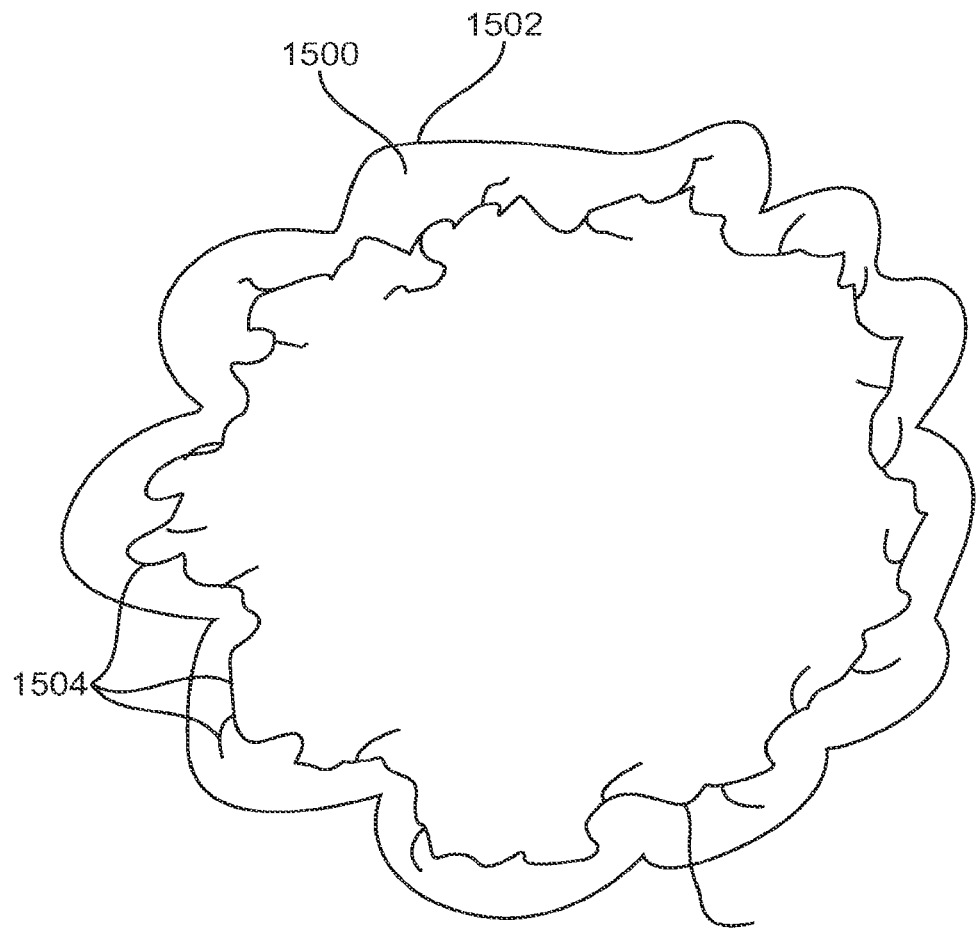
FIG. 15A shows a therapeutic lens comprising structures to adhere the lens to the cornea, according to embodiments of the present invention.

FIG. 15A shows a therapeutic lens 1500 comprising structures to adhere the lens to the cornea. The lens may comprise a perimeter 1502 to increase surface area of the therapeutic lens. The lens may comprise channels with tortuosity 1504 and/or a surface tortuosity so as to increase surface area of the therapeutic lens, for a therapeutic lens comprising water.

Many of the adhesives described above can be reversed with a removal agent. The adhesives used to adhere the layer and/or therapeutic lens to the stroma, Bowman's, epithelium and/or conjunctiva may comprise a removable adhesive that can melt when a removal agent is applied. The removal agent may comprise tissue plasminogen activator (TPA). The adhesive may comprise fibrin, such that the adhesive can melt when the removal agent is applied to the adhesive.

Figure 16A:
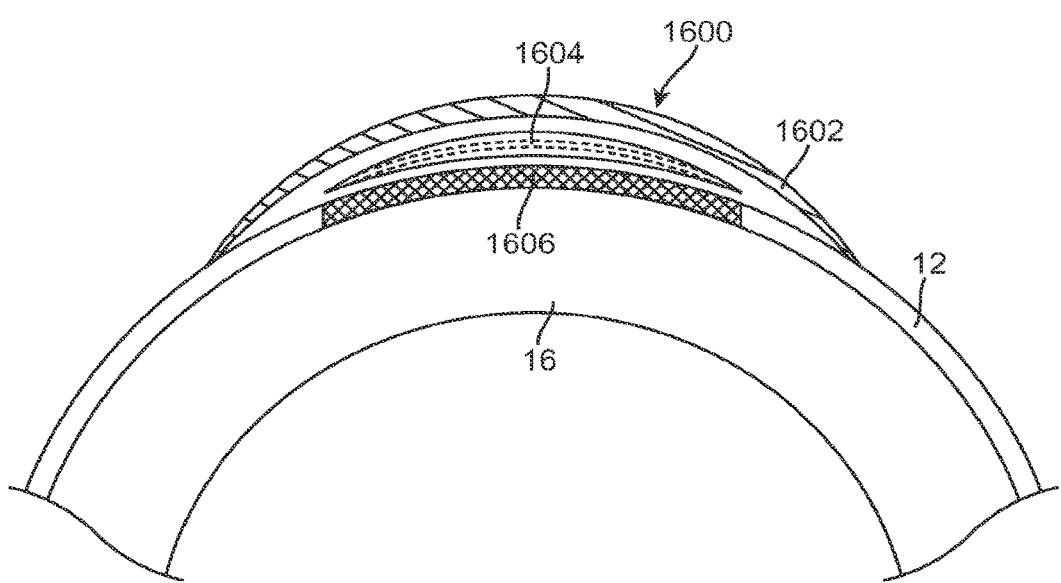
FIG. 16A shows a composite lens comprising a first component and a second component, according to embodiments of the present invention.

FIG. 16A shows a composite lens 1600 comprising a first component and a second component. The first component may comprise a soft lens 1602 composed of known soft lens materials. The second component may comprise a hard lens 1604 composed of known hard lens materials. The soft component can be affixed to the second component. The hard lens can be disposed under the soft lens such that the hard lens is positioned toward the stroma and/or Bowman's membrane of the eye. The hard lens may protect an ablated area from blinking of the eye. Many of the adhesives 1606 described above can be applied to the eye, for example Tisseal. The adhesive can be disposed under the two component lens such that the adhesive is disposed in contact with the stroma and/or Bowman's membrane and in contact with at least the hard lens of the two component lens so as to adhere the two component lens to the eye. Epithelium may be disposed to the periphery of the adhesive in contact with the stroma and/or Bowman's membrane and the adhesive may extend over the epithelium in contact with the epithelium such that the adhesive adheres the second soft lens component to the epithelium. The hard lens may be sized to fit over the ablation zone with a diameter that corresponds to the size of the ablation zone, for example within about one mm of the size of the ablation zone. The soft lens may comprise a diameter greater than the hard lens, such that the soft lens can adhere to the epithelium as described above.

Figure 16B:
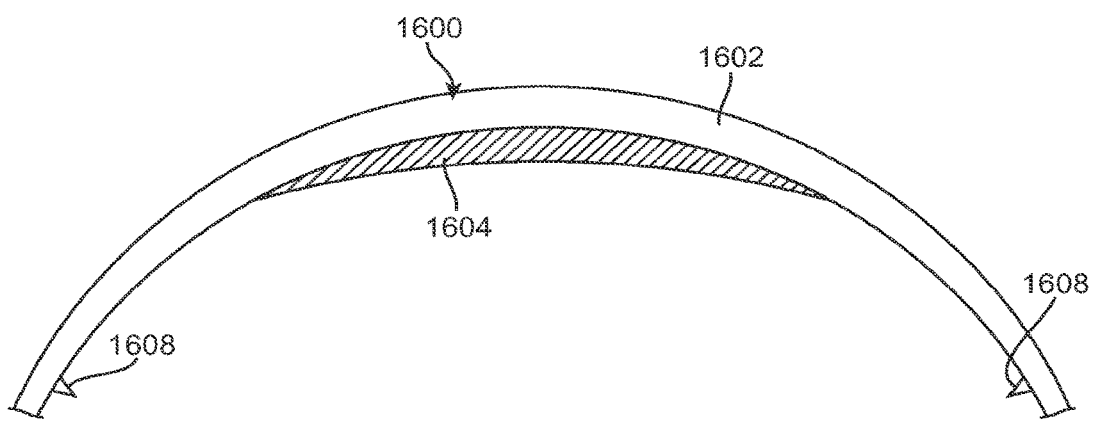
FIG. 16B shows a two component lens in which the second component is configured to adhere to at least one of a cornea or a conjunctiva, according to embodiments of the present invention.

FIG. 16B shows a two component lens in which the second component is configured to adhere to at least one of a cornea 1604 or a conjunctiva. The two component lens comprises a soft lens S 1602 disposed over a hard lens H. The soft lens may comprise at least one peripheral tack 1608 configured for insertion into at least one of a peripheral portion cornea or a conjunctiva. The peripheral portion of the cornea may often comprise an annular portion of the cornea disposed away from the pupil of the eye, such that the peripheral portion of the cornea may not be optically useful for vision. The hard lens may be sized to fit the ablation zone for protection, and the soft lens can be sized to extend across at least a peripheral portion of the cornea and may extend over an annular portion of the conjunctiva to the periphery of the cornea. The hard and soft lens combination can be shaped such that the two component lens comprises no more than about +/−1 Diopter of optical power, so as to allow the patient to see with the ablated surface when the two component lens is placed on the eye, for example following PRK.

The at least one tack may comprise many materials. The tack may comprise a bioerodible or bioabsorbable material, such that the tack adheres the lens to the cornea for a period of time, for example when the epithelium regenerates under the lens, and the material erodes or is absorbed sufficiently to release the lens from the cornea after the epithelium has grown under the lens. Many bioerodible or bioabsorbable materials can be used including poly lactic acid (hereinafter "PLA"). The tack can be configured to erode and/or break or be absorbed after at least three days, for example after at least one week. Alternatively, the tack may comprise a shape memory material, for example, Nitinol or a temperature sensitive shape memory alloy. The shape memory material may facilitate the removal of the lens by allowing the tack to straighten under certain conditions.

Figure 17A:
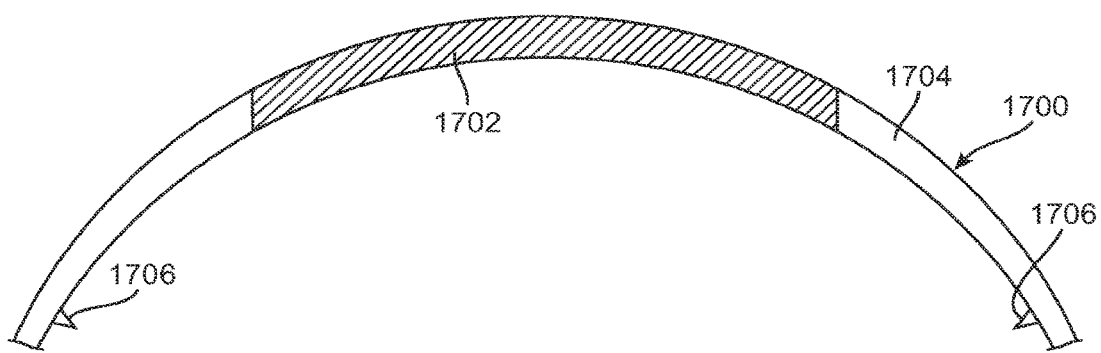
FIG. 17A shows a two component lens with a central circular first component and an annular second component, according to embodiments of the present invention.
Figure 17B:
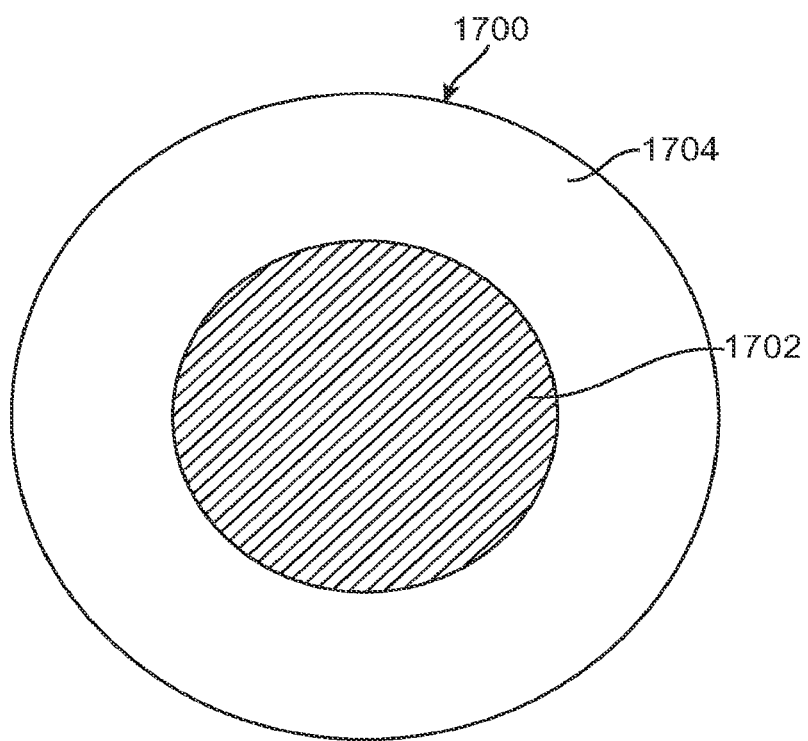
FIG. 17B shows a top view of the lens as in FIG. 17A.

FIGS. 17A and 17B show a two component lens 1700 with a central circular first component and an annular second component. The first component may comprise a hard lens 1702 composed of a known hard lens material. The second component may comprise a soft lens 1704 composed of a known soft lens material. The first component may comprise a circular component with an outer circumference. The second component may comprise a skirt in contact with the first component. For example, the second component may comprise an annular component with an inner circumference having an inner annular diameter and an outer circumference having an outer annular diameter. The inner annular circumference of the second component can be sized to fit the outer circumference of the second component, such that the second component contacts the first component along the inner annular circumference. The first component can be sized to match the ablation zone, for example with a diameter within about 1 mm of an ablation zone. The second component may be configured to extend outward toward the conjunctiva of the eye. The soft lens may comprise at least one peripheral tack 1706 configured for insertion into at least one of a peripheral portion cornea or a conjunctiva.

Figure 17C:
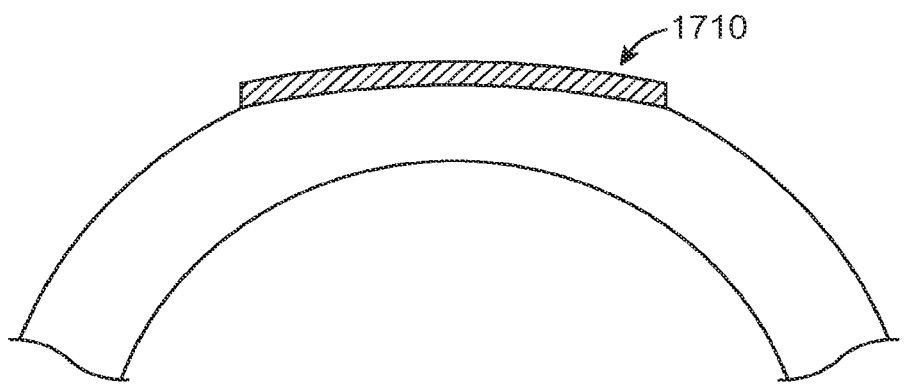
FIG. 17C shows a hard tens with anterior and posterior surface profiles that that correspond to a reshaped cornea, according to embodiments of the present invention.

FIG. 17C shows a hard lens 1710 with anterior and posterior surface profiles that corresponds to a reshaped cornea. The anterior surface profile may track the ablated profile, such that the lens provides optical correction similar to the ablation. The posterior profile of the lens may correspond to the unablated corneal profile at the periphery as described above, such that the posterior profile tracks the unablated profile of the periphery of the eye. The lens may comprise a lens with no more than about +/−1 Diopter of optical power, for example a piano lens with no refractive power centrally. However, the lens can be formed with many optical powers, and the center may be flat with a plateau profile. In some embodiments an adhesive may be placed below the lens to adhere the lens to the ablated bed comprising stroma and/or Bowman's membrane, for example with Tisseal adhesive.

Figure 17D:
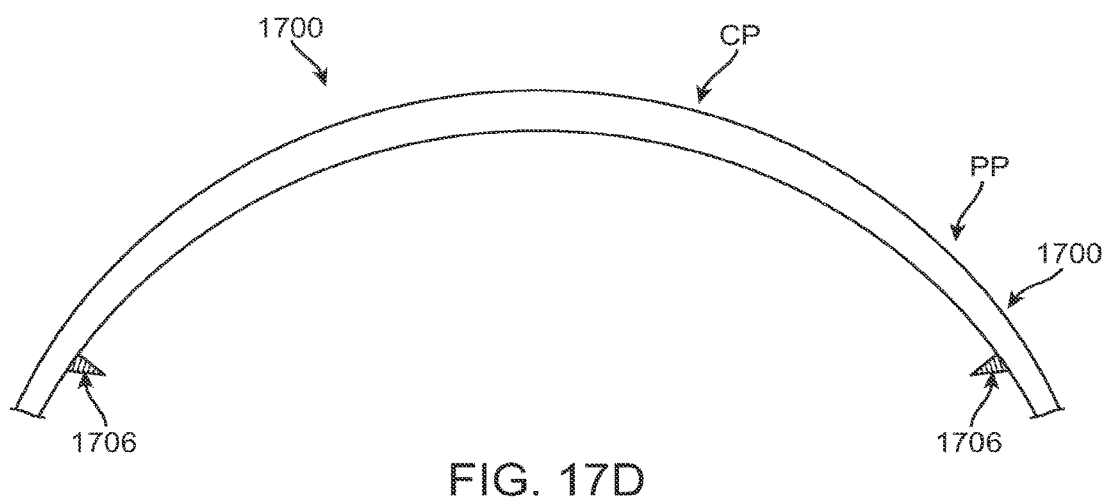
FIG. 17D shows a side profile view of a therapeutic lens with tacks, according to embodiments of the present invention.

FIG. 17D shows a side profile view of a therapeutic lens 1700 with at least one tack 1706. The at least one tack, for example two tacks, may be normal to the posterior surface of the lens, and may be inclined inward or outward, or combinations thereof. The tacks can be inclined inwardly, for example centrally, and may be inclined outwardly toward the periphery, for example outwardly along a radius extending from center of the lens. The tack and lens may be formed from a single material, for example a rigid material such as an RGP material. The tack and lens may comprise separate materials, for example the lens may comprise known soft lens material and the tack may comprise a rigid material. Other materials include shape memory materials such as Nitinol.

The lens comprises a central portion CP composed of an optically transmissive material for vision and a peripheral portion PP to anchor the lens over the cornea. The peripheral portion can be sized to extend over a peripheral portion of the cornea, and may even extend over at least a portion of the conjunctiva. The peripheral portion of the lens can anchor to the cornea and/or conjunctiva with the tacks.

Figure 17E:
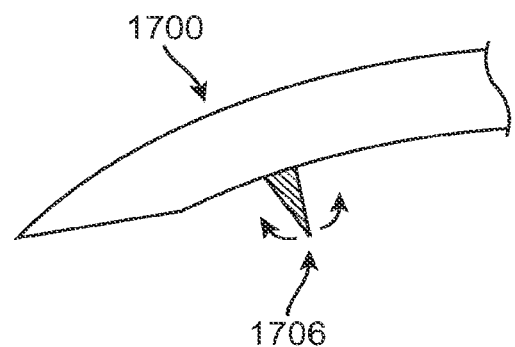
FIG. 17E shows many angles of a tack with a therapeutic lens, according to embodiments of the present invention.

FIG. 17E shows many angles at which a tack 1706 can be positioned in relation to a therapeutic lens 1700. The tack can extend from a base on the bottom surface of the lens to a tip in a direction normal to the surface of the therapeutic lens. The tack may be inclined inward or outward as described above.

Figure 17F:
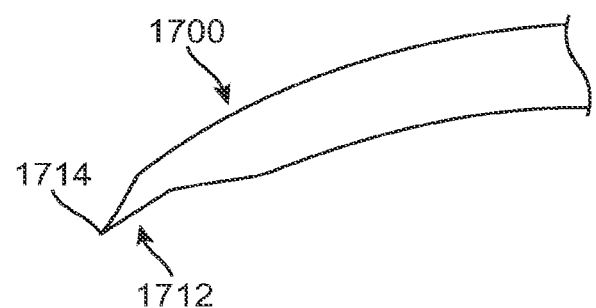
FIG. 17F shows a bevel edge on a therapeutic lens to anchor the therapeutic lens to the tissue.

FIG. 17F shows a bevel edge 1712 on a therapeutic lens 1700 to anchor the therapeutic lens to the tissue. The bevel edge can be configured to adhere the lens to the eye. The bevel may comprise a sharp edge 1714 that penetrates the cornea to adhere the lens to the eye or to tack the lens into the conjunctiva. The beveled edge may comprise a sharp tip to extend into tissue similar to a hypodermic needle.

Figure 17G:
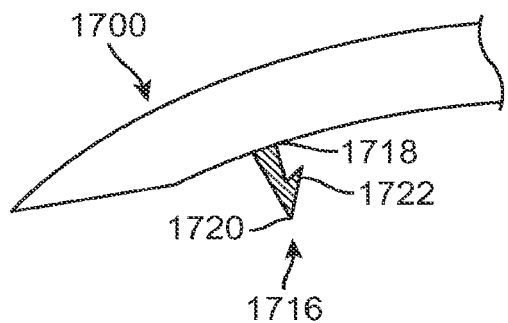
FIG. 17G shows a barbed tack with the tack extending normal to the therapeutic lens surface, according to embodiments of the present invention.

FIG. 17G shows a barbed tack 1716 with the tack configured to extend into the tissue of the eye. The barbed tack can be sized to anchor the tack in the cornea. The tack can extend a distance from the base 1718 to the tip 1720. The distance may correspond to the depth of the tack in tissue. The tack may extend no more than 400 microns, for example when the tack extends normal to the lens surface, so as to avoid penetration of the cornea. In some embodiments, the tack may be sized to extend no more than about 40 microns so as to avoid penetration of the stroma and/or Bowman's membrane.

Figure 17H:
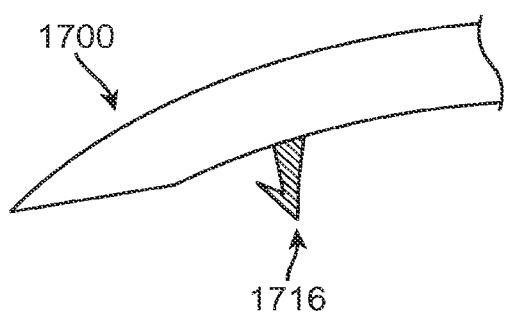
FIG. 17H shows a barbed tack with the barb extending from a base at the therapeutic lens to tip with the tack inclined outward, according to embodiments of the present invention.

FIG. 17H shows a barbed tack 1716 with the barb 1722 extending from a base 1718 at the therapeutic lens to tip 1720 with the tack inclined outward. The barbed tack can be sized and positioned at many locations as described above.

Figure 17I:
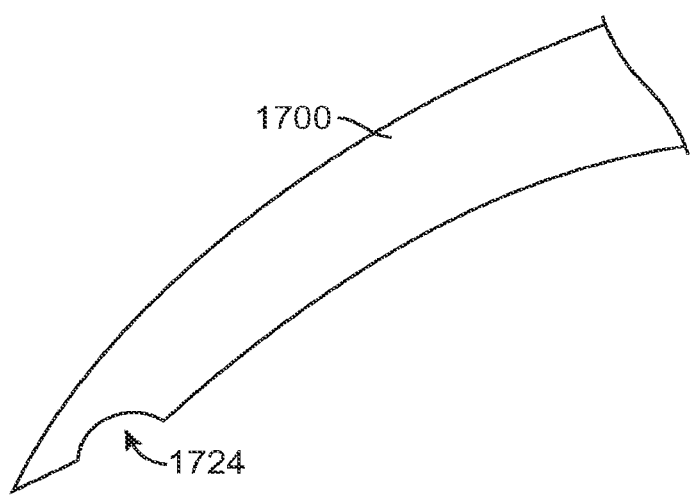
FIG. 17I shows a suction cup anchor, according to embodiments of the present invention.

FIG. 17I shows a suction cup anchor 1724. The suction cup may comprising an indentation in the lens to adhere the lens to the tissue with suction. The suction cup may be disposed on a peripheral portion of the therapeutic lens.

Figure 18:
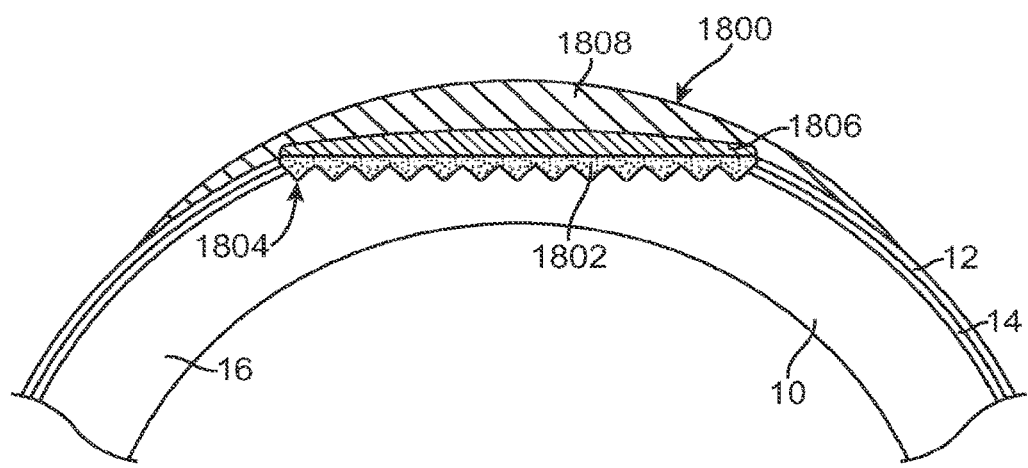
FIG. 18 shows optical smoothing with a two component lens positioned on an eye.

FIG. 18 shows optical smoothing with a two component lens 1800 positioned on an eye. The stroma 16 and/or Bowman's membrane 14 exposed for the ablation process comprises a bed with roughness. An adhesive, for example a fibrin 1802 based adhesive, is disposed over the bed 1804 to smooth the roughness, for example as described above. A two component lens can be positioned over the adhesive, for example with a first hard lens 1806 component in contact with the adhesive and a soft lens 1808 component disposed over the hard lens. The adhesive can be disposed on the bed with sufficient thickness to smooth the roughness, for example about 25 to 75 um, and the two component lens can be positioned on the adhesive such that the hard lens component is positioned over the adhesive with smoothing of the adhesive. Although a two component lens is shown, smoothing can be achieved with many of the lenses, molds and sprays, for example as described above.

Figure 19A:
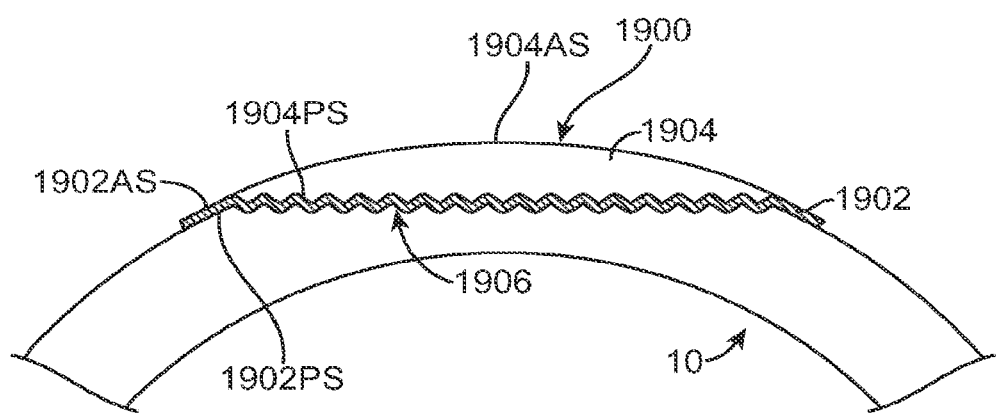
FIG. 19A shows a therapeutic covering comprising a first layer sprayed on the eye and a second layer sprayed over the first layer.

FIG. 19A shows a therapeutic covering 1900 comprising a first layer 1902 sprayed on the eye and a second layer sprayed 1904 over the first layer. The stroma and/or Bowman's membrane ablated with the laser may comprise a bed 1906 with irregularity, for example as described above. The first layer may comprise a thin layer, for example from about 1 to 25 um. The first layer may be sprayed in many ways, for example with jet deposition, electrospray, and/or apertures as described above. The first layer may comprise a hydrophobic material, for example polyethylene glycol-based material. The first layer may comprise an optically clear material and control edema, as described above. The first layer may comprise a substantially water impermeable layer that minimizes and/or inhibits the passage of water through the material into the cornea. The first layer can be sucked down onto the bed comprising the stroma and/or Bowman's membrane, for example with endothelial pumping, in a manner similar to a LASIK flap. The first layer may comprise a uniform thickness such that irregularities of the bed are transferred from a posterior surface of the first layer in contact with the bed to a posterior surface 1902PS of the first layer The posterior surface of the first layer may contact the posterior surface of the second layer 1904PS.

The second layer may comprise a smoothing layer, for example with a thickness from about 10 um to about 200 um to smooth the irregularities of the bed transferred through the first layer. The second layer may be sprayed in many ways, for example with jet deposition, electrospray, and/or apertures as described above. Thus, irregularities from the anterior surface of the first layer 1902AS in contact with the posterior surface of the second layer 1904AS can be smoothed out along the anterior surface of the second layer. This smoothing can be sufficient to provide functional vision for the patient of 20/40 or better, for example 20/25 or better. The second layer may comprise an anterior surface profile with a radius of curvature similar to the ablated bed such that the anterior surface of the second layer provides optical correction for the patient. Although the second layer is shown sprayed on the first layer, the second layer may be applied to the first layer in many ways, for example as a single drop of liquid that spreads over the first layer. The second layer may be adhered to the first layer. The anterior upper surface of the second layer can be smoothed in many ways, for example with molds, as described above.

A therapeutic lens may be placed over the second layer, for example as described above.

FIGS. 19B1 and 19B2 show epithelial growth over at least one layer of a therapeutic covering as in FIG. 19A. The epithelium 12 may grow over the first layer, for example to separate the first layer from the second layer; and the first layer may remain in contact with the bed comprising the stroma and/or Bowman's membrane when the epithelium separates the first, layer from the second layer, as shown in FIG. 19B1. The epithelium may grow over the first layer 1902 and the second layer 1904, for example when the first layer is adhered to the stroma and/or Bowman's membrane and the second layer is adhered with bioadhesive 1908 to the first layer, as shown in FIG. 19B2. The epithelium may grow under the first layer to separate the first layer from the bed comprising the stroma and/or Bowman's membrane, for example when the first layer is adhered to the second layer.

FIG. 19B3 shows epithelial growth under the therapeutic covering as in FIG. 19A.

Figure 20A:
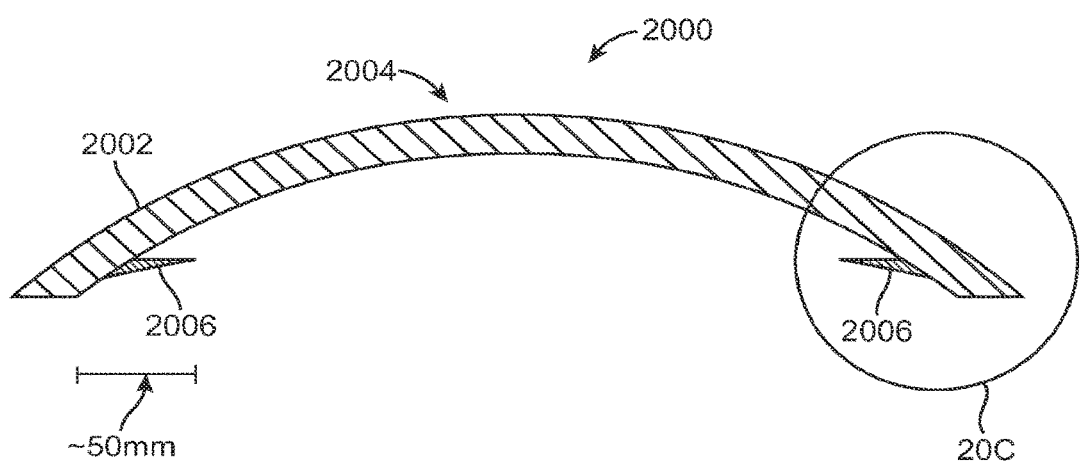
FIG. 20A shows a side profile view of a therapeutic lens with peripheral tacks to adhere the therapeutic lens to the cornea, according to embodiments of the present invention.

FIG. 20A shows a side profile view of a therapeutic lens 2000 with tacks disposed on a peripheral portion 2002 of the lens to adhere the therapeutic lens to the cornea. The therapeutic lens comprises a therapeutic covering for placement on an exposed surface of a cornea of an eye to correct vision of the eye. The therapeutic lens comprises a central optical portion 2004 for patient vision and a peripheral portion to anchor the lens to the eye. The therapeutic lens comprises an optically clear transmissive material, for example many known therapeutic lens materials can be used such as rigid, gas permeable, rigid gas permeable (RGP) and soft lens materials. The therapeutic lens comprises at least one anchor 2006 extending from a periphery of the lens to anchor the lens over the cornea. The therapeutic lens may comprise a center portion for optical effect and placement over the pupil. The peripheral portion can be sized to extend over at least a peripheral portion of the cornea, such that the peripheral portion with the tacks engage a peripheral portion of the cornea. The peripheral portion may extend to the conjunctiva and/or limbus, such that the anchor engages the conjunctiva to anchor the lens over the cornea.

The at least one anchor comprises at least one peripheral tack comprising a base extending to a sharp tip, the base attached to the therapeutic lens. The tack may comprise a length from the base to the tip of about 50 um. This size of the tack can anchor the lens in the epithelium of the cornea or in the conjunctiva without penetrating through the epithelium or conjunctiva, such that the tip of the tack is disposed over the stroma or sclera, for example without penetrating the stroma or sclera. The tack can be configured to penetrate only epithelium, for example with a length from the base to the tip of no more than about 50 microns, for example no more than about 40 microns. The tack can be configured to extend into the corneal stroma so as to anchor with collagenous tissue, for example with a depth of at least about 50 microns and no more than 500 microns, for example with a length from the base to the tip within a range from about 100 microns to 400 microns. The tip may be no more than 500 microns so as to avoid penetrating through the cornea into Descemet's membrane and/or the endothelium. The tack may be formed from a variety of materials including shape memory material such as Nitinol.

The at least one anchor may be inclined. The at least one peripheral tack can be inclined inward toward a center of the lens.

Figure 20B:
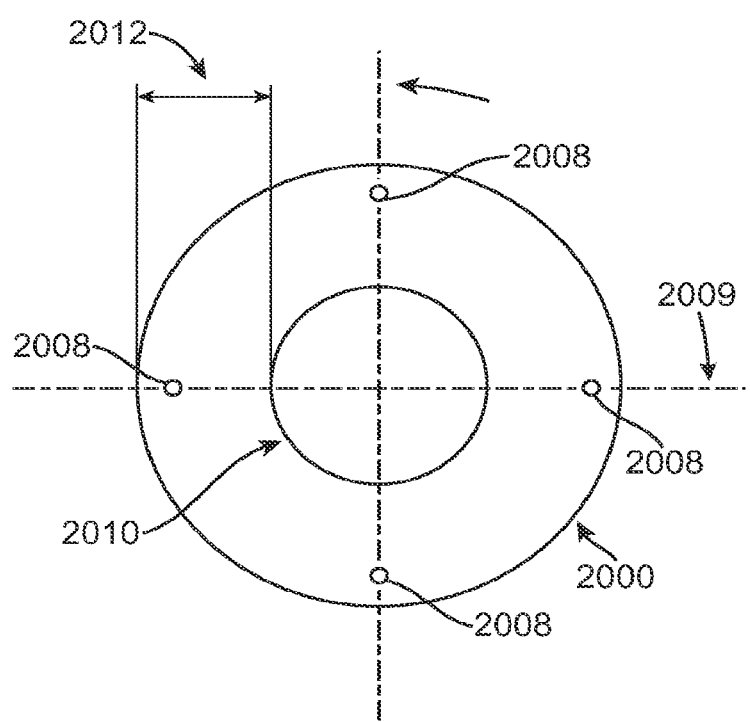
FIG. 20B shows a top view of the therapeutic lens as in FIG. 20A.

FIG. 20B shows a top view of the therapeutic lens 2000 as in FIG. 20A. The at least one anchor 2008 may comprise at least two anchors located on an annular peripheral portion of the lens. The central portion of the lens comprising an optic zone 2010 with optical correction for the patient is shown sized to fit over at least the pupil of the eye for patient vision. The at least two anchors may be symmetrically disposed around the optical portion such that at least two anchors are located on opposite sides of the central portion and pull against each other, for example the at least two anchors disposed along the vertical line. The at least two anchors may comprise equal spacing, for example equal angular and/or circumferential spacing around the central optical portion and along the peripheral portion 2012.

Figure 20C:
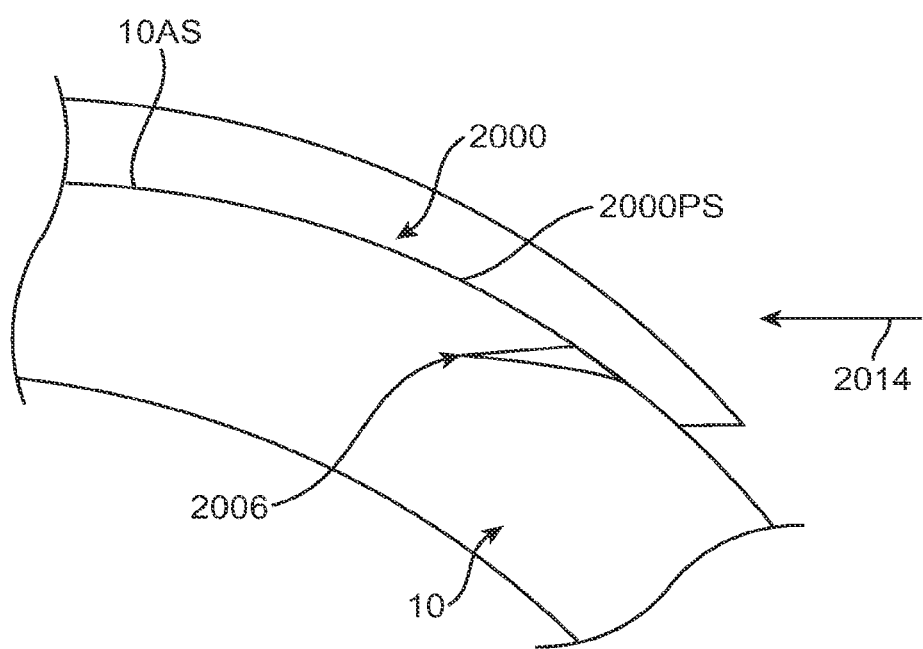
FIG. 20C shows detail of the therapeutic lens similar as in FIGS. 20A and 20B with the lens and inwardly inclined tack configured such that the lens comprises a lens spring with inward tension force to the inwardly inclined tack such that the lens force and tack anchor the lens on the eye.

FIG. 20C shows detail of the therapeutic lens 2000 as in to FIGS. 20A and 20B with the lens and inwardly inclined tack 2006 configured such that the lens comprises a lens spring 2014 with inward tension force to the inwardly inclined tack such that the lens force and tack anchor the lens on the eye. The therapeutic lens can be configured to urge the at least one peripherally inclined tack inward with an elastic force when the lens is positioned on the cornea. The posterior surface of the therapeutic lens 2000PS comprises a base radius of curvature. The anterior surface of the cornea 10AS comprises an anterior radius of curvature. The base radius of curvature of the therapeutic lens may be no more than the anterior radius of curvature of the cornea, such that the peripheral portion of the lens is urged outward by the cornea when the lens is positioned on the eye with force in the anterior to posterior direction. When released, the therapeutic lens can apply a force to the cornea with the peripheral portion, such that the inwardly inclined tack engages the cornea.

Figure 20D:
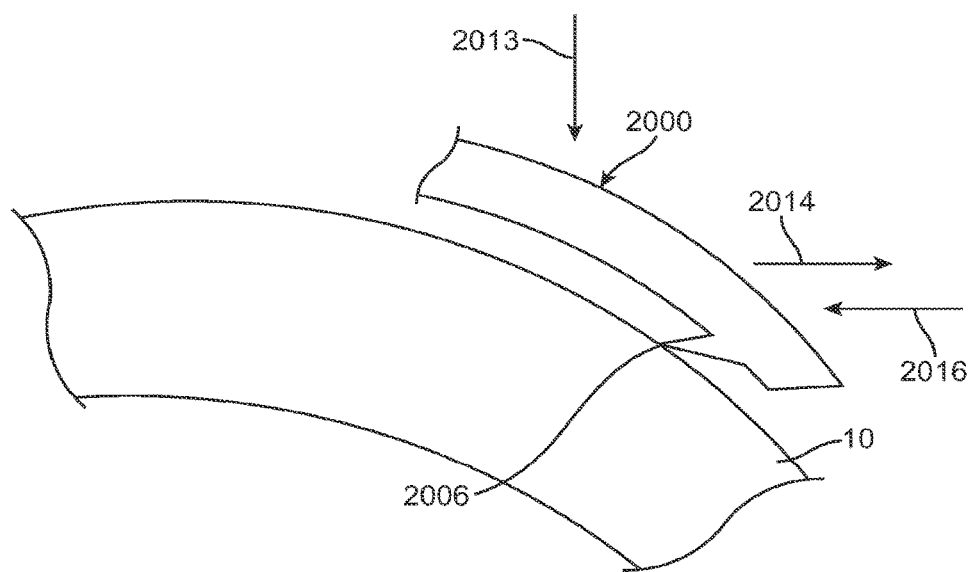
FIG. 20D shows a method of application of a therapeutic lens as in FIGS. 20A and 20B.

FIG. 20D shows a method of application of a therapeutic lens 2000 as in FIGS. 20A and 20B. The method places the therapeutic covering comprising the lens over an exposed surface of a cornea 10 of an eye. A lens as in FIGS. 20A to 20C is provided. The lens is placed on the eye to anchor the lens over the cornea with the at least one anchor. The lens is pushed onto the eye 2013 with at least some force, such that the lens slides along the surface of the cornea and is urged outward 2014, for example with elastic stretching of the lens material. The at least one anchor comprises at least one peripheral tack 2006 inclined inward toward a center of the lens. When the force that pushes the lens into place is removed, the lens retracts elastically 2016 so as to anchor the tack in the cornea and/or conjunctiva.

Figure 20E:
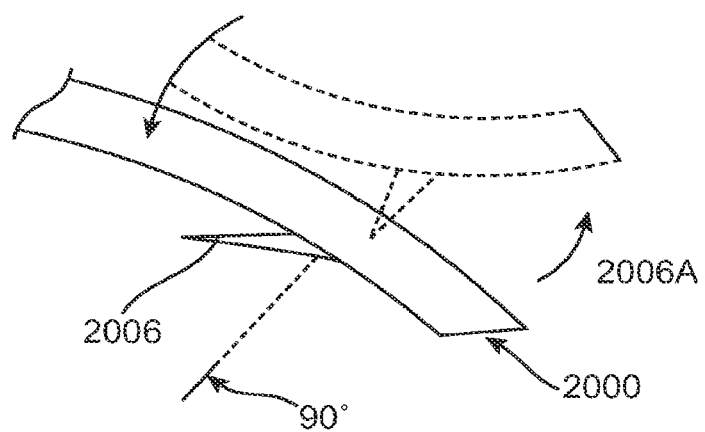
FIG. 20E shows detail of the therapeutic lens as in FIG. 20A with a centrally inclined peripheral tack and removal of the centrally inclined peripheral tack.

FIG. 20E shows detail of the therapeutic lens 2000 as in FIG. 20A with a centrally inclined peripheral tack 2006 and removal of the centrally inclined peripheral tack. The centrally inclined tack is inclined inward relative to a 90 degree surface normal vector. This inclination can hold the lens in position, for example when the lens exerts and centripetal force on the tack. The lens can be removed with deformation and/or rotation of the lens at the periphery, as indicated by the dashed line and arrows. The removal may stretch the lens so as to retract the tack from the tissue of the cornea and/or conjunctiva.

FIG. 20E1 shows the lens 2000 as in FIGS. 20A to 20E in an initial configuration. The lens may comprise a first configuration, for example without deformation, such that the peripheral portion of the lens engages the cornea.

FIG. 20E2 shows the lens 2000 as in FIGS. 20A to 20E1 in an elastically deformed configuration. The lens can be pushed into position, for example with force applied to the lens in an anterior to posterior direction, such that the peripheral portion of the lens 2000P is stretched elastically outward away from a center of the lens to assume a second configuration, for example an elastically deformed configuration, when the lens is placed on the cornea. In the deformed configuration, the radius of curvature of the posterior surface of the lens 2000R may be closer to the radius of curvature of the cornea 10R than when the lens is in the initial configuration without deformation. With the elastic deformation of the lens, the anchor is urged inward to engage tissue with elastic force when the lens is released.

The therapeutic lens covering may be removed. For example, the lens may be stretched outward to pull the tack out of the corneal tissue when the lens is removed. The lens may be stretched outward to remove the tack from the conjunctiva in those embodiments where the peripheral portion is sized to anchor the tack in the conjunctiva. The tack may be formed from a variety of materials, including shape-memory materials such as Nitinol. For example, a heat-sensitive shape-memory material may facilitate removal of the lens by allowing the tack to straighten out under certain temperatures.

Although FIGS. 20A to 20E show a lens sized to engage the cornea with anchors of the lens, the lens can be of a larger size such that the anchors engage the conjunctiva. Such lenses can be anchored to the conjunctiva and removed with similar structures to those used to anchor the cornea and remove from the cornea.

Figure 20F:
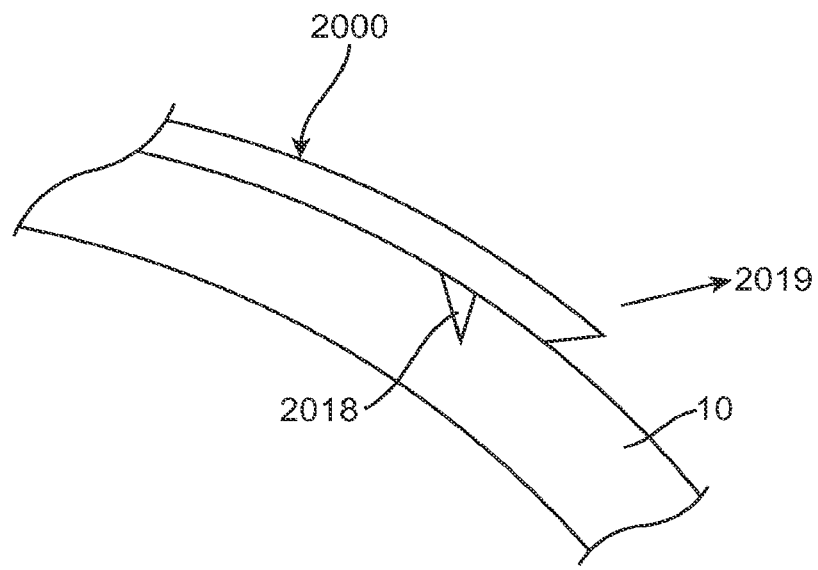
FIGS. 20F and 20G shows detail of a therapeutic lens similar to FIG. 20A with a peripherally inclined tack and insertion and removal of the peripherally inclined tack.
Figure 20G:
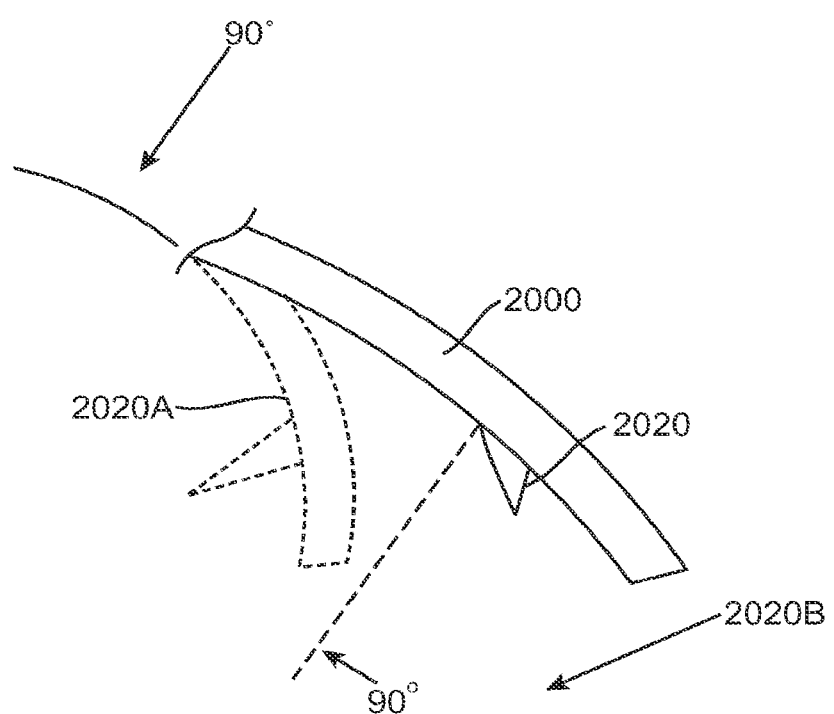

FIGS. 20F and 20G show detail of a therapeutic lens similar to FIGS. 20A and 20B with a peripherally inclined tack 2018 and insertion and removal of the peripherally inclined tack. The at least one peripheral tack can be inclined outward away from a center of the lens. The lens and outwardly inclined tack can be configured such that the lens comprises a lens spring with outward force to the outwardly inclined tack 2020 such that the lens force and tack anchor the lens on the eye. The lens can be anchored to the cornea with at least two, for example at least four, outwardly inclined tacks. The therapeutic lens may comprises a base radius of curvature on the posterior surface and the cornea comprises an anterior radius of curvature. The base radius of curvature may be greater than or equal to the anterior radius of curvature, such that the lens is flatter than the cornea. As the lens is flatter than the cornea, the lens can be deformed, or bent downward at the periphery when positioned on the eye. With this configuration therapeutic lens is configured to urge outward the at least one tack disposed on the peripheral portion with an elastic force when the lens is positioned on the cornea. The therapeutic lens may comprise an inner optical portion for placement over the pupil of the eye and an outer peripheral portion that extends over at least one of a peripheral portion of the cornea or a conjunctiva of the eye when the lens is positioned over the cornea. The at least one anchor can be positioned on the outer peripheral potion so as to extend into the epithelium of at least one of the peripheral cornea or the conjunctiva of the eye when the lens is positioned on the eye. In embodiments where the peripheral portion of the lens is sized to extend the tack into the epithelium above the cornea, the tack may be sized to extend into the cornea. The at least one anchor may have a length sized to extend into the epithelium without extending into the sclera when the outer portion of the lens is sized to engage the epithelium above the conjunctiva. The at least one anchor comprises at least four tacks disposed on the outer portion, for example as described above. The at least one anchor may comprise a variety of materials, for example, a shape memory material such as Nitinol.

Figure 20H:
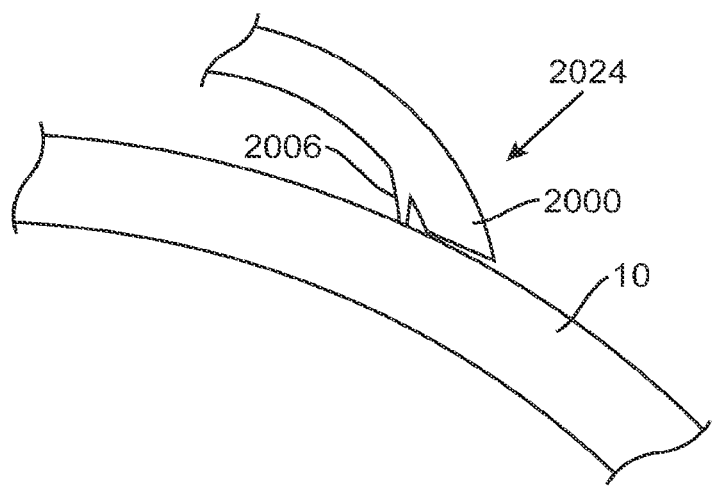

FIGS. 20H, 20H1 and 20H2 show a method of application of a therapeutic lens 2000 as in FIGS. 20F and 20G. The method places therapeutic covering comprising a lens on an exposed surface of a cornea of an eye. The lens may comprise a curved posterior surface and a curved anterior surface, such that the lens comprises no more than about one Diopter of optical power over a central optical portion of the lens. The therapeutic lens may comprise a base radius of curvature on the posterior surface 2020. The cornea may comprise an anterior radius of curvature 2022. In a first configuration as shown in FIG. 20H1, for example without deformation, the base radius of curvature may be greater than or equal to the anterior radius of curvature of the cornea. The lens may be squeezed inward 2024 toward a center of the lens to assume second configuration, for example an elastic squeezed and/or deformed configuration as in FIG. 20H. For example, the lens can be pressed inward 2026 similar to a taco, such that the periphery of the lens is urged inward with force. In the second configuration, the lens can be placed against the cornea and released, and the therapeutic lens urges outward the at least one peripheral tack with an elastic force when the lens is positioned on the cornea and released. When released, the periphery of the lens can move outward toward the first configuration, such that the at least one anchor urges outward 2028 and engages the cornea with elastic force in the released configuration, as shown in FIG. 20H2. The therapeutic lens can be removed, and the lens can be compressed inward 2030 to remove the lack from the cornea when the lens is removed.

Figure 21:
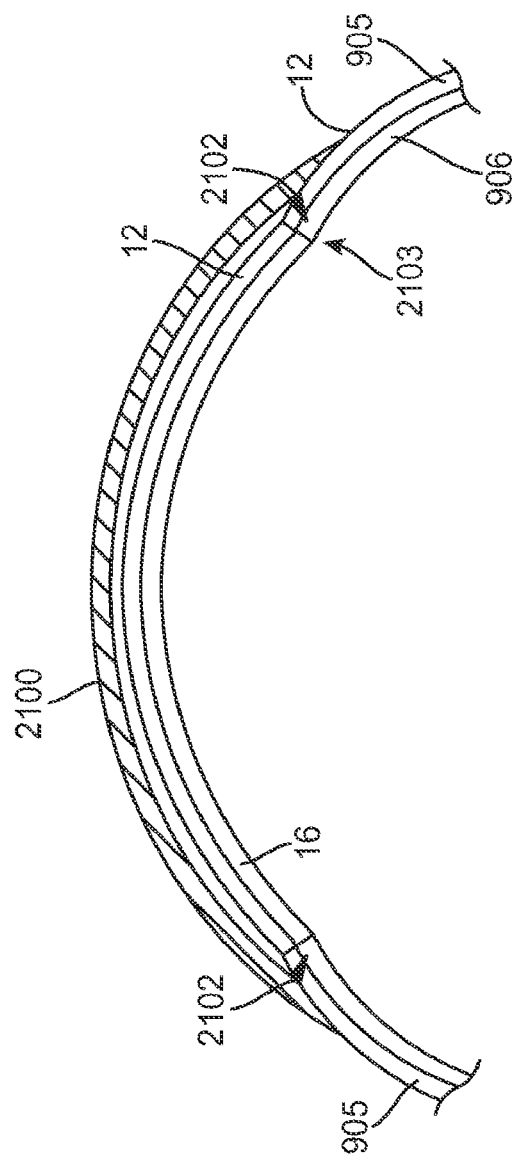
FIG. 21 shows a lens configured to engage a conjunctiva with tacks, according to embodiments of the present invention.

FIG. 21 shows a lens 2100 configured to engage a conjunctiva with tacks 2102. The therapeutic lens can be similar to the embodiments described in FIGS. 20A to 20E, and comprise a peripheral portion that is sized to extend at least partially over the conjunctiva 905, such that the anchor comprising the tack 2102 can extend at least partially into the conjunctiva when the lens is positioned on the eye.

The lenses described above, for example with reference to FIGS. 20A to 20E, can be combined with the tie layers and/or therapeutic layers described above.

Figure 22A:
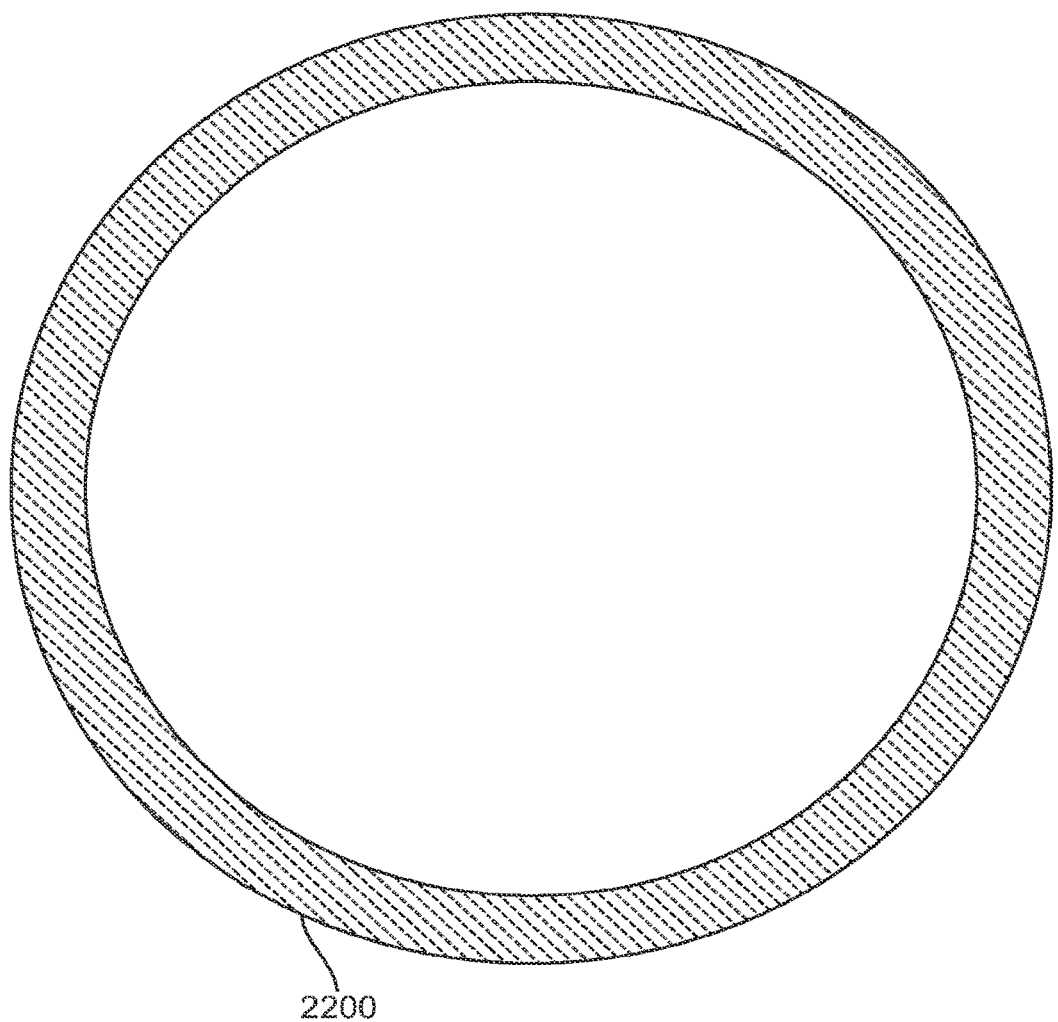
FIG. 22A shows an annular structure for use with a therapeutic lens that extends over at least a peripheral portion of the therapeutic lens to adhere the lens to cornea of the eye, according to embodiments of the present invention.

FIG. 22A shows an annular structure 2200 for use with a therapeutic lens that extends over at least a peripheral portion of the therapeutic lens to adhere the lens to cornea of the eye. The annular structure may comprise an annular band, for example a ring, configured to retain the lens of the eye. The annular hand may comprise many of the adhesive materials, structures and/or anchors described above, such that the annular band is adhered to the eye when placed on the eye.

Figure 22B:
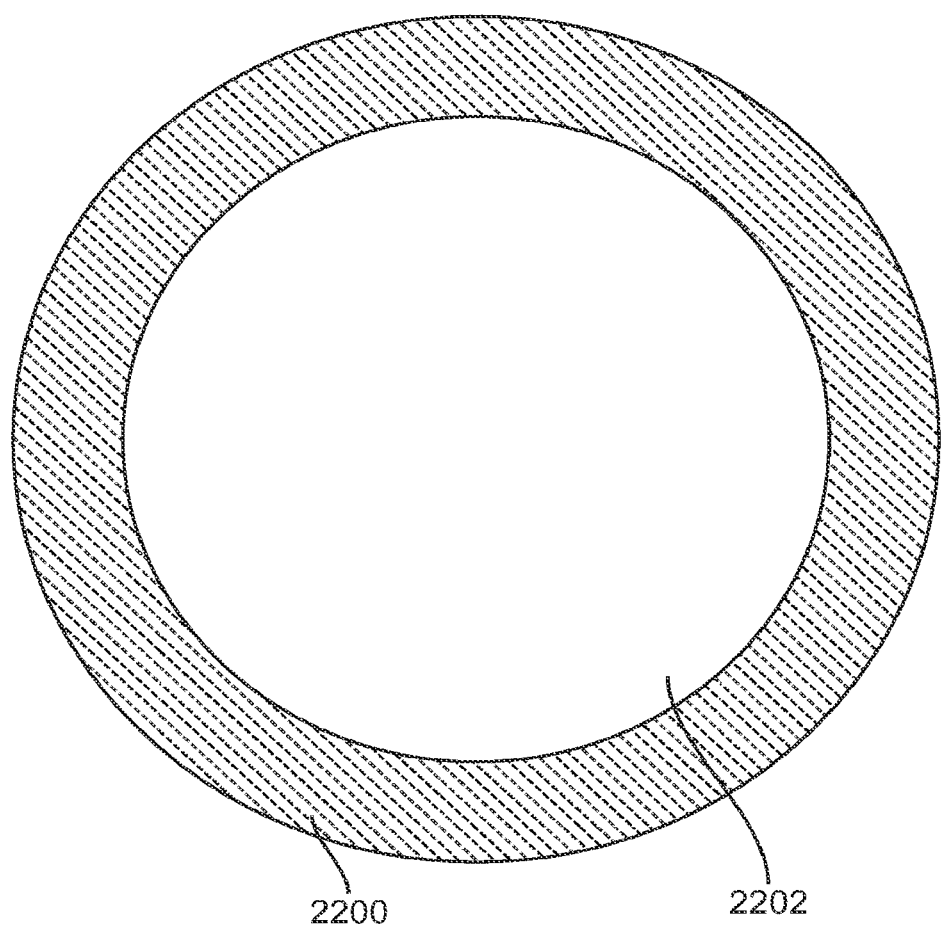
FIG. 22B shows an annular structure as in FIG. 22A over a therapeutic lens to adhere the lens to the eye, according to embodiments of the present invention.

FIG. 22B shows an annular structure 2200 as in FIG. 22A over a therapeutic lens 2202 to adhere the lens to the eye. The annular structure, for example an annular band, may comprise an inner diameter and an outer diameter. The therapeutic lens can be sized with a diameter greater than the inner diameter of the annular structure and less than the outer diameter, such that the annular structure extends over a portion of the therapeutic lens so as to contact the tissue and adhere the lens. The annular structure may comprise a first potion sized to contact the therapeutic lens and a second portion sized to contact the corneal tissue, for example the corneal epithelium.

Figure 22C:
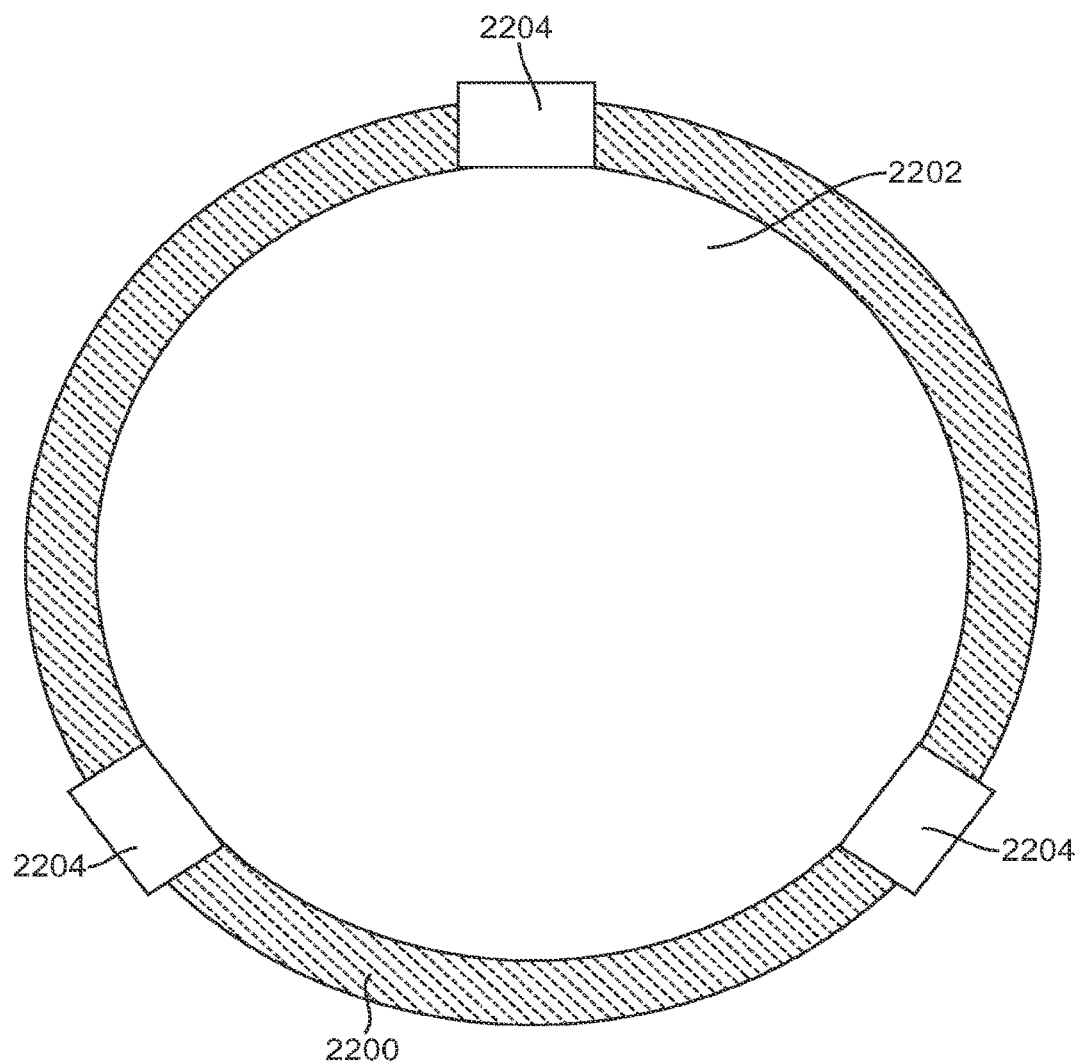
FIG. 22C shows an annular structure with tabs to adhere a therapeutic lens to a cornea, according to embodiments of the present invention.
Figure 22D:
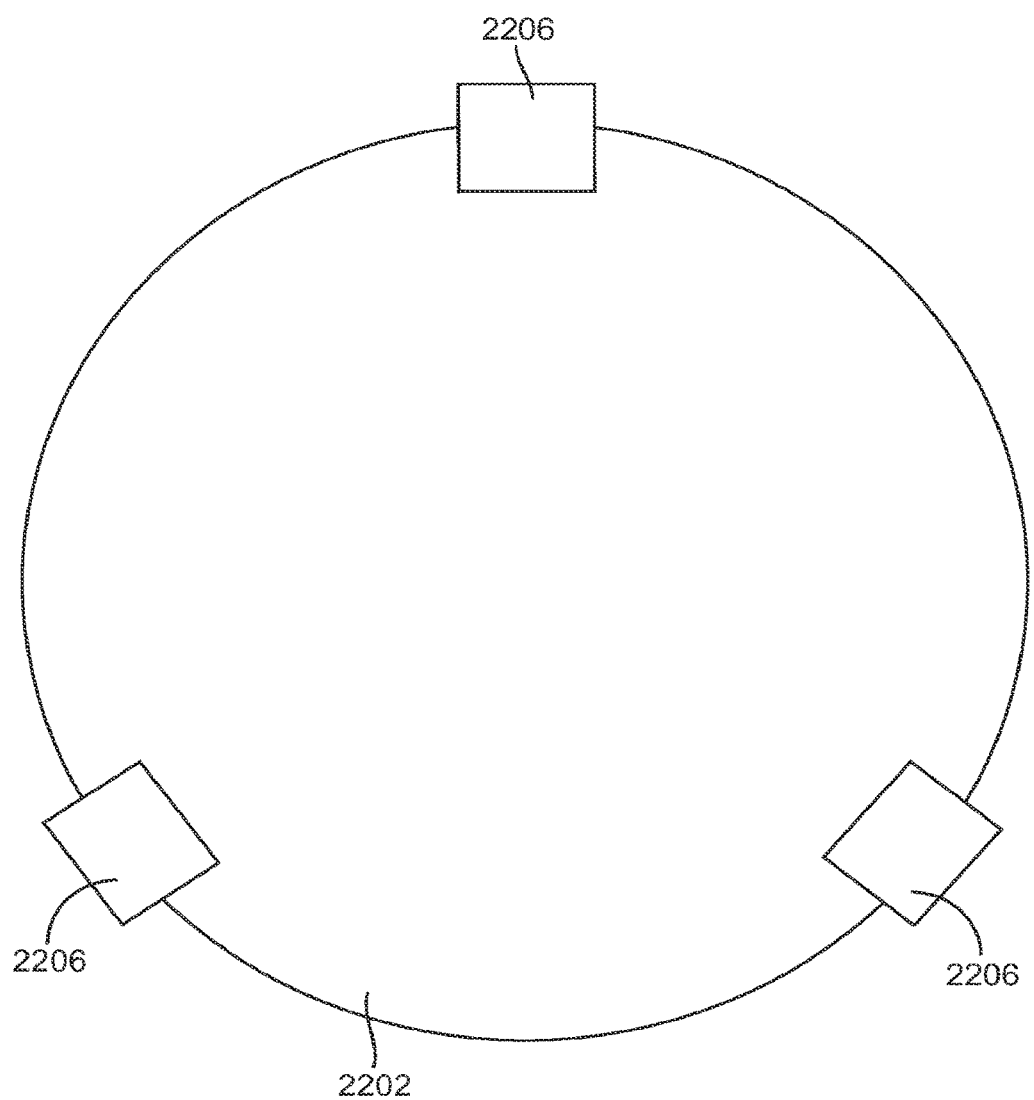
FIG. 22D shows a therapeutic lens with adhesive tabs to adhere to the eye, according to embodiments of the present invention.

FIG. 22C shows an annular structure 2200 with tabs to adhere a therapeutic lens 2202 to a cornea. The annular structure may be similar to the annular structure of FIG. 22B and include adhesive tabs 2204 that can extend outward from the band and downward to engage tissue, such that the tabs are configured to adhere to the epithelium, for example, the epithelium over the stroma and/or conjunctiva. The tabs may comprise many of the adhesive materials, structures and/or anchors described above, such that the annular band is adhered to the eye when placed on the eye. The tabs may be formed from the same material and/or formed from a different material affixed to the annular structure. The tabs may comprise adhesive tape configured to adhere to the epithelium and/or the band. The annular structure 2200 can be placed over the therapeutic lens 2202 to anchor the lens on the cornea, as described above FIG. 22D shows a therapeutic lens with adhesive tabs 2206 to adhere to the eye. The tabs may comprise many of the adhesive materials, structures and/or anchors described above, such that the therapeutic lens is anchored to the eye when the tabs are placed on the eye. For example the tabs may comprise adhesive tape configured to adhere to the epithelium and the therapeutic lens 2202, such that the lens can be adhered to the cornea with the tape.

Figure 23A:
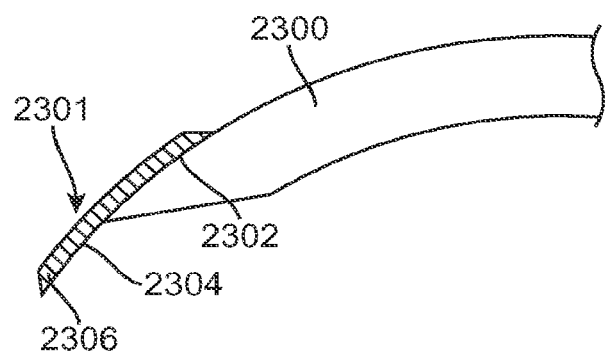
FIG. 23A shows a therapeutic lens with a peripheral adhesive structure disposed on an upper surface of the lens, which structure extends from the upper surface of the lens past an outer periphery of the lens to contact corneal tissue so as to adhere the lens to the eye, according to embodiments of the present invention.

FIG. 23A shows a therapeutic lens 2300 with a peripheral adhesive structure disposed on an upper surface of the lens, which structure 2301 extends from the upper surface of the lens past an outer periphery of the lens to contact corneal tissue so as to adhere the lens to the eye. The peripheral adhesive structure may comprise at least one of the tabs, annular structure, bands or rings described above. The inner portion 2302 may comprise a lower surface with a profile shaped to match the therapeutic lens, for example at least one of a sloped surface or a concave surface with a radius of curvature sized and/or sloped to engage the upper convex surface of the therapeutic lens. The second outer portion 2304 may comprise an adhesive surface 2306 with many of the adhesives described above.

Figure 23B:
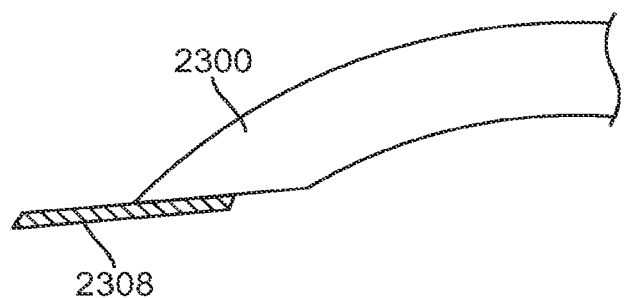
FIG. 23B shows a therapeutic lens with a peripheral adhesive structure disposed on a lower surface of the lens, which structure extends from the lower surface of the lens past an outer periphery of the lens to contact corneal tissue so as to adhere the lens to the eye, according to embodiments of the present invention.

FIG. 23B shows a therapeutic lens 2300 with a peripheral adhesive structure 2308 disposed on a lower surface of the lens, which structure extends from the lower surface of the lens past an outer periphery of the lens to contact corneal tissue so as to adhere the lens to the eye. The peripheral adhesive structure may comprise at least one of the tabs, annular structure, bands or rings described above. The inner portion may comprise an upper surface with a profile shaped to match the therapeutic lens, for example at least one of a sloped surface or a convex surface with a radius of curvature sized and/or sloped to engage the upper concave surface of the therapeutic lens. The second outer portion may comprise an adhesive surface with many of the adhesives described above.

Figure 24A:
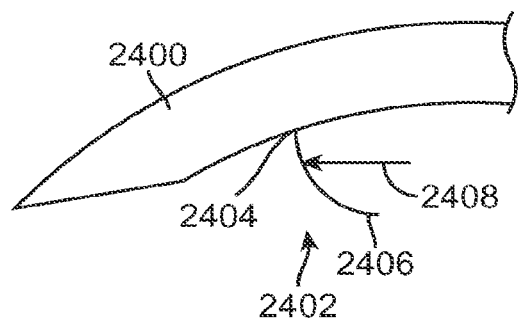
FIG. 24A shows a therapeutic lens comprising a suture tack to anchor the lens to the cornea, according to embodiments of the present invention.

FIG. 24A shows a therapeutic lens 2400 comprising a suture tack 2402 to anchor the lens to the cornea. The suture may extend from a base 2404 along the lower surface of the therapeutic lens to a tip 2406. The suture may comprise a thickness and/or material to penetrate tissue. The suture may extend along a curved arc that corresponds to a radius R 2408 of curvature. The suture can extend with inward inclination from the base to the tip along the arc. The suture can extend many distances from the lower surface of the therapeutic lens. The suture may extend a distance of no more than 400 microns for example 200 microns, and may extend no more than 50 microns to adhere to the epithelium without penetrating the stroma. The suture may comprise, many known suture materials, including known bioerodible or bioabsorbable suture materials. The suture may comprise a bioerodible or bioabsorbable material configured to break or be absorbed after a period of time that corresponds to re-epithelialization of the patient following PRK, for example configured to break after 3 or more days, for example after 7 days.

The suture may be affixed to the therapeutic lens. For example the suture may be formed, for example molded, with the therapeutic lens. The suture may be inserted into the therapeutic lens after the lens is formed, for example and glued to the therapeutic lens.

Figure 24B:
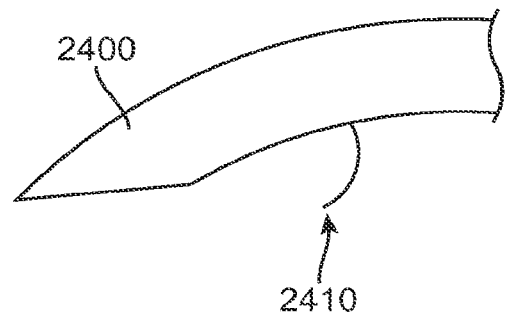
FIG. 24B shows a therapeutic lens comprising a suture tack with outward inclination to anchor the lens to the cornea, according to embodiments of the present invention.

FIG. 24B shows a therapeutic lens 2400 comprising a suture tack 2410 with outward inclination to anchor the lens to the cornea. The suture may extend along an outwardly inclined arc, and may be similar to the curved suture described above. In some embodiments the credible suture may extend normal to surface, for example as described above.

Figure 24C:
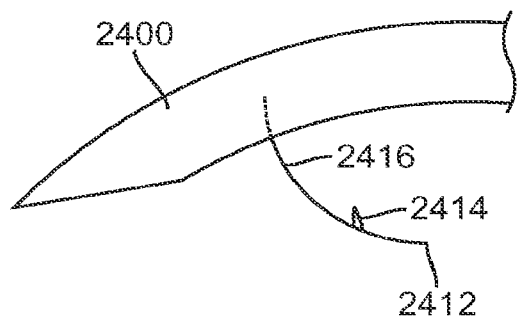
FIG. 24C shows a therapeutic lens comprising a barbed suture to anchor the lens to the cornea, according to embodiments of the present invention.

FIG. 24C shows a therapeutic lens 2400 comprising a barbed suture to anchor the lens to the cornea. The barbed suture can be inclined inward 2412 and may comprise many of the suture characteristics described above. The barbed suture may comprise a bioerodible or bioabsorbable material such that the suture is configured to break or be absorbed and release the lens after an appropriate time, for example three days, or a week, as described above. In some embodiments, the barb can be configured to erode before the suture breaks to facilitate removal.

Figure 24D:
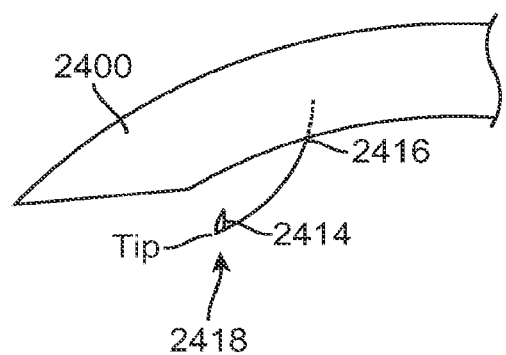
FIG. 24D shows a therapeutic lens comprising a barbed suture with outward inclination to anchor the lens to the cornea, according to embodiments of the present invention.

FIG. 24D shows a therapeutic lens 2400 comprising a barbed suture with outward 2418 inclination to anchor the lens to the cornea. The barbed suture is similar to may of the sutures described above.

Figure 25A:
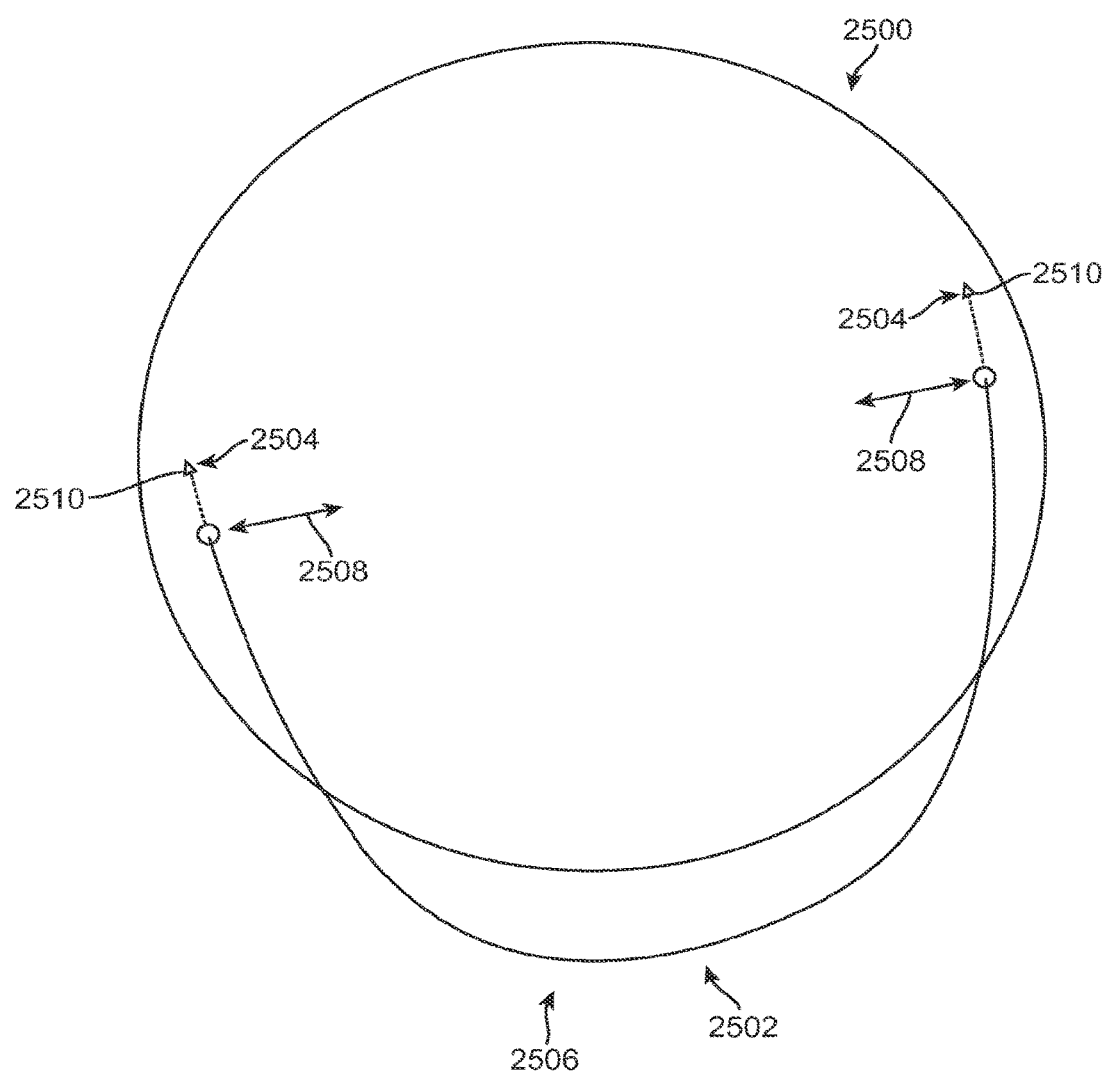
FIG. 25A shows an external elastically deformable structure coupled to a therapeutic lens so as to adhere the lens to the eye, according to embodiments of the present invention.

FIG. 25A shows an external elastically deformable structure 2502 coupled to a therapeutic lens 2500 so as to adhere the lens to the eye. The elastically deformable structure may urge the tacks 2504 into tissue with force, for example with inclined tacks as described above. The elastically deformable member may comprise a band, a loop, a coil, a spring, a suture and many materials such as shape memory materials. The elastically deformable structure can be connected to the tacks, for example tacks as described above, such that the structure exerts force on the tacks. The deformable structure can be used with deformation of the therapeutic lens 2508, for example with a first configuration and a second configuration as described above, such that the therapeutic lens can be adhered on the cornea with force from the elastic structure coupled to the tacks. The structure may comprise a low profile configured to lay along the surface of the cornea and/or conjunctiva. The structure may also fit into a groove on the surface of the therapeutic lens. The tacks may comprise barbs 2510 and/or bioerodible or bioabsorbable materials as described above.

Figure 25B:
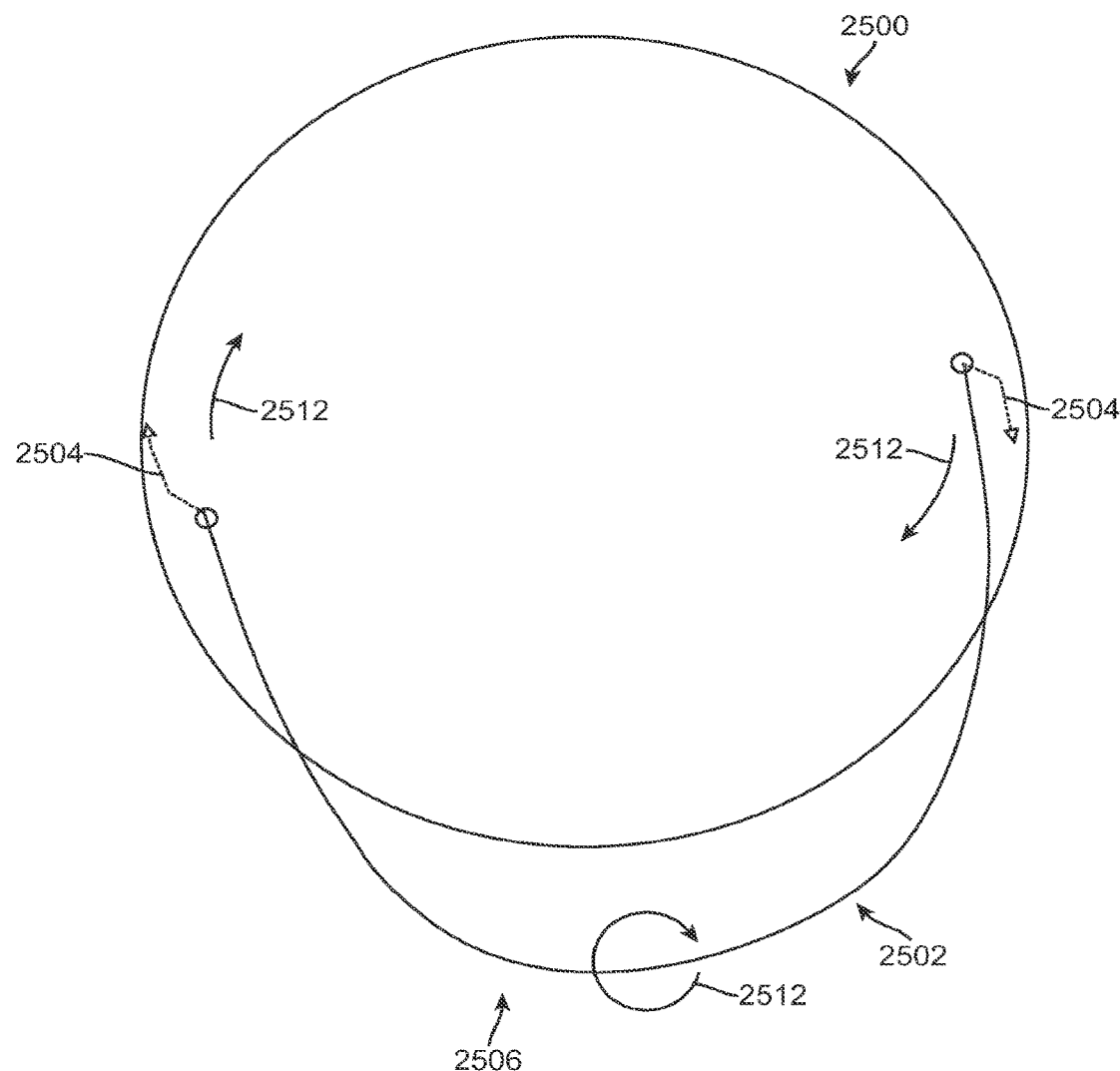
FIG. 25B shows an external elastically deformable structure coupled to tacks inclined at opposing angles to as to adhere the lens to the eye with rotation of the elastically deformable structure, according to embodiments of the present invention.

FIG. 25B shows an external elastically deformable structure 2502 coupled to tacks 2504 inclined at opposing angles to as to adhere the lens to the eye with rotation 2512 of the elastically deformable structure. The tacks may extend from a base to a tip with opposite inclination. For example, a first tack may extend from the base to the tip in a first direction, and the second tack may extend from the base to the tip in a second direction, in which the second direction extends opposite the first direction. The external elastically deformable structure 2502 may comprise a low profile that extends along the cornea and/or conjunctiva when the lens is adhered, for example anchored, to the eye.

Figure 25C:
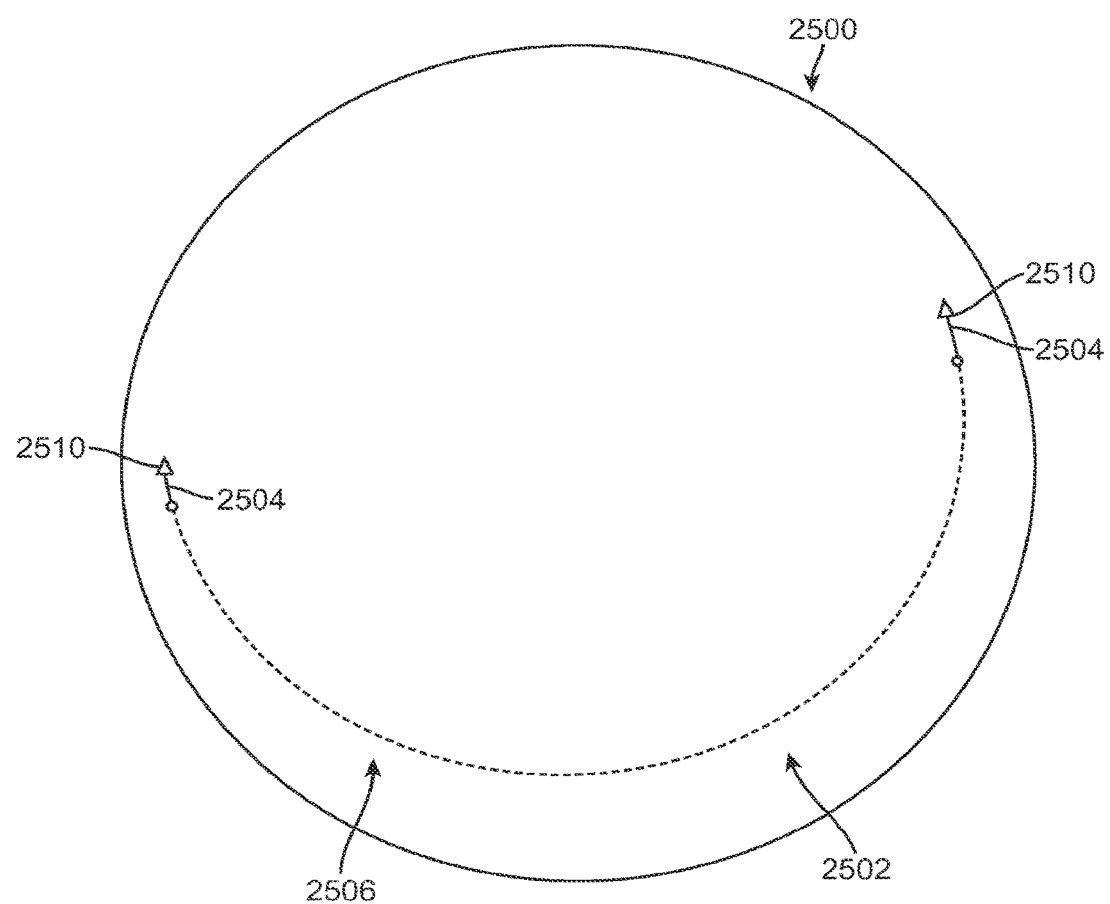
FIG. 25C shows an internal elastically deformable structure coupled to tacks to adhere the lens to the eye, according to embodiments of the present invention.

FIG. 25C shows an internal elastically deformable structure 2502 coupled to tacks to adhere the lens to the eye. The elastically deformable structure and tacks may comprise characteristics similar to the external deformable structure described above. For example the tacks may comprise credible sutures and/or barbs, as described above.

Figure 25D:
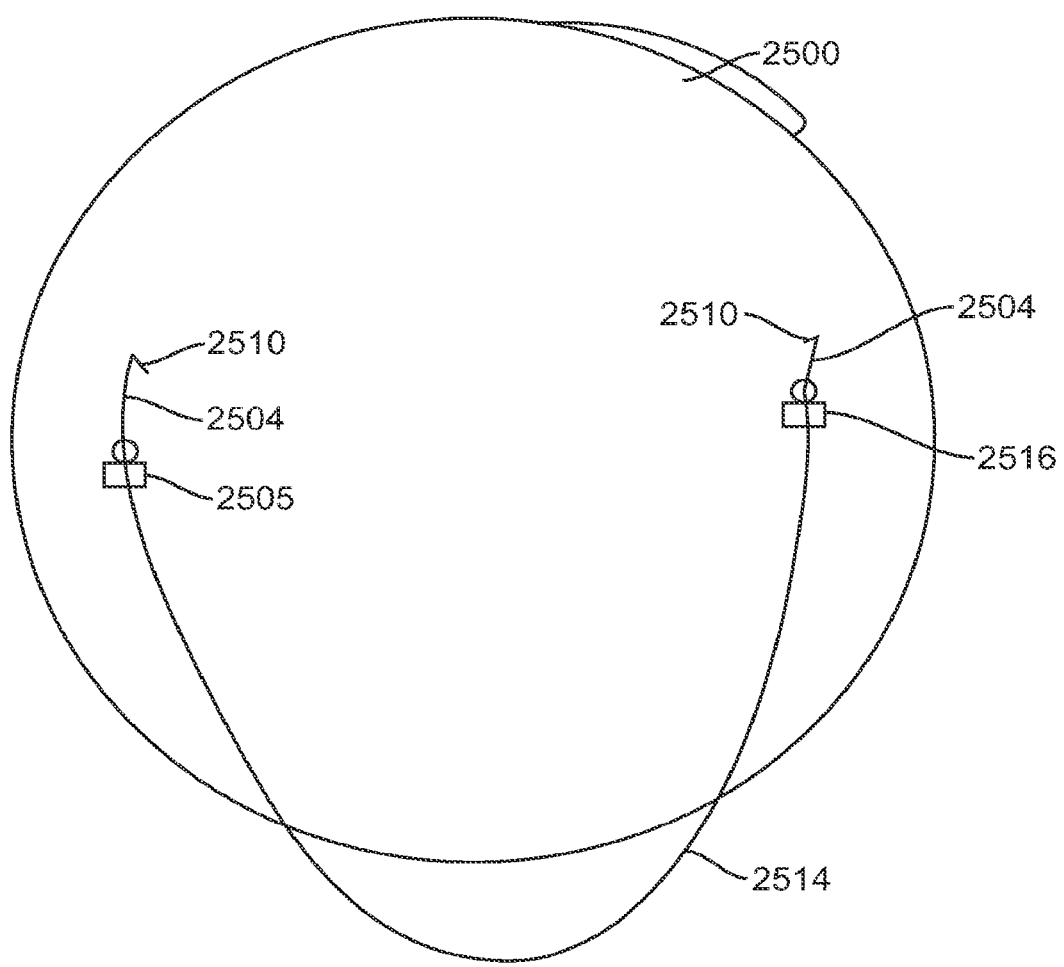
FIG. 25D shows an external tool coupled to tacks with couplings to adhere the lens to the cornea of the eye, according to embodiments of the present invention.

FIG. 25D shows an external insertion tool 2514 coupled to tacks 2504 with couplings to adhere the lens 2500 to the cornea of the eye. The insertion tool may comprise a graspable loop connected to the tack so as to engage each tack with a coupling 2516 connected to the tack. The insertion tool can be separated from each tack at the coupling when the lens is adhered to the eye.

Figure 26A:
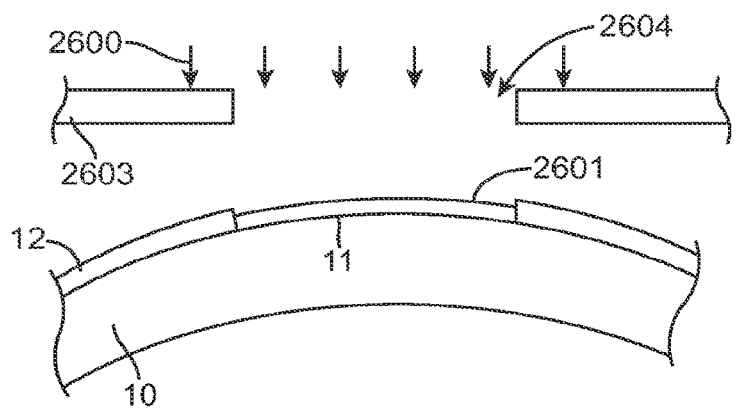
FIGS. 26A to 26D show a method of forming a therapeutic covering, according to embodiments of the present invention.

FIG. 26A to 26D show a method of forming a therapeutic covering. In some embodiments, it may be desirable to form a first covering centrally over the stroma and/or Bowman's and a second outer covering over the epithelium. As shown in FIG. 26A a step applies a first spray 2600 comprising a first material 2602 to the eye. The first material is applied to the exposed stroma 16 and/or Bowman's 14 where tissue has been ablated. An aperture 2604 is placed in front of the eye to form a central pattern comprising a first material. Although an aperture is shown, a jet deposition spray, for example with scanning as described above can be used to deposit the first material. The first central pattern may comprise many of the shapes described above for example at least one of a layer, a lens 2601, or a two or more layer covering. The first material may comprise an adhesive targeted to adhere to the stroma and/or Bowman's membrane, for example a fibrin adhesive commercially available as Tisseal™.

Figure 26B:
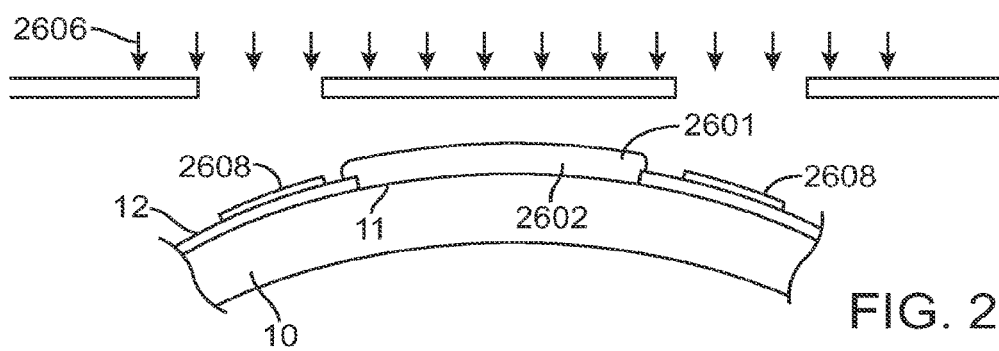
Figure 26C:
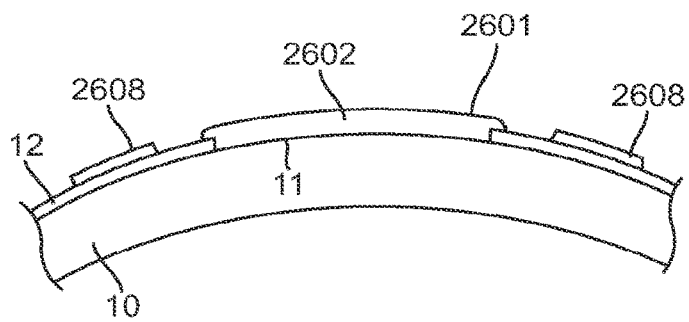

As shown in FIG. 26B, a step applies a second spray 2606 comprising a second material 2608 to the eye away from the ablated region 11 of the eye where epithelium has been removed. The second material may comprise an adhesive targeted to adhere to the epithelium for example a mucoadhesive. While many adhesives may be used, muco-adhesives commercially available as Pharmadur™ may be used, for example as described in U.S. Pat. Nos. 5,814,329; 5,942,243 and 6,958,148; and U.S. Pub No. 2004/0143026, the disclosures of which may be suitable for combination in accordance with some embodiments of the present invention. The second material may comprise micro-particles to be attached to the epithelium, for example with delivery agents as described in U.S. Pat. No. 6,958,158, the disclosure of which may be suitable for combination in accordance with some embodiments of the present invention. The second material is applied to form the second layer on the epithelium with a desired thickness, for example as shown in FIG. 26C. Although an annular pattern is shown, the second material can be applied in many patterns, for example star shaped, cross-hatched and/or oval. In at least some embodiments, the annular pattern extends over the epithelium without extending over the ablated stroma and/or Bowman's.

The first central material may comprise a first therapeutic agent or no therapeutic agent, and the second material may comprise a second therapeutic agent or no therapeutic agent. Work in relation to embodiments of the present invention suggests that at least some therapeutic agents can be delivered effectively over the epithelium that may not be appropriate for release over the ablated tissue surface. The use of a second material comprising a therapeutic agent targeted for placement over the epithelium can allow elution of the therapeutic agent only over the epithelium, such that specific tissues and/or effects can be targeted. For example, an epithelial growth factor can be eluted over the epithelium. In some embodiments, a therapeutic agent appropriate for the stroma can be released over the ablated stroma and/or Bowman's, for example Mitomycin C.

Figure 26D:
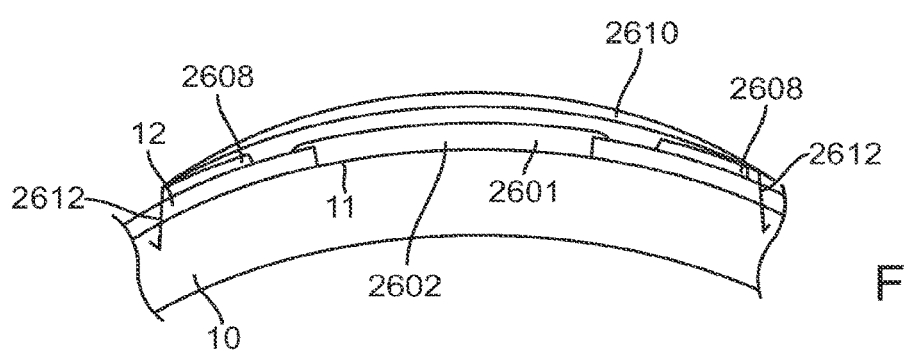

As shown in FIG. 26D, a therapeutic lens 2610 may be placed over the first central 2602 material and second peripheral material 2608. The therapeutic lens may be adhered with the second material. In some embodiments, the second material may allow at least some lateral movement of the therapeutic lens, such that the therapeutic lens may be adhered with a peripheral portion as described above, for example with lacks 2612.

The peripheral material may comprise a sticky material that sticks the therapeutic lens to the cornea so as to allow shear, or sliding, of the lens on the cornea, for example the mucoadhesive and/or micro-particles as described above. An adhesive structure sufficient to resist a blink of the eye lid can be disposed in the peripheral portion of the therapeutic lens to resist shear motion of the therapeutic lens. The adhesive structure may comprise a length sufficient to extend through the layer of second material and contact and even extend into the epithelium, such that motion of the lens from the eyelid can be resisted. The adhesive structure may comprise at least one of microstructures, setae or micro-tacks and many of the structures described above so as to limit shear motion in combination with the peripheral material.

Figure 27A:
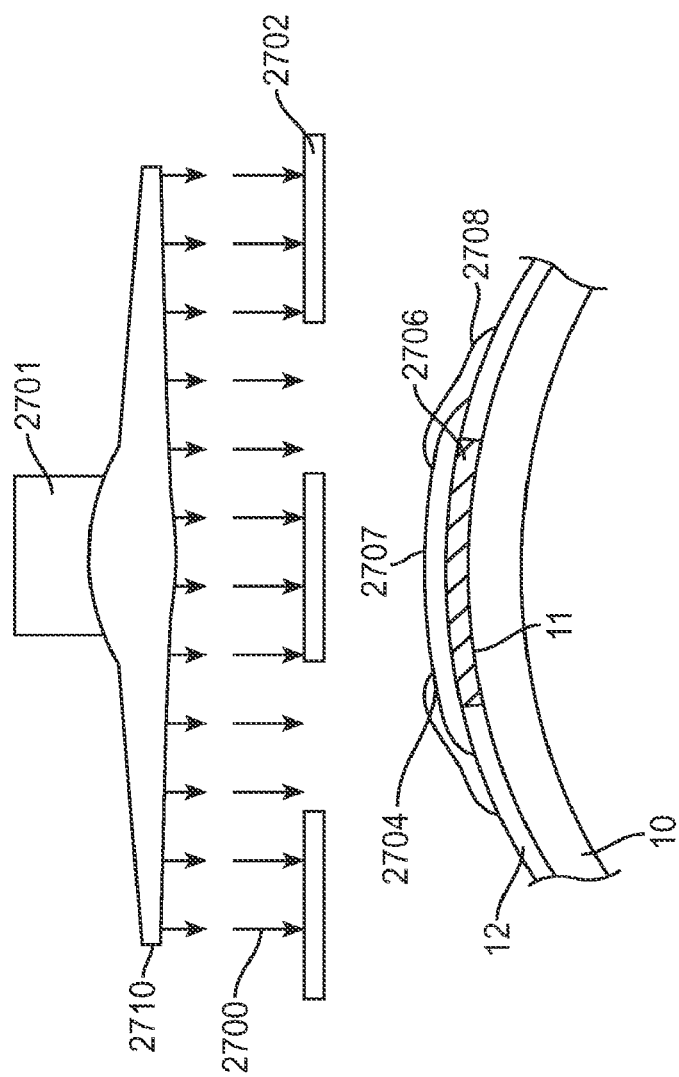
FIG. 27A shows a method of adhering a lens to a cornea, according to embodiments of the present invention.

FIG. 27A shows a method of adhering a lens to a cornea. An adhesive spray 2700 can be sprayed, for example as described above. A mask 2702 comprising an annular aperture can be disposed between a spray source 2701 and the eye, for example as described above. A lens 2704 can be placed on the eye with at least one therapeutic layer 2706 disposed over the ablation 11, for example as described above. Adhesive can be sprayed over a peripheral portion 2708 of the lens. The spray may avoid the central optical portion 2707 of the lens such that the lens remains good optical properties. The adhesive spray 2710 can be disposed in an annular pattern around the periphery of the lens to form a peripheral portion 2708 of the lens in situ, which peripheral portion anchors the lens on the cornea of the eye, for example with adhesion to the epithelium with the peripheral portion. Although an annular mask is shown, the adhesive may be sprayed in many ways, for example with scanning jet deposition as described above. The adhesive can cure on the eye to form the peripheral portion. Many adhesives described above can be sprayed onto the eye and cured to form the peripheral portion, for example a skirt, in situ.

FIG. 28A shows a lens 2800 adhered to the cornea with protrusions comprising peripheral tacks 2802. The cornea comprises a stroma, an epithelium and an epithelial defect 11. The lens comprises a plurality of apertures 2804, or holes, each of which extends through the lens and is sized to receive a tack, the tack can be formed in many ways and may comprise a tip to penetrate tissue and a barb to retain the tack and lens in place until removal. The tack can be sized and extend from the recess of the contact lens 2806 into the stroma, for example such that the tip 2808 and barb 2810 contact corneal stroma for retention, although the tack may also be sized such that the tip and barb contacts a desired tissue for retention, for example Bowman's membrane or the epithelium. The tack may comprise many materials, for example an erodible material as described above. The aperture includes a recess sized to receive a head of the tack, such that the head fits into the recess. The head of the tack fits flush with the anterior surface of the contact lens, such that irritation to the eyelid is minimized, for example when the patient blinks. In some embodiments, an additional annular structure, for example similar to the annular structure shown in FIGS. 22A and 22B above, can be placed over the tacks to inhibit or minimize irritation to the patient eyelid. The lens may comprise many of the lens materials described above, for example a hard lens composed of at least one of known PMMA or RGP materials, and the lens may comprise a soft lens, for example a known hydrogel lens. The lens may comprise the layer of therapeutic material, or a layer of therapeutic material can be positioned between the lens and stroma so as to cover exposed stromal tissue in the region of the epithelial defect.

FIG. 28A1 shows a tack 2802 for use with the lens 2800 as in FIG. 28A. The tack comprises a tip 2808 and a barb 2810 to retain the tack and contact lens with tissue. The tab comprises a head sized to fit into a recess 2806 formed in the contact lens. The tack is sized so as to extend from the head through the aperture 2804 of the contact lens, through the epithelium 12 and into the corneal stroma 16 with contact of the tip and barb in stromal tissue to anchor the contact lens.

FIG. 28B shows a lens 2800 with protrusions 2812 to adhere the lens to the cornea. The lens comprises a central portion for vision and a peripheral portion to adhere the lens to the eye and minimize motion of the lens and therapeutic layer. The lens may comprise many of the lens materials described above, including hard tenses and soft lenses. The peripheral portion comprises a protrusion to adhere, for example to anchor or fix, the lens to the eye. The protrusion extends downward on the lens and is sized to extend into corneal tissue to adhere the lens to the eye. Although one protrusion is shown, many protrusions can extend from the lens to adhere the lens to the eye. The protrusions can be formed in many ways, for example with tacks, as described above, embedded in the lens material.

FIG. 28B-1 shows a protrusion 2812 comprising a tack having tip 2816 and a barb 2814 for use with lenses as in FIGS. 28A and 28B. The protrusion comprises a tack having a tip and a barb, and can be sized to adhere the lens to at least one of stromal, Bowman's or epithelial tissue.

FIG. 28B-2 shows a tack comprising a tack 2802 with a tip 2808 and a barb 2810 for use with lenses as in FIGS. 28A and 28B. The tack comprises a head, a barb and a tip.

FIG. 28B-3 shows a protrusion 2812 comprising a tack having a tip 2818 and an expanded cross section for use with lenses as in FIGS. 28A and 28B. The tip may comprise a blade shaped to penetrate tissue. An enlarged cross section the expanded cross section near the tip can anchor the tack in tissue to adhere the lens to the cornea.

FIG. 28B-4 shows a protrusion 2812 comprising a tip and an expanded cross section for use with a lens as in FIGS. 28A and 28B. The tip 2820 may extend to a point shaped to penetrate tissue. An enlarged cross section the expanded cross section near the tip can anchor the tack in tissue to adhere the lens to the cornea.

Figure 28C:
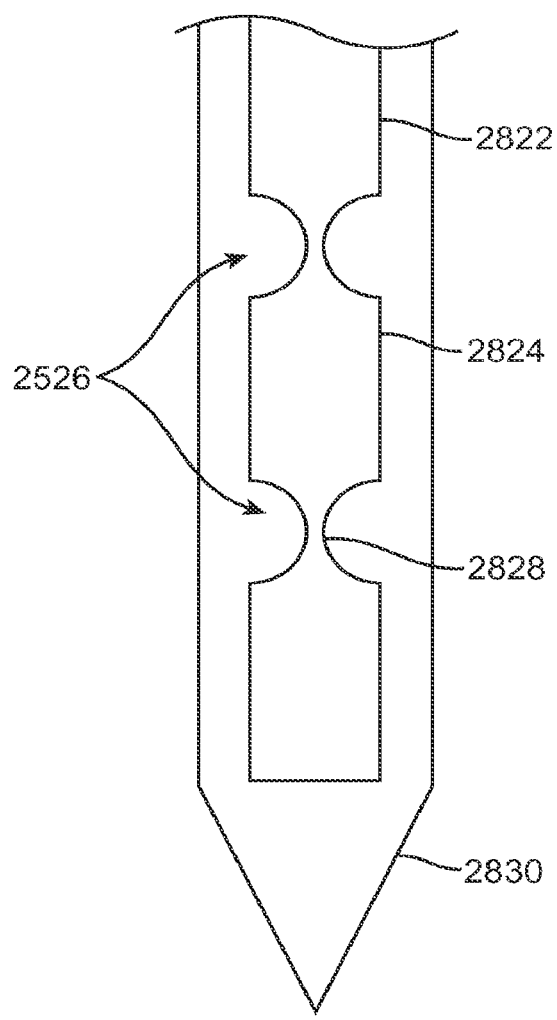
FIG. 28C shows a protrusion comprising syringe tube for use with tenses as in FIGS. 28A and 28B.

FIG. 28C shows a protrusion 2822 comprising syringe tube for use with lenses 2800 as in FIGS. 28A and 28B. The syringe tube 2824 comprises openings 2826 for tissue in growth 2828. A needle 2830 can be used for at least one of insertion or removal of the syringe tube, and the needle comprises a lumen sized to receive the syringe tube.

Figure 28D:
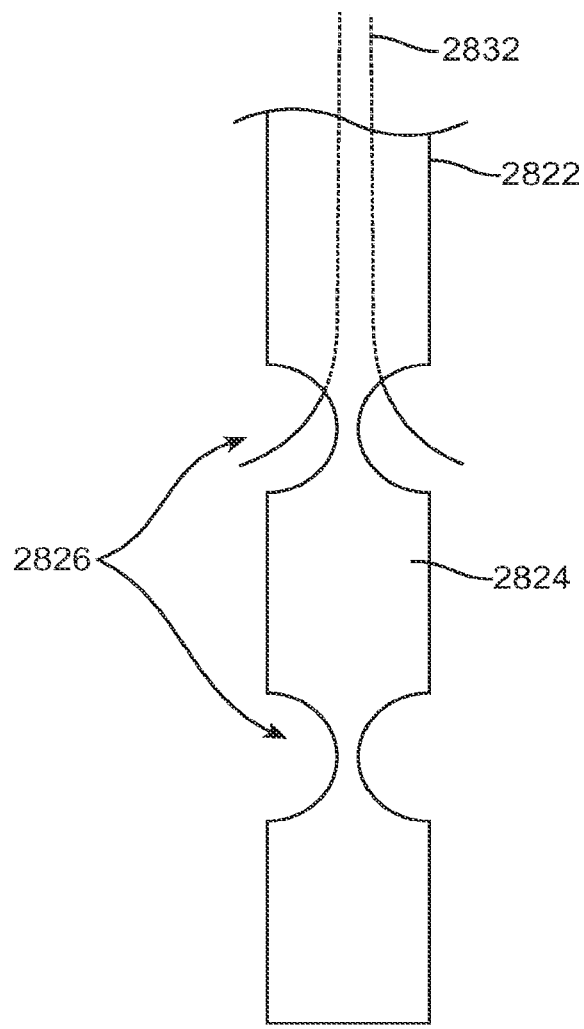
FIG. 28D shows a protrusion comprising syringe tube with at least one of wire or suture inserted therein for use with lenses as in FIGS. 28A and 28B.

FIG. 28D shows a protrusion 2822 comprising syringe tube 2824 with at least one of wire 2832 or suture inserted therein for use with lenses as in FIGS. 28A and 28B. The syringe tube comprises openings 2826 sized to receive and pass the wire. The wire can be inserted into the syringe tube to anchor the syringe tube in the cornea to adhere the lens to the cornea. The wire can be removed prior to removal of the syringe tube to facilitate removal of the syringe tube. In some embodiments, an annular structure, as described above, can be positioned over the lens and wires to protect the eyelid from the wires.

Figure 28E:
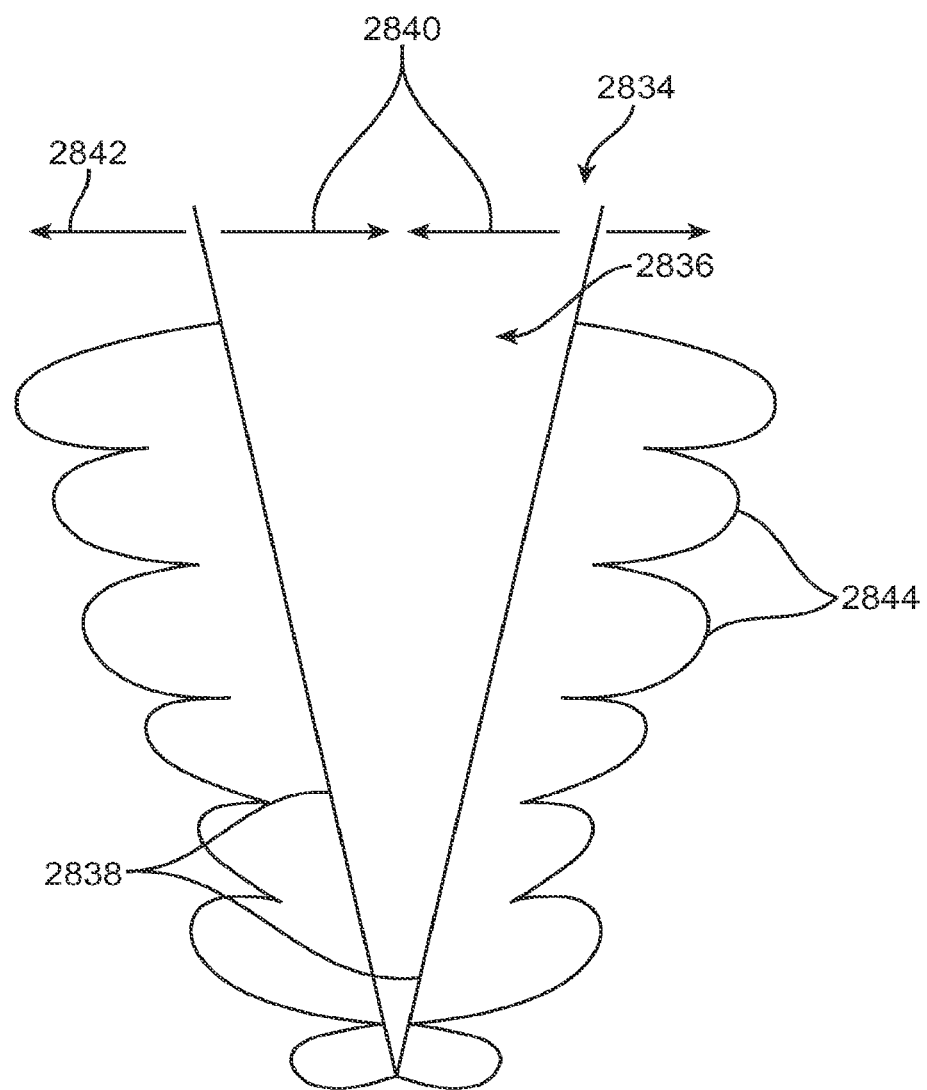
FIG. 28E shows a protrusion comprising a removable wedge for use with lenses as in FIGS. 28A and 28B.

FIG. 28E shows a protrusion 2834 comprising a removable wedge 2836 for use with lenses 2800 as in FIGS. 28A and 28B. The removable wedge comprises elongate members 2838, for example elastic members, such that the wedge can be squeezed 2840 together for insertion and removal, for example when the protrusion passes through an aperture of a contact lens as described above. The wedge may also be at least partially embedded in the contact lens. The elastic member can urge the removable wedge outward 2842 against tissue to anchor the wedge in tissue to adhere the contact lens to the eye. The removable wedge may comprise surface structures 2844 for traction when the elastic members urge the wedge outward. In some embodiments, elongate members comprise a single piece of resilient material and the spring is provided by flexure at a bend in the material.

Figure 28F:
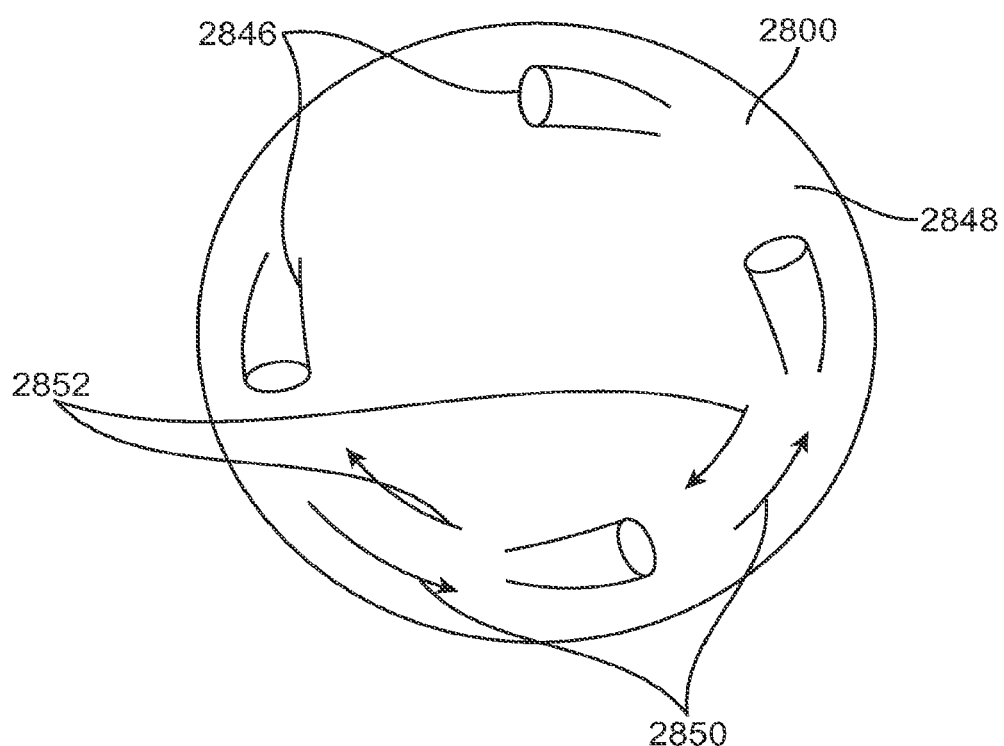
FIG. 28F shows protrusions configured for twisting attachment of the lenses as in FIGS. 28A and 28B.

FIG. 28F shows protrusions 2846 configured for twisting attachment of the lenses 2800 as in FIGS. 28A and 28B. The protrusions may comprise tacks, for example as described above, embedded in the contact lens. The protrusions extend from the lower surface 2848 of the lens at an angle so as to penetrate tissue when the lens is rotated, for example twisted 2850, and pressed against the cornea. For example, counter clockwise rotation of the lens as viewed on the lower surface (clockwise for the surgeon) can result in adherence of the lens to tissue. For removal, the lens can be twisted in an opposite direction 2852, for example clockwise as viewed from the lower surface and counterclockwise for the surgeon, such that both the lens and the lens protrusions are removed from tissue. The removable wedge may function in a remotely similar way to a wall anchor for holding a screw in drywall.

Figure 28G:
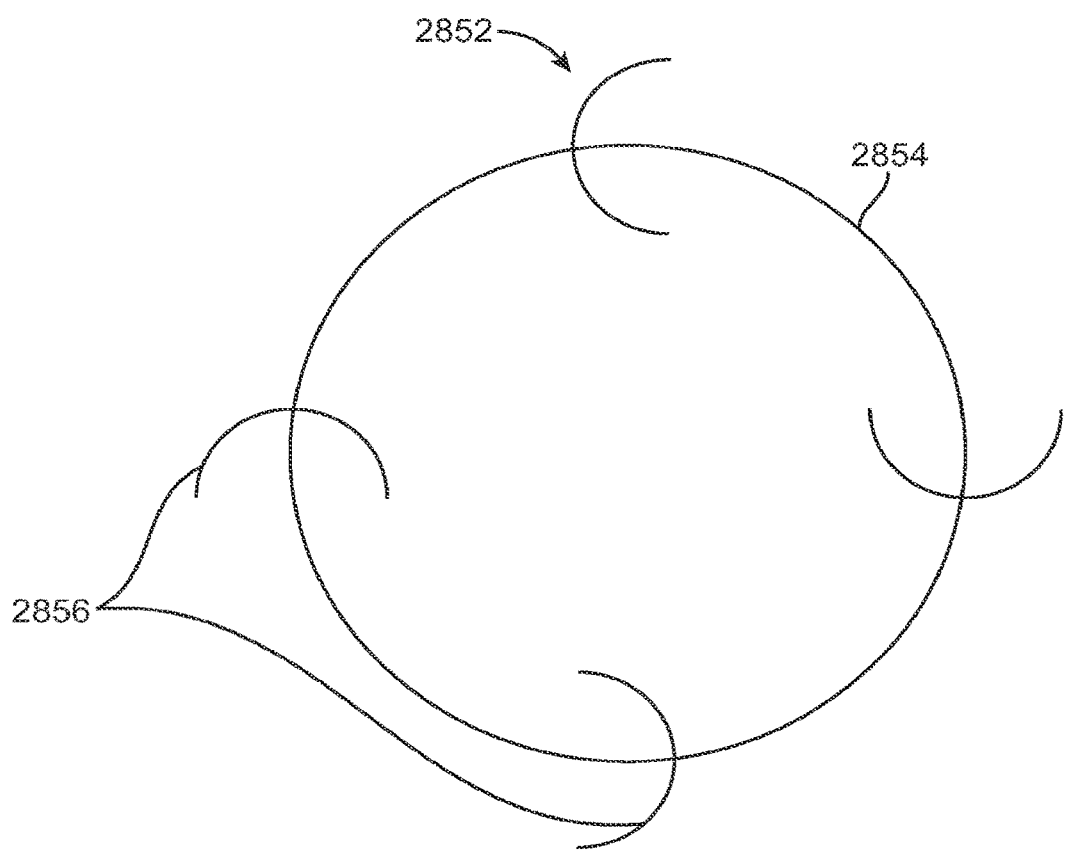
FIG. 28G shows a ring with clip attachment for use with lenses as in FIGS. 28A and 28B.

FIG. 28G shows a ring with clip attachment protrusions 2852 for use with lenses as in FIGS. 28A and 28B. The ring 2854 extends circumferentially and may comprise clips 2856 to attach the ring. Each clip may comprise a pair of protrusions configured to extend downward into the corneal tissue. The ring can be placed on the contact lens near the rim of the lens with the clips extending into the tissue. The ring may also be embedded in the contact lens such that the protrusions extend downward into the tissue.

Figure 28H:
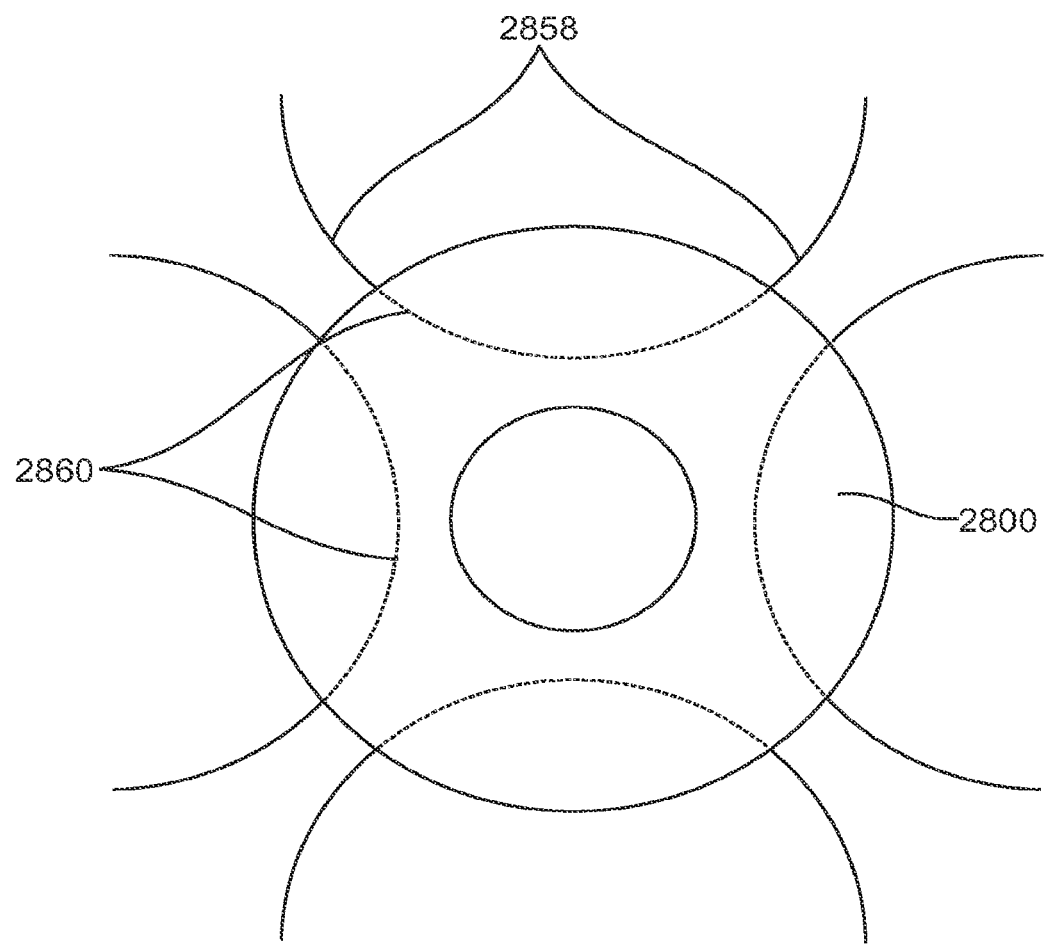
FIG. 28H shows shallow pins for use with lenses as in FIGS. 28A and 28B.

FIG. 28H shows protrusions comprising shallow pins 2858 for use with lenses as in FIGS. 28A and 28B. The shallow pins can be embedded 2860 in the lens 2800, or may extend through apertures formed in the lens. The pins can be sized to extend into at least one of stromal tissue, Bowman's membrane or epithelial tissue.

Figure 28I:
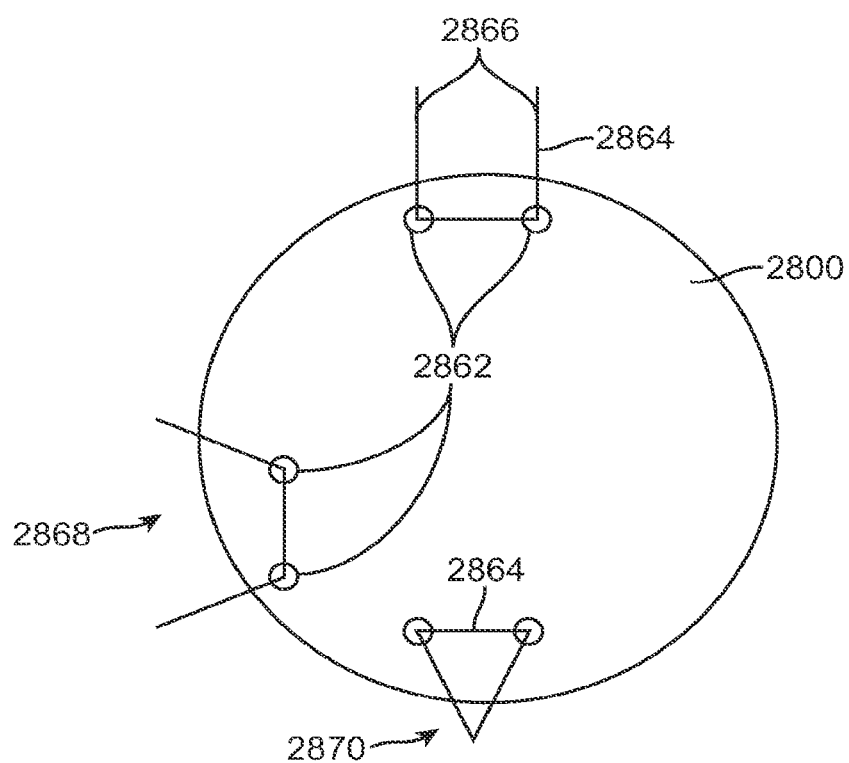
FIG. 28I shows staples for use with lenses as in FIGS. 28A and 28B.

FIG. 28I shows protrusions comprising staples 2864 for use with lenses as in FIGS. 28A and 28B. The staples can be embedded in the lens 2800, and may also be sized to pass through apertures 2862 similar to the tacks described above. The prongs of each staple may extend in a substantially parallel configuration. The prongs 2866 of each staple may be configured to flare out 2868, and the prongs may be configured to flare in 2870, so as to anchor each staple in tissue. The prongs of each flared staple anchored in tissue may also be bent into the parallel configuration for removal.

Figure 28J:
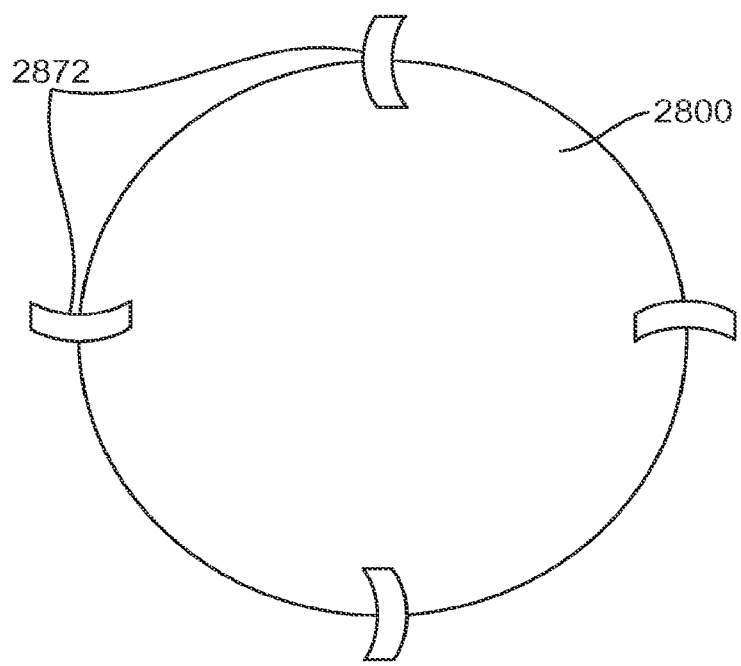
FIG. 28J shows bandage clips to adhere a contact tens to the cornea.

FIG. 28J shows protrusions comprising bandage clips 2872 to adhere a contact lens 2800 to the cornea. The bandage clips may be similar to known commercially available ACE™ bandage clips, and sized to adhere the lens to the cornea. The contact lens can be placed on the cornea of the eye, and each clip then placed on the contact lens and cornea so as to adhere the contact lens to the cornea. The clips may also be at least partially embedded in the contact lens, for example one side of the clip, such that a portion of the clip protrudes from the lens to adhere the lens to the cornea.

Figure 28K:
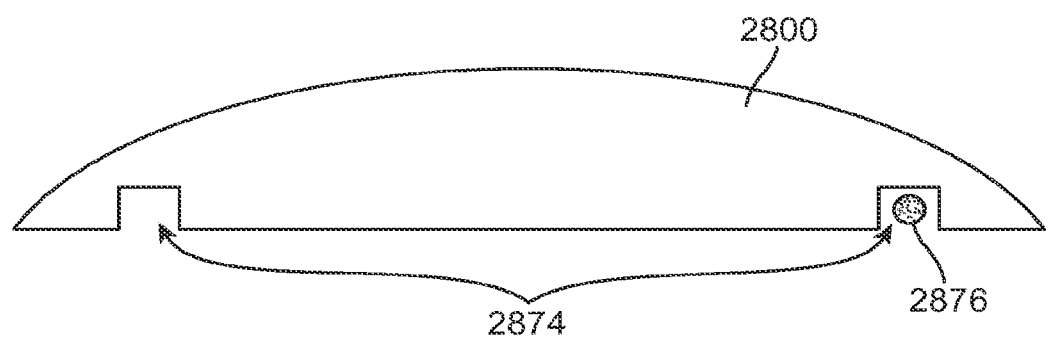
FIG. 28K shows indentations on a lower part of a lens for attachment to the cornea, according to embodiments.

FIG. 28K shows indentations 2874 on a lower surface of a lens 2800 for attachment to the cornea. The indentations on the lower side of the lens can be shaped and sized to receive glue 2876 to adhere the lens to the cornea peripheral to an epithelial defect, similar to the embodiments described above.

Figure 28L:
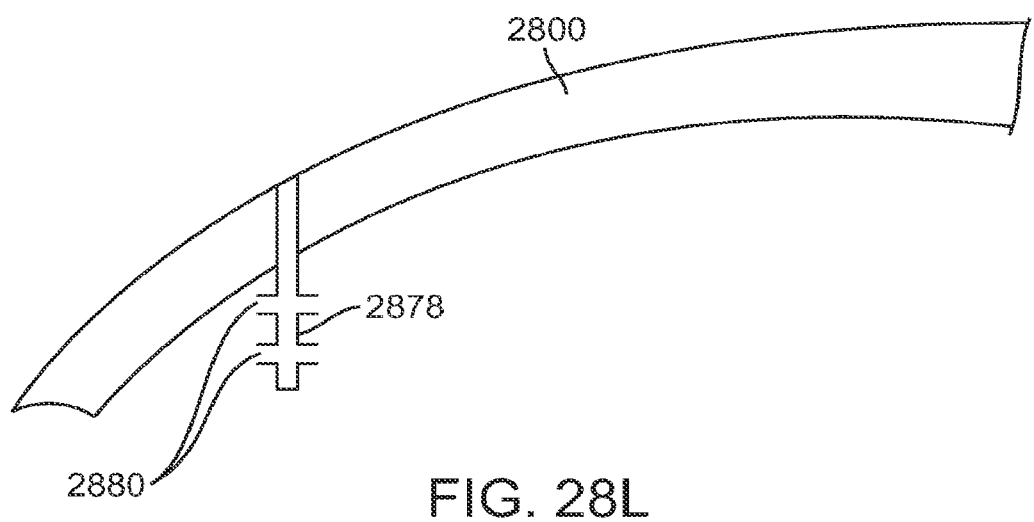
FIG. 28L shows tubing with holes for adhesive to adhere a lens, according to embodiments.

FIG. 28L shows tubing 2878 with holes 2880 for adhesive to adhere a lens 2800. The tubing may comprise a plurality of tubes disposed at many locations on the contact lens. The tubing may comprise a plurality of apertures to pass the glue into the tissue to anchor the tubing and adhere the lens. Each tube comprises at least one channel that may extend from an upper surface of the lens to the apertures to pass glue to contact the tissue, such that an adhesive glue can be injected into the tubing when the tubing is inserted into the tissue.

Figure 28M:
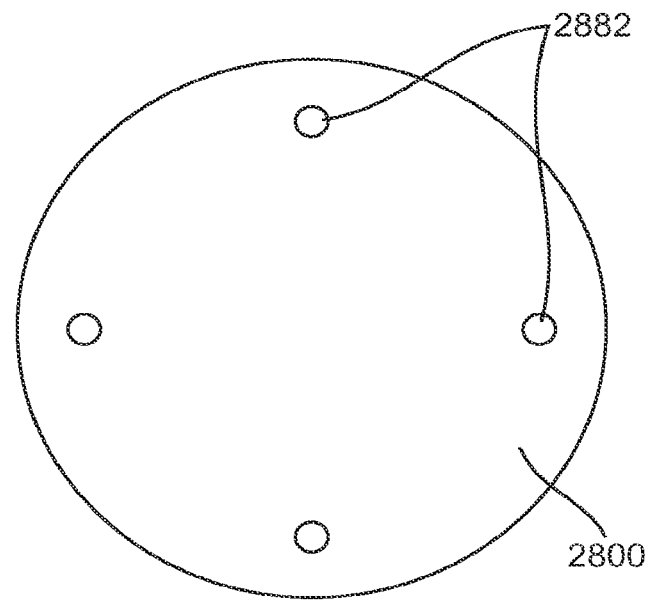
FIG. 28M shows a contact lens with apertures for gluing the lens near the periphery of the lens, according to embodiments.
Figures 1, 28M:
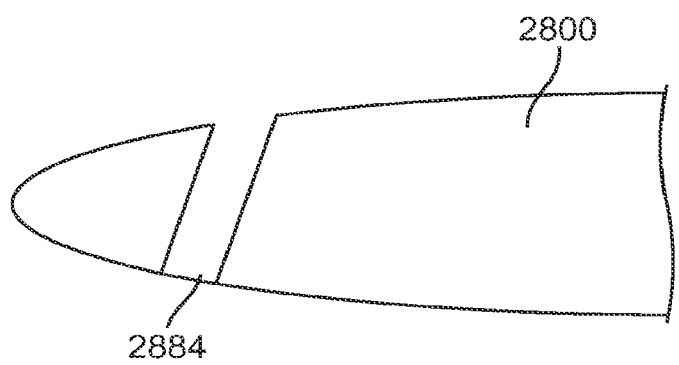
Figures 2, 28M:
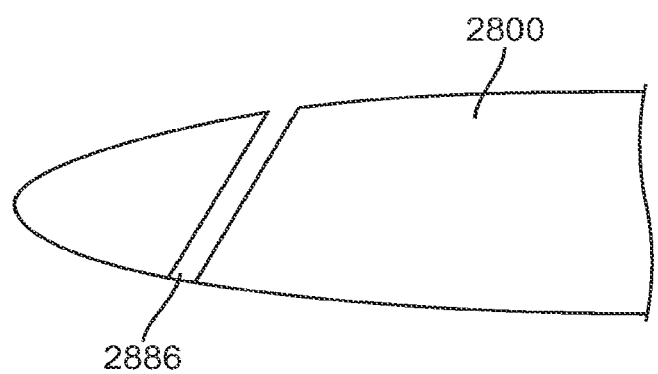

FIG. 28M shows a contact lens 2800 with apertures 2882, or holes, for gluing the lens near the periphery of the lens. The hole extends from the upper surface of the lens to the lower surface of the lens, such that glue can be injected through the hole so as to contact the corneal tissue. The tacks, as described above, may also be sized to pass through the holes to adhere the lens to the cornea. The holes may pass through the lens at many angles, for example normal to the surface, inclined, inclined toward the center of the eye and inclined away from the center of the eye.

FIG. 28M-1 shows a channel 2884 extending normal to a lower surface of a lens 2800 as in FIG. 28M. The channel may comprise a hole, or aperture, that extends through the lens. The channel may comprise a groove that extends along the surface of the lens and may also extend through the lens. The hole may also extend vertically through the lens when the lens is placed on the eye and the patient is supine, for example during eye surgery.

FIG. 28M-2 shows inclined 2886 channel in a lens 2800 as in FIG. 28M. The channel may comprise a hole, or aperture, that extends through the lens from an upper surface of the lens to a lower surface of the lens, such that the hole is inclined away from a center of the eye when the lens is placed on the cornea.

Figure 28N:
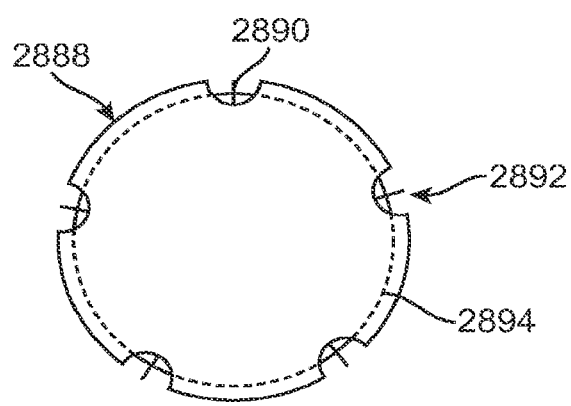
FIG. 28N shows a clipped on lens comprising neurovascular clips supported with a suture bonded and/or molded into a lens and disposed in recesses of the lens, for example cutouts, according to embodiments of the present invention.

FIG. 28N shows a clipped on lens 2888 comprising neurovascular clips 2890 supported with a suture bonded and/or molded into a lens and disposed in recesses of the lens, for example cutouts 2892. A suture can extend circumferentially around the lens to support the clips. The suture 2894 can be affixed to the lens, for example bonded or molded into the lens. The suture can support the neurovascular clips, so as to adhere the lens to the tissue when the neurovascular clips are attached to the tissue.

Figure 28O:
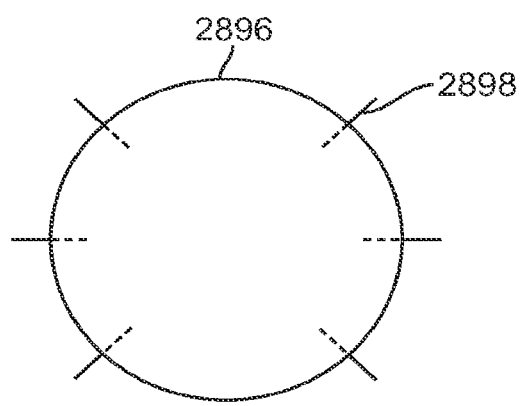
FIG. 28O shows suture needles to adhere the lens to the cornea, according to embodiments of the present invention.

FIG. 28O shows suture needles 2896 to adhere the lens to the cornea. The lens may comprise apertures, for example laser drilled holes 2898, sized to receive the suture needles. The hides can be inclined away from a center of the eye such that the suture needles can be passed through the holes to adhere the lens to the eye when the lens is aligned with the epithelial defect. The suture needles may also be adhered and/or bonded into the lens and extend from the lens such that the needles extend from the lens engage tissue and adhere the lens into position when the lens is placed on the eye.

Figure 28P:
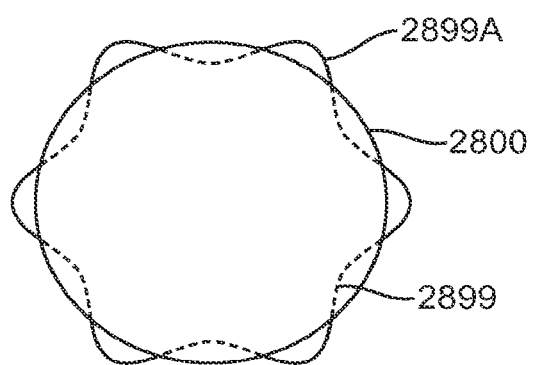
FIG. 28P shows a suture bonded to a lens, for example embedded in the lens, with protrusions of the suture extending from the lens to receive at least one of clips or needles to adhere the lens to the cornea, according to embodiments of the present invention.

FIG. 28P shows a suture bonded 2899 to a lens, for example embedded 2899 in the lens, with protrusions of the suture extending from the lens to receive at least one of clips or needles to adhere the lens to the cornea. The suture 2899A can extend from the lens so as to define an aperture sized to receive clips or needles, for example as described above, to adhere the lens to the cornea.

Figure 28Q:
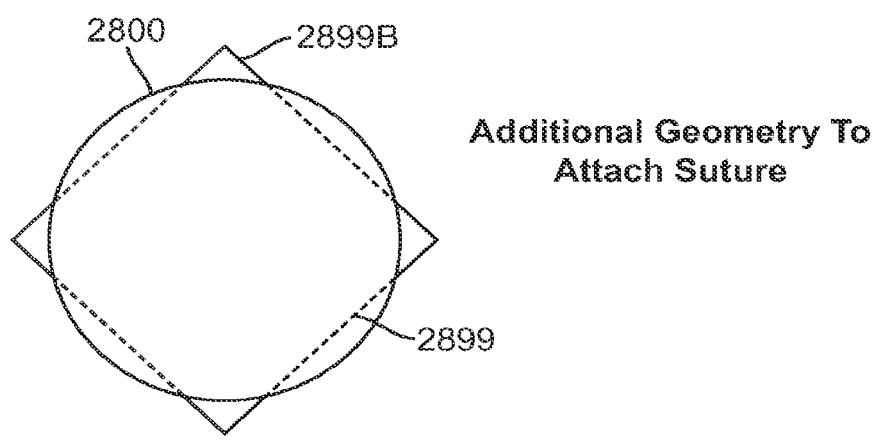
FIG. 28Q shows a suture comprising a rectangular geometry, for example a square geometry, attached to a contact lens with protrusions of the suture extending from the contact lens to adhere the contact lens to the cornea, according to embodiments of the present invention.

FIG. 28Q shows a suture comprising a rectangular geometry 2899B, for example a square geometry, attached to a contact lens with protrusions of the suture extending from the contact lens to adhere the contact lens to the cornea. The suture can extend from the lens to define an aperture sized to receive the clips or needles. The number of protrusions can be determined by the geometry of the suture, for example four protrusions with a square.

Figure 28R:
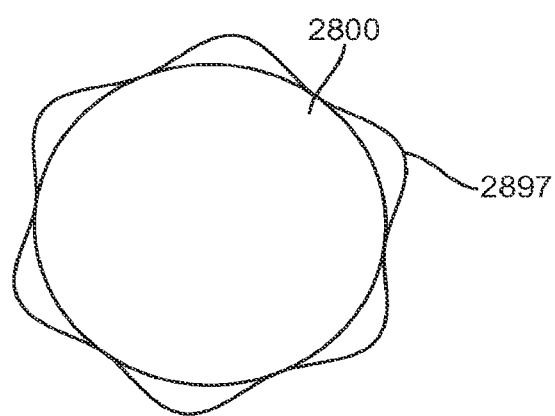
FIG. 28R shows shaped Nitinol extending around a circumference of a contact lens and attached to the lens with portions extending from the lens at attachment locations configured to receive sutures and clips.

FIG. 28R shows shaped Nitinol 2897 extending around a circumference of a contact lens 2800 and attached to the lens with protrusions extending from the lens at attachment locations configured to receive sutures and clips. The attachment locations, or points, can be sized to receive clips and needles to adhere the lens to the cornea.

FIG. 29A shows a covering 2900 sucked down onto the cornea with pumping action from endothelial cells. The covering may comprise a flap, for example a silicone flap. The endothelial pumping of water from the stromal tissue, as described above, pulls the flap covering down onto the stroma and may also pull the flap covering down 2902 against the epithelium. As the stroma 16 is substantially more permeable to water than the epithelium 12, the pulling force from the endothelial pumping can be greater for the portion of the flap covering disposed over the stroma than over the epithelium. As at least some water penetrates the epithelium, the portion of the flap positioned over the epithelium can also be sucked down against the corneal epithelium, although with less force than the portion disposed over the stroma. As the epithelium grows centripetally, the flap is displaced upward and the epithelium grows inward under the flap. The flap may comprise a thin layer of material, for example no more than about 200 um, sized to cover at least part of the epithelial defect 11. The covering may comprise many materials and more than one layer, for example materials and layers as described above.

FIG. 29A-1 shows a thin flap covering 2900 at least one of sealed or adhered 2904 onto the cornea with physiologic pressure 2902 from endothelial pumping. The covering may comprise a thin tens for vision, and the lens may comprise at least a central portion of the covering. The lens can be adapted to conform to the cornea, for example adapted to conform to an exposed ablated surface of the cornea. The central portion of the thin lens covering can be adapted to conform to corneal shapes ablated into the cornea, for example wavefront aberration correction ablated into the cornea, such that the lens covering can provide good vision during healing. The thin lens covering may comprise a hydrophobic material to decrease water flow, for example to inhibit or minimize water flow, through the lens so as to decrease corneal swelling and deturgesce the cornea when the lens is placed on the cornea over the epithelial defect. The thin lens covering may also comprise a hydrophilic portion for contacting the stroma and to at least minimize sliding, even adhere, the hydrophilic portion on the stroma and to facilitate release of the lens over epithelium when the epithelium has regenerated within the zone of epithelial debridement and grown under the covering, for example with PRK patients. The thin lens covering may comprise a peripheral portion configured to seal the lens against the corneal epithelium, for example a peripheral portion configured to seal the lens against corneal epithelium away from a debrided region, for example undebrided epithelium away from an ablation zone with PRK patients. The peripheral portion may comprise a lower surface configured to form a seal against the undebrided epithelium, for example with a hydrophobic surface such as a hydrophobic surface from an elastomer such as silicone. A contact lens, for example as described above, can also be placed over the thin flap lens to hold the covering against the cornea. The thin flap lens covering may comprise many of the materials described above, for example fibrin, bioglue and tissue welding materials.

The thin flap lens covering may comprise many known materials used for contact lenses. For example, the covering may comprise at least one of hydrogel, 2-hydroxyethylmethacrylate (HEMA), methacrylic acid (MA), methyl methacrylate (MMA), N,N-dimethylacrylamide (DMA); N-vinyl pyrrolidone (NVP), phosphorylcholine (PC), poly vinyl alcohol (PVA) or polyvinyl pyrrolidone (PVP), tris-(trimethylsiloxysilyl) propylvinyl carbamate (TPVC); N-carboxyvinyl ester (NCVE); silicone hydrogel, poly[dimethylsiloxyl] di [silylbutanol] bis[vinyl carbamate] (PBVC); silicone, silicate, plasma treated silicone hydrogel, collagen, gelatin, fibrin, bioglue, tisseal, or amniotic membrane. The hydrogel may comprise a polymeric material capable of absorbing water at least 10% by weight, when fully hydrated.

The thin flap lens covering may comprise cured silicone, uncured silicone, or a combination thereof. The cured silicone may comprise silicone that is two-part heat cured and RTV (room temperature vulcanized). For example, polydimethyl siloxane such as NuSil, or poly(dimethyl) (diphenyl) siloxane may be used to mold thin flap lenses, with less than 10% water content so as to increase oxygen diffusion through the covering. A lens may comprise perfluoropolyethers or fluorofocal may work as an oxygen reservoir.

The flap covering may comprise a silicone layer and another layer. As an example, a thinned collagen shield, such as a commercially available ProShield™ collagen shield, can be thinned down by sanding. Silicone may be positioned on one side, for example printed on or wiped on with a blade. An even thinner layer can be achieved applying silicone dissolved in solvent and then removing the solvent through methods known in the art.

The thin flap lens covering may comprise silicone hydrogel which offers good oxygen permeability and allows for the transport of metabolites.

The thin flap lens covering may also comprise gelatin attached thereto. The gelatin may be crosslinked, which can provide the ability to maintain the pre-formed shape of the lens, or non-crosslinked, which can offer the advantage of dispersing under the other materials of the thin flap lens covering. The gelatin may be crosslinked using glutaraldehyde, UV, or riboflavin, and many known methods of cross-linking. A heavily crosslinked gelatin on the anterior surface may be used to promote lubricity on the thin flap lens covering.

Table IIIA shows known monomers for hydrogel contact lens materials that can be incorporated with some of the embodiments described herein, and Table IIIB shows known silicone-hydrogel contact lens materials that can incorporated with some of the embodiments described herein.

TABLE IIIA

Known hydrogel materials and lenses suitable for incorporation with embodiments of the present invention.

| Commercial name | Manufacturer | USAN | Water Content | Monomers |
|---|---|---|---|---|
| Frequency 38 | CooperVision | polymacon | 38.0 | HEMA |
| Optima FW | B&L | polymacon | 38.0 | HEMA |
| Preference | CooperVision | Ietrafilcon | 42.5 | HEMA, MMA, NVP |
| Biomedics 55 | Ocular Sciences | Ocufilcon D | 55.0 | HEMA, MA |
| Focus (1-2 wks) | CIBA Vision | vifilcon | 55.0 | HEMA, PVP, MA |
| 1-Day Acuvue | Vistakon | etafilcon | 58.0 | HEMA, MA |
| Acuvue 2 | Vistakon | etafilcon | 58.0 | HEMA, MA |
| Proclear Compatibles | CooperVision | omafilcon | 62.0 | HEMA, PC |
| Soflens 66 | B&L | alphafilcon | 66.0 | HEMA, NVP |
| Focus Dailies | CIBA Vision | nelfilcon | 69.0 | Modified PVA |
| Soflens One Day | B&L | hilafilcon | 70.0 | HEMA, NVP |
| Precision UV | CIBA Vision | vasurfilcon | 74.0 | MMA, NVP |

TABLE IIIB

Known silicone hydrogel materials and lenses suitable for incorporation with embodiments of the present invention

| | Proprietary name | | |
|---|---|---|---|
| | PureVision | Focus Night & Day | Acuvue Advance |
| United States adopted name | Balafilcon A | Lotrafilcon A | Galyfilcon A |
| Manufacturer | Bausch & Lomb | CIBA Vision | Vistakon |

TABLE IIIB-continued

Known silicone hydrogel materials and lenses suitable for incorporation with embodiments of the present invention

| | Proprietary name | | |
|---|---|---|---|
| | PureVision | Focus Night & Day | Acuvue Advance |
| Center thickness (@-3.00D) mm | 0.09 | 0.08 | 0.07 |
| Water Content | 36% | 24% | 47% |
| Oxygen permeability (x 10-11) | 99 | 140 | 60 |
| Oxygen transmissibility(x 10-9) | 110 | 175 | 86 |
| Modulus (psi)* | 148 | 238 | 65 |
| Surface treatment | Plasma oxidation, producing glassy islands | 25 nm plasma coating with high refractive index | No surface treatment. Internal wetting agent (PVP) |
| FDA Group | III | I | I |
| Principal monomers | NVP, TPVC, NCVE, PBVC | DMA, TRIS siloxane macromere | N/A |

The materials shown in Table IIIA and Table IIIB can be modified in many ways for incorporation in accordance with embodiments of the present invention. In many embodiments, the hydrogel lenses and materials shown in Table IIIA can be modified in many ways, for example to include a hydrophobic layer, such that water permeability is reduced to deturgesce the cornea, and a peripheral structure included to at least one of seal or adhere the lens to the cornea. In many embodiments, the silicone hydrogel lenses and materials shown in Table IIIB can be modified in many ways, for example to include a peripheral hydrophobic surface to suck down against the epithelium and form a seal with the corneal epithelium. The silicone hydrogel materials may comprise less hydrogel and more silicone, so as to decrease the transmission of water through the lens and increase oxygen permeability. The central portion of the above lenses and materials may also comprise a thickness of no more than about 200 um, for example 100 um, and that is substantially uniform, such that the central portion conforms to the ablated cornea with no more than about +/−1 Diopter of optical power from the central portion when the lens is sucked down against the cornea. Many additional modifications will be apparent to one of ordinary skill in the art based on the drawings and descriptions included herein.

A contact lens may be placed over the thin flap lens covering, for example a contact lens adhered to the epithelium as described above.

FIG. 29A-2 shows a thin covering 2900 as in FIG. 29A-1 sized to extend beyond an epithelial debridement area 11. This sizing may facilitate centripetal epithelial in growth under the covering. This size may also form a seal between the covering and the epithelium 12, for example epithelium that is not debrided and includes hemidesmosomes to adhere to the epithelium to the Bowman's membrane. The covering can adhere to the cornea with a physiologic sucking mechanism. A contact lens may be placed over the covering and adhered to the cornea, for example adhered as described above.

FIG. 29A-3 shows a thin covering 2900 as in FIG. 29A-2 size to fit an epithelial debridement area 11. The covering can be sized to fit the epithelial debridement area, for example a circular debridement area. This sizing may provide a seal of the covering with the epithelium around the periphery of the covering similar to a LASIK flap. A portion of the covering may be glued to the epithelium, for example with fibrin glue, to form a hinge. A thin layer of glue may also be placed under the flap covering. Alternatively, the thin covering may be sized smaller than the debrided area. In such a case, the epithelium may grow preferentially under the thin covering. The diameter of the thin covering may be within a range from about 6 to 11 mm or more, and the upper limit of the diameter may be determined by the diameter of the cornea at the limbus, such that the diameter of the thin covering is sized smaller than the diameter of the cornea at the limbus.

FIGS. 29A-4 and 29A-5 shows a thin covering 2900 comprising a hydrophobic portion 2906 to decrease water flow and a hydrophilic portion 2908 to contact ablated stroma. The hydrophobic portion can control edema, for example by decreasing water flow through the covering, even inhibiting water flow through the covering. The hydrophobic portion may also prevent infection by preventing bacteria from accessing the debrided zone. The hydrophilic portion can assist in the sucking down of the flap. As the stroma comprises a hydrophilic material, a hydrophilic surface of the covering to contact the stroma can improve contact of the flap with the ablated stroma and/or Bowman's, and may even adhere the flap to stroma when the cornea is deturgesced by endothelial pumping. The hydrophilic surface of the covering can also increase friction and may decrease sliding of the covering when the cornea is deturgesced by endothelial pumping. As the epithelium grows under the covering, the hydrophilic surface of the covering may contact and hydrophobic surface of the corneal epithelium. This contact of the hydrophilic surface of the covering with the epithelium that may be hydrophobic can facilitate removal of the covering when the epithelium regenerates, and the covering can be separated from the regenerated epithelium such that the regenerated epithelium remains intact on the cornea.

The hydrophobic portion and the hydrophilic portion may comprise, respectively, many hydrophobic and many hydrophilic materials as described herein. For example the hydrophilic portion may comprise a thin covering comprising an amniotic membrane or components of amnion. The amniotic membrane component may be formed from amniotic membranes, for example as known in the art. The amniotic membrane may comprise donor tissue which is adequately tested to prevent transmission of disease and processed so as to maximize resiliency and wound healing properties. At least one other component may be attached to the amniotic membrane. The at least one other component may comprise a second hydrophobic material, so as to help control edema and prevent tear fluid from penetrating to the epithelial defect of the eye. The hydrophobic material component may comprise a silicone polymer, for example room temperature vulcanized silicone, thinly applied by brushing or deposition onto the amniotic membrane. The hydrophobic layer may comprise a biologic tissue grown or adhered to the amniotic layer, such as an epithelial layer.

The hydrophobic portion may be covered by a hydrophilic surface, for example plasma treated, and may also be covered by a hydrophilic layer, for example hyaluronic acid (HA). For example, the amniotic membrane may be covered by a silicone hydrophobic layer, which, in turn, is covered by a hydrophilic or lubricious coating, for example lubricious surface coatings commercially available under the trademark Isurtec™, as provided by Innovative Surface Technology, Inc. of Saint Paul, Minn., and as available from Surmodics of Eden Prairie Minn. Other examples of plasma treatment materials include vinyl pyrrolidone, diols, ethylene glycol and tetraethyl ethylene glycol. The hydrophilic or lubricious coating can reduce friction between the thin covering and the bandage lens or the lid of the eye. The plasma treatment may increase may create a mechanical lock—a layer to seal a surface to which other material can bond—and a layer to increase wettability or lubricity. Examples of materials that can be made to bond following plasma treatment include collagen or gelatin. Plasma treatment may be further cross-linked by using glutaraldehyde. The amniotic membrane comprises an epithelial side, containing an epithelial cell layer, and a stromal or collagen side comprising fibroblast. For various reasons it may be advantageous to leave one or the other of these sides exposed to cover the patient tissue (stroma) and the other covered by a coating such as those described above. For example, the epithelium of the amniotic membrane may be covered with a hydrophilic silicone coating such that the fibroblast containing collagenous layer of the amniotic membrane is exposed for placement against the exposed stromal tissue of the patient. Alternatively, the collagenous fibroblast containing layer of the amniotic membrane may be covered with a hydrophilic silicone coating such that the epithelial layer of the amniotic membrane is exposed for placement against the exposed stromal tissue of the patient.

FIG. 29B-1 shows a silicone flap covering 2910 comprising peripheral portion 2912 and a central portion 2914. The central portion may comprise a thin portion, for example a thin layer, of an elastic material, for example an elastomer such as silicone. The central portion can comprise a hydrophilic surface and may comprise, for example, silicone elastomer treated with surface treatment such as plasma oxidation to produce glassy islands or a 25 nm plasma coating with high reactive index. The peripheral portion can be shaped in many ways and may comprise a peripheral ring 2916 to hold the central portion in place. The peripheral portion may be more rigid than the central portion. The central portion can be configured to adhere to the cornea similar to the contact lens embodiments described above. For example the peripheral portion may comprise many of the above structures to adhere the covering to the cornea, for example including but not limited to at least one of a hydrophobic surface, protrusions, tacks, holes, channels, tubes, wedges, clips, needles, sutures or nitinol.

FIG. 29B-2 shows a flap covering 2910 as in FIG. 29B-1 contacting a stromal tissue surface. The stromal tissue surface may comprise an ablated stromal tissue 11 surface of a PRK patient. The ring 2916 can be positioned on the epithelium 12 away from the epithelial defect. The flap covering, for example the silicone flap covering, can be sucked down onto the stroma with endothelial pumping and displaced as the epithelium advances centripetally.

FIG. 29C shows a curved covering 2920 comprising a curved central portion 2920CP adapted to conform to the cornea and a curved peripheral portion 2920PP to seal against the cornea and placement of the covering on the cornea. The peripheral portion may comprise a lower surface radius of curvature, as described above. The radius of curvature of the lower surface may comprise a value that corresponds to the radius of curvature of the cornea such that the peripheral portion of the lens is fit to the unablated cornea comprising the epithelium. The central portion can be sized to fit over the ablated cornea 11 and may comprise a lower surface with a radius of curvature that approximates the radius of curvature of the cornea after the ablation. For example, the radius of curvature of the central potion may be greater than the radius of curvature of the peripheral portion with a patient receiving a myopic PRK correction. The central portion may comprise a lens, for example a lens with no optical power and uniform thickness 2921, such that the lens can conform to the ablated stromal surface. The covering may comprise a water inhibiting hydrophobic layer 2922 to inhibit or minimize corneal swelling, for example a silicone elastomer layer. The water inhibiting layer may comprise a non-water permeable layer composed of a hydrophilic material, such as silicone hydrogel that minimizes permeability of the layer to water.

The surfaces of the covering can be configured in many ways so as to optimize the adherence of the covering to the cornea. For example, the peripheral portion 2920PP may comprise a hydrophobic surface so as to increase the coefficient of friction such that the peripheral portion comprises a sticky surface to contact and adhere to the corneal epithelium. The covering may comprise a hydrophilic layer 2924 to contact the stroma, for example a hydrophilic surface coating. The inner portion and the outer portion can be sized such that the hydrophobic outer portion contacts the intact epithelium and the inner portion contacts the stroma.

The lens can be fit to the cornea in many ways, for example the lens covering can be selected from among of a plurality of lens coverings, such that the peripheral portion fits the undebrided epithelium. Although the peripheral portion can be fit in many ways, for example a loose fit, the fit may also comprise a tight fit to form a seal, for example with a radius of curvature of the peripheral portion fitting the radius of curvature of the cornea to within about +/−0.1 mm, or about +/−0.5 D for a 44 D peripheral cornea. The tight fit may comprise a steep fit with the radius of curvature of the lens shorter than the radius of curvature of the cornea such that the peripheral portion of the lens that contacts the cornea is steeper than the cornea. The radius of the lens can be determined pre-operatively with known lens fitting techniques, such as fluorescein installation and slip lamp examination.

FIGS. 29C1 to 29C4 show a method of covering an ablated cornea with a covering, according to embodiments of the present invention.

FIG. 29C1 shows a flat casting 2926 of substantially uniform thickness 2928. The flat casting can be formed by curing a material, between plates. The material may comprise many of the materials described above, for example fibrin. The casting can be cut, for example with a trephine to form a circular covering 2930. The casting may be ablated to a desired thickness, for example with an excimer laser.

FIG. 29C2 shows the covering comprising the circular casting 2930 positioned above the cornea, for example a post PRK cornea in a first flat configuration. The covering is aligned with the debrided region, for example the ablated region of the cornea.

FIG. 29C3 shows the covering comprising the circular casting 2930 positioned on the cornea and conforming to corneal surface, for example the ablated stroma 16 and/or Bowman's 14 membrane. The covering is sized to fit within the epithelial defect.

FIG. 29C4 show a contact lens 2934 positioned over the circular covering 2930. The contact lens may comprise many of the contact lenses described above. The contact lens may hold the covering In place over the epithelial defect when the epithelium regenerates.

FIG. 29C5 shows a covering 2930 for use with the method as in FIGS. 29C1-29C4 with the covering sized to extend beyond the debrided area 11. This sizing of the covering may be used with a contact lens, as described above. This sizing may facilitate regeneration of the epithelium 12 over the ablated stroma 11 and may help to seal the covering against the cornea, as described above.

FIG. 29C6 shows in situ ablation 2936 of a covering 2930 to correct vision of a patient after ablation of the stroma 16 to correct vision. The covering can be ablated in situ on the cornea. The covering can be ablated in many ways, for example to thin the covering for conformance to the underlying stromal ablation. The covering may also be ablated so as to shape the covering with optical power to correct vision of the patient. The covering may comprise a conformable covering that conforms to the cornea when the covering is placed on the cornea.

The ablatable covering may comprise many materials, for example as described above. The ablatable covering may comprise collagen combined with polymer such as Neoglycopolymer-crosslinked biopolymer matrix as described by US Pub. No. 2007/002046 in the name of Griffith. The ablatable covering may comprise a biosynthetic matrix as described by US Pub. Nos. 2006/0246113; 2006/013050 and 2006/0134170 in the name of Griffith. The ablatable covering may also comprise collagen hydrogels.

FIG. 29C7 shows ablation of a covering 2930 prior to placement on the cornea. The covering can be ablated 2938, for example to thin the covering to conform with the cornea.

FIG. 29C8-1 shows a curved covering 2930 adapted to conform to the cornea and placement of the covering on a debrided and ablated cornea. The covering comprises a peripheral portion 2930PP to contact the epithelium 12 and a central portion 2930CP to contact the stroma 16 and/or Bowman's. The peripheral portion of the covering can be fit to the cornea, for example as described above. The lower surface of the covering may comprise a radius, radius as described above, that is substantially similar for the central and peripheral portions.

FIG. 29C8-2 shows the covering 2930 of FIG. 29C8-1 conforming to the ablated surface contour. The central portion 2930CP of the covering can be sucked down against (lie stroma 16 and/or Bowman's membrane such that the covering conforms to the ablated surface. The central portion may comprise a thin material of substantially uniform thickness to conform to the ablated cornea when the central portion is sucked down against the cornea with endothelial pumping and deturgescence. The covering may also be sufficiently thin and soft so as to conform to the epithelium 12 around the boundary of the epithelial defect.

FIG. 29C8-3 shows the covering 2930 of FIG. 29C8-1 conforming to wavefront aberrations 2940 ablated into a corneal surface to correct aberrations of the eye. The aberration ablated into the eye may comprise aberrations ablated in response to aberration measured with a wavefront aberrometer such as a known Hartmann/Shack wavefront aberrometer 2942. The aberration may comprise many known aberrations such as spherical aberrations and coma.

FIG. 29D shows an erodible covering 2944. The covering can be configured to erode such that the cover erodes inwardly away from the regenerating corneal epithelium. The covering may comprise an outer portion, for example a peripheral portion, configured to erode at a first rate and an inner portion, for example a central portion, configured to erode at a second rate. For example, the outer portion can be configured to erode within 24 hours of placement on the eye and the inner portion is configured to erode 48 hours after placement on the eye. The outer portion erosion rate is faster than the inner erosion rate to erode the outer portion of the covering before the inner portion of the covering. Such erosion can be helpful to improve fitting of the covering to the exposed ablation surface, for example when the epithelium advances centripetally. For example, the covering may comprise a first portion configured to erode in 12 hours, a second portion 2946 configured to erode in 24 hours 2948, a third portion configured to erode in 48 hours 2950 and a fourth portion configured to erode in 72 hours 2952.

The outer portion, for example the first portion, may comprise a first amount of crosslinking, and the inner portion, for example the second portion, may comprise a second amount of cross linking to erode the outer portion before the inner portion. The cross-linking can be configured in many ways, for example with known crosslinking such as that used to manufacture 12 hour, 24 hour, 48 hour and 72 hour collagen shields. A collagen shields that is known erode is the ProShield™ available from Alcon Laboratories, Inc.; such a shield can be modified to incorporate zones that erode at different times and rates.

The outer portion and the inner portion may comprise many arrangements of portions of the covering. For example, the outer portion may comprise a first outer portion and a second outer portion peripheral to the first outer portion, and the inner portion may comprise a first inner portion and a second inner portion with the second inner portion disposed inward from the first inner portion.

FIG. 29E1 shows a covering 2954 with a hydrophobic layer and a hydrophilic layer. The covering comprises an upper surface 2956 and a lower surface 2958. The covering also comprises a hydrophobic layer 2960 and a hydrophilic layer 2962. The hydrophobic layer and the hydrophilic layer are each disposed between the upper surface and the lower surface. The hydrophilic layer is disposed closer to the lower surface and may comprise the lower surface, and the hydrophobic layer is disposed closer to the upper surface and may comprise the upper surface. The hydrophobic layer and the hydrophilic layer each comprise a thickness, and the thickness of each layer can be configured in many ways to enhance the performance of the covering. For example, at least one of the hydrophilic layer or the hydrophobic layer comprises at least one monolayer, and the at least one monolayer comprises a thickness 2964 of no more than about 40 nm.

The hydrophilic layer may comprise the functions of encouraging healthy epithelial growth, taking metabolites, and cushioning the cornea. The hydrophilic layer may comprise many known hydrophilic materials, surfaces and coatings and can be formed in many ways and may comprise a known coating. Hydrophilic coatings, surfaces and materials are commercially available from Surmodics, Hydromer Biocoat, Horsham Pa., Hyluran, Hydromer, and the coating may comprise hyaluronic acid (HA) coatings, monolayers and a plasma treated surface. The hydrophilic layer may comprise an optically transparent gel comprising at least about 10% water. The gel may comprise a non-water containing hydrophilic gel, for example NuSil, a very soft silicone that can be formulated so as to promote re-epithelialization by minimizing the force needed to disconnect the stroma from the thin therapeutic covering. The hydrophilic layer may also comprise gelatin. In some embodiments, the hydrophilic layer can comprise not more than about 10 um thickness, for example about 40 nm thickness. The hydrophilic layer may also comprise dots that fulfill the above-stated functions of the hydrophilic layer.

The hydrophobic coating or surface layer may comprise many known hydrophobic materials, surfaces and coatings. Hydrophobic coatings, surfaces and materials are known and may comprise, for example, a plasma treated surface and a mono-layer, a hydrophobic material such as silicone.

FIG. 29E2 shows a covering 2954 with a hydrophobic upper layer 2960 and a hydrophilic lower layer with the lower hydrophilic layer 2962 thicker than the upper hydrophobic layer. The hydrophobic layer and the hydrophilic layer each comprise a thickness. The hydrophilic layer thickness can be at least about twice the thickness of the hydrophobic layer. For example the hydrophilic layer can be at least about ten times as thick as the hydrophobic layer. The hydrophobic layer may comprise a monolayer, for example a monolayer no more than about 40 nm thick. The thicker hydrophilic layer may have some advantages. For example, the thicker hydrophilic layer comprises a water density that is hyperosmotic relative to the normal hydration of the cornea, such that the cornea can be dried with the hyperosmotic hydrophilic layer.

FIG. 29E3 shows a covering 2954 with a hydrophobic upper layer 2960 and a hydrophilic lower layer 2962 with the upper layer thicker than the hydrophobic layer. For example, the hydrophilic layer may comprise a thickness no more than about half a thickness of the hydrophobic layer. The thicker hydrophobic layer may be useful with embodiments where it is desirable to decrease changes in thickness of the covering due to hydration of the underlying cornea. Also, the increased thickness of the hydrophobic layer can decrease permeability to water and increase oxygen permeability, for example when the hydrophobic layer comprises silicone.

FIG. 29E4 shows a covering 2954 with a hydrophobic upper 2964 monolayer opposite a hydrophilic lower monolayer 2966. The covering with at least one monolayer may comprise two monolayers, and the hydrophobic layer and the hydrophilic layer may each comprise one of the two monolayers. The two monolayers can be tied together with a crosslinker such that the two monolayers are positioned opposite each other. The covering comprising the two monolayers can be very thin, for example about 100 nm. A very thin monolayer can conform to the cornea, for example to the epithelium, and may conform to the cornea with a substantially uniform thickness so that the patient can benefit from optical correction ablated into a stromal surface.

FIG. 29E5 shows a covering 2954 comprising a hydrophilic upper layer 2968, hydrophobic inner layer 2970 and a hydrophilic lower layer 2972. The covering comprises the second hydrophilic layer. The second hydrophilic layer may comprise an upper surface and the first hydrophilic layer may comprise a lower surface. The hydrophobic layer is disposed between the first hydrophilic layer and the second hydrophilic layer. A covering with an upper surface comprising a hydrophilic layer can help the tear film spread uniformly over the upper surface which can improve patient vision and decrease friction with at least one of a contact lens or the eyelid that contacts the upper surface and may move relative to the upper surface, for example when the patient blinks. The hydrophobic layer, for example silicone, may inhibit the flow of water through the covering. The lower hydrophilic surface may help the lower surface stick to exposed stroma, and may facilitate removal of the covering when the epithelium is regenerated.

FIGS. 29F1 and 29F2 show a covering 2974 with inner channels 2976 to pass tear liquid from an outer opening to an inner portion. The covering may comprise an inner portion, for example a central portion 2974CP, configured for placement over an epithelial defect. The covering may also comprise an outer portion, for example a peripheral portion 2974PP, configured for placement on the epithelium away from the defect. The covering may comprise at least one channel 2976 extending along the outer portion to pass fluid. The at least one channel can extend from a peripheral opening 2976PO located near an outer boundary of the peripheral portion to an inner opening 2976IO located within a central potion of the covering. The at least one channel may comprise a tube, for example a capillary, extending from an outer boundary of the outer portion to the inner portion. The capillary can draw fluid, for example a liquid such as water, through the peripheral portion to the central portion. The capillaries can be sized such that the water passed through the capillaries is no more than water passed through the epithelium such that the cornea is deturgesced with endothelial pumping. The fluid may also comprise a gas, for example when the covering is removed. Vacuum pressure of the central portion may be reduced during covering removal when gas travels through the channel to the central portion, so as to reduce vacuum pressure under the central portion of the covering.

FIG. 29F3 shows a covering with lower surface 2974LS channels 2976 to pass tear liquid from an outer opening 2976PG to an inner portion 2976IO.

FIG. 29G shows a covering 2978 comprising an inner portion 2978CP and a peripheral portion 2978PP, in which holes 2980, also referred to as apertures, extend from an upper surface to a lower surface to pass liquid to remove the covering. The holes comprise an example of at least one channel comprising a plurality of apertures extending through a thickness of the outer portion.

FIG. 29H shows a covering 2982 with a rough lower surface 2984 and a smooth upper surface 2986. The covering and corneal tissue may be roughened in many ways. For example, the lower surface can be microshaped using a femtosecond laser or an excimer laser. Work in relation to embodiments of the present invention indicates that microshaping of the covering and/or recipient Bowman's 14 and/or stroma 16 can provide adhesion. The lower surface can be roughened with mechanical roughening such as scraping. The ablated corneal surface 11 of the recipient cornea may also be ablated and/or treated with a femtosecond laser or additional ablation so as to microfinish the surface with roughness. Microfinishing may provide increased surface area so as to adhere the covering to the stroma and/or Bowman's with Van der Waals forces.

In many embodiments, the ablated surface comprises a roughness and the lower surface of the covering comprises a similar roughness. As both surfaces comprise comparable roughness, for example roughness on the order of about a micron, contact between the two surfaces can cause friction that can minimize sliding of the covering over the ablated surface when the covering is held against the ablated surface, for example with at least one of a contact lens or suction.

The lower surface can be configured for friction with the ablated stroma in many ways. For example the lower surface can be roughened, may comprise nano structures, and may comprise interlocking structures. The lower surface may comprise structures configured to interlock with collage for adhesion, for example small protrusions, such as hairs, hooks, or pokers that extend downward to go around collagen fibers. The protrusions may comprise a density per square mm, and the density per square mm can be configured for the desired amount of adhesion and removal. A first force, or first pressure, may be used to apply the covering to the ablated stroma, and a second force, or second pressure, required for removal. The second force can be configured such that the covering is lifted by the epithelium when the epithelium regenerates.

The covering comprising the rough lower surface can be adhered to the lower surface, for example with fibrin. The covering may also be configured to crosslink to the stroma, for example with riboflavin. Many of the above adhesives can stick to the stroma and slough off the epithelium when the epithelium regenerates. With both cross-linking and adhesives, the epithelium can grow under the covering so as to dislodge the covering when the epithelium grows centripetally during regeneration.

The covering can be removed with a solution that dissolves an adhesive. For example, the covering can be adhered with fibrin and a drop of a fibrin dissolving substance applied when the epithelium has regenerated. For example the fibrin dissolving substance may comprise known tissue plasminogen activator (TPA) or a known plasmin.

The covering may comprise a layer to inhibit water penetration, for example as described above, such that the endothelium can maintain corneal deturgescence when the covering is positioned on the eye, as described above.

The covering may comprise an upper surface comprising an upper surface portion, for example a central upper surface portion. The covering may comprise a lower surface comprising a lower surface portion disposed opposite the upper surface portion.

The upper surface portion may be smoother than the lower surface portion. The lower surface portion may comprise a first amount of roughness for friction against the ablated stromal surface. This roughness of the lower surface can provide friction so as to resist sliding of the lower the lower surface portion along the stromal surface, for example when the patient blinks. The upper surface portion may comprise a second amount of roughness. The second amount of roughness can be less than the first amount of roughness, so as to slide the upper surface portion along at least one of a contact lens or an eyelid, for example when the patient blinks. This differential roughness of the upper and lower surfaces can retain the covering against the ablated stroma and minimize sliding of the covering against the ablated stroma, so as to decrease patient and irritation.

The lower surface portion may be configured in many ways to comprise the first amount of roughness and the upper surface portion may be configured in many ways to comprise the second amount of roughness. For example, the first amount of roughness may be at least about twice the second amount of roughness. The upper surface portion comprises an optically smooth sur face. For example, the optically smooth surface of the tipper surface portion may comprise an RMS roughness for visual acuity of about 20/25 or better. The lower surface portion may comprise an optically rough surface. For example, the optically rough surface may comprise an RMS roughness for a visually acuity less than about 20/25 or better before the covering is placed against the cornea, and a visual acuity of at least about 20/25 or better when the covering is placed on the cornea. The lower surface portion may comprise a material having an index of refraction within a range from about 1.36 to about 1.40, such that the visual quality of the covering is improved when the covering is positioned against the ablated corneal surface.

FIG. 29H1 shows a covering 2982 with interlocking structures 2988. The interlocking structures may comprise barbs, hooks, and/or protrusions extending from a base on the covering to an enlarged distal end.

FIG. 29H2 shows a covering 2982 with nanostructures 2990A. The nanostructures may comprise many structures, for protrusions and indentations such as castellation. In some embodiments, the nanostructures may comprise setae and/or fibers with spatulas on the end, so as to increase surface area and provide charge on the nanostructure of the covering and/or cornea, for example with Van der Waals forces. Nanostructures with adhesive properties suitable for incorporation in accordance with some embodiments of the present invention are described in U.S. Pat. No. 7,229,685. Such nanostructures can be provided on the covering and/or the cornea to adhere the covering to the cornea. The nanostructures can be disposed on a peripheral portion of the covering disposed away from a central vision correcting portion of the covering.

FIG. 29H3 shows an amniotic membrane 2990A2 tissue layer suitable for incorporation with the therapeutic coverings 2982 as described above. The amniotic membrane comprises an epithelium 2990A4, a basement membrane 2990A6, a compact layer 2990A8, and a fibroblast-containing collagenous layer 2990A10. The amniotic membrane may comprise at least one hydrophilic collagenous layer suitable for combination with a hydrophobic layer, as described herein. For example, the amniotic membrane may comprise the hydrophilic material of the coverings of FIGS. 29A1 to 29H.

The hydrophobic layer of the covering may be combined in many ways with the hydrophilic layer comprising amniotic membrane material. The hydrophilic layer comprising amniotic membrane material may comprise at least one of a layer of amniotic membrane tissue, particles of amniotic membrane attached to the hydrophobic layer, a film of amniotic membrane material coated onto a hydrophobic layer, a blend of amniotic membrane material and a known contact lens material, a hydrophilic material treated with an amniotic solution so as to trap tissue repair and growth factors in the hydrophilic material. The hydrophobic layer may comprise a contact lens with at least one hydrophobic layer, for example a silicone contact lens. The hydrophilic layer may comprise the amniotic membrane tissue layer, and the hydrophobic layer may contact the epithelium of the amniotic membrane. Alternatively, the hydrophobic layer may contact the collagenous fibroblast-containing layer of the amniotic tissue layer The hydrophobic layer may be formed on either the epithelium layer or the fibroblast-containing layer, for example by applying NuSil RTV Silicone to one of the layers and scraping with a squeegee to form the hydrophobic layer on the hydrophilic layer in contact with the hydrophilic amniotic membrane layer. The hydrophilic layer comprising amniotic membrane may be applied to a layer of hydrophobic material, for example similar to the application of amniotic membrane, amniotic particles, amniotic solution to form an amniotic film, and amniotic solution to entrap tissue repair and growth factors in a contact lens as described in Examples 1 to 6 of U.S. Pat Nos. 5,932,205 and 6,143,315, the disclosures of which may be suitable for combination in accordance in accordance with some embodiments of the present invention. The hydrophilic layer may comprise optically clear collagen material, for example as described in US Pub. 20030187515 and US Pub. 20040048796, the disclosure of which may be suitable for combination in accordance with some embodiments of the present invention.

FIG. 29I shows a covering 2990A10 with charge to retain the covering on the cornea. Charge on the covering 2990A12 and cornea can adhere the cornea to the covering. Work in relation to embodiments of the present invention suggests that disruption of collagen fibers can provide charge to promote adhesion. The stroma 16 and/or Bowman's 14 can be ablated with the excimer laser, for example with PRK, and the covering may comprise disrupted fibers, for example collagen fibers disrupted with at least one of an excimer laser or femtosecond laser. Chemical treatment and/or scintillation may also be employed to promote adhesion of the covering and cornea with charge. In some embodiments, the charge may comprise intermolecular forces, for example Van der Waals forces at the interface between the covering and the Bowman's membrane and/or stroma.

FIG. 29J1 shows a covering 2990A14 comprising a plurality of zones configured to release a drug for each of one, two and three days, according to embodiments of the present invention. The covering may comprise an outer portion 2990A14PP without the drug 2990A16, and an inner portion configured to release the drug. The inner portion configured to release the drug may comprise a first inner portion configured to release the drug for a first time 2990A18, for example one day, and a second inner portion configured to release the drug for a second time 2990A20, for example two days. The first inner portion may comprises a first length across, for example about five mm, and the second inner portion may comprise a second length across, for example about 3 mm. The first time can be less than the second time such that more drug is released from the second inner portion, for example the two day portion, as the epithelium advances centripetally to cover the epithelial defect Additional drug release portions can be used for example a portion configured to release drug for three days. This configuration may allow for drugs to be released directly toward the stroma from a lower surface of the covering. Alternatively, the covering may comprise a hydrophobic lower surface with an inner zone that may extend along the debrided zone and then slowly release drugs towards the stroma.

The drug may comprise many of the drugs described above, for example at least one of steroids, anti-inflammatories, antibiotics or analgesics. For example the drug may comprise the analgesic, and the analgesic may comprise at least one of gabapentin, proparacaine, lidocaine, or tetracaine or a derivative thereof. The covering may also release metabolites, for example, glucose, to aid in the healing process of the epithelium.

FIG. 29J2 shows the covering 2990A14 of FIG. 29J1 on a cornea two days after ablation. The epithelium 14 has advanced centripetally to partially cover the ablation zone 11. The epithelium has advanced toward the two day portion of the covering 2990A20. Experiments of re-epithelialization rates and sizes at times following surgery can be conducted on an empirical number of patients to determine the size and times of the inner portions. The size and time can be configured such that a majority of the drug is released from each portion before the epithelium advances centripetally to each portion so as to inhibit or minimize contact of the drug releasing portion with the epithelium. Mathematical modeling and simulations can be conducted to determine the effectiveness and optimize the configuration of the drug releasing portions.

FIG. 29K1 shows a covering 2990A26 configured for a tight fit with a cornea. The tight fit may decrease swelling of the cornea. The covering comprises a lower surface with covering radius 2990A26CR. For a tight fit, the covering radius is substantially the same as the radius of the cornea 2990A28, for example to within about 0.05 mm of a peripheral portion of the cornea. The tight fit may comprise a steep fit, with the radius of the contact lens less than the radius of the cornea such that the lower surface of the covering is steeper than the peripheral surface of the cornea near the periphery of the cornea. The covering radius of the outer portion may comprise many sizes and can be sized to stretch the outer portion of the covering when the outer portion of the covering is placed against a peripheral portion of cornea away from the epithelial defect. For example the covering radius of curvature can be no more than, or even less than, a radius of curvature of cornea 11CR. A covering radius of curvature can cause the covering to engage the cornea with an outer peripheral portion of the covering. The outer portion of the covering may comprise an elastic material such that the outer portion is adapted to stretch and form a seal with an unablated portion of the cornea when the outer portion contacts the unablated portion of the cornea.

FIG. 29K2 shows the covering 2990A26 of FIG. 29K1 placed on the cornea with the light fit such that the covering conforms to the ablated stroma 11. The covering may also conform to the inner edge of the epithelium 12. The peripheral outer portion of the covering may stretch more than the central portion of the covering such that the peripheral portion may exert a greater force on the cornea to seal the cornea.

The light fit lens may be enhanced by heating the cornea and lens, for example by about 1 to 2 degrees Centigrade. The diameter of the covering may be less than 13 mm or more than 15 mm to enhance the tight fit. The covering may be thicker in the outer periphery and thinner inward near the center to enhance the tight fit, and may comprise an outer rim.

FIG. 29L shows a covering 2990A30 with a light transmitting 2990A32 central portion 2990A34 and a non-light transmitting 2990A36 peripheral portion 2990A38. The inner portion may comprise many of the optically transparent materials as described above and a smooth optical surface for patient vision. The peripheral outer portion may comprise an optically non-transmissive material, for example at least one of an absorbing material or a scattering material. For example, a patient may be fitted with covering where the diameter of the light transmitting central portions are of different diameters, for example 1-3 mm for the smaller diameter and 3-5 mm for the larger one. The covering with the larger diameter light transmitting portion would allow such a patient to see under low light conditions, while the covering with the smaller diameter light transmitting portion would allow such patient to see with a smaller pupil so as to increase a depth of field of images and may also decrease optical effects due to the epithelium as the epithelium advances centripetally.

FIGS. 29M1A and 29M1C show a covering 2990A40 comprising outer structures, for example peripheral structures to inhibit or minimize motion of the covering on the cornea and a bandage lens 2990A42 positioned over the covering. The covering can be adapted to conform to the cornea, as described above, and may comprise a smooth upper optical surface and a lower surface with roughening to inhibit or minimize motion, as described above. The covering comprises at least two, for example four, radially extending protrusions configured to inhibit or minimize at least one of rotation or lateral motion of the covering over the cornea. The outer structures may comprise at least one of apertures or protrusions 2990A44. The outer structures can be configured to extend along an inner surface of a bandage covering, for example a bandage lens, such that the bandage lens can exert force on the covering near the outer structure. The outer structure may form an interstitial space that can be filled by the cornea, and the outer structure may indent the cornea slightly so as to form an interlocking fit with the outer structure. The covering may comprise a covering material harder than corneal tissue, for example at least one of Bowman's membrane, the epithelium or the stroma, so as to deform the cornea or form an interstitial space between the cornea and the lens.

FIG. 29M1B shows a cross sectional view of the covering 2990A40 and bandage lens 2990A42 of FIG. 29M1A placed on a cornea. The covering conforms to the cornea under the bandage contact lens, also referred to as a shield. The covering comprises features to inhibit or minimize, for example twisting, of the lens axially and lateral forces, for example from an eyelid during blinking. Experimental studies have indicated that the cornea can conform, for example indent, in response to a covering placed under a contact lens. For example, the epithelium can smooth the interface between the covering and the ablated surface. The cornea can fill in around the covering, for example into the interstitial space between the covering and contact lens, and the covering may slightly indent the cornea, so as to form an interlock with the cornea. The deformed and/or filling cornea in conjunction with the structure of the covering can form an interlocking structure, so as to inhibit or minimize at least one of rotation or lateral motion of the covering along the surface of the cornea. The force holding the covering or therapeutic lens to the cornea is greater than the force adhere the therapeutic lens to the bandage lens without the use of an adhesive, while allowing the epithelium to heal at the point of adherence between the therapeutic lens and the debrided zone. Alternative embodiments of a non-moving lens include a piano, vaulting, silicone scleral lens, silicone lenses and RGP lenses.

FIG. 29M1D shows a covering 2990A40, similar to the covering of FIG. 29M1A, comprising aperture 2990A46 structures to inhibit or minimize motion of the covering on the cornea. The aperture structures can be positioned away from the epithelial defect 11 when the covering is placed on the cornea following PRK, for example outside an epithelial debrided zone. The covering may also be sized to fit within the epithelial debridement, for example as described above. The aperture structures may comprise many shapes of apertures, for example elongate apertures, arcuate apertures, oval apertures, rectangular apertures or square apertures.

FIG. 29M1E shows a covering 2990A40, similar to the covering of FIG. 29M1A, comprising protruding aperture structures 2990A48 to inhibit or minimize motion of the covering on the cornea, in which the aperture structures 2990A50 can be positioned away from the epithelial defect when the covering is placed on the cornea following PRK;

FIG. 29M1F shows a plan view of the covering 2990A40 of FIGS. 29M1A to 29M1C.

FIG. 29M1G shows a covering, similar to the covering of FIG. 29M1A, comprising circular aperture structures to inhibit or minimize motion of the covering on the cornea, in which the aperture structures can be positioned away from the epithelial defect when the covering is placed on the cornea following PRK;

FIG. 29M1H shows covering 2990A40, similar to the covering of FIG. 29M1A, comprising protruding radially elongate structures 2990A56 to inhibit or minimize motion of the covering on the cornea, in which the protruding radially elongate structures can be positioned away from the epithelial defect when the covering is placed on the cornea following PRK.

FIG. 29N shows a therapeutic covering 2990 comprising an outer portion 2992 configured to conform to the cornea so as to seal the covering over the cornea and an non-conforming inner portion 2994 configured to retain an optical shape and smooth the cornea for vision. The inner portion 2994 comprises an upper surface 2994U and a lower surface 2994L. The outer portion 2992 comprises an upper surface 2992U and a lower surface 2992L. The covering may comprise an upper hydrophilic layer along each of the upper surfaces, a middle hydrophobic layer along each of the inner and outer portions, and a lower hydrophilic layer along each of the inner and outer portions. The hydrophobic and hydrophobic layers can be similar to those described above. While many hydrophilic coatings can be used, the lubricous coating may comprise commercially available N-vinyl pyrrolidone (NVP), polyamine based coatings, methacrylate based coatings, and lubricous coatings commercially available from Surmodics Inc., Tri-Star Plastics Inc, and AST Products Inc. The hydrophilic coating may comprise phosphorylcholine technology, for example a coating commercially available from Vertellus.

The covering comprises a thickness sufficient to inhibit water through the covering and sufficient to maize swelling related to hypoxia of the cornea, for example within a range from about 20 to about 200 microns. For example, the covering may comprise an oxygen permeability, also referred to as Dk, of at least about 350, for example 400 or even 500 or more. For example, the covering may comprise a hydrophobic NuSil inner layer configured to transport oxygen and inhibit passage of water, and upper and lower hydrophilic layers, respectively, as described above. The silicone layer may comprise, for example, dimethyl diphenyl methyl vinyl silicone. The hardness of the covering, the thicknesses and oxygen can be configured by one of ordinary skill in the art to provide the sealing, water barrier, oxygen and optical functions to reduce edema based on the teachings described herein.

The thin lens covering comprises four characteristics that provide; a barrier against tear liquid entering the debrided zone, high oxygen permeability, and a good optical zone in the center of the lens, and an environment that encourages healthy epithelial re-growth. For example, silicone may have a very high oxygen permeability. The thin lens covering layer may comprise hydrophobic silicone may be covered with a hydrophilic lower layer to encourage healthy epithelial re-growth. The silicone layer may be coated on the lid side with a hydrophilic lubricant that that provides good tear film optics by smoothing the tear film, and which exhibits superior oxygen permeability.

The inner portion 2994 can be configured in many ways to provide the optical surface, water barrier, and high oxygen transport. The central portion can be configured to retain the optical surface, even when the epithelium underneath is somewhat irregular in many ways. For example, the inner portion may comprise a thickness from about 50 to about 200 microns. The inner portion may comprise a hardness durometer parameter within a range from about Shore A 30 to about Shore A 70, such that the inner portion retains the optical surface.

The outer portion 2992 can be configured in many ways to seal the covering against the epithelium and provide barrier function. For example, the outer portion may comprise a thickness from about 20 to about 100 microns, and may comprise a Shore A hardness durometer parameter within a range from about 20 to about 60.

The covering 2990 can be configured in many ways so as to seal the cornea. The outer portion and inner portion comprise a radius of curvature 2990R. The radius of curvature 2990R can be the same for both the inner portion and the outer portion. For example, the radius of each the inner portion and the outer portion may comprise about 7.5 mm. Alternatively, the inner portion may comprise a radius of curvature fit to the ablation profile, and the outer portion may comprise a radius of curvature fit to the unablated peripheral epithelium corresponding to the pre-ablation radius of curvature, as described above.

FIG. 29N-1 shows the therapeutic covering as in FIG. 29N adhered to a cornea after PRK with endothelial suction. The inner portion 2994 is positioned over the ablation 20. The inner portion can be sized smaller than the ablation such that the outer portion 2992 extends at least partially over the ablation and the edge of the epithelium. The outer portion 2992 extends over the boundary of the ablation 20B and the edge of epithelium 12 so as to conform to the epithelium and the edge of the ablation such that the lens is sealed on the cornea.

FIG. 29N-2 shows the outer portion therapeutic covering as in FIGS. 29N and 29N-1 conforming to the cornea over the undebrided epithelium and over the edge of the ablation 20B. The outer portion can comprise a size and a thickness so as to conform with the epithelium at the edge of the epithelial defect 12E and at the edge of the ablation 20B. For example, the thickness may comprise about 20 um at the periphery of the outer portion and extend to the central portion with an increasing thickness to about 50 microns. The outer portion may comprise a Shore A durometer hardness parameter of about 20 to about 40. The thickness can be increased as the durometer is decreased. For example, the thickness may extend from about 20 um at the periphery to about 100 microns near the inner portion. As the endothelial suction may not take effect immediately, contact tens may be positioned over the covering 2990 to retain the covering such that the covering can be pulled down ward against the epithelium with endothelial suction so as to seal the covering. The covering 2990 may be retained with many structures, adhesives and photosensitizers as described above.

FIG. 29N-3 shows the inner portion of the therapeutic covering as in FIGS. 29N and 29N-1 with an optical surface disposed over regenerating corneal epithelium. The optical surface may comprise upper surface 2994U of inner portion 2994L. Work in relation to embodiments suggests that the epithelium can be somewhat irregular during regeneration, and that this irregularity can contribute to decreased vision. Inner portion 2994 comprises sufficient rigidity such that the inner portion retains the optical shape of the surfaces. For example, when irregular epithelium regenerated under the inner portion, the inner portion may separate slightly from the ablated surface such that the inner portion floats on the regenerating epithelium. As the regenerated epithelium may be subject to suction of the endothelium due so sealing and endothelial pumping, the irregular epithelium can be smoothed by the lower optical surface of the inner portion so as to improve patient vision, for example to about 20/30 or better when the epithelium has regenerated at three days post-op. As the epithelium may continue to smooth after re-epithelialization, the covering may be positioned on the cornea for more than three days, for example 7 days or more and even one month.

The upper and lower surfaces of the inner portion can be curved in many ways to provide functional patient vision of at least 20/40 (metric 6/12) or better, for example 20/30 (metric 6/9) or better. For example the inner portion may comprise an optical power within a range from about −1 D to about +1 D. The lower surface 2994U may comprise a radius of curvature so as to correspond to the ablation 20, as described above.

FIG. 29O shows a therapeutic covering as in FIG. 29N comprising a covering molded with a homogeneous material, in which the outer portion comprises a thickness configured to conform with the cornea and in which the inner portion comprises thickness configured to retain the optical shape. The outer portion 2992 may comprise a thickness of no more than about 100 microns. For example the outer portion may comprise a thickness of about 50 microns at the boundary with the inner portion, and linearly taper from 50 microns at the boundary with the inner portion to about 20 microns at the periphery of the outer portion. The inner portion may comprise a thickness of no more than about 200 microns. For example, the inner portion may comprise a thickness of about 100 microns. Many materials can be used as described above. For example, the single piece covering may comprise silicone having a water content within a range from about 0.1% to about 10%, for example no more than about 1%, and a hardness Shore A durometer parameter within a range from about 20 to about 70, for example about 30.

FIG. 29P shows a therapeutic covering as in FIG. 29N comprising a covering molded with a first outer material and a second inner material, in which the outer portion 2992 comprises a first hardness configured to conform with the cornea and in which the inner portion 2994 comprises second hardness configured to retain the optical shape. The outer material may comprise many materials as described above. For example, the outer material may comprise silicone having a hardness Shore A durometer parameter from about 20 to about 40, and the inner material may comprise silicone having a hardness durometer parameter from about 40 to about 70.

FIG. 29Q shows a therapeutic covering as in FIG. 29N comprising a first outer portion composed of a first material affixed to a second inner portion composed of a second material, in which the outer portion comprises a first hardness configured to conform with the cornea and in which the inner portion comprises second hardness configured to retain the optical shape. The central inner portion may comprise a rigid central portion, of a higher durometer, of 3-4 mm in diameter to improve visual acuity in patients. This optically clear central portion may be up to 6 mm in diameter, for example. The central inner portion may provide optical power when placed on the eye, although patients receiving refractive vision correction such as PRK may not benefit from such refractive power such that the inner lens portion may comprise no more than about +/−1 Diopter of optical power. The center portion may comprise many materials, for example an RGP material. The peripheral outer portion may comprise a less rigid material, of a lower durometer, than the central portion so as to conform to the cornea along the epithelium and around the debrided edge and the edge of the ablation. Since optical clarity may not play a substantial role in the peripheral portion, the peripheral portion may comprise a transparent or opaque material. For example the peripheral portion may comprise an opaque material so as to define an aperture of the inner portion, for example a pinhole as described above.

FIG. 29R shows a covering comprising an annular configuration with the inner portion 2994 comprising an optic zone with a lower surface composed of a hydrophobic material configured for placement over the epithelial defect and the outer portion 2992 comprising a lower surface having a hydrophilic material configured to contact the epithelium. The diameter of the hydrophilic layer may have greater than the diameter of the hydrophobic layer so as to allow the hydrophilic layer to contact the epithelium when the inner hydrophobic layer is sucked down over the debrided area of the cornea.

Work in relation to embodiments suggests that silicone can store oxygen, and that silicone can diffuse from the hydrophobic layer to the cornea. Therefore, the therapeutic covering positioned on the eye may comprise oxygen that can diffuse to the cornea.

The thin therapeutic lens coverings as described above, may comprise the thin flap lens placed on the eye in a dry configuration to facilitate handing.

FIGS. 30A to 30C show a method of forming an annular band with protrusions to attach a contact lens to the cornea.

FIG. 30A shows an isometric cutaway view showing the lay up of thin walled positive form 3000 (0.032" metal walled cup) with hole 3002 permitting 0.005" wire 3004 to exit the region of flowing plastic 3006, which is in between the solid base 3008 and the cup.

FIG. 30B shows a cross sectional view showing the layup prior to the application of heat (200° C.) with 0.005" wire pressed against polycarbonate strip.

FIG. 30C shows a cross sectional view showing the layup after the application of heat, with the 0.005" wire 3004 now embedded into the polycarbonate strip 3006 which has flowed to fill the gap supported by the thickness of the wire.

FIG. 30D shows a method 30D00 of treating a PRK patient with a therapeutic covering. A step 30D05 measures the patient correction, for example a vision correction. A step 30D10 determines an ablation profile in response to the vision correction. A step 30D15 places a speculum in the eye of the patient, for example a physician placing the speculum in the eye of the patient to keep the eyelids separated and the cornea exposed. A step 30D20 removes the epithelium, for example with known methods as described above. A step 30D25 ablates the eye to correct vision, for example with known ablation profiles as described above. A step 30D30 places a therapeutic covering on the eye. The therapeutic covering may be placed on the eye after ablation and before the eye is hydrated when the speculum is placed against the eyelids. When the speculum is placed against the eyelids, the eyelids cannot blink to hydrate the eye and the cornea may dry. The covering may comprise an amount of hydration that is dryer than normally hydrated corneal tissue that comprises about 85% water, so as to adhere the covering to the stromal tissue. For example, the covering may comprise hyperosmotic hydration relative to the normally hydrated cornea, so as to adhere the covering to the cornea. A step 30D35 conforms the covering to the ablated corneal surface. The covering can be conformed to the corneal surface when positioned on the corneal surface, for example with pressure to the covering. A step 30D40 places a contact lens over the eye, for example a contact lens as described above. The covering may form a seal with the corneal epithelium when the covering conforms to the cornea. A step 30D45 adheres the contact lens to the cornea, for example as described above. A step 30D50 hydrates the eye, for example with saline from an artificial source. A step 30D55 removes the speculum from the eye, such that the patient can blink. A step 30D60 deturgesces the cornea, for example with endothelial pumping. A step 30D65 adheres the covering to the cornea with endothelial suction. A step 30D70 decreases pain, decreases swelling and improves vision, for example in response to deturgescence of the cornea. A step 30D75 regenerates the epithelium, for example such that the epithelium grows over the ablated corneal stroma and/or Bowman's membrane. A step 30D80 hydrates the contact lens, for example in preparation for removal of the contact lens. A step 30D85 removes the contact lens. A step 30D90 hydrates the therapeutic covering, for example in preparation for removal of the therapeutic covering. Another step can be to apply an oil, such as silicone oil to the eye, for example when the covering comprises silicone. A step 30D95 removes the covering so as to separate the covering from the underlying regenerated epithelium, such that the underlying regenerated epithelium remains intact over the ablated stroma and/or epithelium.

It should be appreciated that the specific steps illustrated in FIG. 30D provide a particular method of treating a PRK patient with a therapeutic covering, according to an embodiment of the present invention. Other sequences of steps may also be performed according to alternative embodiments. For example, alternative embodiments of the present invention may perform the steps outlined above in a different order. Moreover, the individual steps illustrated in FIG. 30D may include multiple sub-steps that may be performed in various sequences as appropriate to the individual step. Furthermore, additional steps may be added or removed depending on the particular applications. One of ordinary skill in the art would recognize many variations, modifications, and alternatives.

EXPERIMENTAL

The following studies are examples of empirical studies that can be performed on an appropriate number of patients to determine the clinical efficacy of the embodiments as described herein.

Although the below studies list specific testing steps, alternate testing steps may be used; some testing steps may comprise sub-steps and the studies can be performed with fewer steps than stated. Although specific numbers of patients are listed, these numbers are merely examples of patient numbers for use to determine empirically the clinically effectiveness of embodiments of the present invention.

Title:
Reducing Corneal Edema for Improving Vision in Patients Following Photorefractive Keratectomy (PRK)
Background:
PRK is a well established procedure for refractive correction for close to 20 years. One of its main draw backs is deteriorated visual acuity during the first postoperative days. Surface irregularity of the ablated area, epithelial initial irregular growth pattern and anterior stromal edema may play a role in such reduced vision. If stromal edema can be reduced during the first post-operative days, vision can be preserved. To establish what is the role of edema in vision recovery following PRK it can be important to establish whether dehydrating the cornea of the post-operative edema can significantly improve vision in patients following PRK. Dehydration of edematous corneas using Glycerin solution, a hyperosmotic agent, can be performed in the ophthalmologist's office to reduce edema when such edema obscures objects seen through the cornea. Glycerin can have a short lasting effect (minutes) and may temporarily dehydrate the edematous cornea. The purpose of this study is to examine if reduction of corneal edema using glycerin can improve patient's vision following PRK.

Study Objective:

Determine if reducing stromal edema can improve vision is patients during the initial post operative days following PRK.

Study Population:

At least 10 patients who underwent PRK.

Study Duration:

One day (single encounter visit ~2 hours)

Study Design:

A prospective non-randomized comparative case-control study

Inclusion Criteria:
1. Patients who underwent bilateral PRK for myopic correction.
2. Age 18-60.
3. Evidence of an epithelial defect.
4. Pre-operative Best Corrected Visual Acuity (BCVA) 20/40 or better.
5. BCVA on study day 2 lines or less than their pre-operative BCVA.
6. Willing to sign an informed consent Exclusion Criteria:
1. Any other anterior segment abnormality other than that associated with PRK.
2. Any abnormalities associated with the eye lids.

Example Methods:
1. Patients following PRK will be examined 1 day following PRK at the outpatient clinic.
2. Aside from the procedure described below no alteration in patient management in the post PRK period will be made.
3. One eye will be randomly selected to be the study eye while the other will serve as control.
4. Following detailed explanation and signing an informed consent form each patient will perform the following:
   a. Anterior segment examination. Specifically evidence for stromal edema will be assessed;
   b. BE: Pachymetry (to assess corneal thickness);
   c. BE: Following topical anesthetics (Localin™) BCVA will be measured using standard Snellen VA chart while standard bandage therapeutic lens in on;
   d. Study eye: Removal of therapeutic lens and placement of hyperosmotic Glycerin solution on the cornea;
   e. Study eye: Pachymetry to verify corneal dehydration (in case not substantial repeat previous step);
   f. Study eye: Re-placement of bandage therapeutic lens;
   g. BE: BCVA will be measured using standard Snellen VA chart while standard bandage therapeutic lens in on at 1 min, 5 min, 10 min, 20 min and 30 min;
   h. BE: Pain assessment (scale of 1-10) at 1 min, 5 min, 10 min, 20 min and 30 min;
   i. BE: Pachymetry at 5 min and 30 min;
   j. Anterior segment examination following the last VA exam.
5. Follow-up visit: all patients will be examined 1 and 6 days following the procedure.

Example Outcome Measures:
1. Relative difference in BCVA between study eye and non-study eye pre and post glycerin placement.
2. Difference in BCVA in study eye between pre and post glycerin placement
3. Correlation between Pachymetry measurements and BCVA.
4. Relative difference in pain between study eye and non-study eye pre and post glycerin placement.

Title: Therapeutic Lens for Mitigating Pain Following Photorefractive Keratectomy (PRK)

Background:

PRK is a well established procedure for refractive correction for close to 20 years. Its main draw backs are severe pain associated with it during the first postoperative days and delayed visual recovery. Standard means for mitigating pain are use of local non-steroidal anti-inflammatory agents, systemic pain killers and bandage therapeutic lens. While these measures are somewhat helpful, the many patients still complain of severe pain which causes them a significant burden (to the extent of causing sleepless nights, inability to open their eye lids, inability to work and more).

The main cause for pain may be that following epithelial debridement in preparation for PRK nerve endings are exposed and during the initial post operative days until the epithelium heals rubbing of eye lids against the wound causes severe pain. While standard bandage therapeutic lens may reduce pain to some extent, it still freely moves on the eye thus rubbing exposed nerve endings.

Gluing the therapeutic lens may prevent such rubbing and may potentially significantly reduce such pain. Fibrin glue (Tisseal™, Baxter Healthcare Corporation, Glendale, Calif.) can be used to glue the therapeutic lens to the cornea. The purpose of this study is to examine if gluing a therapeutic lens to the cornea using fibrin glue can reduce pain in such patients.

Study Objective:

Determine if a therapeutic lens bonded on the cornea following PRK can reduce pain associated with the epithelial defect during the initial period following PRK.

Study Population:

At least 10 patients who underwent PRK.

Study Duration:

One day

Study Design:

A prospective non-randomized comparative case-control study

Inclusion Criteria:
1 Patients who underwent bilateral PRK for myopic correction.
2 Age 18-60.
3 Evidence of an epithelial defect.
4 Patient complains of significant pain.
5 Willing to sign an informed consent.

Exclusion Criteria
1 Any other anterior segment abnormality other than that associated with PRK.
2 Any abnormalities associated with the eye lids.

Example Methods
1 Patients following PRK will be examined 1 day following PRK at the outpatient clinic.

2 Aside from the procedure described below no alteration in patient management in the post PRK period will be made.
3 One eye will be randomly selected to be the study eye while the other will serve as control.
4 Following detailed explanation and signing an informed consent form each patient will perform the following:
   a. Both eyes (BE) anterior segment examination;
   b. BE: Visual acuity (VA) using standard Snellen VA chart with standard bandage therapeutic lens:
   c. BE: Subjective pain assessment (1 to 10 scale) with standard bandage therapeutic lens;
   d. BE: Subjective discomfort assessment (1 to 10 scale) with standard bandage therapeutic lens;
   e. Study eye: Removal of bandage therapeutic lens;
   f. Study eye: Corneal photography with and without fluorescein;
   g. Study eye: Following short acting local anesthetic (Localin™) and while the patient is in supine position a standard bandage therapeutic lens will be attached to corneal epithelium using fibrin glue;
   h. Study eye: Anterior segment examination at 0 hr, 1 hr, 2 hr and 4 hr following the procedure;
   i. Corneal photography at 0 hr and 4 hr following the procedure;
   j. Visual acuity using standard Snellen VA chart with standard bandage therapeutic lens at 0 hr, and 4 hr following the procedure;
   k. BE: Subjective pain assessment (1 to 10 scale) with glued-on standard bandage therapeutic lens at 1 hr, 2 hr and 4 hr following the procedure;
   l. BE: Subjective discomfort assessment (1 to 10 scale) with glued-on standard bandage therapeutic lens at 1 hr, 2 hr and 4 hr following the procedure;
   m. Study eye: Removal of standard bandage glued-on therapeutic lens following the 4 hr examination;
   n. Study eye: Anterior segment examination following the removal of therapeutic lens;
   o. Corneal photography following the removal of therapeutic lens;
   p. Placement of standard (non-glued) bandage therapeutic lens.
5 Follow-up visit: all patients will be examined 1 and 6 days following the procedure.

Example Outcome 3 Measures:
1 Relative change in pain before and after placing the glued-on therapeutic lens between study eye and non-study eye.
2 Relative change in discomfort before and after placing the glued-on therapeutic lens between study eye and non-study eye.
3 Difference in study eye between pre procedure and post-procedure pain.

Title: Corneal Coating for Mitigating Pain Following Photorefractive Keratectomy (PRK)

Background:

PRK is a well established procedure for refractive correction for close to 20 years. Its main draw backs can be severe pain associated with it during the first postoperative days and delayed visual recovery. Means for mitigating pain are use of local non-steroidal anti-inflammatory agents, systemic pain killers and bandage therapeutic lens. While these measures are somewhat helpful, many patients still complain of severe pain which causes them a significant burden (to the extent of causing sleepless nights, inability to open their eye lids, inability to work and more).

The main cause for pain may be that following epithelial debridement in preparation for PRK nerve endings are exposed and during the initial post operative days until the epithelium heals rubbing of eye lids against the wound causes severe pain. While standard bandage contact may reduce pain to some extent, it still freely moves on the eye thus rubbing exposed nerve endings. A biocompatible material that can adhere to the cornea and not move during blinking and eye movement has the potential to significantly reduce pain after PRK.

Fibrin glue (Tisseal™, Baxter Healthcare Corporation, Glendale, Calif.) can be used to coat the exposed surface of the cornea. The purpose of this study is to examine if coating the wounded area using fibrin glue can reduce pain in such patients.

Study Objective:

Determine if a thin layer of fibrin glue placed on the cornea following PRK can reduce pain associated with the epithelial defect during the initial period following PRK.

Study Population;

At least 10 patients who underwent PRK.

Study Duration:

Five days

Study Design:

A prospective non-randomized comparative case-control study

Inclusion Criteria:
1 Patients who underwent bilateral PRK for myopic correction.
2 Age 18-60.
3 Evidence of an epithelial defect.
4 Patient complains of significant pain.
5 Willing to sign an informed consent.

Exclusion Criteria
1 Any other anterior segment abnormality other than that associated with PRK.
2 Any abnormalities associated with the eye lids.

Example Methods
1 Patients following PRK will be examined 1 day following PRK at the outpatient clinic
2 Aside from the procedure described below no alteration in patient management in the post PRK period will be made.
3 One eye will be randomly selected to be the study eye while the other will serve as control.
4 Following detailed explanation and signing an informed consent form each patient will perform the following:
   a Both eyes (BE) anterior segment examination;
   b BE: Visual acuity (VA) using standard Snellen VA chart with standard bandage therapeutic lens;
   c BE: Subjective pain assessment (1 to 10 scale) with standard bandage therapeutic lens;
   d BE: Subjective discomfort assessment (1 to 10 scale) with standard bandage therapeutic lens;
   e Study eye: Removal of bandage therapeutic lens;
   f Study eye: Corneal photography with and without fluorescein;
   g Study eye: Following short acting local anesthetic (Localin) and while the patient is in supine position a thin layer of fibrin glue will be applied to the wound area;
   h Study eye: Anterior segment examination at 0 hr, 1 hr, 2 hr and 4 hr, 1 day, 2 days, 3 days and 4 days following the procedure;
   i BE: Corneal photography with fluorescein at 0 hr and 4 hr, 1 day, 2 days, 3 days and 4 days following the procedure;

j Visual acuity using standard Snellen VA chart 0 hr, and 4 hr, 1 day, 2 days, 3 days and 4 days following the procedure following the procedure;

k BE: Subjective pain assessment (1 to 10 scale) at 1 hr, 2 hr and 4 hr, 1 day, 2 days, 3 days and 4 days following the procedure;

l BE: Subjective discomfort assessment (1 to 10 scale) at 1 hr, 2 hr and 4 hr 1 day, 2 days, 3 days and 4 days following the procedure.

Example Outcome Measures:

1 Relative change in pain before and after placing fibrin glue between study eye and non-study eye.

2 Relative change in discomfort before and after placing fibrin glue between study eye and non-study eye.

3 Difference in study eye between pre-procedure and post-procedure pain (1 hr, 2 hr and 4 hr only).

Animal studies may be also conducted in accordance with the embodiments described above.

It should be appreciated that the protocols shown above provide a particular method of testing therapeutic coverings, according to some embodiments of the present invention. Other embodiments may also be tested in accordance with at least some aspects of the above testing protocols. Furthermore, additional embodiments may be tested in combination or removed depending on the particular applications. One of ordinary skill in the art would recognize many variations, modifications, and alternatives.

FIG. 31A shows measured corneal edema immediately following PRK surgery and one day post-op with PRK patients. The corneal edema can be measure with pachymetry by comparing the pre-op values to the post-op values. The day of surgery, day 0, the edema is about 100 um in the measure patients. At one day post-op, the swelling is about 140 um. This data shows the cornea swells following PRK both the day of surgery and the following day.

FIG. 31B shows a model for corneal swelling with PRK patients as in FIG. 31A. After PRK the epithelium has an epithelial defect 11 that allows water to enter the cornea 10 through the ablated stroma 16. This water passes through the cornea and is pumped from the cornea by the corneal endothelium 18. The amount of water that enters the cornea through the epithelial defect can exceed the pumping rate of the corneal endothelium, such that the cornea swell, for example in an anterior portion of the stroma 16 where the cornea is ablated.

FIG. 32A shows measured corneal edema immediately following LASIK surgery and one day post-op with LASIK patients. The day of surgery, day 0, the corneal swelling is about 100 um, similar to the PRK patients. At one day post-op the corneal swelling is about 30 um. The 110 um difference in swelling between the PRK corneas and the LASIK corneas shows that PRK corneas swell more than LASIK corneas, at least for the first day post-op. As LASIK patients report less pain and have better vision at one day post-op than PRK patients, this data shows that swelling of the cornea can significantly effect patient comfort and may also effect patient vision.

FIG. 32B shows a model for corneal swelling with LASIK patients as in FIG. 31A. With LASIK, a flap 3200 of corneal tissue is cut and moved to the side with a hinge that connects the flap to the cornea, and the exposed stromal tissue 16 ablated is ablated 11. The flap is repositioned on the cornea over the stromal ablation. As the flap retains the corneal epithelium, the flap may comprise a barrier to water entry of the corneal stroma. At surgery, the epithelium has not regenerated between the flap and the cornea, such that water can enter at the margin of the flap 3204. At one day post-op for LASIK, the epithelium can cover the margin of the flap to seal the cornea, such that the endothelium can effectively deturgesce the cornea so as to decrease swelling. Consequently, the cornea swells less with LASIK at one day post-op and patients report less pain and better vision.

FIGS. 33A and 33B show pre-op and post-op pachymetry measurements on patients with a Pentacam™ to determine corneal edema at one day post-op. A Pentacam™ is a known device for mapping the thickness of the cornea and is commercially available from Oculus, Inc. of Lynwood, Wash. FIG. 33A shows the pre-op pachymetry map of a patient that is a −1.25 myope. The combined thickness of the pre-operative cornea comprising the endothelium, stroma, Bowman's membrane and epithelium is 524 um. The pre-operative thickness includes 60 um of corneal epithelium that is debrided. The thickness of the post operative cornea is 537 um. The edema of the cornea can be calculated from the change in pachymetry, the thickness of the epithelium and the thickness of the ablation. The pre-operative cornea comprises a stromal thickness of about 464 microns, and is ablated with about 24 microns, such that the pachymetry should be about 440 um post-op. The measured corneal thickness is about 537 um post-op, which is 97 microns more than the theoretical pachymetry post-op due to swelling of the stroma.

FIGS. 34A and 34B show pre-op and post-op pachymetry measurements on patients with a OCT to determine corneal edema at one day post-op OCT, also referred to as optical coherence tomography, is a known and commercially available method of measuring corneal thickness. FIG. 34A shows the pre-operative corneal thickness as 458 microns, which includes 60 um of epithelium. The cornea was ablated with a targeted ablation depth of 24 microns. FIG. 34B show's the post-ablation stromal thickness to be 514 microns by OCT. Without swelling, the post-operative corneal thickness would have been 434 um (518–60–24) microns. The measured thickness of 514 microns indicates approximately 80 microns of corneal swelling.

FIG. 35 shows loss of visual acuity and cornea edema with PRK for patients the day of surgery within about one hour of surgery, measured in accordance with the above protocols. For example, patient one OD (ocular dexter, or right eye), shows a pre-op corrected visual acuity of 20/25. One day post op the vision is 20/50 with a bandage lens (BL) and 20/50 with a rigid gas permeable lens (RGP). Therefore, post-op this patient has lost about 3 lines of visual acuity at one day post op. The edema based on OCT is about 70 um. The left eye, OS, of patient 1 shows similar results. Patients 2 and 3 show similar results.

FIG. 36 shows loss of visual acuity and cornea edema with PRK patients one day after surgery, measure in accordance with the above protocols. These data show a loss of visual acuity and corneal swelling similar to FIG. 35. The edema of patient 1 OS is about 166 microns, and the edema of patient 2 OD is about 104. The last row shows the change in corneal edema from the day of surgery to the first day post-op (Baseline Pa@PRK day—Pa@1st day). The visual acuity of patient 2 with the right eye is 20/40 without a bandage lens (BL) and is correctable to 20/22 with a bandage lens, which indicates that post-operative swelling of the cornea can effect visual acuity.

Also, the patients were treated with glycerin and Healon® to determine the effect of corneal drying, in accordance with the above protocols. These data show that glycerin with a bandage contact lens can improve visual acuity (VA wo/BL Gly 1) with the first application at about 1 minute, which show visual acuity without a bandage lens improving by two lines in both the right and left eyes of patient 1 from about 20/50 and 20/66, respectively, to about 20/33 and 20/40. Subsequent applications of glycerin did not improve visual acuity (VA wo/BL+Gly 2). This may be due to penetration of the corneal stroma by the glycerin so as to decrease the hyperosmotic effect of the glycerin on the stroma. The subsequent treatment of the eyes with Healon, which has a higher molecular weight than glycerin, may not penetrate the stroma and may be effective to reduce swelling, for example as a filler material as described above. The initial testing with Healon (VA+RGB+Healon) did showed an improvement in vision over the second application in glycerin in both eyes of patient 1, and not with the right eye of patient 3. Further experiments and refinements can be made on an empirical number of patients.

FIG. 37 shows decrease in corneal edema and increase in visual acuity in response to glycerin applied to an initial sample of patient eyes so as to reduce swelling and improve visual acuity, in patients tested in accordance with the above protocols. Series 1 corresponds to visual acuity 20/xx and series 2 corresponds to cornea thickness.

FIG. 38A-38D show clinical pictures of a flat covering on a human cornea with the covering conforming to the curved cornea of the patient and a contact lens placed over the covering.

FIG. 38A shows a picture of a thin flap fibrin lens covering placed on the epithelium of a patient in accordance with the above protocols. In this particular experiment, the properties of the fibrin lens were evaluated on a cornea with an intact epithelium to demonstrate a flat lens adapted to conform the curvature of a cornea. The flat fibrin lenses were manufactured as described herein below with reference to the materials fabricated for testing of the US Air Force resolution target, described herein below. The edge of the lens 3800 is visible in FIG. 38A.

FIG. 38B shows a picture of the lens coveting of FIG. 38A on the patient with a bandage contact lens (BCL) placed over the thin fibrin flap covering after 15 minutes. A small air bubble 3802 is visible under the bandage contact lens at the edge of the fibrin covering.

FIG. 38C shows a picture of the lens covering of FIGS. 38A and 38B on the patient with a bandage contact lens (BCL) placed over the thin fibrin flap covering after 60 minutes. The edge of the thin fibrin lens 3804 is barely visible in the picture.

FIG. 38D shows a picture of the lens covering of FIGS. 38A, 38B and 38C on the patient with a bandage contact lens (BCL) placed over the thin fibrin flap covering after 90 minutes. The edge of the thin fibrin lens 3806 is barely visible in the picture. It was observed in this eye that the fibrin covering made a small indentation indicative of pressure applied to the covering with the contact lens, such that the covering can be located at substantially the same location so as to resist a blink of an eyelid, and may be configured to adhere to and/or seal the cornea as described above.

FIGS. 38E-1 and 38E-2 show OCT images of the covering of FIGS. 38A-38D with a contact lens 3808 placed over the cornea and the covering 3810 conforming to the cornea. FIG. 38E-1 shows an OCT image of the center of the cornea and shows the bandage contact lens placed over the thin fibrin lens covering with the covering conforming to the surface of the cornea. FIG. 38E-2 shows an OCT image of the edge of the thin lens 3812 covering under the bandage contact lens, with the thin fibrin lens covering conforming to the shape of the cornea.

Examples of additional covering materials that can be tested for conformance to the cornea and optical properties include 8 configurations were as follows: Hydrogel and PET; Dialysis Membrane (3 mm); Collagen (sheepskin); Tisseal™ Sheet (5 mm); BioGlue Sheet (3 mm); Tisseal™ Sheet (8 mm); Air Dried; Hydrogel CL (5 mm and 8 mm trephine); Lamellar "LASIK" Flap Created.

FIGS. 39A to 39C show optical images through casting of a U.S. Air Force resolution target and improvements in optical characteristics of the castings in response to improvements to the casting materials and process. FIG. 39A shows a standard formulation of fibrin. FIG. 39B shows a custom formulation of fibrin. FIG. 39C shows a cast custom formulation. These optical images show that the optical quality of the fibrin formulation can be improved significantly with the custom formulation and casting.

1. Standard Fibrin Formulation Membrane:

The fibrinogen component of a standard fibrin sealant such as Tisseal™ (Baxter Biosurgery) is reconstituted with half of the supplied aprotinin solution at 37° C. on a heated stir plate such as Fibrotherm™, Baxter Biosurgery, by stirring for at least 5 minutes. Once the lyophilize is completely dissolved, the solution is allowed to sit for at least 30 minutes until all entrapped air bubbles have dissipated. The thrombin component is reconstituted with the supplied 40 mM CaCl2 solution, then diluted 9:1 v/v with more 40 mM CaCl2, to produce a 50 unit/mL thrombin solution. Each component is loaded into syringes, taking care to not introduce air bubbles, and mounted into a dual syringe tissue adhesive applicator such as DuploJect from Baxter Biosurgery. An applicator tip either with or without an in-line static mixer, is attached to the end of the syringe joiner piece. Glass slides are prepared by adhering w/medical device grade cyanoacrylate metal shim strips (approximately 25 um thick) along the edges, then washing and rinsing. An amount of the two part mixture is then applied to the glass slide sufficient to cover it, then another clean glass slide without shim strips is placed atop the solution and pressed down gently but firmly onto the shim strips. The glass slide assembly containing the entrapped fibrin is allowed to incubate at room temperature overnight. Once the gel has dried, the glass slides are pried apart, the fibrin rinsed with saline, and peeled off, then washed and rinsed in several changes of sterile saline and allowed to dry again and trephined to produce circular implants. The membranes are then placed in appropriate packaging and sterilized by gamma radiation (approximately 25 kGy). Prior to application onto the cornea, the membrane is rehydrated with saline.

2. Optically Clear Custom Fibrin Formulation Membrane:

To produce an optically clear fibrin membrane, the fibrinogen component of the fibrin sealant is reconstituted with only half of the supplied aprotinin solution in the same manner as for the standard formulation. The thrombin is reconstituted with 300 mM NaCl and 40 mM to produce a 50 U/mL solution. The membrane production then proceeds in the same manner as for the standard fibrin formulation.

3. BSA-Glutaraldehyde Membrane:

Sterile 30% bovine serum albumin (Sigma-Aldrich) is loaded into a syringe. A 4% glutaraldehyde solution is prepared and loaded into a second syringe. Both components are loaded onto a dual syringe tissue adhesive applicator such as DuploJect from Baxter Biosurgery) either with or without a static inline mixer. The membrane is then produced in the same manner as for the fibrin membranes, except more rinsing is used in order to remove unbound glutaraldehyde prior to gamma sterilization.

The optical and conforming properties of the covering can be improved with and improved casting process based on empirical laboratory and clinical studies, such that the covering can provide improved vision, for example 20/20 vision through the covering as measured with the air force resolution target. An improved casting process may comprise improving the mixing of the two solutions (fibrinogen and thrombin). For example by using a static mixer attached to the applicator. That way inhomogeneities in the ratios between the two components can be minimized or eliminated completely. A person can cast other fibrin formulations this way and the cast formulation can appear much more visually homogeneous. Such casting formulations can be made by one of ordinary skill in the art with time to do make this specific formulation, which can be the very clear fibrin. Further, laser ablation to affect further thinning of the material can result in improved optical quality, for example by rendering the covering clearer and this improvement may be quantified, for example by measuring the minimum angle of resolution of images through the covering. Also, gamma irradiation of the cast membrane can clarify the covering further. This has been observed with the clinical material as these materials have been laser thinned and gamma irradiated before human use.

FIG. 40 shows a picture of an annular band, or skirt with a wire made with the method of FIGS. 30A to 30C that can be placed over a contact lens to adhere the contact lens to the cornea. The annular hand is clearly visible in the picture. The wire extends horizontally along the band and is embedded in the band as described above. The wire successfully penetrated the underlying contact lens and anchored in the underlying stroma. The annular band can be adhered to a contact lens, for example and RGP contact lens so as to adhere the contact lens to the cornea with the annular band.

Pain Management:

Experimentally it has been observed that edema can be caused by both a lack of water barrier function and decrease of oxygen. The thin lens covering can provide pain management both mechanically and metabolically. From a mechanical standpoint, the thin lens covering can provide a barrier against rubbing between the debrided zone and the inside of the eye lid. The thin lens covering may also comprise a barrier sealed against the epithelium so as to inhibit water entering the debrided area. From a metabolic standpoint, the thin lens covering comprises oxygen permeability so as to provide the oxygenation needed for corneal epithelium healing. For epithelial re-growth of the debrided epithelium, the oxygen requirement of the epithelium growing over the defect can much higher than for intact epithelium. Without adequate oxygenation, the epithelium may shifts the metabolic pathway away from producing the carbon dioxide to producing lactic acid. The lactic acid can cause hyperosmosis in the epithelial and stromal layers and draw water into these layers which, in turn, may cause the cornea to swell. The decreased oxygen of the cornea may also cause nerve activation manifested by pain, for example nerve activation due to increase swelling.

FIGS. 41A, 41B and 41C shows uncorrected visual acuity, corneal edema, and epithelial defect area over time for patients treated with a therapeutic covering as described above, and control patients receiving a commercially available therapeutic bandage lens loosely fit to the cornea in accordance with known clinical methods of post PRK patient treatment. These data were obtained from clinical studies undertaken with PRK patients in accordance with the above described protocols. The data are shown for 17 patients for the control group and 10 test patients receiving the tested device.

Data are shown of patients' uncorrected visual acuity readings from 0 to 72 hours post-PRK. The data shows the UCVA of 17 control patients wearing either Oasys Acuvue or Night & Day CIBA Vision silicone hydrogel bandage lenses. Ten patients wore a thin lens flap covering comprising NuSil and plasma treated with carboxylated surface on the front surface, covered by a silicone hydrogel bandage lens for the acuity reading. The UCVA measurements were taken at 0, 4, 24, 48 and 72 hours. The patients wearing a silicone thin lens flap and on top of it a silicone hydrogel bandage contact lens for the purpose of the UCVA measurement, had better UCVA than the control group wearing a bandage lens only; at 72 hours the UCVA values for both sets of patients largely corresponded The uncorrected visual acuity of the patients with the test silicone covering had a mean uncorrected visual acuity (20/XX) of 0.5 at about 1 hour post-op, and the controls with the hydrogel bandage had a mean visual acuity of about 0.4 at about 1 hour post-op. At one day post-op, the test patients had an acuity of about 0.75 and the controls had a visual acuity of about 0.55. At two days post-op the test patients had a visual acuity of about 0.60 and the control patients had a visual acuity of about 0.45. These data show that the therapeutic covering can improve vision at a plurality of days comprising days one and two post-op, and one of ordinary skill in the art can improve vision based on the teachings described herein. At day three post-op, the test patients and the control patients each have similar visual acuities of about 0.6. Work in relation to the tested embodiments suggests that the regenerated epithelium at day three may comprise some irregularities, and that one can improve the optical surface of the covering so as to improve the patient vision at day three based on the teachings described herein.

Data of patients' edema are shown from 0-72 hours post-PRK. The data shows the edema thickness (in um) of 17 control patients wearing either Oasys Acuvue or Night & Day CIBA Vision silicone hydrogel bandage lenses. Ten patients wore a thin lens flap covering comprising NuSil and plasma treated with carboxylated hydrocarbon surface on the front surface. The patients wearing a silicone thin lens flap had less edema than the control group wearing a bandage lens only; at 72 hours the edema values for both sets of patients were quite close.

The mean edema of the test patients with the lest silicone covering was about 70 um at about 1 hour post-op, and the controls with the hydrogel bandage had a mean edema of about 80 um at about 1 hour post-op. The edema was calculated based on the pre-op corneal thickness as compared to post-op, and the calculated edema corrected for the ablation depth and the epithelial thickness. The mean edema of the test patients with the test silicone covering was about 15 um, about 3%, at about 4 hours post-op, and the controls with the hydrogel bandage had a mean edema of about 45 um, about 10%, at about 4 hours post-op. The mean edema of the test patients with the test silicone covering was about 3 um at about 24 hours post-op, less than 1%, and the controls with the hydrogel bandage had a mean edema of about 45 um, about 10%, at about 24 hours post-op. The mean edema of the test patients with the test silicone covering was about 5 um, about 1%, at about 48 hours post-op, and the controls with the hydrogel bandage had a mean edema of about 45%, about 10%, at about 48 hours post-op. Therefore, the test therapeutic covering reduced the mean edema to about 1% or less for a plurality days comprising days one and two and the control patients showed an edema of about 10% at these time periods. The mean edema of the test patients with the test silicone covering was about 15 um, about 3%, at about 72 hours post-op, and the controls with the hydrogel bandage had a mean edema of about 10 um, about 2%, at about 72 hours post-op. Work in relation to these studies suggest that oxygen permeability of the test covering may contribute to the corneal edema at day three post-op. Based on the teachings described herein, a person of ordinary skill in the art can decrease the permeability to decrease the edema of patients at day three post-op to within about 20 um, about 2%, or less, for example within about 10 um, about 1%. The thickness of the covering may be decreased so as to increase the oxygen permeability Dk parameter, and the parameter determined empirically.

Data are shown patients' epithelial defect size from 0-72 hours post-PRK. The data shows the edema thickness (in um) of 17 control patients wearing either Oasys Acuvue or Night & Day CIBA Vision silicone hydrogel bandage lenses. Ten patients wore a thin lens flap covering comprising NuSil and plasma treated with carboxylated hydrocarbon surface on the front surface. The patients wearing a silicone thin lens flap had a larger epithelial defect size from 24 to approximately 72 hours than the control group wearing a bandage lens only; at 72 hours the epithelial defect had closed for both the control and the thin lens flap patients.

The mean epithelial defect area of the test patients with the test silicone covering was about 15 mm$^2$ at about 24 hours post-op, and the controls with the hydrogel bandage had a mean epithelial defect area of 15 mm$^2$ at about 24 hour post-op. The mean epithelial defect area of the test patients with the test silicone covering was about 5 mm$^2$ at about 48 hours post-op, and the controls with the hydrogel bandage had a mean epithelial defect area of 2 mm$^2$ at about 48 hour post-op. The mean epithelial defect area of the test patients with the test silicone covering was about 0 mm$^2$ at about 72 hours post-op, and the controls with the hydrogel bandage had a mean epithelial defect area of 0 mm$^2$ at about 24 hour post-op, such that both groups were substantially re-epithelialized by day three post-op. Further studies can be conducted to determine whether a covering with an increased oxygen permeability can result in faster repithelialization.

FIG. 42 shows an optical coherence tomography image of the clinically tested therapeutic covering adhered to an eye so as to remodel the epithelium near the edge of the 9 mm diameter covering. The image also shows a bandage lens positioned over the covering. The image shows the covering adhered to the epithelium such that the covering induced an irregularity of the epithelium near the edge of the covering. The epithelium has grown over the covering slightly at the periphery and extends under the covering for a substantial distance, such that the cornea is sealed with the covering and the epithelium. The covering was adhered to the eye with the bandage lens removed. This data shows the covering adhered to the cornea with endothelial suction. A person of ordinary skill in the art will recognize that the periphery of the covering may be thinned so as to inhibit or minimize the irregularity of the epithelium at the periphery, based on the teachings described herein. As the endothelial suction was sufficient to induct the peripheral irregularity of the epithelium, the rigidity of the inner portion may be configured to smooth the epithelium, based on the teachings described herein.

FIG. 42A shows an optical coherence tomography image of a therapeutic covering conforming to an epithelial layer of a PRK patient at 24 hours post-op. The covering conforms to the epithelial defect, so as to seal the cornea. The covering comprises a silicon material having a thickness of about 50 um and a Shore A durometer of about 30. The epithelium is shown growing under the covering and continued to grow such that the eye re-epithelialized under the covering.

FIG. 43 shows an optical coherence tomography image of a therapeutic covering conforming to a de-epithelialized porcine eye. The pig eye was enucleated and debrided. The diameter of the debrided zone is approximately 2.5 mm. The thickness of the epithelium is shown as approximately 0.06 mm.

The thin lens flap covering comprises NuSil grade 4930 and with a carboxylated plasma treated anterior surface has been draped over the debrided zone. The thin lens flap covering conforms to the surface of the eye, leaving no gaps between the posterior/bottom part of the lens mid the surface of the cornea. The covering is shown conforming to irregularities of the cornea, including irregularities of the epithelium and stroma, such as the boundary of the epithelial defect. The covering comprised a thickness of about 50 um and a Shore A durometer of about 30. These data suggest suitable parameters for the peripheral portion such that the peripheral portion can conform to irregularities of the epithelium so as to seal the cornea, and that the inner portion may comprise a durometer of more than 30 when the inner portion is no more than about 50 um thick.

A person of ordinary skill in the art can conduct empirical studies to determine material properties, coatings and dimensions of a therapeutic covering for use after photorefractive keratectomy so as to provide improved water barrier function, decreased pain and increased visual acuity for days one to three post-op, even from days one to seven post-op. For example, a decreased thickness of the flap can result in decreased edema at three days post-op and may improve visual acuity at three days post-op. For example, parameters can be determined for a therapeutic covering so as to decrease average edema to no more than about 5%, decrease average pain, and provide an average visual acuity of at least about 20/30 or better in a population of patients for days one to three post. For example, the above experimental findings indicate that a thinner silicone flap can decrease swelling at days 1 and 3 post-op.

Clinical studies in accordance with the above described embodiments have shown that the cornea may comprise may corneal irregularities following PRK, and that the covering can decrease many of these irregularities. The irregularities can correspond to optical aberrations that decrease patient vision. In the first one to three days following PRK, the cornea can swell. The swelling of the corneal stroma can result in stromal irregularities. For example the stroma can swell so as to produce a central island, which can resolve when swelling is decreased and the epithelium covers the stroma and/or Bowman's. A central island may comprise an under ablated central portion that produces optical aberrations. Also, the boundary at the edge of the ablation may comprise a stroma irregularity. Clinical studies the Pentacam™ and topography systems have shown epithelial irregularities comprising the edge of the epithelial defect, and the epithelium can be somewhat irregular, even though the epithelium can cover the cornea. The epithelial irregularities may last for at least one week following PRK.

The empirical studies may comprise laboratory studies, for example of conformance of a covering to a target shape. For example, the covering can be placed over a 7.5 mm radius of curvature surface with a 2 mm hole in the middle of the test surface to simulate a corneal irregularity. With a inner portion that may be more soft than ideal, the inner portion may droop over the hole. The hardness and/or thickness of the inner portion can be increased such that the inner portion retains the optical shape and does not droop over the hole. For example, experiments have suggested that a 50 um uniform thickness covering with a Shore A durometer of 30 may droop slightly such that a thicker and/or harder covering may provide improved clinical results. Patients may be tested subsequent to laboratory testing to optimize empirically the parameter of the therapeutic covering so as to achieve the above stated functions such as edema less than 5% and visual acuity of 20/30 or better.

An example of a therapeutic covering in accordance with the above may comprise a single piece of molded silicon having a water content of no more than about 2%, an outer portion with an outer size of about 7 to 9 mm across, for example 8 mm diameter, an inner portion with a size of about 3 to 5 mm across, for example 4 mm diameter. The silicone may comprise hardness corresponding to a Shore A durometer from within a range about 30 to about 70, for example a uniform hardness corresponding to a durometer of about 40. The thickness of the outer portion at the periphery may comprise about 10 to 40 microns across, for example 20 microns. The thickness can gradually increase toward an inner boundary of the outer portion having a thickness within a range from about 40 to 80 microns. The central portion may comprise an uniform thickness within a range from about 80 to 120 microns across, for example 100 microns. The covering comprising the molded single piece can be coated on the upper surface with a hydrophilic layer, for example a lubricous coating, and coated on the lower surface with a hydrophilic layer, for example a lubricous coating. The outer portion of the covering can conform to and seal against the undebrided epithelium and the peripheral Bowman's membrane with endothelial suction, as described above, and the central portion comprises an optical surface for vision which does not conform to irregularities of the epithelium or the ablated stroma. The oxygen permeability and corresponding Dk of the covering can exceed 350, for example 400 or even 500 or more, so as to inhibit or minimize pain and swelling when the epithelium regenerates.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims and the full scope of the equivalents thereof.

What is claimed is:

1. A covering to treat a cornea of an eye of a patient, said cornea comprising an epithelium, and said covering comprising:
   an inner portion comprising an inner rigidity, an inner thickness, and an inner durometer; and
   an outer portion comprising an outer rigidity,
   wherein said inner rigidity is greater than said outer rigidity,
   wherein said inner durometer is within a range of Shore 20A to Shore 70A, and
   wherein said covering, when applied to said cornea, is configured to adhere to said cornea to reduce swelling of said cornea.

2. The covering of claim 1, wherein said covering is configured to be applied to said cornea when a speculum is positioned against an eyelid of said eye.

3. The covering of claim 2, wherein said cornea comprises a dried portion, wherein a portion of said covering is configured to adhere to said dried portion of said cornea, and wherein said portion of said covering comprises a less than physiological amount of hydration.

4. The covering of claim 1, wherein said cornea comprises an ablation profile and wherein said covering is configured to conform to said ablation profile when adhered to said cornea.

5. The covering of claim 1, wherein said covering comprises a laser-ablateable material.

6. The covering of claim 1, wherein said covering is configured to form a seal between said cornea and at least a portion of said covering to decrease water flow into said cornea.

7. The covering of claim 1, further comprising an outer periphery configured to allow said epithelium to grow over at least a portion of said outer periphery.

8. The covering of claim 7, wherein said epithelium is disposed under said outer periphery when said epithelium grows over said at least portion of said outer periphery.

9. The covering of claim 1, wherein said covering is configured to be placed on said cornea over an epithelial defect of said epithelium.

10. The covering of claim 9, wherein said covering is configured to be removed from said cornea when said epithelial defect is healed.

11. The covering of claim 10, wherein said covering is configured to separate from said cornea and from said epithelium when said covering is removed from said cornea.

12. The covering of claim 11, wherein said covering is configured to loosen from said epithelium when water is provided to said eye.

13. The covering of claim 1, wherein said covering comprises a hydrophobic lower surface configured to inhibit sliding of said covering on said cornea.

14. The covering of claim 6, wherein said covering comprises a substantially water impermeable material configured to deturgesce or inhibit swelling of said cornea when said seal is formed.

15. The covering of claim 6, wherein said cornea comprises an epithelial defect and wherein said covering comprises a lower surface or a lower material configured to suck down against a stroma of said cornea and to adhere to said stroma when said seal is formed.

16. The covering of claim 15, wherein said lower surface or said lower material is configured to adhere substantially less to said epithelium than to said stroma.

17. The covering of claim 1, wherein said covering comprises a substantially oxygen permeable material.

18. The covering of claim 17, wherein said lower surface or said lower material comprises a radius of curvature corresponding to a radius of curvature of said cornea.

19. The covering of claim 1, wherein said covering comprises an optical power within a range from about −5 Diopters (D) to about +5 D.

20. The covering of claim 1, wherein said covering comprises an optical power within a range from about −1 D to about +1 D.

21. The covering of claim 6, wherein said cornea comprises an epithelial defect and an ablated stroma, said ablated stroma having been subjected to photorefractive PRK, and wherein said covering is configured to form said seal over an unablated region of said epithelium.

22. The covering of claim 21, wherein said covering comprises a surface or a material configured to inhibit water flow through said covering and to deturgesce said cornea when said seal is formed.

23. The covering of claim 22, wherein said inner portion comprises a hydrophilic surface configured to adhere said covering to said ablated stroma when said seal is formed and to release said covering from said epithelium when said epithelium regenerates and covers said epithelial defect.

24. The covering of claim 1, wherein said inner thickness is within a range from 5 micrometers (μm) to 200 μm.

25. The covering of claim 1, wherein the covering comprises a therapeutic lens.

\* \* \* \* \*